US007576099B2

(12) United States Patent
Kelly et al.

(10) Patent No.: US 7,576,099 B2
(45) Date of Patent: *Aug. 18, 2009

(54) AMIDE DERIVATIVES AS ION-CHANNEL LIGANDS AND PHARMACEUTICAL COMPOSITIONS AND METHODS OF USING THE SAME

(75) Inventors: Michael G. Kelly, Thousand Oaks, CA (US); John Kincaid, San Mateo, CA (US); Matthew Duncton, San Francisco, CA (US); Kiran Sahasrabudhe, Fall Church, VA (US); Satyanarayana Janagani, Santa Clara, CA (US); Ravindra B. Upasani, San Jose, CA (US); Guoxian Wu, Palo Alto, CA (US); YunFeng Fang, San Diego, CA (US); Jianhua He, legal representative, Foster City, CA (US); Zhi-Liang Wei, Foster City, CA (US); Carl Kaub, San Mateo, CA (US)

(73) Assignee: Renovis, Inc., South San Francisco, CA (US)

( * ) Notice: Subject to any disclaimer, the term of this patent is extended or adjusted under 35 U.S.C. 154(b) by 479 days.

This patent is subject to a terminal disclaimer.

(21) Appl. No.: 11/362,451

(22) Filed: Feb. 24, 2006

(65) Prior Publication Data

US 2006/0194801 A1  Aug. 31, 2006

Related U.S. Application Data

(60) Provisional application No. 60/656,984, filed on Feb. 28, 2005, provisional application No. 60/710,445, filed on Aug. 23, 2005.

(51) Int. Cl.
C07D 215/16  (2006.01)
C07D 413/02  (2006.01)
A61K 31/47  (2006.01)

(52) U.S. Cl. ............... 514/311; 546/152; 546/159; 514/313

(58) Field of Classification Search ............. 546/152, 546/159; 514/311, 313
See application file for complete search history.

(56) References Cited

U.S. PATENT DOCUMENTS

| 3,346,584 | A | 10/1967 | Manning et al. |
| 3,424,760 | A | 1/1969 | Helsley et al. |
| 3,424,761 | A | 1/1969 | Helsley et al. |
| 3,798,226 | A | 3/1974 | Kanji et al. |
| 4,393,225 | A | 7/1983 | Hayashi et al. |
| 4,430,423 | A | 2/1984 | Aoki et al. |
| 4,579,866 | A | 4/1986 | Stevenosn et al. |
| 4,642,308 | A | 2/1987 | Cotrel et al. |
| 4,760,161 | A | 7/1988 | Durette et al. |
| 5,559,141 | A | 9/1996 | Karjalainen et al. |
| 5,693,672 | A | 12/1997 | Weichert et al. |
| 5,968,946 | A | 10/1999 | Maryanoff et al. |
| 6,034,107 | A | 3/2000 | Hirai et al. |
| 6,083,987 | A | 7/2000 | Nishino et al. |
| 6,221,865 | B1 | 4/2001 | Sebti et al. |
| 6,262,104 | B1 | 7/2001 | Dondio et al. |
| 6,331,640 | B1 | 12/2001 | Fotouhi et al. |
| 6,414,145 | B1 | 7/2002 | Boyle et al. |
| 6,486,156 | B1 | 11/2002 | Arnould et al. |
| 6,656,971 | B2 | 12/2003 | Wu et al. |
| 6,803,384 | B2 | 10/2004 | Fotouhi et al. |
| 6,831,175 | B2 | 12/2004 | Li et al. |
| 7,217,728 | B2 | 5/2007 | Fotouhi et al. |
| 7,432,281 | B2 | 10/2008 | Kelly et al. |
| 2002/0052512 | A1 | 5/2002 | Fotouhi et al. |
| 2002/0165275 | A1 | 11/2002 | Wu et al. |
| 2003/0199511 | A1 | 10/2003 | Li et al. |
| 2003/0220495 | A1 | 11/2003 | Boyle et al. |
| 2004/0006236 | A1 | 1/2004 | Fotouhi et al. |
| 2004/0110802 | A1 | 6/2004 | Thorarensen et al. |
| 2004/0116399 | A1 | 6/2004 | Zhu et al. |
| 2004/0142953 | A1 | 7/2004 | DeLorme et al. |
| 2004/0157919 | A1 | 8/2004 | Wu et al. |
| 2004/0235888 | A1 | 11/2004 | Yamamori et al. |
| 2005/0080119 | A1 | 4/2005 | Fotouhi et al. |
| 2005/0165028 | A1 | 7/2005 | Norman et al. |

(Continued)

FOREIGN PATENT DOCUMENTS

| DE | 2502588 | 7/1976 |
| EP | 0 172 083 | 2/1986 |
| EP | 0 347 000 | 12/1989 |
| EP | 0 401 903 | 12/1990 |
| GB | 2226313 | 6/1990 |

(Continued)

OTHER PUBLICATIONS

Thomas A. Godwin (Gastrointestinal Diseases, <http://edcenter.med.cornell.edu/CUMC_PathNotes/Gastrointestinal/Gastrointestinal.html>, 51 pages), downloaded on Jul. 7, 2005.*

(Continued)

Primary Examiner—Kahsay T Habte
(74) Attorney, Agent, or Firm—Jones Day

(57) ABSTRACT

Compounds are disclosed that have a formula represented by the following:

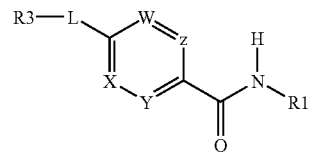

The compounds may be prepared as pharmaceutical compositions, and may be used for the prevention and treatment of a variety of conditions in mammals including humans, including by way of non-limiting example, pain, inflammation, traumatic injury, and others.

24 Claims, 6 Drawing Sheets

U.S. PATENT DOCUMENTS

| | | | |
|---|---|---|---|
| 2005/0222200 | A1 | 10/2005 | Kelly et al. |
| 2006/0020131 | A1 | 1/2006 | Raeppel et al. |
| 2006/0035939 | A1 | 2/2006 | Koga et al. |
| 2006/0111353 | A1 | 5/2006 | Weichert et al. |
| 2006/0154988 | A1 | 7/2006 | Andersen et al. |
| 2006/0194801 | A1 | 8/2006 | Kelly et al. |
| 2007/0099956 | A1 | 5/2007 | Kikuchi et al. |
| 2007/0105943 | A1 | 5/2007 | Nakamoto et al. |
| 2008/0300243 | A1 | 12/2008 | Kelly et al. |
| 2008/0312237 | A1 | 12/2008 | Kelly et al. |

FOREIGN PATENT DOCUMENTS

| | | | |
|---|---|---|---|
| JP | 11-171848 | | 6/1999 |
| JP | 2001-139550 | | 5/2001 |
| JP | 2002-055409 | | 2/2002 |
| JP | 2005-314347 | | 11/2005 |
| WO | WO 92/09285 | | 6/1992 |
| WO | WO 96/32015 | | 10/1996 |
| WO | WO 97/14681 | | 4/1997 |
| WO | WO 97/29079 | | 8/1997 |
| WO | WO 97/45402 | | 12/1997 |
| WO | WO 97/48694 | | 12/1997 |
| WO | WO 98/50029 | | 11/1998 |
| WO | WO 98/50030 | | 11/1998 |
| WO | WO 98/50031 | | 11/1998 |
| WO | WO 99/02497 | | 1/1999 |
| WO | WO 99/41235 | | 8/1999 |
| WO | WO 99/48492 | | 9/1999 |
| WO | WO 00/15213 | | 3/2000 |
| WO | WO 00/54759 | | 9/2000 |
| WO | WO 00/69849 | | 11/2000 |
| WO | WO 01/10380 | | 2/2001 |
| WO | WO 01/10381 | | 2/2001 |
| WO | WO 01/19798 | | 3/2001 |
| WO | WO 01/21160 | | 3/2001 |
| WO | WO 01/21615 | | 3/2001 |
| WO | WO 01/51456 | | 7/2001 |
| WO | WO 01/55115 | | 8/2001 |
| WO | WO 01/62737 | | 8/2001 |
| WO | WO 01/64642 | | 9/2001 |
| WO | WO 01/82916 | | 11/2001 |
| WO | WO 02/08221 | | 1/2002 |
| WO | WO 02/16317 | * | 2/2002 |
| WO | WO 02/16318 | | 2/2002 |
| WO | WO 02/16319 | | 2/2002 |
| WO | WO 02/16517 | * | 2/2002 |
| WO | WO 02/44126 | | 6/2002 |
| WO | WO 02/051397 | | 7/2002 |
| WO | WO 02/053101 | | 7/2002 |
| WO | WO 02/059080 | | 8/2002 |
| WO | WO 02/064547 | | 8/2002 |
| WO | WO 02/064568 | | 8/2002 |
| WO | WO 02/070494 | | 9/2002 |
| WO | WO 02/094766 | | 11/2002 |
| WO | WO 03/013516 | | 2/2003 |
| WO | WO 03/015774 | | 2/2003 |
| WO | WO 03/016254 | | 2/2003 |
| WO | WO 03/018536 | | 3/2003 |
| WO | WO 03/024448 | | 3/2003 |
| WO | WO 03/040174 | | 5/2003 |
| WO | WO 03/048101 | | 6/2003 |
| WO | WO 03/051366 | | 6/2003 |
| WO | WO 03/068749 | | 8/2003 |
| WO | WO 2004/002481 | | 1/2004 |
| WO | WO 2004/009549 | | 1/2004 |
| WO | WO 2004/022536 | | 3/2004 |
| WO | WO 2004/024710 | | 3/2004 |
| WO | WO 2004/062601 | | 7/2004 |
| WO | WO 2004/069792 | | 8/2004 |
| WO | WO 2004/096784 | | 11/2004 |
| WO | WO 2005/009962 | | 2/2005 |
| WO | WO 2005/016277 | | 2/2005 |
| WO | WO 2005/019176 | | 3/2005 |
| WO | WO 2005/033079 | | 4/2005 |
| WO | WO 2005/046683 | | 5/2005 |
| WO | WO 2005/115977 | | 12/2005 |
| WO | WO 2006/093832 | | 9/2006 |
| WO | WO 2007/100758 | | 9/2007 |

OTHER PUBLICATIONS

Chalmers (TiPS vol. 17, pp. 166-172 Apr. 1996).*
ISA/PCT International Search Report dated Jan. 29, 2007, for International Application No. PCT/US2006/006615.
IPEA/PCT International Preliminary Report on Patentability dated May 21, 2007, for International Application No. PCT/US2006/006615.
PCT International Search Report, dated Sep. 28, 2007, for International Application No. PCT/US2007/004912, filed Feb. 22, 2007.
PCT International Preliminary Report on Patentability, dated Oct. 20, 2008, for International Application No. PCT/US2007/004912, filed Feb. 22, 2007.
PCT International Search Report, dated Mar. 28, 2005, for International Application No. PCT/US2004/033163, filed Oct. 7, 2004.
U.S. P.T.O. Non-Final Office Action dated Oct. 16, 2007, in U.S. Appl. No. 10/961,483, filed Oct. 7, 2004.
U.S.P.T.O. Interview Summary between Examiner, Zinna N. Davis, and Rahul Pathak, dated Apr. 21, 2008, in U.S. Appl. No. 10/961,483, filed Oct. 7, 2004.
U.S.P.T.O. Notice of Allowance and Fees Due dated Apr. 24, 2008, in U.S. Appl. No. 10/961,483, filed Oct. 7, 2004.
U.S.P.T.O. Supplemental Notice of Allowability dated Jul. 28, 2008, in U.S. Appl. No. 10/961,483, filed Oct. 7, 2004.
Alonso et al., 1997, "Lithiated 3-Aminoalkyl Sulfones as Mono and Dinucleophiles in the Preparation of Nitrogen Heterocycles: Application to the Synthesis of Capazepine," Tetrahedron, vol. 53:4791.
Baston et al., 2003 "Cyclohex-1-ene Carboxylic Acids: Synthesis and Biological Evaluation of Novel Inhibitors of Human 5α Reductase," Arch. Pharm. Pharm. Med. Chem., 1:31-38.
Brisdon et al., "Hydrofluorocarbon 245fa: A Versatile New Synthon in Alkyne Chemistry," Chem. Comm., 2002, pp. 2420-2421.
Dorsett et al., 1970, "Aminoalkenylbenzenesulfonamides with Hypotensive and Histamine-Releasing Properties," J. Med. Chem., 13(6):895-900.
Fanta, Paul E., "Sodium Nitromalonaldehyde Monohydrate," Organic Syntheses, Collective vol. 4, p. 844. ©1963 Organic Synthesis, Inc.
Fu et al., 2002, "Peptidyl Aldehydes as Reversible Covalent Inhibitors of Protein Tyrosine Phosphatases," Biochemistry, 41:10700-10709.
Hutter et al., "QSAR of Human Steriod 5α-Reductase Inhibitors: Where are the Differences Between Isoenzyme Type 1 and 2?" QSAR Comb. Sci., 23:406-415.
Ikeda et al., 2002, "Cobalt-Catalyzed Heck-Type Reaction of Alkyl Halides with Styrenes," J. Am. Chem. Soc., 124:6514-6515.
Janusz et al., 1993, Vanilloids. 1. Analogs of Capsacin with Antinociceptive and Antiinflammatory Activity, J. Med. Chem., vol. 36:2595.
Marchand et al., 1999, "Synthesis and Electrochemical Behaviour of New Polythiophenes Branched with Sulfonamides for Solid Phase Synthesis," New J. Chem., 23:869-875.
Vlad et al., 2002, "Improved Synthesis of 2,2'-Bipyrimidine," J. Org. Chem., vol. 67:6550-6552.
Walpole et al., 1994, "The Discovery of Capsazine, the First Competitive Antagonist of the Sensory Neuron Excitants Capsacain and Resiniferatoxin," Journal of Medicinal Chemistry, vol. 37:1942-1957.
Yoneda et al, 1990, Preparation of 1-Aryl- or 1-Alkenyl-2-(perfluoroalkyl)acetylenes), Bull. Chem. Soc. Jpn., vol. 63:2124-2126.

* cited by examiner

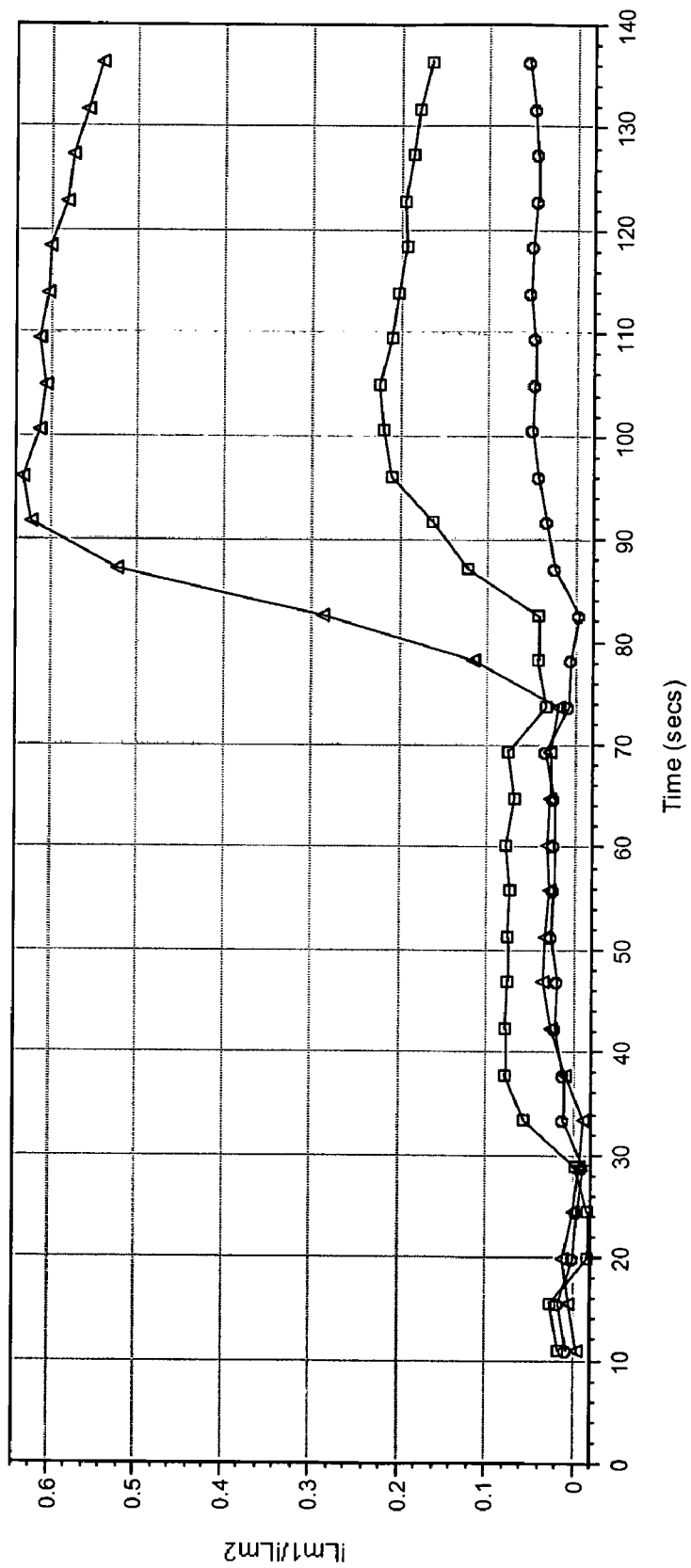

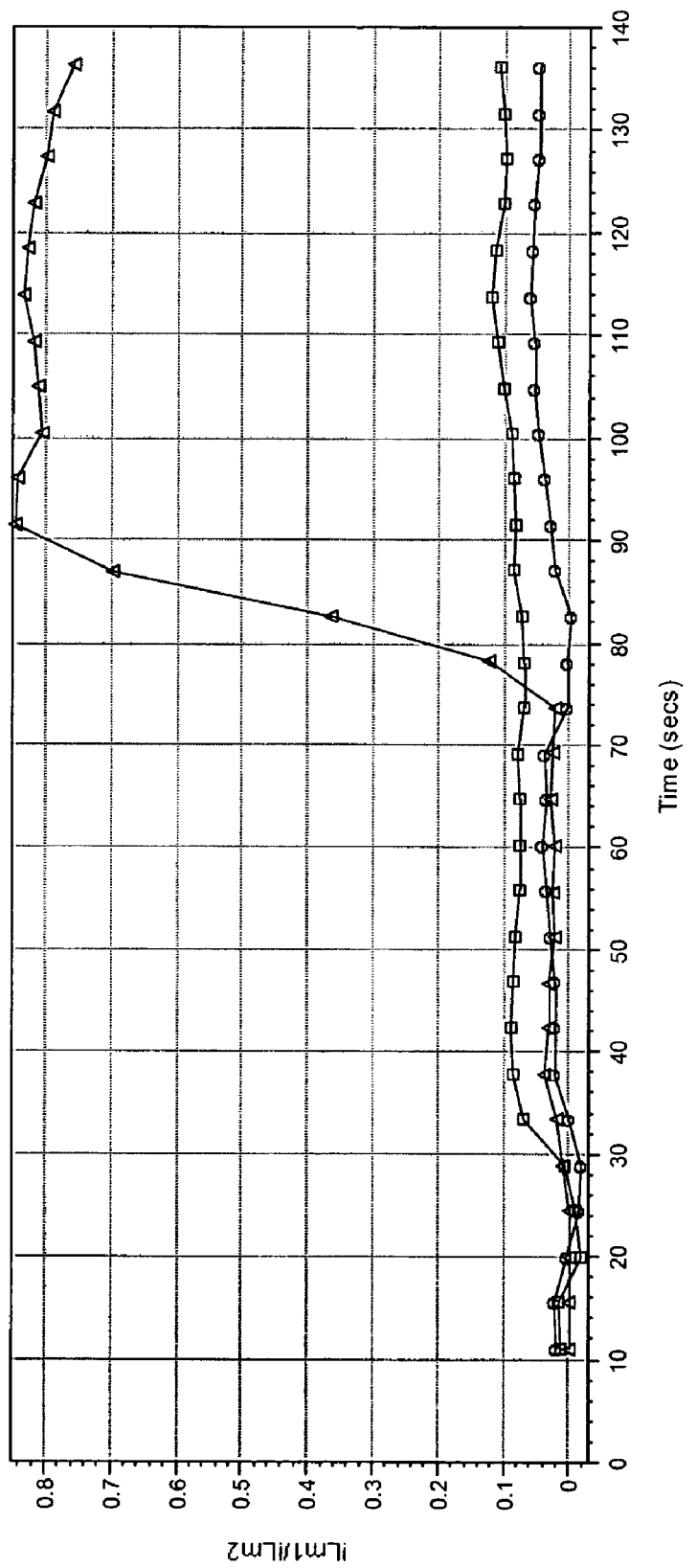

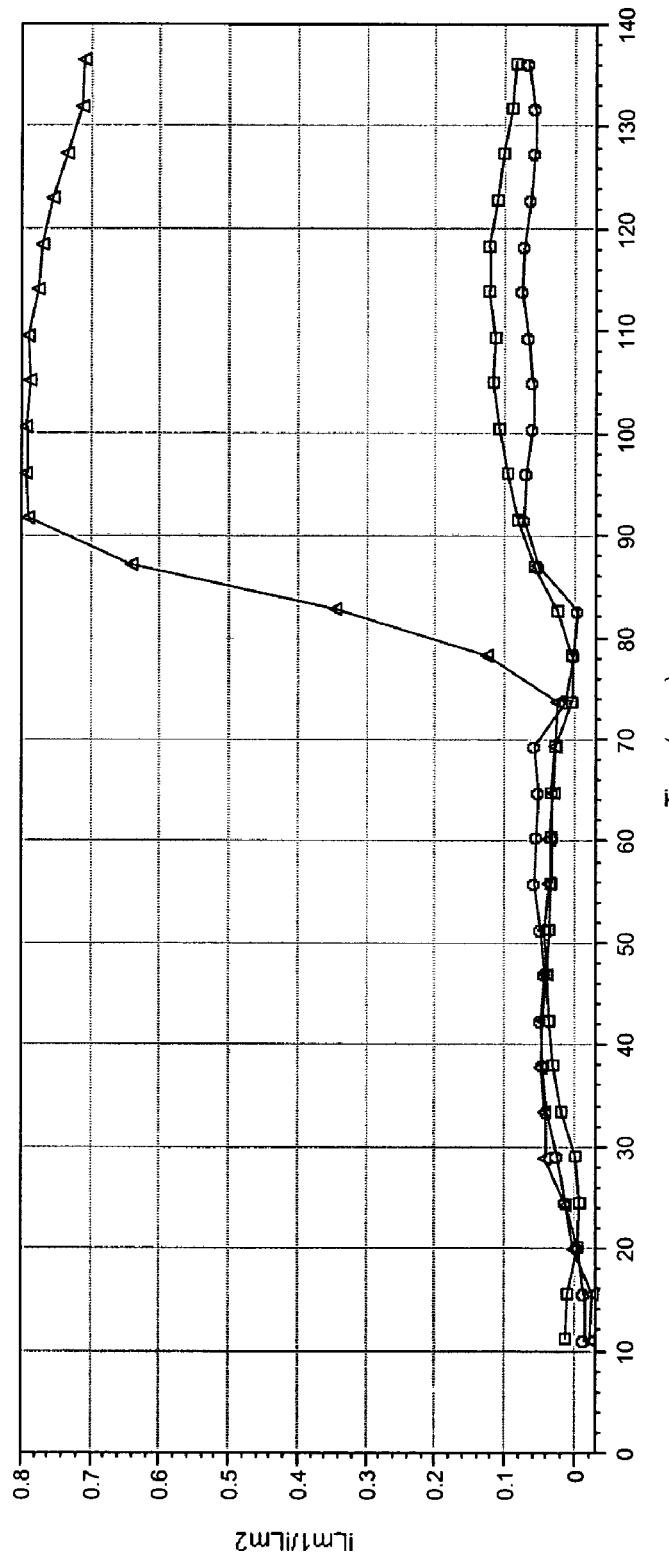

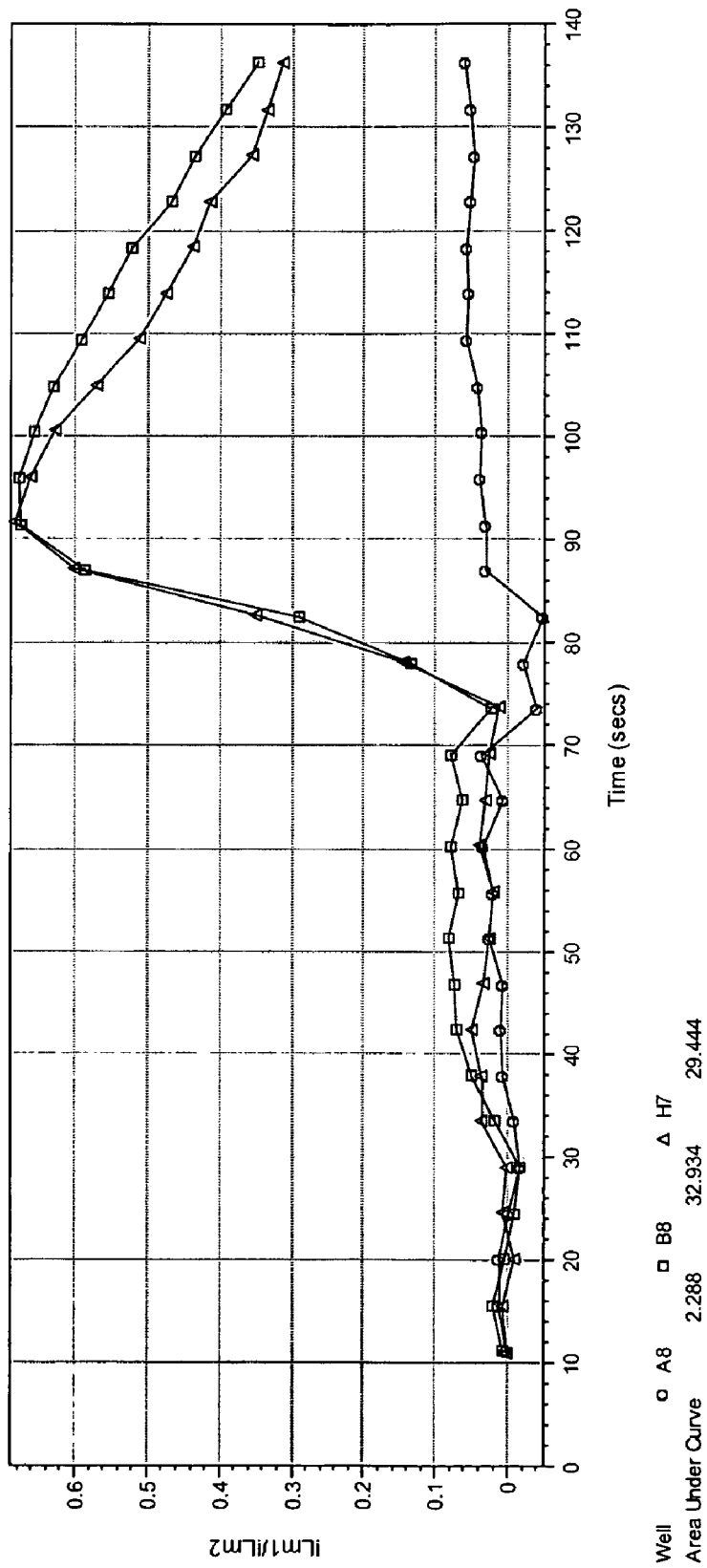

AMIDE DERIVATIVES AS ION-CHANNEL LIGANDS AND PHARMACEUTICAL COMPOSITIONS AND METHODS OF USING THE SAME

RELATED APPLICATIONS

The instant application claims the benefit under 35 U.S.C. §119 of U.S. Provisional Application No. 60/656,984, filed Feb. 28, 2005, and U.S. Provisional Application No. 60/710,445, filed Aug. 23, 2005, the contents of each of which are hereby incorporated by reference in their entirety.

FIELD OF THE INVENTION

This invention relates to novel compounds and to pharmaceutical compositions containing such compounds. This invention also relates to methods for preventing and/or treating pain and inflammation-related conditions in mammals, such as (but not limited to) arthritis, Parkinson's disease, Alzheimer's disease, stroke, uveitis, asthma, myocardial infarction, the treatment and prophylaxis of pain syndromes (acute and chronic or neuropathic), traumatic brain injury, acute spinal cord injury, neurodegenerative disorders, alopecia (hair loss), inflammatory bowel disease, urinary incontinence, chronic obstructive pulmonary disease, irritable bowel disease, osteoarthritis, and autoimmune disorders, using the compounds and pharmaceutical compositions of the invention.

BACKGROUND OF THE INVENTION

Studies of signaling pathways in the body have revealed the existence of ion channels and sought to explain their role. Ion channels are integral membrane proteins with two distinctive characteristics: they are gated (open and closed) by specific signals such as membrane voltage or the direct binding of chemical ligands and, once open, they conduct ions across the cell membrane at very high rates.

There are many types of ion channels. Based on their selectivity to ions, they can be divided into calcium channel, potassium channel, sodium channel, etc. The calcium channel is more permeable to calcium ions than other types of ions, the potassium channel selects potassium ions over other ions, and so forth. Ion channels may also be classified according to their gating mechanisms. In a voltage-gated ion channel, the opening probability depends on the membrane voltage, whereas in a ligand-gated ion channel, the opening probability is regulated by the binding of small molecules (the ligands). Since ligand-gated ion channels receive signals from the ligand, they may also be considered as "receptors" for ligands.

Examples of ligand-gated ion channels include nAChR (nicotinic acetylcholine receptor) channel, GluR (glutamate receptor) channel, ATP-sensitive potassium channel, G-protein activated channel, cyclic-nucleotide-gated channel, etc.

Transient receptor potential (TRP) channel proteins constitute a large and diverse family of proteins that are expressed in many tissues and cell types. This family of channels mediates responses to nerve growth factors, pheromones, olfaction, tone of blood vessels and metabolic stress et al., and the channels are found in a variety of organisms, tissues and cell types including nonexcitable, smooth muscle and neuronal cells. Furthermore, TRP-related channel proteins are implicated in several diseases, such as several tumors and neurodegenerative disorders and the like. See, for example, Minke, et al., *APStracts* 9:0006P (2002).

Nociceptors are specialized primary afferent neurons and the first cells in a series of neurons that lead to the sensation of pain. The receptors in these cells can be activated by different noxious chemical or physical stimuli. The essential functions of nociceptors include the transduction of noxious stimuli into depolarizations that trigger action potentials, conduction of action potentials from primary sensory sites to synapses in the central nervous system, and conversion of action potentials into neurotransmitter release at presynaptic terminals, all of which depend on ion channels.

One TRP channel protein of particular interest is the vanilloid receptor. Also known as VR1, the vanilloid receptor is a non-selective cation channel which is activated or sensitized by a series of different stimuli including capsaicin, heat and acid stimulation and products of lipid bilayer metabolism (anandamide), and lipoxygenase metabolites. See, for example Smith, et al., *Nature,* 418:186-190 (2002). VR1 does not discriminate among monovalent cations, however, it exhibits a notable preference for divalent cations with a permeability sequence of $Ca^{2+}>Mg^{2+}>Na^+=K^+=Cs^+$. $Ca^{2+}$ is especially important to VR1 function, as extracellular $Ca^{2+}$ mediates desensitization, a process which enables a neuron to adapt to specific stimuli by diminishing its overall response to a particular chemical or physical signal. VR1 is highly expressed in primary sensory neurons in rats, mice and humans, and innervates many visceral organs including the dermis, bones, bladder, gastrointestinal tract and lungs. It is also expressed in other neuronal and non-neuronal tissues including the CNS, nuclei, kidney, stomach and T-cells. The VR1 channel is a member of the superfamily of ion channels with six membrane-spanning domains, with highest homology to the TRP family of ion channels.

VR1 gene knockout mice have been shown to have reduced sensory sensitivity to thermal and acid stimuli. See, for example, Caterina, et al. *Science,* 14:306-313 (2000). This supports the concept that VR1 contributes not only to generation of pain responses but also to the maintenance of basal activity of sensory nerves. VR1 agonists and antagonists have use as analgesics for the treatment of pain of various genesis or etiology, for example acute, inflammatory and neuropathic pain, dental pain and headache (such as migraine, cluster headache and tension headache). They are also useful as anti-inflammatory agents for the treatment of arthritis, Parkinson's Disease, Alzheimer's Disease, stroke, uveitis, asthma, myocardial infarction, the treatment and prophylaxis of pain syndromes (acute and chronic [neuropathic]), traumatic brain injury, spinal cord injury, neurodegenerative disorders, alopecia (hair loss), inflammatory bowel disease, irritable bowel disease and autoimmune disorders, renal disorders, obesity, eating disorders, cancer, schizophrenia, epilepsy, sleeping disorders, cognition, depression, anxiety, blood pressure, lipid disorders, osteoarthritis, and atherosclerosis.

Compounds, such as those of the present invention, which interact with the vanilloid receptor can thus play a role in treating or preventing or ameliorating these conditions.

A wide variety of Vanilloid compounds of different structures are known in the art, for example those disclosed in European Patent Application Numbers, EP 0 347 000 and EP 0 401 903, UK Patent Application Number GB 2226313 and International Patent Application, Publication Number WO 92/09285. Particularly notable examples of vanilloid compounds or vanilloid receptor modulators are capsaicin or trans 8-methyl-N-vanillyl-6-nonenamide which is isolated from the pepper plant, capsazepine (Tetrahedron, 53, 1997, 4791) and olvanil or- N-(4-hydroxy-3-methoxybenzyl)oleamide (J. Med. Chem., 36, 1993, 2595).

International Patent Application, Publication Number WO 02/08221 discloses diaryl piperazine and related compounds which bind with high selectivity and high affinity to vanilloid receptors, especially Type I Vanilloid receptors, also known as capsaicin or VR1 receptors. The compounds are said to be useful in the treatment of chronic and acute pain conditions, itch and urinary incontinence.

International Patent Application, Publication Numbers WO 02/16317, WO 02/16318 and WO 02/16319 suggest that compounds having a high affinity for the vanilloid receptor are useful for treating stomach-duodenal ulcers.

International Patent Application, Publication No. WO 2005/046683, published May 26, 2005, commonly owned, discloses a series of compounds that have demonstrated activity as VR-1 antagonists, and that are suggested as being useful for the treatment of conditions associated with VR-1 activity.

U.S. Pat. Nos. 3,424,760 and 3,424,761 both describe a series of 3-Ureidopyrrolidines that are said to exhibit analgesic, central nervous system, and pyschopharmacologic activities. These patents specifically disclose the compounds 1-(1-phenyl-3-pyrrolidinyl)-3-phenyl urea and 1-(1-phenyl-3-pyrrolidinyl)-3-(4-methoxyphenyl) urea respectively. International Patent Applications, Publication Numbers WO 01/62737 and WO 00/69849 disclose a series of pyrazole derivatives which are stated to be useful in the treatment of disorders and diseases associated with the NPY receptor subtype Y5, such as obesity. WO 01/62737 specifically discloses the compound 5-amino-N-isoquinolin-5-yl-1-[3-(trifluoromethyl)phenyl]-1H-pyrazole-3-carboxamide. WO 00/69849 specifically discloses the compounds 5-methyl-N-quinolin-8-yl-1-[3-(trifluoromethyl)phenyl]-1H-pyrazole-3-carboxamide, 5-methyl-N-quinolin-7-yl-1-[3-trifluoromethyl)phenyl]-1H-pyrazole-3-carboxamide, 5-methyl-N-quinolin-3-yl-1-[3-(trifluoromethyl)phenyl]-1H-pyrazole-3-carboxamide, N-isoquinolin-5-yl-5-methyl-1-[3-(trifluoromethyl)phenyl]-1H-pyrazole-3-carboxamide, 5-methyl-N-quinolin-5-yl-1-[3-(trifluoromethyl)phenyl]-1H-pyrazole-3-carboxamide, 1-(3-chlorophenyl)-N-isoquinolin-5-yl-5-methyl-1H-pyrazole-3-carboxamide, N-isoquinolin-5-yl-1-(3-methoxyphenyl)-5-methyl-1H-pyrazole-3-carboxamide, 1-(3-fuorophenyl)-N-isoquinolin-5-yl-5-methyl-1H-pyrazole-3-carboxamide, 1-(2-chloro-5-trifluoromethylphenyl)-N-isoquinolin-5-yl-5-methyl-1N-pyrazole-3-carboxamide, 5-methyl-N-(3-methylisoquinolin-5-yl)-1-[3-(trifluoromethyl) phenyl]-1N-pyrazole-3-carboxamide, 5-methyl-N-(1,2,3,4-tetrahydroisoquinolin-5-yl)-1-[3-(trifluoromethyl)phenyl]-1H-pyrazole-3-carboxamide.

German Patent Application Number 2502588 describes a series of piperazine derivatives. This application specifically discloses the compound N-[3-[2-(diethylamino) ethyl]-1,2-dihydro-4-methyl-2-oxo-7-quinolinyl]-4-phenyl-1-piperazinecarboxamide.

We have now discovered that certain compounds have surprising potency and selectivity as VR-1 antagonists. The compounds of the present invention are considered to be particularly beneficial as VR-1 antagonists as certain compounds exhibit improved aqueous solubility and metabolic stability.

SUMMARY OF THE INVENTION

It has now been found that compounds such as those set forth herein, are capable of modifying mammalian ion channels such as the VR1 cation channel. Accordingly, the present compounds are potent VR1 antagonists with analgesic activity by systemic administration. The compounds of the present invention may show less toxicity, good absorption, good half-life, good solubility, low protein binding affinity, less drug-drug interaction, a reduced inhibitory activity at HERG channel, reduced QT prolongation and good metabolic stability. This finding leads to novel compounds having therapeutic value. It also leads to pharmaceutical compositions having the compounds of the present invention as active ingredients and to their use to treat, prevent or ameliorate a range of conditions in mammals such as but not limited to pain of various genesis or etiology, for example acute, chronic, inflammatory and neuropathic pain, dental pain and headache (such as migraine, cluster headache and tension headache).

Accordingly, in a first aspect of the invention, compounds are disclosed that are capable of modifying ion channels, in vivo, having a formula I:

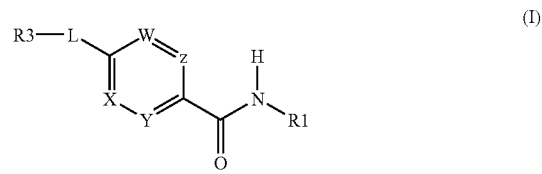

wherein:
each of W, Z, Y and X is independently N or $CR^4$;
L is —$(CR^5{=}CR^6)$— or —$(C{\equiv}C)$—;
$R^1$ is substituted or unsubstituted bicycloaryl or bicycloheteroaryl;
$R^3$ is $C_1$-$C_6$ alkyl, hydroxyl $C_1$-$C_6$ alkyl, halo $C_1$-$C_6$ alkyl, heteroalkyl, aryl, cycloalkyl, cycloheteroalkyl, heteroaryl, aralkyl, or heteroaralkyl;
each $R^4$ is independently hydrogen, $C_1$-$C_6$ alkyl, hydroxyl $C_1$-$C_6$ alkyl, $C_2$-$C_6$ acyl, $C_2$-$C_6$ acylamino, $C_1$-$C_6$ alkylamino, $C_1$-$C_6$ alkylthio, $C_1$-$C_6$ alkoxy, $C_1$-$C_6$ alkoxycarbonyl, $C_1$-$C_6$ alkylarylamino, aryl $C_1$-$C_6$ alkyloxy, amino, aryl, aryl $C_1$-$C_6$ alkyl, sulfoxide, sulfone, sulfanyl, aminosulfonyl, arylsulfonyl, sulfuric acid, sulfuric acid ester, dihydroxyphosphoryl, aminohydroxyphosphoryl, azido, carboxy, carbamoyl, carboxyl, cyano, cycloheteroalkyl, dialkylamino, halo, heteroaryloxy, heteroaryl, heteroalkyl, hydroxyl, nitro or thio; and
each of $R^5$ and $R^6$ is independently H, halo, $C_1$-$C_6$ alkyl, hydroxyl $C_1$-$C_6$ alkyl, hetero $C_1$-$C_6$ alkyl, aryl, heteroaryl, aralkyl, or heteroaralkyl.

or a pharmaceutically acceptable salt, solvate or prodrug thereof;

and stereoisomers and tautomers thereof.

In a further embodiment of the invention, compounds of formula IA, hereinafter referred to as compounds of formula IA', $R^3$-L represents the moiety: $CR^3R^6{=}CR^5$

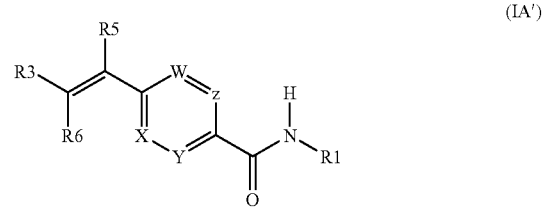

wherein $R^3$ is as defined for compounds of formula I and $R^5$ and $R^6$ are independently selected from hydrogen, halo, $C_1$-$C_6$ alkyl, hydroxyl $C_1$-$C_6$ alkyl, hetero $C_1$-$C_6$ alkyl, aryl, heteroaryl, aralkyl and heteroaralkyl.

In certain specific compounds $R^3$ is selected from $C_1$-$C_6$ alkyl, hydroxyl $C_1$-$C_6$ alkyl, substituted or unsubstituted $C_3$-$C_6$ cycloalkyl, substituted or unsubstituted aryl and substituted or unsubstituted aralkyl; and each $R^5$ and $R^6$ are independently selected from hydrogen, halo and substituted and unsubstituted $C_1$-$C_6$ alkyl; and 0-3 groups selected from W, Z, X and Y represent N.

In compounds of formula IA', $R^5$ and $R^6$ may, for example, independently represent hydrogen, halo, $C_1$-$C_6$ alkyl or hydroxyl $C_1$-$C_6$ alkyl. Preferably $R^5$ and $R^6$ represent hydrogen.

In another particular embodiment of compounds of formula IA hereinafter referred to as compounds of formula IA", $R^3$-L represents the moiety $R^3C\equiv C-$.

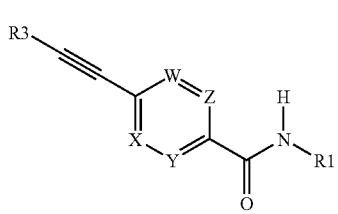

(IA")

In compounds of formula I, IA' and IA", W, Z, X and Y may for example each represent $CR^4$ especially CH. Alternatively X may represent N and W, Z and Y may each represent $CR^4$. In another example set of compounds each of X, Y and Z represents $CR^4$ especially CH. In another example set of compounds W is N. In yet another example set of compounds Y is N.

Generally in compounds of formula I, L is preferably $-(C=C)-$ or $-C\equiv C-$. Thus in one example set of compounds L represents $-(C=C)-$. In another example set of compounds L represents $-C\equiv C-$.

In compounds of formula I, IA' and IA", $R^1$ may for example represent substituted or unsubstituted bicycloaryl or bicycloheteroaryl, e.g. substituted naphthyl, quinoline, isoquinoline or tetrahydroquinoline. Examples of substituents include alkyl, alkyl(OH), —COOH, C(Me)$_3$, CH(Me)$_2$, halo, CF$_3$, cyano and methoxy. Alternatively, $R^1$ may represent substituted or unsubstituted tetrahydroisoquinoline or benzodioxane.

In compounds of formula I, IA' and IA", $R^3$ may for example represent $CR^{6'}R^7R^8$ wherein $R^{6'}$ represents hydrogen, halo, $C_1$-$C_6$ alkyl or hydroxyl $C_1$-$C_6$ alkyl; each of $R^7$ and $R^8$ is independently halo, $C_1$-$C_6$ alkyl or hydroxyl $C_1$-$C_6$ alkyl; or $R^7$ and $R^8$ together form a substituted or unsubstituted $C_3$-$C_8$ cycloalkyl ring. For example $R^7$ may represent lower alkyl (e.g. methyl). For example $R^8$ may represent lower alkyl (e.g. methyl). In particular examples, $R^{6'}$ may represent hydrogen and $R^7$ and $R^8$ may represent methyl. Alternatively each of $R^{6'}$, $R^7$ and $R^8$ may represent methyl. Alternatively each of $R^{6'}$, $R^7$ and $R^8$ may represent fluoro. Alternatively $R^{6'}$ may represent hydrogen and $R^7$ and $R^8$ together form a cyclopropyl ring.

In further embodiment of the compounds of formula I, IA, IA' and IA", $R^3$ may for example represent substituted or unsubstituted aryl or heteroaryl.

In a first alternative embodiment of the compounds of formula IA, $R^3$ is CF$_3$, n-propyl, or a group of the formula

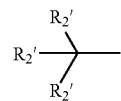

wherein $R^{2'}$ is hydrogen or alkyl; and wherein two $R^{2'}$ may join together to form a cycloalkyl or cycloheteroalkyl ring of 3-8 atoms; provided at least two of $R^{2'}$ are alkyl.

With respect to the compounds of formula I, $R^1$ may be substituted or unsubstituted naphthyl, or alternatively, substituted or unsubstituted tetrahydronaphthyl. Further, $R^1$ may also be substituted or unsubstituted bicycloheteroaryl, and in a particular embodiment, the bicycloheteroaryl may be selected from the group consisting of tetrahydroquinoline, tetrahydroisoquinoline, benzodioxane, benzopyran, indole and benzimidazole. More particularly, the bicycloheteroaryl may be quinoline, isoquinoline, benzodioxane, and benzoxazine. In a particular embodiment, the substitution on the bicycloheteroaryl is selected from the group consisting of hydrogen, alkyl, trifluoromethyl, halo, methoxy, trifluoromethoxy, amino and carboxy. In a yet further particular embodiment, the substitution on bicycloheteroaryl is selected from the group consisting of tert-butyl, cyano, trifluoroalkyl, halo, nitro, methoxy, amino and carboxy.

In yet another particular embodiment, with respect to the compounds of formula I, $R^1$ may be substituted or unsubstituted isoquinolin-5-yl, quinolin-3-yl, benzodioxan-6-yl or benzoxazin-6-yl.

In yet another particular embodiment, with respect to the compounds of formula I, $R^1$ may be substituted or unsubstituted:

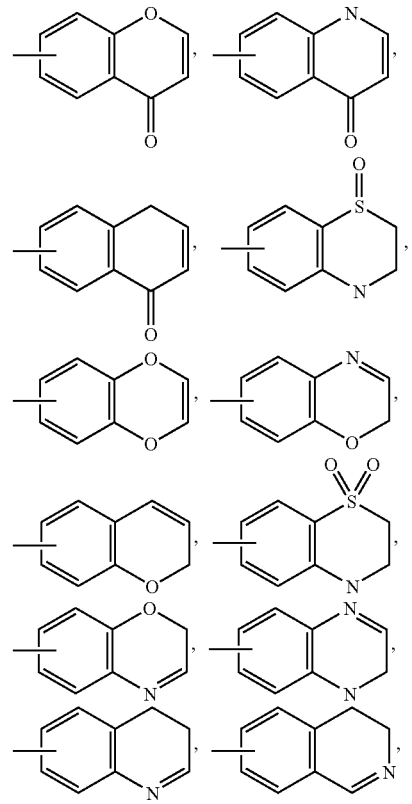

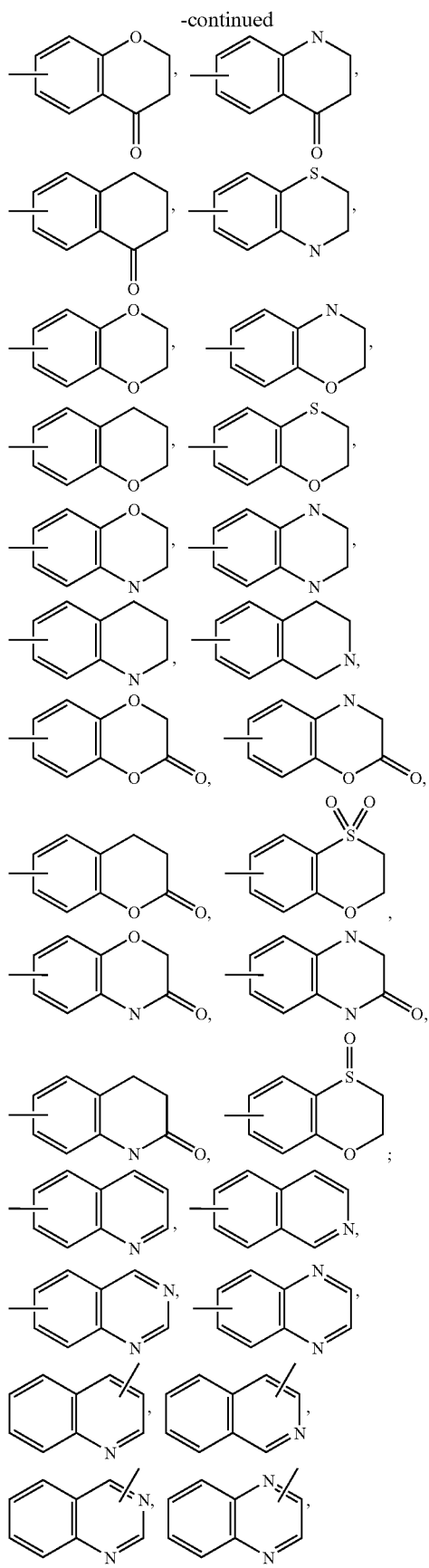
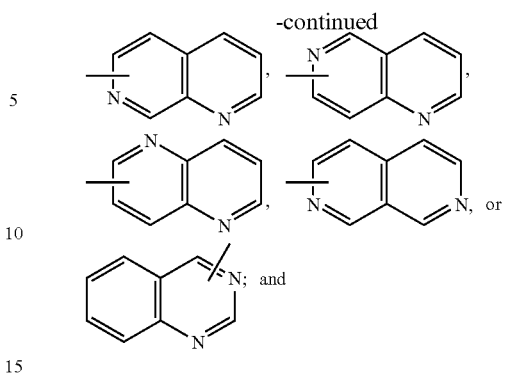
wherein, when feasible, the ring N can further be substituted with H or alkyl.
In yet another particular embodiment, with respect to the compounds of formula I, $R^1$ may be substituted or unsubstituted:
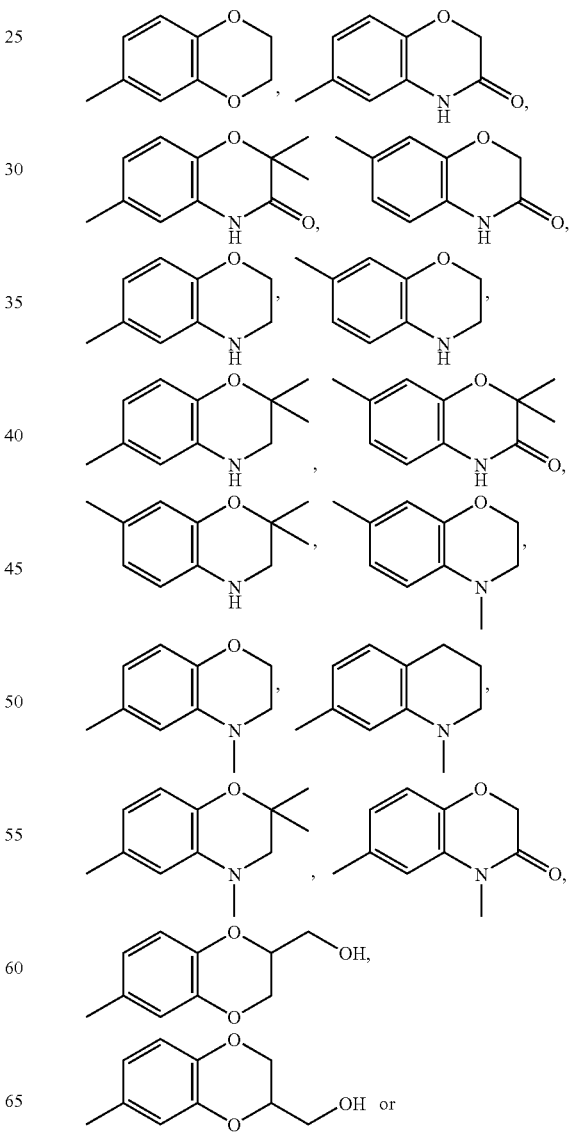

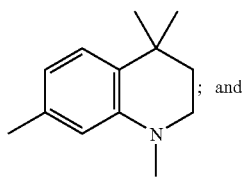

wherein, when feasible, the ring N can further be substituted with H or alkyl.

In yet another particular embodiment, with respect to the compounds of formula I, $R^1$ may be substituted or unsubstituted:

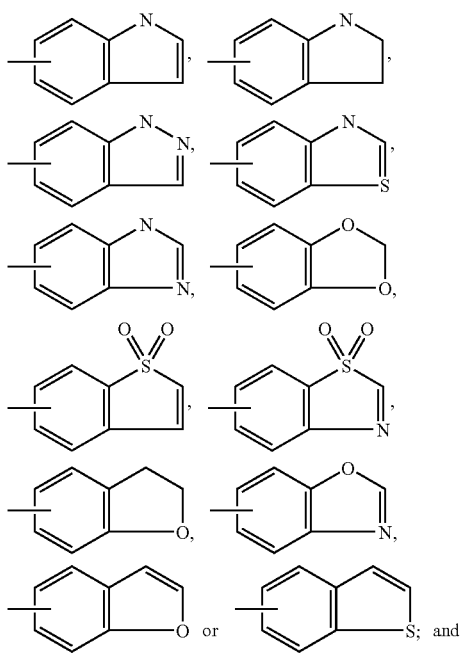

wherein, when feasible, the ring N can further be substituted with H or alkyl.

In yet another particular embodiment, with respect to the compounds of formula I, $R^3$ may be substituted or unsubstituted cyclopropyl.

In yet further particular embodiment, with respect to the compounds of formula I, $R^3$ may be $CF_3$.

In yet further particular embodiments, the compounds of the invention are set forth and may be selected from a comprehensive listing of such compounds, set forth later on herein in Table 1. The Table contains in excess of 200 compounds that have been or can be synthesized and have as a group, demonstrated activity in their capacity of modifying ion channels, in vivo, and thereby functioning in the therapeutic applications set forth herein in relation to capsaicin and the vanilloid receptor.

In a further aspect of the invention, compounds are disclosed that are capable of modifying ion channels, in vivo, having a formula I-I:

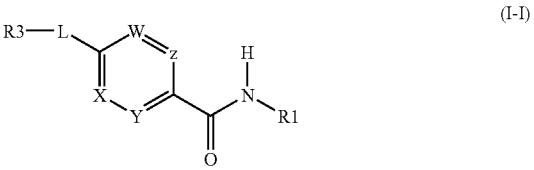

wherein:

each of W, Z, Y and X is independently N or $CR^4$;

L is substituted or unsubstituted —($CR^5$=$CR^6$)— or —(C≡C)—;

$R^1$ is substituted bicycloaryl or bicycloheteroaryl;

$R^3$ is $C_1$-$C_6$ alkyl, hydroxyl $C_1$-$C_6$ alkyl, halo $C_1$-$C_6$ alkyl, heteroalkyl, aryl, cycloalkyl, cycloheteroalkyl, heteroaryl, aralkyl, or heteroaralkyl;

each $R^4$ is independently hydrogen, $C_1$-$C_6$ alkyl, hydroxyl $C_1$-$C_6$ alkyl, acylamino, alkylamino, alkylthio, alkoxy, alkoxycarbonyl, alkylarylamino, arylalkyloxy, amino, aryl, arylalkyl, sulfoxide, sulfone, sulfanyl, aminosulfonyl, arylsulfonyl, sulfuric acid, sulfuric acid ester, dihydroxyphosphoryl, aminohydroxyphosphoryl, azido, carboxy, carbamoyl, cyano, cycloheteroalkyl, dialkylamino, halo, heteroaryloxy, heteroaryl, heteroalkyl, hydroxyl, nitro or thio; and each of $R^5$ and $R^6$ is independently H, halo, $C_1$-$C_6$ alkyl, hydroxyl $C_1$-$C_6$ alkyl, heteroalkyl, aryl, heteroaryl, aralkyl, or heteroaralkyl, or a pharmaceutically acceptable salt, solvate or prodrug thereof; and stereoisomers and tautomers thereof.

In a further embodiment of the invention, compounds of formula I-IA, hereinafter referred to as compounds of formula IA', $R^3$-L represents the moiety: $CR^3R^6$=$CR^5$

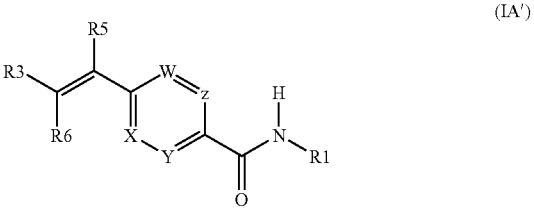

wherein $R^3$ is as defined for compounds of formula I and $R^5$ and $R^6$ are independently selected from hydrogen, halo, $C_1$-$C_6$ alkyl, hydroxyl $C_1$-$C_6$ alkyl, cycloalkyl, heteroalkyl, aryl, heteroaryl, aralkyl and heteroaralkyl.

In certain specific compounds $R^3$ is selected from $C_1$-$C_6$ alkyl, hydroxyl $C_1$-$C_6$ alkyl, substituted or unsubstituted $C_1$-$C_6$ cycloalkyl, substituted or unsubstituted aryl and substituted or unsubstituted aralkyl; and each $R^5$ and $R^6$ are independently selected from hydrogen, halo and substituted and unsubstituted $C_1$-$C_6$ alkyl; and 0-3 groups selected from W, Z, X and Y represent N.

In compounds of formula IA', $R^5$ and $R^6$ may, for example, independently represent hydrogen, halo, $C_1$-$C_6$ alkyl or hydroxyl $C_1$-$C_6$ alkyl. Preferably $R^5$ and $R^6$ represent hydrogen.

In another particular embodiment of compounds of formula I-IA hereinafter referred to as compounds of formula IA", $R^3$-L represents the moiety $R^3$C≡C—.

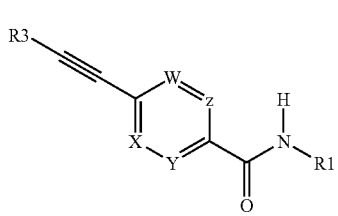

(IA'')

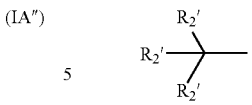

wherein $R^{2'}$ is hydrogen or alkyl; and wherein two $R^{2'}$s may join together to form a cycloalkyl or cycloheteroalkyl ring of 3-8 atoms; provided at least two of $R^{2'}$ are alkyl.

In compounds of formula I-I, IA' and IA'', W, Z, X and Y may for example each represent $CR^4$, especially CH. Alternatively X may represent N and W, Z and Y may each represent $CR^4$. In another exemplary set of compounds, each of X, Y and Z represents $CR^4$, especially CH. In another example set of compounds W is N. In yet another exemplary set of compounds, Y is N.

In another exemplary set of compounds of formula I-I, IA' and IA'', each of W, X and Z represents $CR^4$ especially CH and Y represents $CR^{4'''}$. In this example set $R^{4'''}$ may for example represent substituted alkyl, halo, sulfone, alkoxy, or amino. Particularly, $R^{4'''}$ may represent substituted alkyl or halo. More particularly, $R^{4'''}$ may be methyl, chloro, trifluoromethyl or fluoro.

In another exemplary set of compounds of formula I-I, IA' and IA'', each of W and X represents $CR^4$ especially CH and each of Y and Z represent $CR^{4'''}$. In this example set each $R^{4'''}$ may for example represent substituted alkyl, halo, alkoxy, or amino. Particularly, $R^{4'''}$ may represent substituted alkyl or halo. More particularly, $R^{4'''}$ may be methyl, trifluoromethyl, chloro or fluoro.

Generally in compounds of formula I-I, L is preferably —C=C— or —C≡C—. Thus in one exemplary set of compounds, L represents —(C=C)—. In another exemplary set of compounds, L represents —C≡C—.

In compounds of formula I-I, IA' and IA'', $R^1$ may for example represent substituted bicycloaryl or bicycloheteroaryl, e.g. substituted benzopyranyl, benzoxazine, benzothiazine, indolyl, indazolyl, methylenedioxyphenyl, quinolinyl, isoquinolinyl, carbazolyl, naphthalene, tetrahydronaphthalene, tetrahydroquinolinyl, tetrahydroisoquinolinyl, dihydroquinolinyl, or dihydroisoquinolinyl. Examples of substituents include alkyl, alkyl(OH), —COOH, C(Me)$_3$, CH(Me)$_2$, halo, CF$_3$, cyano and methoxy. Alternatively, $R^1$ may represent substituted or unsubstituted benzoxazine, dihydrobenzoxazine, benzodioxine or benzodioxane.

In compounds of formula I-I, IA' and IA'', $R^3$ may for example represent $CR^{6'}R^7R^8$ wherein $R^{6'}$ represents hydrogen, halo, $C_1$-$C_6$ alkyl or hydroxyl $C_1$-$C_6$ alkyl; each of $R^7$ and $R^8$ is independently halo, $C_1$-$C_6$ alkyl or hydroxyl $C_1$-$C_6$ alkyl; or $R^7$ and $R^8$ together form a substituted or unsubstituted $C_3$-$C_8$ cycloalkyl ring. For example, $R^7$ may represent lower alkyl (e.g. methyl). For example $R^8$ may also represent lower alkyl (e.g. methyl). In particular examples, $R^{6'}$ may represent hydrogen and $R^7$ and $R^8$ may represent methyl. Alternatively each of $R^{6'}$, $R^7$ and $R^8$ may represent methyl. Alternatively each of $R^{6'}$, $R^7$ and $R^8$ may represent fluoro. Alternatively $R^{6'}$ may represent hydrogen and $R^7$ and $R^8$ together form a cyclopropyl ring.

In a further embodiment of the compounds of formula I-I, IA, IA' and IA'', $R^3$ may for example represent substituted or unsubstituted aryl or heteroaryl.

In a first alternative embodiment of the compounds of formula IA, $R^3$ is CF$_3$, n-propyl, or a group of the formula With respect to the compounds of formula I-I, IA' and IA'', $R^1$ may be substituted naphthyl, or alternatively, substituted tetrahydronaphthyl. Further, $R^1$ may also be substituted bicycloheteroaryl, and in a particular embodiment, the bicycloheteroaryl may be selected from the group consisting of tetrahydroquinoline, tetrahydroisoquinoline, benzoxazine, dihydrobenzoxazine, benzodioxine, dihydrobenzodioxine, benzopyran, indole and benzimidazole. More particularly, the bicycloheteroaryl may be quinoline, isoquinoline, benzodioxine, and benzoxazine. In a particular embodiment, the substitution on the bicycloheteroaryl is selected from the group consisting of hydrogen, alkyl, trifluoromethyl, halo, methoxy, trifluoromethoxy, amino and carboxy. In a yet further particular embodiment, the substitution on bicycloheteroaryl is selected from the group consisting of substituted alkyl, cyano, trifluoroalkyl, halo, nitro, methoxy, amino and carboxy. More particularly, the substitution on bicycloheteroaryl is selected from alkyl substituted with hydroxyl or amino. Most particularly, the substitution on bicycloheteroaryl is hydroxyalkyl, for example, hydroxymethyl, hydroxyethyl or hydroxypropyl.

In yet another particular embodiment, with respect to the compounds of formula I-I, IA' and IA'', $R^1$ may be substituted or unsubstituted:

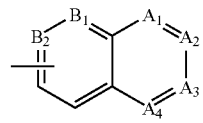

wherein each of $A^1$, $A^2$, $A^3$, $A^4$, $B^1$ and $B^2$ is independently $CR^{4'}$ and N;

and each of $R^{4'}$ is independently H, substituted or unsubstituted lower alkyl, halo, hydroxyl, alkoxy, substituted alkoxy, amino, substituted amino, or hydroxyalkyl. More particularly, $R^1$ may be substituted or unsubstituted:

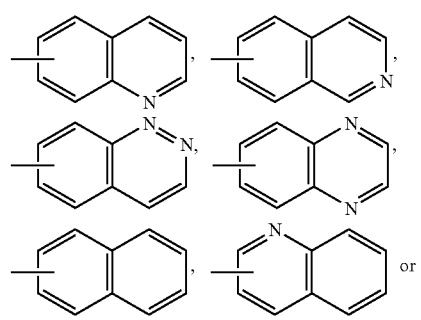

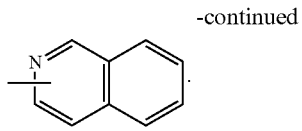

In yet another particular embodiment, with respect to the compounds of formula I-I, IA' and IA", $R^1$ may be substituted:

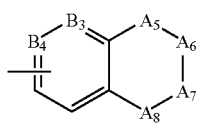

wherein each of $A^5$ and $A^8$ is independently $CR^{4'}R^{4'}$, $NR^{4'}$, O, S, SO or $SO_2$;

each of $A^6$ and $A^7$ is independently $CR^{4'}$, $NR^{4'}$, $CR^{4'}R^{4'}$ or CO; each of $B^3$ and $B^4$ is independently $CR^{4'}$ and N; when $R^{4'}$ is attached to C, each of $R^{4'}$ is independently H, $C_1$-$C_6$ alkyl, halo, or hydroxy $C_1$-$C_6$ alkyl, and when $R^{4'}$ is attached to N, each of $R^{4'}$ is independently H or $C_1$-$C_6$ alkyl; and the dotted bond represents a single or a double bond. More particularly, $R^1$ may be substituted or unsubstituted:

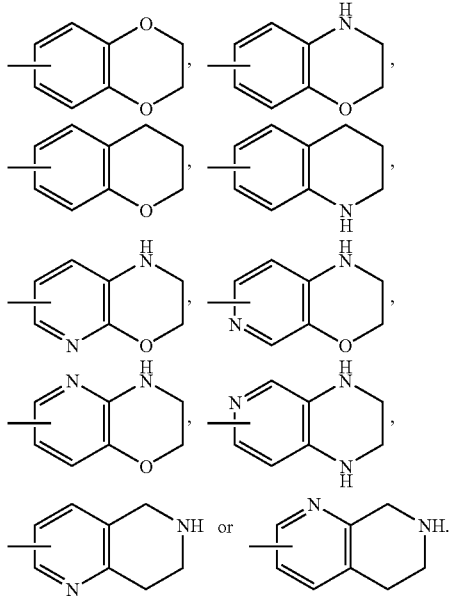

In yet another particular embodiment, with respect to the compounds of formula I-I, IA' and IA", $R^1$ may be substituted or unsubstituted:

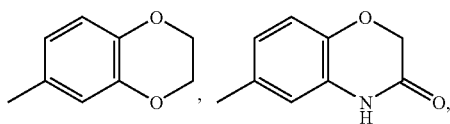

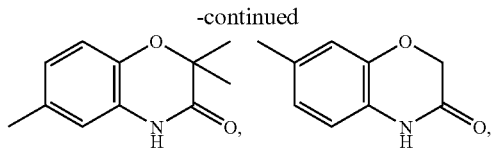

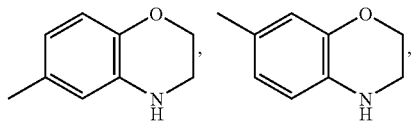

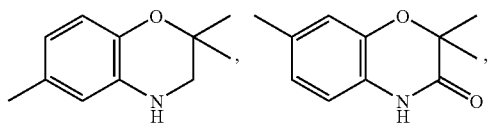

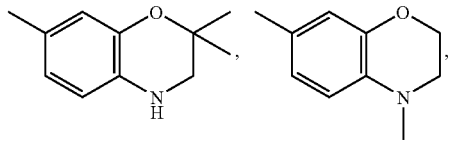

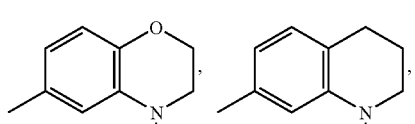

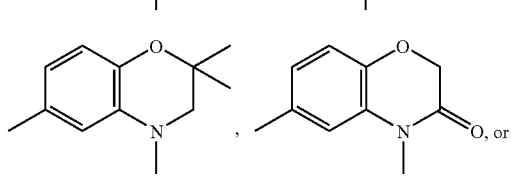

In yet another particular embodiment, with respect to the compounds of formula I-I, IA' and IA", $R^1$ may be substituted or unsubstituted:

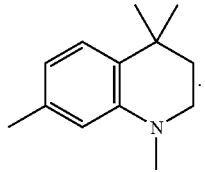

wherein each of $A^9$, $A^{10}$ and $A^{11}$ is independently $CR^{4'}$, $CR^{4'}R^{4'}$, CO, CS, N, $NR^{4'}$, O, S, SO or $SO_2$;
each of $B^5$ and $B^6$ is independently $CR^4$ and N;
when $R^{4'}$ is attached to C, each of $R^{4'}$ is independently H, $C_1$-$C_6$ alkyl, halo, or hydroxy $C_1$-$C_6$ alkyl, and when $R^{4'}$ is attached to N, each of $R^{4'}$ is independently H or $C_1$-$C_6$ alkyl; and
each of the dotted bonds independently represents a single or a double bond. More particularly, $R^1$ may be substituted or unsubstituted:

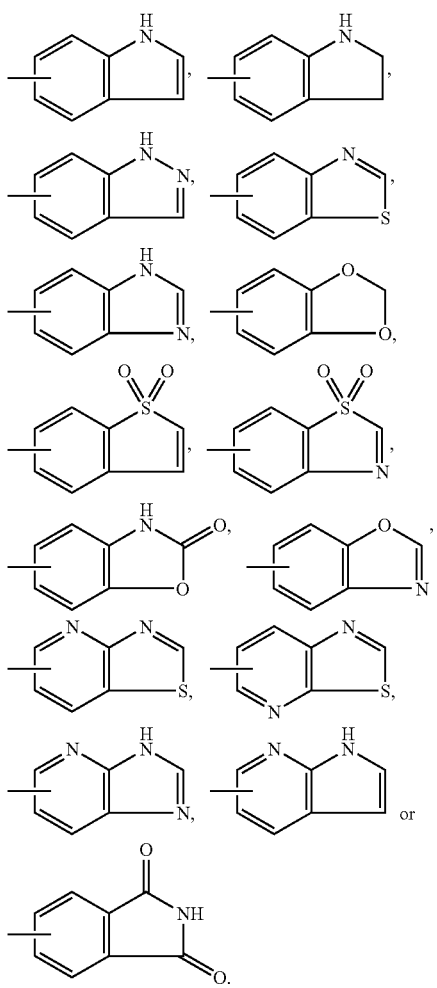

In yet another particular embodiment, with respect to the compounds of formula I-I, IA' and IA", $R^1$ may be substituted or unsubstituted:

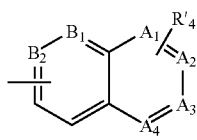

wherein each of $A^1$, $A^2$, $A^3$, $A^4$, $B^1$ and $B^2$ is independently CH and N; and $R^{4'}$ is substituted or unsubstituted lower alkyl. More particularly, $R^{4'}$ is $C_1$-$C_6$ alkyl or hydroxy $C_1$-$C_6$ alkyl.

In yet another particular embodiment, with respect to the compounds of formula I-I, IA' and IA", $R^1$ may be substituted

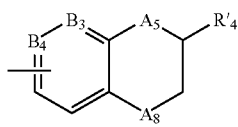

wherein each of $A^5$ and $A^8$ is independently $CH_2$, CHMe, NH, NMe, O, S, SO or $SO_2$; and $R^{4'}$ is $C_1$-$C_6$ alkyl or hydroxy $C_1$-$C_6$ alkyl.

In yet another particular embodiment, with respect to the compounds of formula I-I, IA' and IA", $R^1$ may be substituted

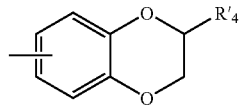

wherein $R^{4'}$ is substituted alkyl. More particularly, $R^{4'}$ is $C_1$-$C_6$ alkyl or hydroxy $C_1$-$C_6$ alkyl.

In yet another particular embodiment, with respect to the compounds of formula I-I, IA' and IA", $R^1$ may be substituted

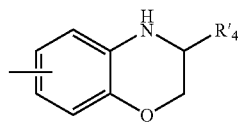

wherein $R^{4'}$ is substituted alkyl. More particularly, $R^{4'}$ is $C_1$-$C_6$ alkyl or hydroxy $C_1$-$C_6$ alkyl.

In yet another particular embodiment, with respect to the compounds of formula I-I, IA' and IA", $R^1$ may be substituted

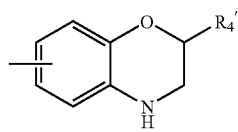

wherein $R^{4'}$ is substituted alkyl. More particularly, $R^{4'}$ is $C_1$-$C_6$ alkyl or hydroxy $C_1$-$C_6$ alkyl.

In yet another particular embodiment, with respect to the compounds of formula I-I, IA' and IA", $R^1$ may be substituted

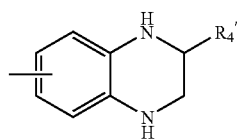

wherein $R^{4'}$ is substituted alkyl. More particularly, $R^{4'}$ is $C_1$-$C_6$ alkyl or hydroxy $C_1$-$C_6$ alkyl.

In yet another particular embodiment, with respect to the compounds of formula I-I, IA' and IA", $R^1$ may be substituted

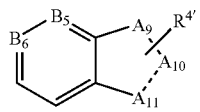

wherein each of $A^9$, $A^{10}$ and $A^{11}$ is independently CH, $CH_2$, N, NH, O, or S; each of $B^5$ and $B^6$ is independently CH and N;

each of $R^{4'}$ is independently H, $C_1$-$C_6$ alkyl or hydroxy $C_1$-$C_6$ alkyl; and each of the dotted bonds independently represents a single or a double bond.

In yet another particular embodiment, with respect to the compounds of formula I-I, IA' and IA", $R^1$ may be substituted

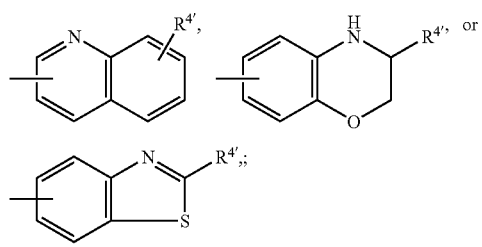

and wherein $R^{4'}$ is independently H, $C_1$-$C_6$ alkyl, halo, or hydroxy $C_1$-$C_6$ alkyl.

In yet another particular embodiment, with respect to the compounds of formula I-I, IA' and IA", $R^1$ may be substituted dihydrobenzodioxin-6-yl or dihydrobenzoxazin-6-yl.

In yet another particular embodiment, with respect to the compounds of formula I-I, IA' and IA", $R^1$ may be substituted or unsubstituted:

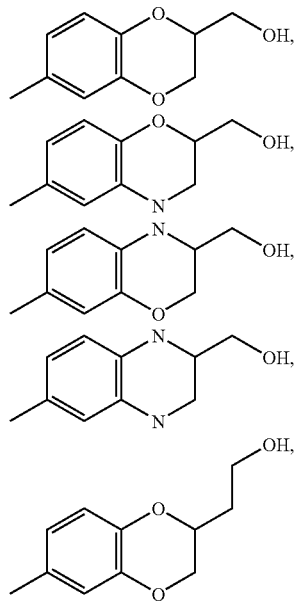

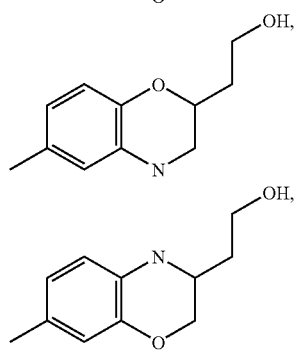

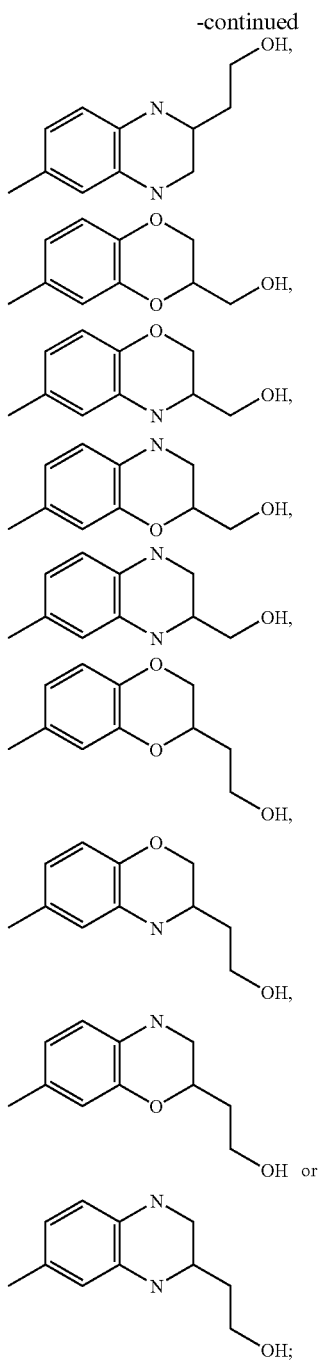

wherein, when feasible, the ring N can further be substituted with H or $C_1$-$C_6$ alkyl.

In yet another particular embodiment, with respect to the compounds of formula I-I, IA' and IA", $R^1$ may be substituted or unsubstituted:

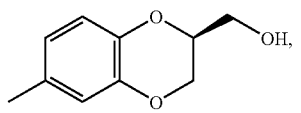

-continued
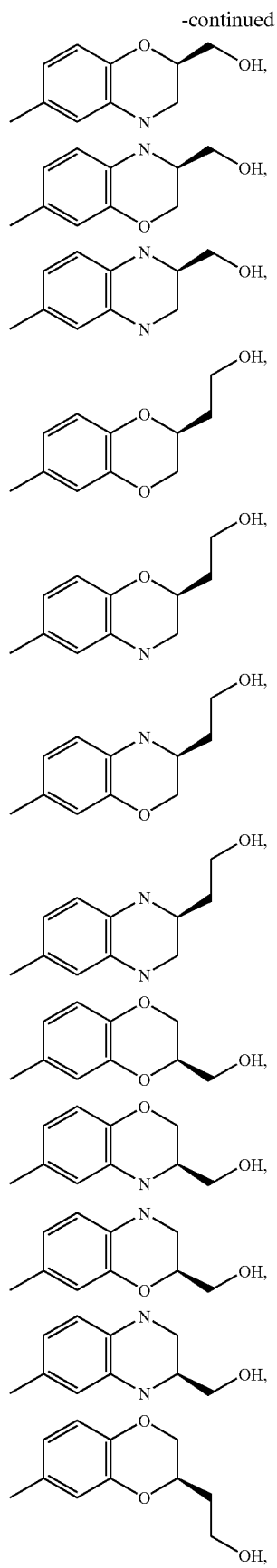
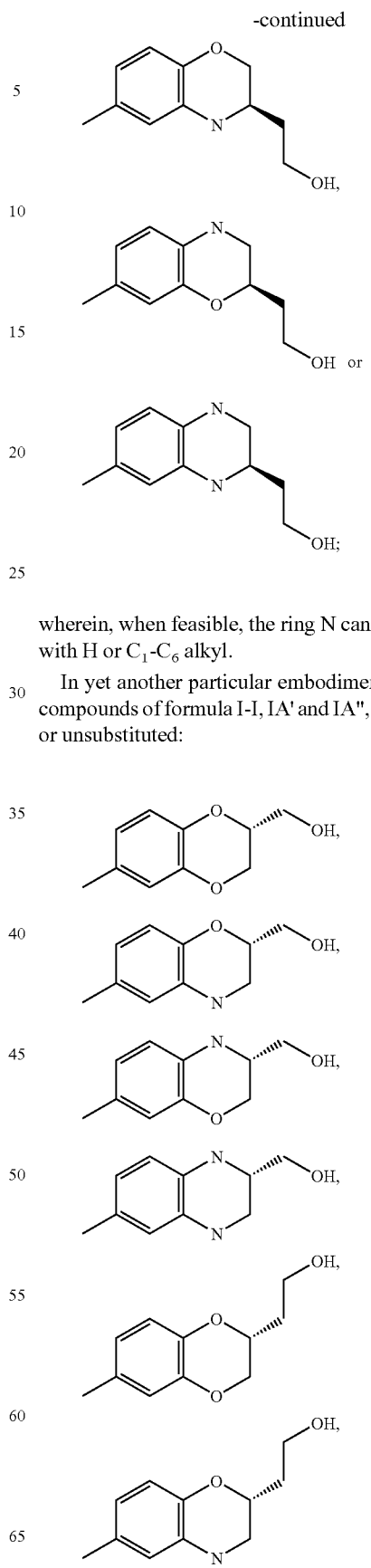
wherein, when feasible, the ring N can further be substituted with H or $C_1$-$C_6$ alkyl.
In yet another particular embodiment, with respect to the compounds of formula I-I, IA' and IA", $R^1$ may be substituted or unsubstituted:

-continued

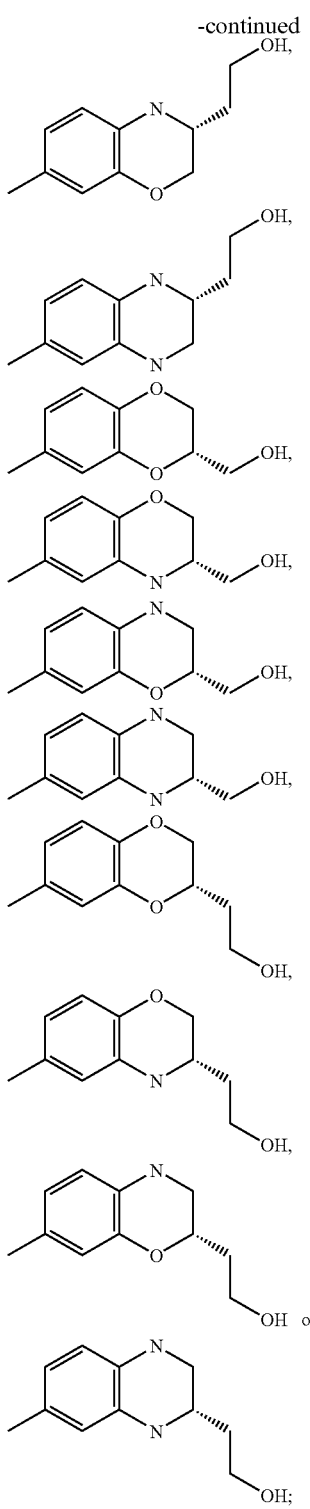

wherein, when feasible, the ring N can further be substituted with H or alkyl.

In yet another particular embodiment, with respect to the compounds of formula I-I, IA' and IA'', $R^{4'}$ may be hydroxy $C_1$-$C_6$ alkyl. In a more particular embodiment thereof, $R^{4'}$ may be —$(CH_2)_n$—OH; and n may be selected from 1-3. In a further embodiment thereof, $R^{4'}$ may be —$CH_2OH$.

In yet another particular embodiment, with respect to the compounds of formula I-I, IA' and IA'', $R^1$ may be:

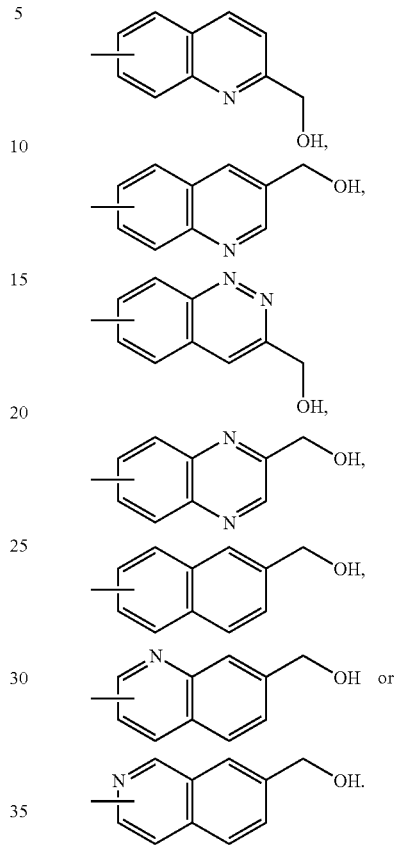

In yet another particular embodiment, with respect to the compounds of formula I-I, IA' and IA'', $R^1$ may be:

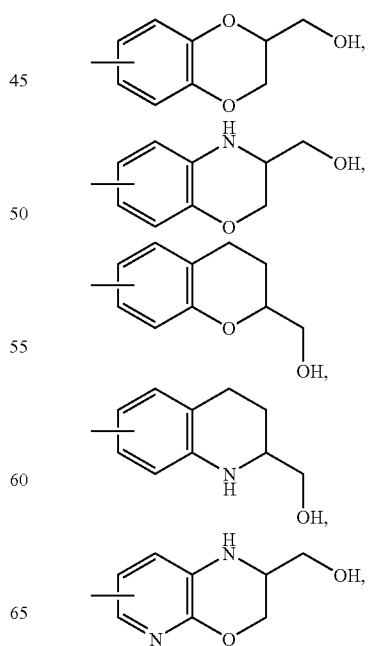

-continued

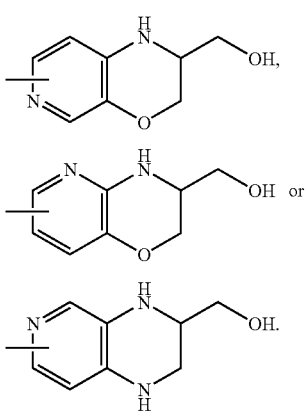

In yet another particular embodiment, with respect to the compounds of formula I-I, IA' and IA", $R^1$ may be:

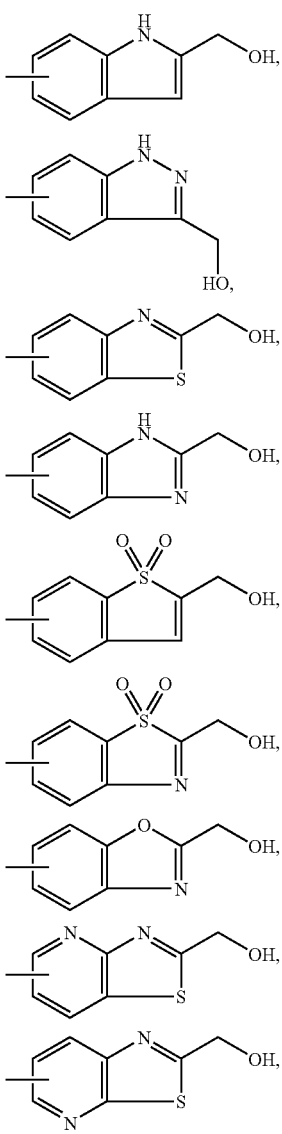

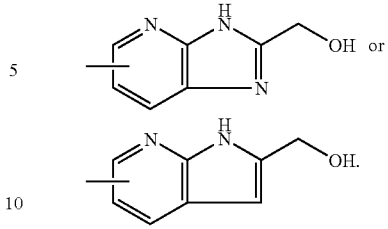

In yet another embodiment, with respect to the compounds of formula I-I, IA' and IA", $R^3$ may be substituted or unsubstituted cycloalkyl. More particularly, $R^3$ may be substituted or unsubstituted cyclopropyl, cyclobutyl, cyclopentyl, or cyclohexyl.

In yet another particular embodiment, with respect to the compounds of formula I-I, IA' and IA", $R^3$ may be cyclopropyl.

In yet further particular embodiment, with respect to the compounds of formula I-I, IA' and IA", $R^3$ may be $CF_3$ or $CHF_2$. More particularly $R^3$ may be $CF_3$.

In yet another particular embodiment, with respect to the compounds of formula I-I, IA' and IA", $R^3$ may be t-Bu or isopropyl. More particularly $R^3$ may be t-Bu.

In yet another embodiment, the present invention provides amide compounds according to formula II.

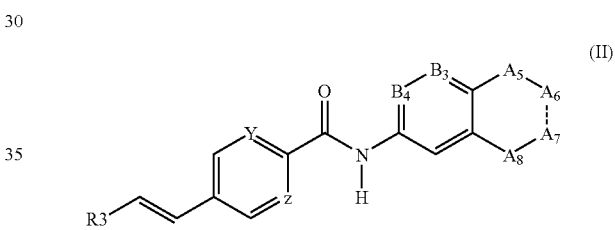

wherein $R^3$ is t-Bu, $CF_3$ or cyclopropyl; Z and Y are independently C—H, C—F, C—Cl, C—Me, C—$SO_2$Me or C—OMe; $B^3$ and $B^4$ are independently $CR^{4'}$ or N; and wherein each of $A^5$ and $A^8$ is independently $CR^{4'}R^{4'}$, $NR^{4'}$, O, S, SO or $SO_2$; each of $A^6$ and $A^7$ is independently $CR^{4'}$, $NR^{4'}$, $CR^{4'}R^{4'}$ or CO; each of $R^{4'}$ is independently H, substituted or unsubstituted alkyl or aryl; and the dotted bond represents a single or a double bond. In one particular embodiment, each $R^{4'}$ is independently H, substituted or unsubstituted alkyl.

In yet another embodiment, the present invention provides amide compounds according to formula III.

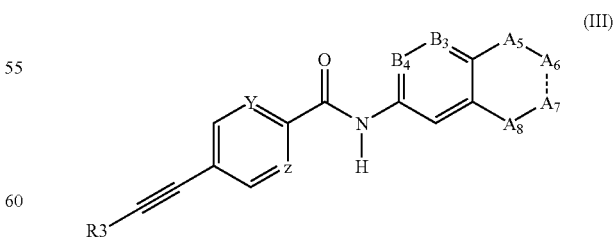

wherein $R^3$ is t-Bu, $CF_3$ or cyclopropyl; Z and Y are independently C—H, C—F, C—Cl, C—Me, C—$SO_2$Me or C—OMe; $B^3$ and $B^4$ are independently $CR^{4'}$ or N; and wherein each of $A^5$ and $A^8$ is independently $CR^{4'}R^{4'}$, $NR^{4'}$, O, S, SO or SO$_2$; each of A$^6$ and A$^7$ is independently CR$^{4'}$, NR$^{4'}$, CR$^{4'}$R$^{4'}$ or CO; each of R$^{4'}$ is independently H, substituted or unsubstituted alkyl or aryl; and the dotted bond represents a single or a double bond. In one particular embodiment, each of R$^{4'}$ is independently H, substituted or unsubstituted alkyl.

In yet another embodiment, the present invention provides amide compounds according to formula IV.

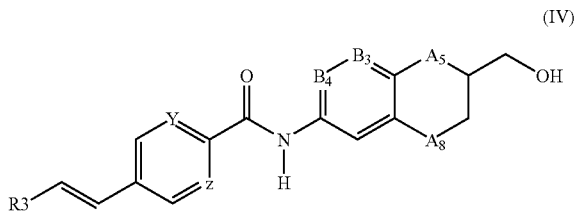

(IV)

wherein R$^3$ is t-Bu, CF$_3$ or cyclopropyl; Z and Y are independently C—H, C—F, C—Cl, C—Me, C—SO$_2$Me or C—OMe; B$^3$ and B$^4$ are independently CR$^{4'}$ or N; and A$^5$ and A$^8$ are independently O or NH.

In one particular embodiment, with respect to the compounds of formula IV, R$^3$ may be t-Bu. In another particular embodiment, with respect to the compounds of formula IV, R$^3$ may be CF$_3$. In another particular embodiment, with respect to the compounds of formula IV, R$^3$ may be cyclopropyl.

In one particular embodiment, with respect to the compounds of formula IV, Y and Z both may be C—H. In another particular embodiment, with respect to the compounds of formula IV, Y is C—H and Z is C—F or C—Cl. In another particular embodiment, with respect to the compounds of formula IV, Y is C—H and Z is C—F. In another particular embodiment, with respect to the compounds of formula IV, Y is C—H and Z is C—Cl. In a further particular embodiment, with respect to the compounds of formula IV, Y is C—H and Z is C—Me or C—OMe. In one particular embodiment, with respect to the compounds of formula IV, Y and Z both may be C—F. In one particular embodiment, with respect to the compounds of formula IV, Y and Z both may be C—Cl. In yet another particular embodiment, with respect to the compounds of formula IV, Y and Z both may be C—Me.

In one particular embodiment, with respect to the compounds of formula IV, A$^5$ and A$^8$ both may be O. In one particular embodiment, with respect to the compounds of formula IV, A$^5$ and A$^8$ both may be NH. In one particular embodiment, with respect to the compounds of formula IV, A$^5$ may be O and A$^8$ may be NH. In one particular embodiment, with respect to the compounds of formula IV, A$^5$ may be NH and A$^8$ may be O.

In yet another embodiment, the present invention provides amide compounds according to formula V.

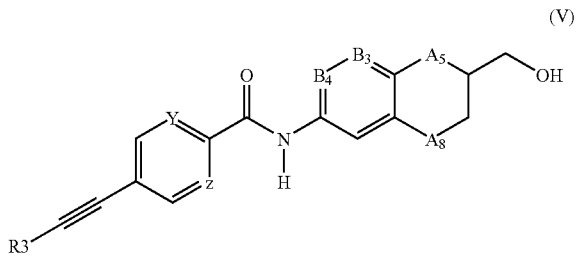

(V)

wherein R$^3$ is t-Bu, CF$_3$ or cyclopropyl; Z and Y are independently C—H, C—F, C—Cl, C—Me, C—SO$_2$Me or C—OMe; B$^3$ and B$^4$ are independently CR$^{4'}$ or N; and A$^5$ and A$^8$ are independently O or NH.

In one particular embodiment, with respect to the compounds of formula V, R$^3$ may be t-Bu. In another particular embodiment, with respect to the compounds of formula V, R$^3$ may be CF$_3$. In another particular embodiment, with respect to the compounds of formula V, R$^3$ may be cyclopropyl.

In a particular embodiment, with respect to compounds of formula V, Y and Z both may be C—H. In another particular embodiment, with respect to the compounds of formula V, Y is C—H and Z is C—F or C—Cl. In another particular embodiment, with respect to compounds of formula V, Y is C—H and Z is C—F. In a further particular embodiment, with respect to the compounds of formula V, Y is C—H and Z is C—Cl. In another particular embodiment, with respect to compounds of formula V, Y is C—H and Z is C—Me or C—OMe.

In a particular embodiment, with respect to the compounds of formula V, Y and Z both may be C—F. In one particular embodiment, with respect to the compounds of formula V, Y and Z both may be C—Cl. In yet another particular embodiment, with respect to the compounds of formula IV, Y and Z both may be C—Me.

In one particular embodiment, with respect to the compounds of formula V, A$^5$ and A$^8$ both may be O. In one particular embodiment, with respect to the compounds of formula V, A$^5$ and A$^8$ both may be NH. In one particular embodiment, with respect to the compounds of formula V, A$^5$ may be O and A$^8$ may be NH. In one particular embodiment, with respect to the compounds of formula V, A$^5$ may be NH and A$^8$ may be O.

In a further aspect, the present invention provides compounds according to formula (VI):

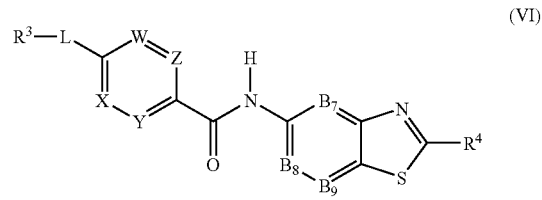

(VI)

or a pharmaceutically acceptable salt, solvate or prodrug thereof, and stereoisomers and tautomers thereof, wherein:
each of W, Z, Y and X is independently N or CR$^4$; each of B$^7$, B$^8$ and B$^9$ is independently N or CR$^4$;
L is —(CR$^5$=CR$^6$)— or —(C≡C)—; R$^3$ is C$_1$-C$_6$ alkyl, hydroxyl C$_1$-C$_6$ alkyl, halo C$_1$-C$_6$ alkyl, heteroalkyl, aryl, cycloalkyl, cycloheteroalkyl, heteroaryl, aralkyl, or heteroaralkyl; each R$^4$ is independently hydrogen, C$_1$-C$_6$ alkyl, hydroxyl C$_1$-C$_6$ alkyl, C$_2$-C$_6$ acyl, C$_2$-C$_6$ acylamino, C$_1$-C$_6$ alkylamino, C$_1$-C$_6$ alkylthio, C$_1$-C$_6$ alkoxy, C$_1$-C$_6$ alkoxycarbonyl, C$_1$-C$_6$ alkylarylamino, aryl C$_1$-C$_6$ alkyloxy, amino, aryl, aryl C$_1$-C$_6$ alkyl, sulfoxide, sulfone, sulfanyl, aminosulfonyl, arylsulfonyl, sulfuric acid, sulfuric acid ester, dihydroxyphosphoryl, aminohydroxyphosphoryl, azido, carboxy, carbamoyl, cyano, cycloheteroalkyl, di C$_1$-C$_6$ alkylamino, halo, heteroaryloxy, heteroaryl, heteroalkyl, hydroxyl, nitro or thio; each of R$^5$ and R$^6$ is independently H, halo, C$_1$-C$_6$ alkyl, hydroxyl C$_1$-C$_6$ alkyl, heteroalkyl, aryl, heteroaryl, aralkyl, or heteroaralkyl; and R$^{4'}$ is C$_1$-C$_6$ alkyl or hydroxyl C$_1$-C$_6$ alkyl.

In certain embodiments according to formula (VI), $R^3$ is $CR^{6'}R^7R^8$ wherein $R^{6'}$ is hydrogen, halo, $C_1$-$C_6$ alkyl or hydroxyl $C_1$-$C_6$ alkyl; each of $R^7$ and $R^8$ is independently halo or substituted or unsubstituted $C_1$-$C_6$ alkyl; or $R^7$ and $R^8$ together form a substituted or unsubstituted $C_3$-$C_8$ cycloalkyl ring. For example, $R^7$ may represent lower alkyl (e.g. methyl). For example $R^8$ may also represent lower alkyl (e.g. methyl). In particular examples, $R^{6'}$ may represent hydrogen and $R^7$ and $R^8$ may represent methyl. Alternatively each of $R^{6'}$, $R^7$ and $R^8$ may represent methyl. Alternatively each of $R^{6'}$, $R^7$ and $R^8$ may represent fluoro. Alternatively, $R^{6'}$ may represent hydrogen and $R^7$ and $R^8$ together may form a cyclopropyl ring. In certain embodiments, $R^3$ is selected from the group consisting of $CF_3$, t-Bu and cycloalkyl. In particular embodiments, $R^3$ is $CF_3$. In particular embodiments, $R^3$ is t-Bu. In particular embodiments, $R^3$ is selected from the group consisting of cyclopropyl, cyclobutyl, cyclopentyl and cyclohexyl. In particular embodiments, $R^3$ is cyclopropyl.

In compounds of formula (VI), $R^5$ and $R^6$ may, for example, independently represent hydrogen, halo, $C_1$-$C_6$ alkyl or hydroxyl $C_1$-$C_6$ alkyl. Preferably $R^5$ and $R^6$ represent hydrogen. Generally in compounds of formula (VI), L is preferably —(C═C)— or —C≡C—. Thus in one exemplary set of compounds, L represents —(C═C)—. In another exemplary set of compounds, L represents —C≡C—.

In certain embodiments according to formula (VI), each of $B^7$, $B^8$ and $B^9$ is N or $CR^4$ wherein $R^4$ is selected from the group consisting of substituted alkyl, halo, alkoxy, or amino. In certain embodiments, each of $B^7$, $B^8$ and $B^9$ is $CR^4$. In certain embodiments, $R^4$ is independently H, $CH_3$, $CF_3$, Cl, or F. In certain embodiments, each $R^4$ is H.

In compounds of formula (VI), W, Z, X and Y may for example each represent $CR^4$, especially CH. Alternatively X may represent N and W, Z and Y may each represent $CR^4$. In another exemplary set of compounds, each of X, Y and Z represents $CR^4$, especially CH. In another example set of compounds W is N. In yet another exemplary set of compounds, Y is N.

In another exemplary set of compounds of formula (VI), each of W, X and Z represents $CR^4$ especially CH and Y represents $CR^{4''}$. In this example set $R^{4''}$ may for example represent substituted alkyl, halo, alkoxy, or amino. Particularly, $R^{4''}$ may represent substituted alkyl or halo. More particularly, $R^{4''}$ may be methyl, chloro or fluoro.

In another exemplary set of compounds of formula (VI), each of W and X represents $CR^4$ especially CH and each of Y and Z represent $CR^{4''}$. In this example set each $R^{4''}$ may for example represent substituted alkyl, halo, alkoxy, or amino. Particularly, $R^{4''}$ may represent substituted alkyl or halo, and more particularly, methyl, chloro or fluoro.

In certain embodiments according to formula (VI), each of W and X is N or $CR^4$, each of Y and Z is N or $CR^{4''}$ and each $R^{4''}$ is independently selected from hydrogen, alkyl, trihaloalkyl and halo. In certain embodiments, each of $R^{4''}$ is independently H, $CH_3$, $CF_3$, Cl, or F. In certain embodiments, each $R^4$ is H.

In certain embodiments according to formula (VI), each of W, X, and Z is N or CH, and Y is C—$CH_3$, C—Cl, or C—F.

In certain embodiments according to formula (VI), $R^{4'}$ is hydroxyl substituted alkyl. In certain embodiments according to formula (VI), $R^{4'}$ is —$(CH_2)_n$—OH wherein n is selected from 1-6. In certain embodiments according to formula (VI), $R^{4'}$ is $CH_2OH$.

In certain embodiments according to formula (VI), L is —(C═C)— or —C≡C—; each W, X, and Y is CH; Z is $CR^{4''}$ and wherein $R^{4''}$ is lower alkyl; $R^3$ is selected from the group consisting of $CF_3$, t-Bu and cyclopropyl; and $R^{4'}$ is hydroxyl substituted alkyl. In certain embodiments according to formula (VI), L is —(C═C)— or —C≡C—; each W, X, and Y is CH; Z is $CR^{4''}$ and wherein $R^{4''}$ is methyl; $R^3$ is selected from the group consisting of $CF_3$, tBu and cyclopropyl; and $R^{4'}$ is hydroxyl substituted alkyl.

In certain embodiments according to formula (VI), L is —(C═C)— or —C≡C—; each W, X, and Y is CH; Z is $CR^{4''}$ and wherein $R^{4''}$ is methyl; $R^3$ is selected from the group consisting of $CF_3$, t-Bu and cyclopropyl; and $R^{4'}$ is —$(CH_2)_n$—OH wherein n is an integer from 1 to 6. In certain embodiments according to formula (VI), L is —(C═C)— or —C≡C—; each W, X, and Y is CH; Z is $CR^{4''}$ and wherein $R^{4''}$ is methyl; $R^3$ is selected from the group consisting of $CF_3$, t-Bu and cyclopropyl; and $R^{4'}$ is $CH_2OH$.

In certain embodiments according to formula (VI), L is —(C═C)— or —C≡C—; each W, X, and Y is CH; Z is $CR^{4''}$ and wherein $R^{4''}$ is methyl; $R^3$ is $CF_3$; and $R^{4'}$ is $CH_2OH$. In certain embodiments according to formula (VI), L is —(C═C)— or —C≡C—; each W, X, and Y is CH; Z is $CR^{4''}$ and wherein $R^{4''}$ is methyl; $R^3$ is t-Bu; and $R^{4'}$ is $CH_2OH$. In certain embodiments according to formula (VI), L is —(C═C)— or —C≡C—; each W, X, and Y is CH; Z is $CR^{4''}$ and wherein $R^{4''}$ is methyl; $R^3$ is cyclopropyl; and $R^{4''}$ is $CH_2OH$.

In yet further particular embodiments, the compounds of the invention are set forth and may-be selected from a comprehensive listing of such compounds, set forth later on herein in Table 1. The Table contains in excess of 200 compounds that have been or can be synthesized and have as a group, demonstrated activity in their capacity of modifying ion channels, in vivo, and thereby functioning in the therapeutic applications set forth herein in relation to capsaicin and the vanilloid receptor.

The compounds of the present invention are useful for the treatment of inflammatory pain and associated hyperalgesia and allodynia. They are also useful for the treatment of neuropathic pain and associated hyperalgesis and allodynia (e.g. trigeminal or herpetic neuralgia, diabetic neuropathy, causalgia, sympathetically maintained pain and deafferentation syndromes such as brachial plexus avulsion). The compounds of the present invention are also useful as anti-inflammatory agents for the treatment of arthritis, and as agents to treat Parkinson's Disease, Alzheimer's Disease, stroke, uveitis, asthma, myocardial infarction, traumatic brain injury, spinal cord injury, neurodegenerative disorders, alopecia (hair loss), inflammatory bowel disease and autoimmune disorders, renal disorders, obesity, eating disorders, cancer, schizophrenia, epilepsy, sleeping disorders, cognition, depression, anxiety, blood pressure, lipid disorders, and atherosclerosis.

In one aspect, this invention provides compounds which are capable of modifying ion channels, in vivo. Representative ion channels so modified include voltage-gated channels and ligand-gated channels, including cation channels such as vanilloid channels.

In a further aspect, the present invention provides pharmaceutical compositions comprising a compound of the invention, and a pharmaceutical carrier, excipient or diluent. In this aspect of the invention, the pharmaceutical composition can comprise one or more of the compounds described herein.

In a further aspect of the invention, a method is disclosed for treating mammals, including humans, as well as lower mammalian species, susceptible to or afflicted with a condition from among those listed herein, and particularly, such condition as may be associated with e.g. arthritis, uveitis, asthma, myocardial infarction, traumatic brain injury, acute spinal cord injury, alopecia (hair loss), inflammatory bowel disease and autoimmune disorders, which method comprises administering an effective amount of one or more of the pharmaceutical compositions just described.

In yet another method of treatment aspect, this invention provides a method of treating a mammal susceptible to or afflicted with a condition that gives rise to pain responses or that relates to imbalances in the maintenance of basal activity of sensory nerves. Compounds have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with neurodegenerative diseases and disorders such as, for example Parkinson's disease, Alzheimer's disease and multiple sclerosis; diseases and disorders which are mediated by or result in neuroinflammation such as, for example traumatic brain injury, stroke, and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; irritable bowel syndrome, over active bladder, respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; alopecia (hair loss); obesity; lipid disorders; cancer; blood pressure; spinal cord injury; and renal disorders method comprises administering an effective condition-treating or condition-preventing amount of one or more of the pharmaceutical compositions just described.

In additional aspects, this invention provides methods for synthesizing the compounds of the invention, with representative synthetic protocols and pathways disclosed later on herein.

Other objects and advantages will become apparent to those skilled in the art from a consideration of the ensuing detailed description, in conjunction with the following illustrative drawings.

BRIEF DESCRIPTION OF THE DRAWINGS

FIG. 3: Graph depicts significant inhibition of the Capsaicin induced intracellular calcium response, under described experimental conditions, by 3 nM of Compound 96.

FIG. 4: Graph depicts significant inhibition of the Capsaicin induced intracellular calcium response, under described experimental conditions, by 3 nM of Compound 45.

FIG. 5: Graph depicts significant inhibition of the Capsaicin induced intracellular calcium response, under described experimental conditions, by 3 nM of Compound 233.

FIG. 6: Graph depicts significant inhibition of the Capsaicin induced intracellular calcium response, under described experimental conditions, by 3 nM of Compound 167.

DETAILED DESCRIPTION OF THE INVENTION

Definitions

Figure 1:
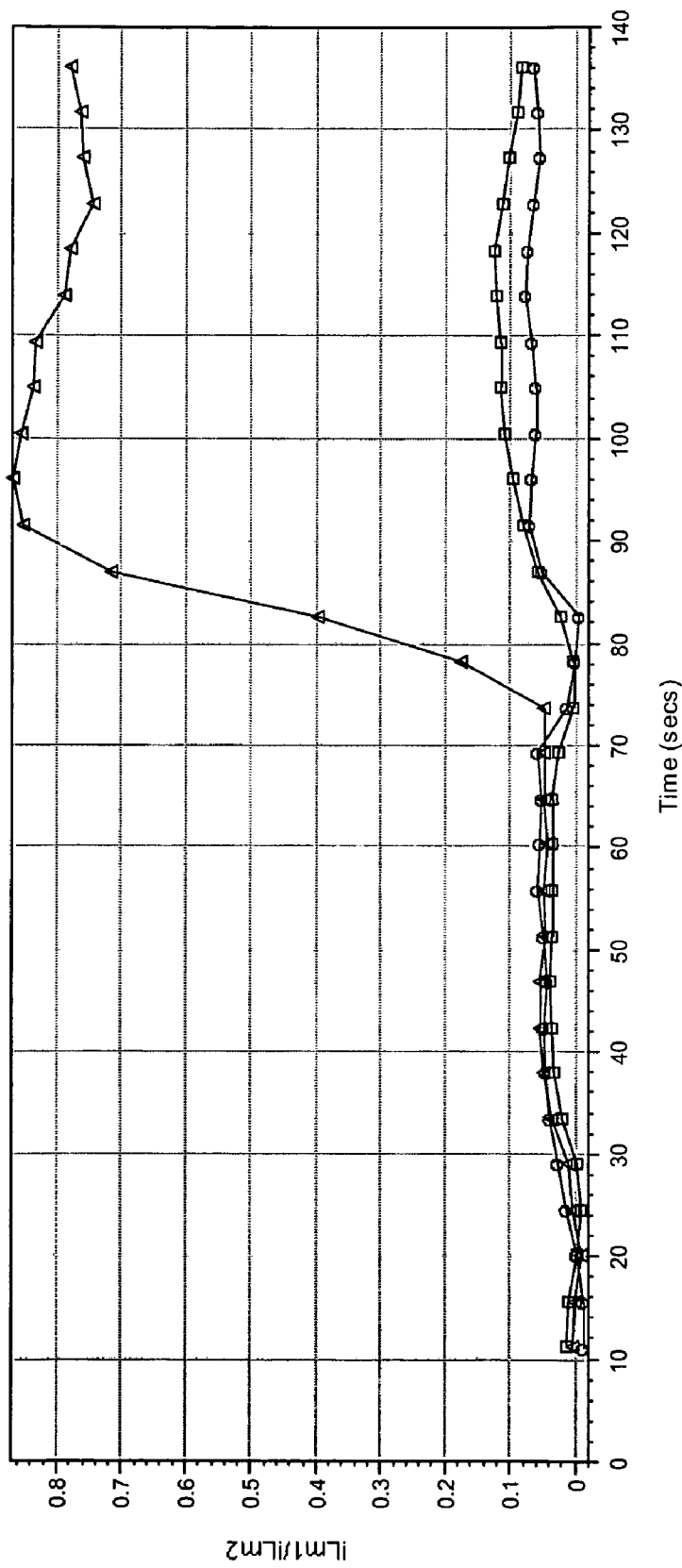
FIG. 1: Graph depicts significant inhibition of the Capsaicin induced intracellular calcium response, under described experimental conditions, by 3 nM of Compound 225.
Figure 2:
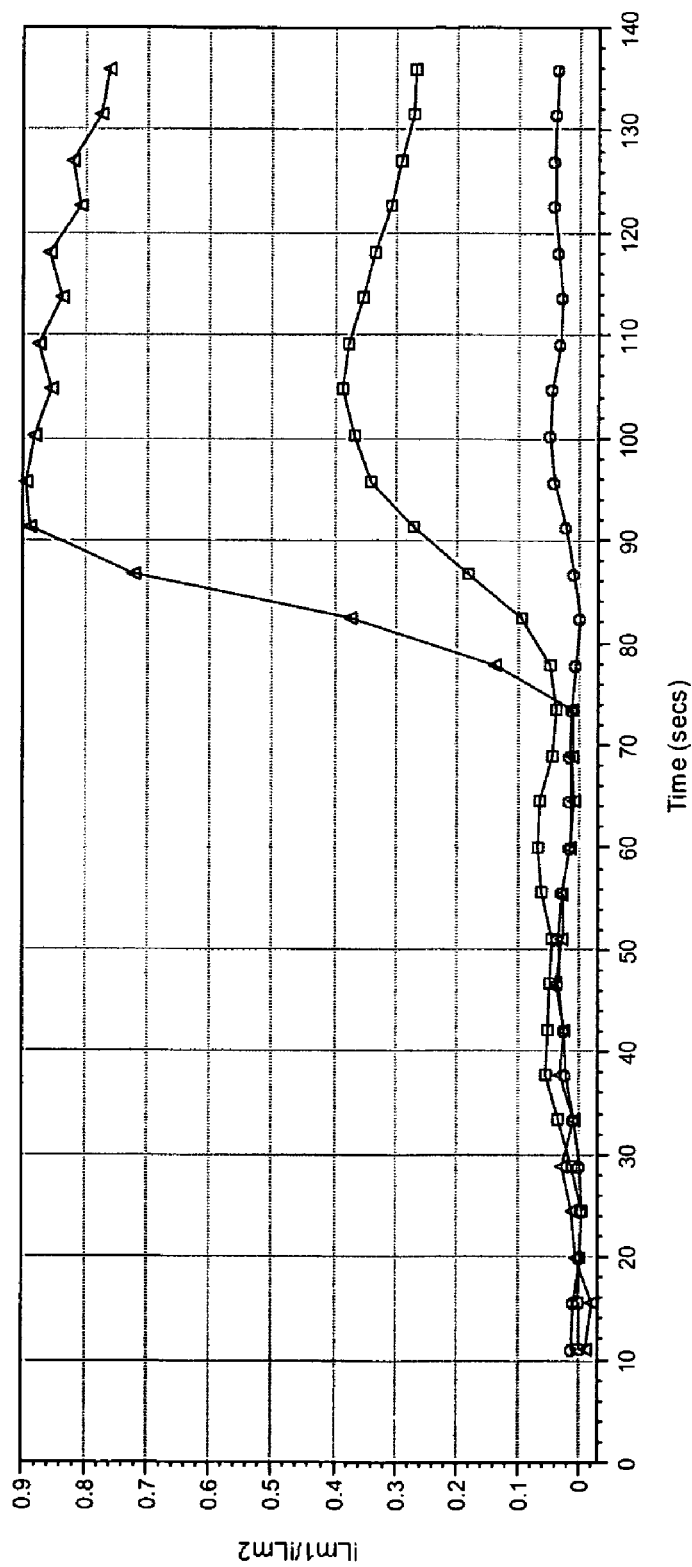
FIG. 2: Graph depicts significant inhibition of the Capsaicin induced intracellular calcium response, under described experimental conditions, by 3 nM of Compound 187.

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope. By way of non-limiting example, such substituents may include e.g. halo (such as fluoro, chloro, bromo), —CN, —CF$_3$, —OH, —OCF$_3$, $C_2$-$C_6$ alkenyl, $C_3$-$C_6$ alkynyl, $C_1$-$C_6$ alkoxy, aryl and di-$C_1$-$C_6$ alkylamino.

"Acyl" refers to a radical —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

"Acylamino" refers to a radical —NR'C(O)R, where R' is hydrogen, alkyl, cycloalkyl, cycloheteroalkyl, aryl, arylalkyl, heteroalkyl, heteroaryl, heteroarylalkyl and R is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)R where R is hydrogen, alkyl, aryl or cycloalkyl.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxy" refers to the group —OR where R is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —NRC(O)OR' where R is hydrogen, alkyl, aryl or cycloalkyl, and R' is alkyl or cycloalkyl.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkenylene, alkynyl and alkynylene. Aliphatic groups typically have from 1 or 2 to about 12 carbon atoms.

"Alkyl" refers to monovalent saturated aliphatic hydrocarbyl groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyls" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated aliphatic hydrocarbyl groups particularly having up to about 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having up to about 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH=CH—), the propenylene isomers (e.g., —CH=CHCH$_2$— and —C(CH$_3$)=CH— and —CH=C(CH$_3$)—) and the like.

"Alkynyl" refers to acetylenically unsaturated hydrocarbyl groups particularly having up to about 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" or "acyl" as used herein refers to the group R—C(O)—, where R is hydrogen or alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-NR'R", wherein each of R' and R" are independently selected from hydrogen and alkyl.

"Arylamino" refers to the group aryl-NR'R", wherein each of R' and R" are independently selected from hydrogen, aryl and heteroaryl.

"Alkoxyamino" refers to a radical —N(H)OR where R represents an alkyl or cycloalkyl group as defined herein.

"Alkoxycarbonyl" refers to a radical —C(O)-alkoxy where alkoxy is as defined herein.

"Alkylarylamino" refers to a radical —NRR' where R represents an alkyl or cycloalkyl group and R' is an aryl as defined herein.

"Alkylsulfonyl" refers to a radical —S(O)$_2$R where R is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)R where R is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —SR where R is an alkyl or cycloalkyl group as defined herein that may be optionally substituted as defined herein. Representative examples include, but are not limited to, methylthio, ethylthio, propylthio, butylthio, and the like.

"Amino" refers to the radical —NH$_2$.

"Substituted amino" includes those groups recited in the definition of "substituted" herein, and particularly refers to the group —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R)$_2$ is an amino group.

"Aminocarbonyl" refers to the group —C(O)NRR where each R is independently hydrogen, alkyl, aryl and cycloalkyl, or where the R groups are joined to form an alkylene group.

"Aminocarbonylamino" refers to the group —NRC(O)NRR where each R is independently hydrogen, alkyl, aryl or cycloalkyl, or where two R groups are joined to form an alkylene group.

"Aminocarbonyloxy" refers to the group —OC(O)NRR where each R is independently hydrogen, alkyl, aryl or cycloalky, or where the R groups are joined to form an alkylene group.

"Arylalkyloxy" refers to an —O-arylalkyl radical where arylalkyl is as defined herein.

"Arylamino" means a radical —NHR where R represents an aryl group as defined herein.

"Aryloxycarbonyl" refers to a radical —C(O)—O-aryl where aryl is as defined herein.

"Arylsulfonyl" refers to a radical —S(O)$_2$R where R is an aryl or heteroaryl group as defined herein.

"Azido" refers to the radical —N$_3$.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidime, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particlar bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —C(O)N(R)$_2$ where each R group is independently hydrogen, alkyl, cycloalkyl or aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —OR where R is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NRR' where R and R' independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C=C)—.

"Ethylene" refers to substituted or unsubstituted —(C—C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —NO$_2$.

"Substituted" refers to a group in which one or more hydrogen atoms are each independently replaced with the same or different substituent(s). Typical substituents include, but are not limited to, —X, —R$^{14}$, —O$^-$, =O, —OR$^{14}$, —SR$^{14}$, —S$^-$, =S, —NR$^{14}$R$^{15}$, =NR$^{14}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{14}$, —OS(O$_2$)O$^-$, —OS(O)$_2$R$^{14}$, —P(O)(O$^-$)$_2$, —P(O)(OR$^{14}$)(O$^-$), —OP(O)(OR$^{14}$)(OR$^{15}$), —C(O)R$^{14}$, —C(S)R$^{14}$, —C(O)OR$^{14}$, —C(O)NR$^{14}$R$^{15}$, —C(O)O$^-$, —C(S)OR$^{14}$, —NR$^{16}$C(O)NR$^{14}$R$^{15}$, —NR$^{16}$C(S)NR$^{14}$R$^{15}$, —NR$^{17}$C(NR$^{16}$)NR$^{14}$R$^{15}$ and —C(NR$^{16}$)NR$^{14}$R$^{15}$, where each X is independently a halogen; each R$^{14}$, R$^{15}$, R$^{16}$ and R$^{17}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{18}$R$^{19}$, —C(O)R$^{18}$ or —S(O)$_2$R$^{18}$ or optionally R$^{18}$ and R$^{19}$ together with the atom to which they are both attached form a cycloheteroalkyl or substituted cycloheteroalkyl ring; and R$^{18}$ and R$^{19}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

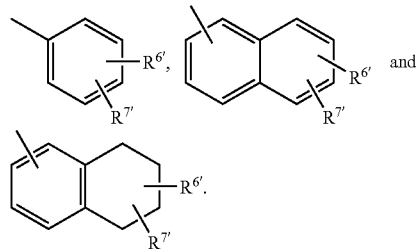

In these formulae one of R$^{6'}$ and R$^{7'}$ may be hydrogen and at least one of R$^{6'}$ and R$^{7'}$ is each independently selected from alkyl, alkenyl, alkynyl, cycloheteroalkyl, alkanoyl, alkoxy, aryloxy, heteroaryloxy, alkylamino, arylamino, heteroarylamino, NR$^{10}$COR$^{11}$, NR$^{10}$SOR$^{11}$, NR$^{10}$SO$_2$R$^{14}$, COOalkyl, COOaryl, CONR$^{10}$OR$^{11}$, CONR$^{10}$OR$^{11}$, NR$^{10}$R$^{11}$, SO$_2$NR$^{10}$R$^{11}$, S-alkyl, S-alkyl, SOalkyl, SO$_2$alkyl, Saryl, SOaryl, SO$_2$aryl; or R$^{6'}$ and R$^{7'}$ may be joined to form a cyclic ring (saturated or unsaturated) from 5 to 8 atoms, optionally containing one or more heteroatoms selected from the group N, O or S. R$^{10}$, R$^{11}$, and R$^{12}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-20 membered heteroaryl, with 5-10 membered heteroaryl being particularly preferred. Particlar heteroaryl groups are those derived from thiophene, pyrrole, benzothiophene, benzofuran, indole, pyridine, quinoline, imidazole, oxazole and pyrazine.

Examples of representative heteroaryls include the following:

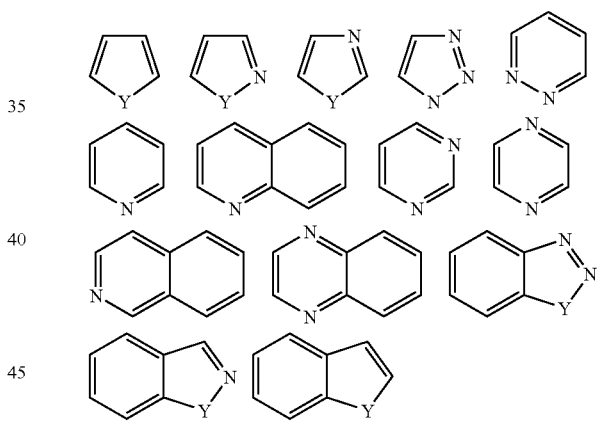

wherein each Y is selected from carbonyl, N, NR$^4$, O, and S.

Examples of representative cycloheteroalkyls include the following

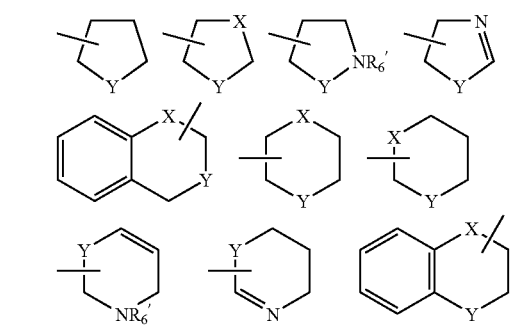

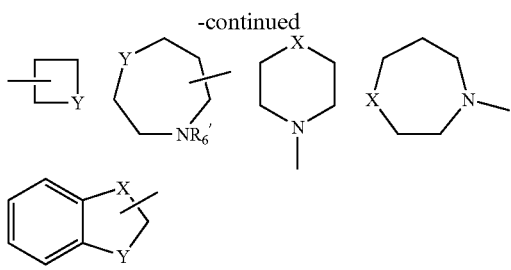

wherein each X is selected from $CR^4{}_2$, $NR^4$, O and S; and each Y is selected from $NR_4$, O and S, and where $R^{6'}$ is $R^2$.

Examples of representative cycloheteroalkenyls include the following:

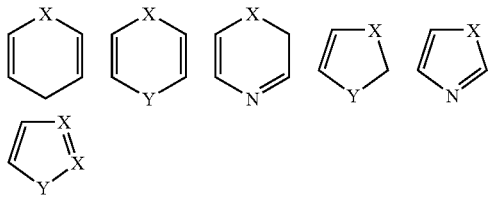

wherein each X is selected from $CR^4$, $NR^4$, O and S; and each Y is selected from carbonyl, N, $NR^4$, O and S.

Examples of representative aryl having hetero atoms containing substitution include the following:

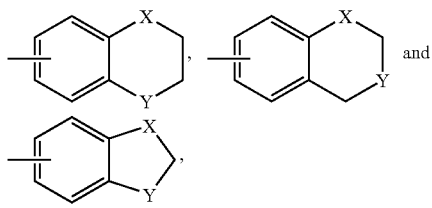

wherein each X is selected from C—$R^4$, $CR^4{}_2$, $NR^4$, O and S; and each Y is selected from carbonyl, $NR^4$, O and S.

"Hetero substituent" refers to a halo, O, S or N atom-containing functionality that may be present as an $R^4$ in a $R^4C$ group present as substituents directly on A, B, W, X, Y or Z of the compounds of this invention or may be present as a substituent in the "substituted" aryl and aliphatic groups present in the compounds.

Examples of hetero substituents include:
-halo,
—$NO_2$, —$NH_2$, —NHR, —$N(R)_2$,
—NRCOR, —NRSOR, —$NRSO_2R$, OH, CN,
—$CO_2H$,
—R—OH, —O—R, —COOR,
—$CON(R)_2$, —CONROR,
—$SO_3H$, —R—S, —$SO_2N(R)_2$,
—S(O)R, —$S(O)_2R$, wherein each R is independently an aryl or aliphatic, optionally with substitution. Among hetero substituents containing R groups, preference is given to those materials having aryl and alkyl R groups as defined herein. Preferred hetero substituents are those listed above.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

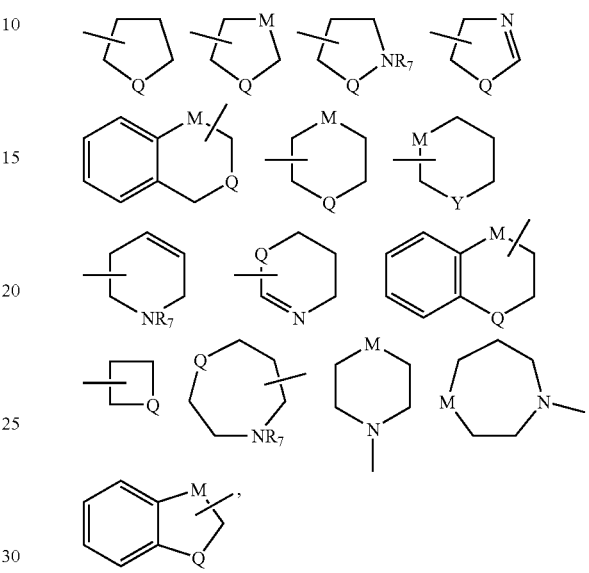

optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives. In the examples, M is $CR^7$, $NR^2$, O, or S; Q is O, $NR^2$ or S. $R^7$ and $R^8$ are independently selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Dihydroxyphosphoryl" refers to the radical —PO(OH)$_2$.

"Substituted dihydroxyphosphoryl" includes those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the radical —PO(OH)NH$_2$.

"Substituted aminohydroxyphosphoryl" includes those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Thioalkoxy" refers to the group —SR where R is alkyl.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Sulfanyl" refers to the radical HS—. "Substituted sulfanyl" refers to a radical such as RS— wherein R is any substituent described herein.

"Sulfonyl" refers to the divalent radical —S(O$_2$)—. "Substituted sulfonyl" refers to a radical such as R—(O$_2$)S— wherein R is any substituent described herein. "Aminosulfonyl" or "Sulfonamide" refers to the radical H$_2$N(O$_2$)S—, and "substituted aminosulfonyl" "substituted sulfonamide" refers to a radical such as R$_2$N(O$_2$)S— wherein each R is independently any substituent described herein.

"Sulfone" refers to the group —SO$_2$R. In particular embodiments, R is selected from H, lower alkyl, alkyl, aryl and heteroaryl.

"Thioaryloxy" refers to the group —SR where R is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Representative enol—keto structures and equilibrium are illustrated below:

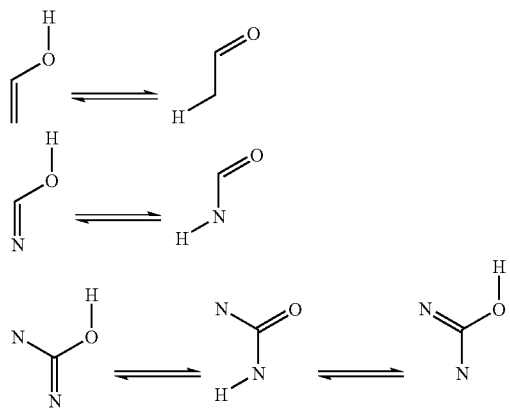

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Compounds

As set forth earlier herein, the compounds of the present invention are useful for preventing and/or treating a broad range of conditions, among them, arthritis, Parkinson's disease, Alzheimer's disease, stroke, uveitis, asthma, myocardial infarction, the treatment and prophylaxis of pain syndromes (acute and chronic or neuropathic), traumatic brain injury, acute spinal cord injury, neurodegenerative disorders, alopecia (hair loss), inflammatory bowel disease and autoimmune disorders or conditions in mammals.

In order that the invention described herein may be more fully understood, the following structures representing compounds typical of the invention are set forth. It should be understood that these examples are for illustrative purposes only and are not to be construed as limiting this invention in any manner.

Accordingly, additional groups of particular compounds are provided. Thus, and as discussed earlier herein, suitable compounds capable of modifying ion channels in vivo, may be selected from those listed in Tables 1-1 and 1-2, below, and may be prepared either as shown or in the form of a pharmaceutically acceptable salt, solvate or prodrug thereof; and stereoisomers and tautomers thereof. All such variants are contemplated herein and are within the scope of the present invention.

In certain aspects, the present invention provides prodrugs and derivatives of the compounds according to the formulae above. Prodrugs are derivatives of the compounds of the invention, which have cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

ASSAY METHODS

Chronic Constriction Injury Model (CCI Model):

Male Sprague-Dawley rats (270-300 g; B. W., Charles River, Tsukuba, Japan) are used. The chronic constriction injury (CCI) operation is performed according to the method described by Bennett and Xie (Bennett, G. J. and Xie, Y. K. Pain, 33:87-107, 1988). Briefly, animals are anesthetized with sodium pentobarbital (64.8 mg/kg, i.p.) and the left common sciatic nerve is exposed at the level of the middle of the thigh by blunt dissection through the biceps femoris. A portion of the sciatic nerve proximal to its trifurcation is freed of adhering tissue and 4 ligatures (4-0 silk) are tied loosely around it with about 1 mm space. A sham operation is performed as same as CCI surgery except for sciatic nerve ligation. Two weeks after surgery, mechanical allodynia is evaluated by application of von Frey hairs (VFHs) to the plantar surface of the hind paw. The lowest amount of force of VFH required to elicit a response is recorded as the paw withdrawal threshold (PWT). VFH testing is performed at 0.5, 1 and 2 hr post-dosing. Experimental data are analyzed using Kruskal-Wallis test followed by Dunn's test for multiple comparisons or Mann-Whitney U-test for paired comparison.

Caco-2 Permeability

Caco-2 permeability is measured according to the method described in Shiyin Yee, Pharmaceutical Research, 763 (1997).

Caco-2 cells are grown on filter supports (Falcon HTS multiwell insert system) for 14 days. Culture medium is removed from both the apical and basolateral compartments and the monolayers are preincubated with pre-warmed 0.3 ml apical buffer and 1.0 ml basolateral buffer for 0.75 hour at 37° C. in a shaker water bath at 50 cycles/min. The apical buffer consists of Hanks Balanced Salt Solution, 25 mM D-glucose monohydrate, 20 mM MES Biological Buffer, 1.25 mM $CaCl_2$ and 0.5 mM $MgCl_2$ (pH 6.5). The basolateral buffer consists of Hanks Balanced Salt Solution, 25 mM D-glucose monohydrate, 20 mM HEPES Biological Buffer, 1.25 mM $CaCl_2$ and 0.5 mM MgCl2 (pH 7.4). At the end of the preincubation, the media is removed and test compound solution (10 µM) in buffer is added to the apical compartment. The inserts are moved to wells containing fresh basolateral buffer and incubated for 1 hr. Drug concentration in the buffer is measured by LC/MS analysis.

Flux rate (F, mass/time) is calculated from the slope of the cumulative appearance of substrate on the receiver side and apparent permeability coefficient (Papp) is calculated from the following equation:

$$Papp\ (cm/sec) = (F*VD)/(SA*MD)$$

where SA is surface area for transport (0.3 cm$^2$), VD is the donor volume (0.3 ml), MD is the total amount of drug on the donor side at t=0. All data represent the mean of 2 inserts. Monolayer integrity is determined by Lucifer Yellow transport.

Human Dofetilide Binding

Cell paste of HEK-293 cells expressing the HERG product can be suspended in 10-fold volume of 50 mM Tris buffer adjusted at pH 7.5 at 25° C. with 2 M HCl containing 1 mM $MgCl_2$, 10 mM KCl. The cells are homogenized using a Polytron homogenizer (at the maximum power for 20 seconds) and centrifuged at 48,000 g for 20 minutes at 4° C. The pellet is resuspended, homogenized and centrifuged once more in the same manner. The resultant supernatant is discarded and the final pellet is resuspended (10-fold volume of 50 mM Tris buffer) and homogenized at the maximum power for 20 seconds. The membrane homogenate is aliquoted and stored at −80° C. until use. An aliquot is used for protein concentration determination using a Protein Assay Rapid Kit and ARVO SX plate reader (Wallac). All the manipulation, stock solution and equipment are kept on ice at all time. For saturation assays, experiments are conducted in a total volume of 200 µl. Saturation is determined by incubating 20 µl of [3H]-dofetilide and 160 µl of membrane homogenates (20-30 µg protein per well) for 60 min at room temperature in the absence or presence of 10 µM dofetilide at final concentrations (20 µl) for total or nonspecific binding, respectively. All incubations are terminated by rapid vacuum filtration over polyetherimide (PEI) soaked glass fiber filter papers using Skatron cell harvester followed by two washes with 50 mM Tris buffer (pH 7.5 at 25° C.). Receptor-bound radioactivity is quantified by liquid scintillation counting using a Packard LS counter.

For the competition assay, compounds are diluted in 96 well polypropylene plates as 4-point dilutions in semi-log format. All dilutions are performed in DMSO first and then transferred into 50 mM Tris buffer (pH 7.5 at 25° C.) containing 1 mM $MgCl_2$, 10 mM KCl so that the final DMSO concentration became equal to 1%. Compounds are dispensed in triplicate in assay plates (4 µl). Total binding and nonspecific binding wells are set up in 6 wells as vehicle and 10 µM dofetilide at final concentration, respectively. The radioligand is prepared at 5.6× final concentration and this solution is added to each well (36 µl). The assay is initiated by addition of YSi poly-L-lysine Scintillation Proximity Assay (SPA) beads (50 µl, 1 mg/well) and membranes (110 µl, 20 µg/well). Incubation is continued for 60 min at room temperature. Plates are incubated for a further 3 hours at room temperature for beads to settle. Receptor-bound radioactivity is quantified by counting Wallac MicroBeta plate counter.

HERG Assay

HEK 293 cells which stably express the HERG potassium channel are used for electrophysiological study. The methodology for stable transfection of this channel in HEK cells can be found elsewhere (Z. Zhou et al., 1998, Biophysical Journal, 74, pp 230-241). Before the day of experimentation, the cells are harvested from culture flasks and plated onto glass coverslips in a standard Minimum Essential Medium (MEM) medium with 10% Fetal Calf Serum (FCS). The plated cells are stored in an incubator at 37° C. maintained in an atmosphere of 95% $O_2$/5% $CO_2$. Cells are studied between 15-28 hrs after harvest.

HERG currents are studied using standard patch clamp techniques in the whole-cell mode. During the experiment the cells are superfused with a standard external solution of the following composition (mM); NaCl, 130; KCl, 4; $CaCl_2$, 2; $MgCl_2$, 1; Glucose, 10; HEPES, 5; pH 7.4 with NaOH. Whole-cell recordings are made using a patch clamp amplifier and patch pipettes which have a resistance of 1-3 MOhm when filled with the standard internal solution of the following composition (mM); KCl, 130; MgATP, 5; $MgCl_2$, 1.0; HEPES, 10; EGTA 5, pH 7.2 with KOH. Only those cells with access resistances below 15MΩ and seal resistances >1 GΩ is accepted for further experimentation. Series resistance compensation is applied up to a maximum of 80%. No leak subtraction was done. However, acceptable access resistance depended on the size of the recorded currents and the level of series resistance compensation that can safely be used. Following the achievement of whole cell configuration and sufficient time for cell dialysis with pipette solution (>5 min), a standard voltage protocol was applied to the cell to evoke membrane currents. The voltage protocol is as follows. The membrane was depolarized from a holding potential of −80 mV to +40 mV for 1000 ms. This is followed by a descending voltage ramp (rate 0.5 mV msec-1) back to the holding potential. The voltage protocol is applied to a cell continuously throughout the experiment every 4 seconds (0.25 Hz). The amplitude of the peak current elicited around −40 mV during the ramp is measured. Once stable evoked current responses are obtained in the external solution, vehicle (0.5% DMSO in the standard external solution) is applied for 10-20 min by a peristalic pump. Provided there were minimal changes in the amplitude of the evoked current response in the vehicle control condition, the test compound of either 0.3, 1, 3, 10 mM is applied for a 10 min period. The 10 min period included the time which supplying solution is passing through the tube from solution reservoir to the recording chamber via the pump. Exposure time of cells to the compound solution is more than 5 min after the drug concentration in the chamber well reaches the intended concentration. There is a subsequent wash period of a 10-20 min to assess reversibility. Finally, the cells are exposed to high dose of dofetilide (5 mM), a specific IKr blocker, to evaluate the insensitive endogenous current.

All experiments are performed at room temperature ($23\pm 1°$ C.). Evoked membrane currents are recorded on-line on a computer, filtered at 500-1 KHz (Bessel −3 dB) and sampled at 1-2 KHz using the patch clamp amplifier and a specific data analyzing software. Peak current amplitude, which generally occurs at around −40 mV, is measured off line on the computer.

The arithmetic mean of the ten values of amplitude is calculated under vehicle control conditions and in the presence of drug. Percent decrease of IN in each experiment is obtained by the normalized current value using the following formula: IN=(1−ID/IC)×100, where ID is the mean current value in the presence of drug and IC is the mean current value under control conditions. Separate experiments are performed for each drug concentration or time-matched control, and arithmetic mean in each experiment is defined as the result of the study.

Half-Life in Human Liver Microsomes (HLM)

Test compounds (1 μM) were incubated with 3.3 mM $MgCl_2$ and 0.78 mg/mL HLM (HL101) in 100 mM potassium phosphate buffer (pH 7.4) at 37° C. on the 96-deep well plate. The reaction mixture was split into two groups, a non-P450 and a P450 group. NADPH was only added to the reaction mixture of P450 group. An aliquot of samples of P450 group was collected at 0, 10, 30, and 60 min time point, where 0 min time point indicated the time when NADPH was added into the reaction mixture of P450 group. An aliquot of samples of non-P450 group was collected at −10 and 65 min time point. Collected aliquots were extracted with acetonitrile solution containing an internal standard. The precipitated protein was spun down in centrifuge (2000 rpm, 15 min). The compound concentration in supernatant was measured by LC/MS/MS system.

The half-life value was obtained by plotting the natural logarithm of the peak area ratio of compounds/internal standard versus time. The slope of the line of best fit through the points yields the rate of metabolism (k). This was converted to a half-life value using following equations:

Half-life=1n 2/k

Mono-Iodoacetate (MIA)-Induced OA Model

Male 6-weeks-old Sprague-Dawley (SD, Japan SLC or Charles River Japan) rats are anesthetized with pentobarbital. Injection site (knee) of MIA is shaved and cleaned with 70% ethanol. Twenty-five ml of MIA solution or saline is injected in the right knee joint using a 29 G needle. The effect of joint damage on the weight distribution through the right (damaged) and left (untreated) knee is assessed using an incapacitance tester (Linton Instrumentation, Norfolk, UK). The force exerted by each hind limb is measured in grams. The weight-bearing (WB) deficit is determined by a difference of weight loaded on each paw. Rats are trained to measure the WB once a week until 20 days post MIA-injection. Analgesic effects of compounds are measured at 21 days after the MIA injection. Before the compound administration, the "pre value" of WB deficit is measured. After the administration of compounds, attenuation of WB deficits is determined as analgesic effects.

Complete Freund's Adjuvant (CFA) Induced Thermal and Mechanical Hyperalgesia in Rats Thermal Hyperalgesia Male 6-week-old SD rats are used. Complete Freund's adjuvant (CFA, 300 mg of Mycobacterium Tuberculosis H37RA (Difco, Mich.) in 100 μL of liquid paraffin (Wako, Osaka, Japan)) is injected into the plantar surface of a hind paw of the rats. Two days after CFA-injection, thermal hyperalgesia is determined by method described previously (Hargreaves et al., 1988) using the plantar test apparatus (Ugo-Basil, Varese, Italy). Rats are adapted to the testing environment for at least 15 minutes prior to any stimulation. Radiant heat is applied to the plantar surface of a hind paw and paw withdrawal latencies (PWL, seconds) are determined. The intensity of radiant heat is adjusted to produce the stable PWL of 10 to 15 seconds. The test compound is administered in a volume of 0.5 mL per 100 g body weight. PWL are measured after 1, 3 or 5 hours after drug administration.

Mechanical Hyperalgesia

Male 4-week-old SD rats are used. CFA (300 mg of Mycobacterium Tuberculosis H37RA (Difco, Mich.) in 100 μL of liquid paraffin (Wako, Osaka, Japan)) is injected into the plantar surface of a hind paw of the rats. Two days after CFA-injection, mechanical hyperalgesia is tested by measuring paw withdrawal threshold (PWT, grams) to pressure using the analgesy-Meter (Ugo-Basil, Varese, Italy). The animals are gently restrained, and steadily increasing pressure is applied to the dorsal surface of a hind paw via a plastic tip. The pressure required to elicit paw withdrawal is determined. The test compound is administered in a volume of 0.5 mL per 100 g body weight. PWT are measured after 1, 3 or 5 hours after drug administration.

Pharmaceutical Compositions

When employed as pharmaceuticals, the amide compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by a variety of routes including by way of non limiting example, oral, rectal, transdermal, subcutaneous, intravenous, intramuscular and intranasal. Depending upon the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdemnal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences.*

The following formulation examples illustrate representative pharmaceutical compositions of this invention. The present invention, however, is not limited to the following pharmaceutical compositions.

Formulation 1—Tablets

A compound of formula I is admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2—Capsules

A compound of formula I is admixed as a dry powder with a starch diluent in an approximate 1:1 weight ratio. The mixture is filled into 250 mg capsules (125 mg of active compound per capsule).

Formulation 3—Liquid

A compound of formula 1 (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

The compound of formula I is admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5—Injection

The compound of formula I is dissolved or suspended in a buffered sterile saline injectable aqueous medium to a concentration of approximately 5 mg/ml.

Formulation 6—Topical

Stearyl alcohol (250 g) and a white petrolatum (250 g) are melted at about 75° C. and then a mixture of a compound of formula I (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds are used as therapeutic agents for the treatment of conditions in mammals. Accordingly, the compounds and pharmaceutical compositions of this invention find use as therapeutics for preventing and/or treating neurodegenerative, autoimmune and inflammatory conditions in mammals including humans.

In a method of treatment aspect, this invention provides a method of treating a mammal susceptible to or afflicted with a condition associated with arthritis, uveitis, asthma, myocardial infarction, traumatic brain injury, acute spinal cord injury, alopecia (hair loss), inflammatory bowel disease and autoimmune disorders, which method comprises administering an effective amount of one or more of the pharmaceutical compositions just described.

In yet another method of treatment aspect, this invention provides a method of treating a mammal susceptible to or afflicted with a condition that gives rise to pain responses or that relates to imbalances in the maintenance of basal activity of sensory nerves. Compounds have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with neurodegenerative diseases and disorders such as, for example Parkinson's disease, Alzheimer's disease and multiple sclerosis; diseases and disorders which are mediated by or result in neuroinflammation such as, for example traumatic brain injury, stroke, and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; alopecia (hair loss); obesity; lipid disorders; cancer; blood pressure; spinal cord injury; and renal disorders method comprises administering an effective condition-treating or condition-preventing amount of one or more of the pharmaceutical compositions just described.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound or its derivative, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of a neurodegenerative, autoimmune or inflammatory condition, the compounds or thier derivatives of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other active derivatives. A VR1 antagonist may be usefully combined with another pharmacologically active compound, or with two or more other pharmacologically active compounds, particularly in the treatment of pain. For example, a VR1 antagonist, particularly a compound of formula (I), or a pharmaceutically acceptable salt or solvate thereof, as defined above, may be administered simultaneously, sequentially or separately in combination with one or more agents selected from:

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an H1 antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-ydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiramate or valproate;

a tachykinin (NK) antagonist, particularly an NK-3, NK-2 or NK-1 antagonist, e.g. (aR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4- morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rinonabant, meclinertant, Miraxion® or sarizotan;

a beta-adrenergic such as propranolol;

a local anaesthetic such as mexiletine;

a corticosteroid such as dexamethasone;

a 5-HT receptor agonist or antagonist, particularly a 5-HT1B/1D agonist such as eletriptan, sumatriptan, naratriptan, zolmitriptan or rizatriptan;

a 5-HT2A receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R, 12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1a,3a,5a)(3-amino-methyl-bicyclo[3.2.0]hept-3-yl)-acetic acid, (3S,5R)-3_aminomethyl-5_methyl-heptanoic acid, (3S,5R)-3_amino-5_methyl-heptanoic acid, (3S,5R)-3_amino-5_methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[-1-(1H-tetrazol-5-ylmethyl)-cycloheptyl]-methylamine, (3S,4S)-(1-aminomethyl-3,4-dimethyl-cyclopentyl)-acetic acid, (3S,5R)-3 aminomethyl-5 methyl-octanoic acid, (3S,5R)-3_amino-5_methyl-nonanoic acid, (3S,5R)-3_amino-5_methyl-octanoic acid, (3R,4R,5R)-3-amino-4,5-dimethyl-heptanoic acid and (3R,4R,5R)-3-amino-4,5-dimethyl-octanoic acid;

a cannabinoid;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buproprion metabolite hydroxybuproprion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S, 5Z)-2-amino-2-methyl-7-[(1-iminoethyl)amino]-5-heptenoic acid, 2-[[(1R,3S)-3-amino-4-hydrox-1-(5-thiazolyl)-butyl]thio]-5-chloro-3-pyridinecarbonitrile; 2-[[(1R, 3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl]benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxymethyl]-1-methyl-2-quinolone (ZD-2138), or 2,3,5-trimethyl-6-(3-pyridylmethyl), 1,4-benzoquinone (CV-6504);

a sodium channel blocker, such as lidocaine;

a 5-HT3 antagonist, such as ondansetron;

and the pharmaceutically acceptable salts and solvates thereof.

In as much as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Preparation of the Compounds

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis,* Second Edition, Wiley, N.Y., 1991, and references cited therein.

The target compounds are synthesized by known reactions outlined in the following schemes. The products are isolated and purified by known standard procedures. Such procedures include (but are not limited to) recrystallization, column chromatography or HPLC.

In this specification, especially in "General Synthesis" and "Examples", the following abbreviations can be used:
DCM dichloromethane
DME 1,2-dimethoxyethane, dimethoxyethane
DMF N,N-dimethylformamide
DMSO dimethyl sulfoxide
EDC 1-ethyl-3-(3'-dimethylaminopropyl) carbodiimide hydrogen chloride)
HOBt 1-hydroxybenzotriazole
EtOAc ethyl acetate
EtOH ethanol
MeOH methanol
THF tetrahydrofuran
TFA trifluoroacetic acid Preparation of Acid Building Blocks Preparation of Substituted Benzoic Acids

Intermediate 1

Preparation of (E)-4-(3,3-dimethylbut-1-enyl)benzoic acid

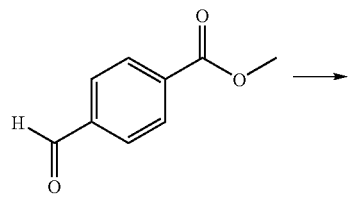

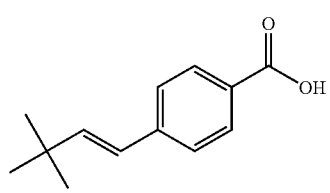

To a cooled (0° C.) and well stirred suspension of 4-carboxy benzaldehyde (2.0 g, 13.32 mmol) in anhydrous THF (90 mL) is added 33.3 mmol of neopentyl magnesium chloride in hexane during 20 minutes and the mixture is stirred at the same temperature for an additional two hours before being quenched with satyrated ammonium chloride solution. Most of the THF is evaporated and the aqueous mixture is treated with conc. HCl (50 mL) and the mixture is heated to reflux for 2 hours. The mixture is then cooled to ambient temperature and extracted with methylene chloride (2×100 mL), the organic layer is dried over sodium sulfate and concentrated to obtain the desired compound.

Intermediate 2

Preparation of (E)-4-(3-methylbut-1-enyl)benzoic acid

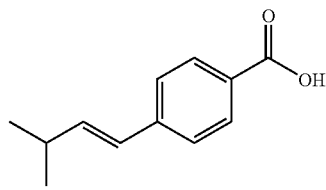

4-Carboxybenzaldehyde (1.0 g, 6.66 mmol) was dissolved in anhydrous tetrahydrofuran (50 mL) and cooled to 0° C. To the mixture was added isobutylmagnesium chloride (16 mL, 32 mmol, 2.0 M solution in THF). The reaction mixture was warmed to room temperature and stirred for 2 hours. The solution was acidified with 50% sulfuric acid in water and the THF was removed under vacuum. The aqueous phase was extracted twice with dichloromethane. The combined organic layers were washed with brine, dried (MgSO$_4$), filtered and evaporated to give the desired compound (950 mg) as grey powder.

m/z=192 (M+1)

Intermediate 3

Preparation of (Z)-4-(4,4-dimethylpent-2-en-2-yl)benzoic acid

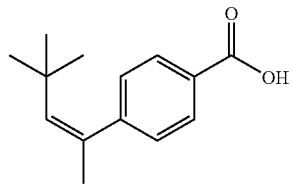

4-Carboxybenzaldehyde (1.0 g, 6.66 mmol) was dissolved in anhydrous tetrahydrofuran (50 mL) and cooled to 0° C. To the mixture was added 2,2-dimethylpropanemagnesium chloride (10.7 mL, 32 mmol, 3.0 M solution in diethyl ether). The reaction mixture was warmed to room temperature and stirred for 2 hours. The solution was acidified with 2N HCl and the solvents were removed under vacuum. The aqueous phase was extracted twice with dichloromethane. The combined organic layers were washed with brine, dried (MgSO$_4$), filtered and concentrated under vacuum to give a grey powder. The grey powder was dissolved in acetone (10 mL) and Jone's Reagent was added (10 mL). The solvent was evaporated and the residue was dissolved in diethyl ether and washed with brine and water, dried (MgSO$_4$), filtered and concentrated under vacuum to give a white solid. The white solid (730 mg) was re-suspended in anhydrous THF. To the solution was added methylmagnesium bromide(3.3 mL, 10 mmol, 3.0 M solution in diethyl ether). The reaction mixture was warmed to room temperature and stirred for 2 hours. The solution was acidified with 50% sulfuric acid in water and the THF was removed under vacuum. The aqueous phase was extracted twice with dichloromethane and the combined organic layers were washed with brine, dried (MgSO$_4$), filtered and evaporated under vacuum to give the product (600 mg) as a grey powder. m/z=219 (M+1).

Intermediate 4

Preparation of 6-(3,3-dimethylbut-1-ynyl)nicotinic acid

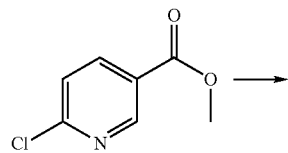

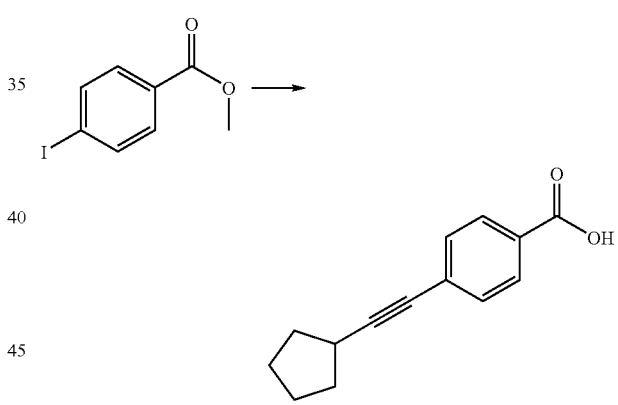

6-Chloronicotinic acid methyl ester (500 mg; 2.93 mmol) was suspended in 1,4-dioxane (3 ml) in a 5 ml reaction vial. To the vessel was added dichlorobis(triphenylphosphine) palladium(ii) (70 mg; 3 mol %), copper iodide (12 mg), n,n-diisopropylethylamine (0.63 ml; 3.5 mmol) and 3,3-dimethylbut-1-yne (0.44 ml; 3.5 mmol). The vessel was sealed and the mixture was heated at 80° C. for 24 hrs. The solvents were evaporated to dryness and 20 ml of tetrahydrofuran and 20 ml of 10N NaOH was added. The mixture was stirred at room temperature for 30 minutes and the solvent was evaporated. The basic layer was acidified with concentrated HCl and extracted three times with EtOAc. The organic layers were washed with brine and dried over Na$_2$SO$_4$, filtered and evaporated to give the desired product as a brown powder (590 mg; 99%).

Intermediate 5

Preparation of 4-(3,3-Dimethylbut-1-ynyl)benzoic acid

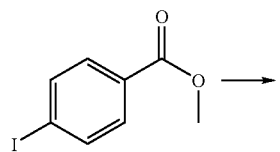

-continued

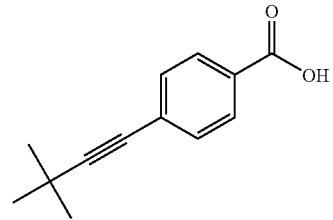

4-iodobenzoic acid methyl ester (500 mg; 1.9 mmol) was suspended in 1,4-dioxane (3 mL) in a 5 mL reaction vial. To the vessel was added dichlorobis(triphenylphosphine)palladium(II) (44 mg; 3 mol %), copper iodide (7.5 mg), N,N-diisopropylethylamine (0.39 mL; 3.5 mmol) and 3,3-dimethylbut-1-yne (0.275 mL; 3.5 mmol). The vessel was sealed and the mixture was heated at 80° C. for 24 hrs. The solvents were evaporated to dryness and 20 mL of tetrahydrofuran and 20 mL of 10N NaOH was added. The mixture was stirred at room temperature for 30 minutes and the solvent was evaporated. The basic layer was acidified with concentrated HCl and extracted three times with EtOAc. The organic layers were washed with brine and dried over Na$_2$SO$_4$, filtered and evaporated to give the desired product as a brown powder (210 mg; 28%). m/z=203 (M+1).

Intermediate 6

Preparation of 4-(cyclopentylethynyl)benzoic acid

The same procedure was followed as for 4-(3,3-dimethylbut-1-ynyl)benzoic acid, with the exception that ethynylcyclopentane was used in place of 3,3-dimethylbut-1-yne.

Intermediate 7

Preparation of 4-(3,3,3-Trifluoropropenyl)benzoic acid

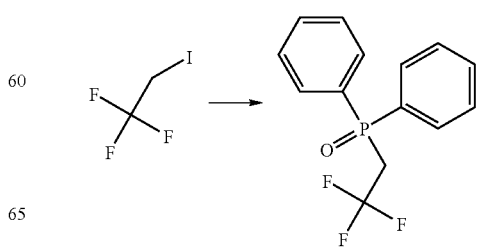

A mixture of ethyl diphenylphosphonite (1.98 g; 5.8 mmol) and 2,2,2-trifluoroethyl iodide (6.1 g; 29 mmol) was stirred at room temperature under nitrogen for 24 hrs. The excess reagents were removed under vacuum. The residue was purified on silica gel using a 0-100% hexane-ethyl acetate gradient to give the target as a white powder (800 mg; 49%). m/z=286 (M+1).

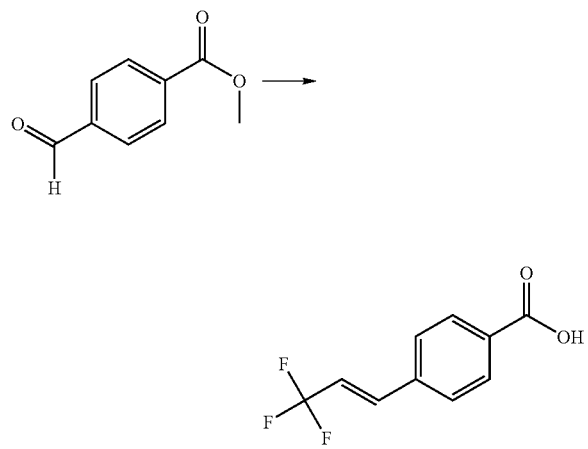

4 Å molecular sieves (7 g; activated powder) were suspended in 8.8 ml of 1.0 m tbaf in thf and stirred overnight at room temperature under nitrogen. To the solution was added methyl 4-formylbenzoate (160 mg; 0.97 mmol) and 2,2,2-trifluoroethyldiphenylphosphine oxide (415 mg; 1.46 mmol) in 10 ml of anhydrous thf. After stirring overnight, the solvents were evaporated to dryness. The residue was dissolved in EtOAc and washed with water and brine. The organic was dried over $Na_2SO_4$, filtered and evaporated. The residue was dissolved in 10 ml of thf and 10 ml of 1N NaOH and refluxed for 30 minutes. The mixture was acidified with concentrated HCl and extracted three times with EtOAc. The organic layers were washed with brine and dried over $Na_2SO_4$, filtered and evaporated to give the desired product as a brown powder (125 mg; 60%). M/z=217 (m+1).

Intermediate 8

Preparation of 4-(3,3,3-trifluoroprop-1-ynyl)benzoic acid

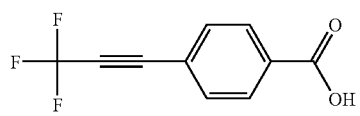

(3,3,3-Trifluoroprop-1-ynyl)triphenylstannane

The triphenylstannane derivative was prepared using a modified procedure of Brisdon (*Chem. Commun.* 2002, 2420-2421). Accordingly, 1,1,1,3,3-pentafluoropropane (2.0 g, 14.9 mmol) was condensed into a 500 mL three neck round bottom flask containing ether (20 mL) cooled to −15° C. The mixture was maintained below −10° C. while n-BuLi (2.5 M in hexanes, 16.08 mL, 40.2 mmol) was added. After the reaction was stirred for 10 minutes at −10° C., triphenyl tin chloride (5 g, 13.4 mmol) was added as a solution in ether, maintaining −10° C. The mixture was slowly warmed to room temperature and allowed to stir for an additional 4 hours. An excess of hexanes (300 mL) was added and then the settled mixture was filtered through Celite®. Concentration of the filtered solution in vacuo afforded a pale yellow solid which was purified by column chromatography ($SiO_2$: ether/hexanes, 1:10) affording 5.2 g (78%) of the triphenylstannane derivative as an off white solid.

Methyl 4-(3,3,3-trifluoroprop-1-ynyl)benzoate

To a 20 mL microwave reaction vial was added methyl 4-iodobenzoate (1 g, 3.8 mmol), toluene (5 mL), tetrakis(triphenylphosphine) Pd(0) (0.44 g, 0.38 mmol), and (3,3,3-trifluoroprop-1-ynyl)triphenylstannane (2.52 g 5.7 mmol). The mixture was heated at 120° C. for 30 minutes, allowed to cool, and reduced in vacuo. The remaining residue was taken up in ethyl acetate (20 mL), washed with water (2×50 mL) and brine (2×50 mL), and purified by column chromatography ($SiO_2$: ethyl acetate/hexanes, 1:10) to afford 0.680 grams (78%) of the benzoate as a yellow oil.

4-(3,3,3-Trifluoroprop-1-ynyl)benzoic acid

To a 100 mL round bottom flask was added 4-(3,3,3-trifluoroprop-1-ynyl)benzoate (0.68 g, 2.9 mmol), lithium hydroxide (0.71 g, 29 mmol), and methanol (30 mL): water (10 mL). The mixture was stirred at room temperature for 30 minutes, heated at reflux for 1 hour, and reduced in vacuo. Water (100 mL) was added and the mixture was cooled to 0° C. HCl (10 N) was added slowly to the stirred solution until the pH of the solution reached 5. A yellow precipitate formed and was filtered, washed with cold water (3×100 mL), and dried under vacuum to afford 0.540 g (86%) of 4-(3,3,3-trifluoroprop-1-ynyl)benzoic acid as a light yellow solid.

Intermediate 9

Preparation of 4-(cyclopropylethynyl)benzoic acid

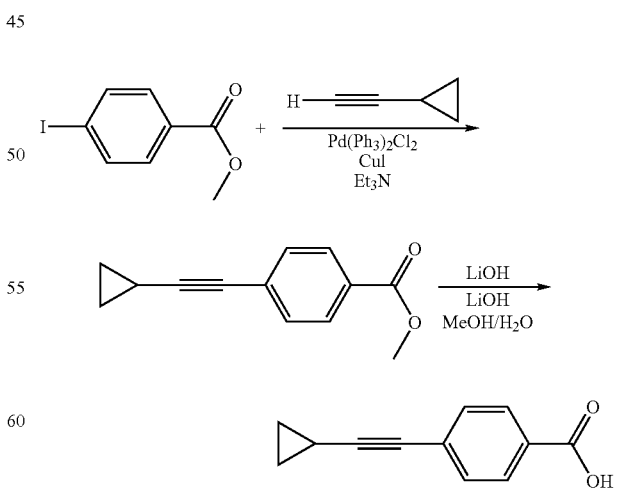

The above compound was prepared using the same procedure as 4-(cyclopropylethynyl)-2-methylbenzoic acid, except methyl 4-iodobenzoate was used as the starting material.

Intermediate 10

Preparation of 4-(3,3-dimethylbut-1-ynyl)-3-(2-morpholinoethoxy)benzoic acid

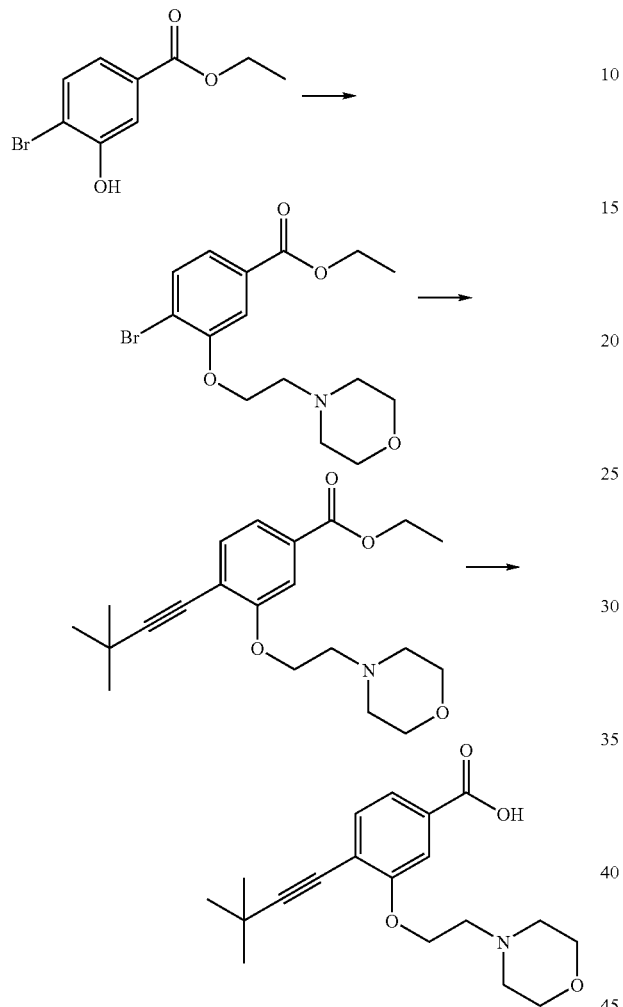

Ethyl 3-(2-morpholinoethoxy)-4-bromobenzoate

Ethyl 4-bromo-3-hydroxybenzoate (1.5 g, 6.12 mmol), potassium carbonate (2.5 g, 18.37 mmol) and 4-(2-chloroethyl)morpholine hydrochloride (1.4 g, 7.35 mmol) were placed in 50 mL DMF and the reaction was heated at 80° C. for 18 h. The mixture was cooled and partitioned between EtOAc and water. The organic layer was separated, washed with water, brine, dried (Na$_2$SO$_4$), filtered, and the filtrate was concentrated to an oil. Purification by column chromatography on silica gel using 0-50% EtOAc/hexane as eluent gave the product (1.0 g, 47%) as a colorless oil.

Ethyl 3-(2-morpholinoethoxy)-4-(3,3-dimethylbut-1-ynyl)benzoate

Ethyl 3-(2-morpholinoethoxy)-4-bromobenzoate (0.5 g, 1.4 mmol), 1-butyne, 3,3-dimethyl-(3.43 mL, 2.8 mmol) copper(I) iodide (27 mg, 0.14 mmol) and bis(triphenylphosphine)palladium(II) chloride (0.19 g, 0.28 mmol) were placed in 50 mL triethylamine and stirred in a sealed tube at room temperature for 20 h. The reaction was diluted with MeOH and filtered through Celite®., then the filtrate was concentrated to an oil. Purification by column chromatography on silica gel using 75% EtOAc/hexane as eluent gave the product (0.34 g, 67%) of as a brown solid. m/z=360 (M+1).

4-(3,3-dimethylbut-1-ynyl)-3-(2-morpholinoethoxy)benzoic acid

Ethyl 3-(2-morpholinoethoxy)-4-(3,3-dimethylbut-1-ynyl)benzoate (0.34 g, 0.95 mmol) and LIOH (68 mg, 2.84 mmol) were placed in a 3:1 mixture of methanol:water (30 mL) and heated at 60° C. for 3.5 h. The reaction was cooled and concentrated in vacuo to a volume of 20 mL. The mixture was placed in an ice-water bath and acidified to pH 5 with conc. HCl. A white solid precipitated which was filtered and washed thoroughly with water. The solid was dried in a vacuum oven to give the product (0.24 g, 70%) as a solid. m/z=330.1 (M−1).

Intermediate 11

Preparation of 4-(3,3-dimethylbut-1-ynyl)-3-ethoxybenzoic acid

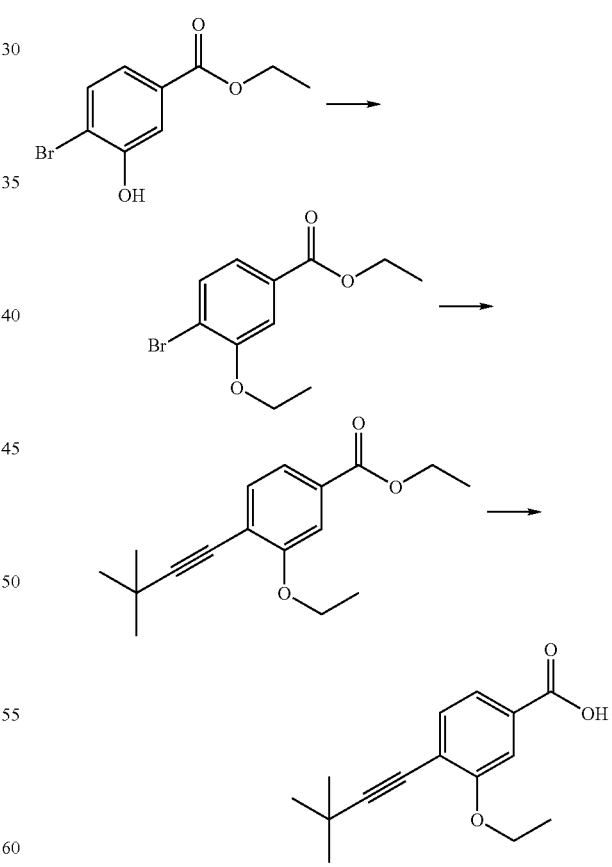

Ethyl 4-bromo-3-ethoxybenzoate

Ethyl 4-bromo-3-hydroxybenzoate (prepared according to M. I. Dawson et al WO 2003048101; 0.5 g, 2.04 mmol), potassium carbonate (0.84 g, 6.12 mmol) and iodoethane (0.2 mL, 2.45 mmol) were placed in 50 mL DMF and the reaction was heated at 80° C. for 18 h. The mixture was cooled and partitioned between EtOAc and water. The organic layer was separated, washed with water, brine, dried (Na$_2$SO$_4$), filtered, and the filtrate was concentrated under vacuum to an oil. The oil was purified by column chromatography using EtOAc/hexane (0-50%) as eluent to give the product (0.35 g, 62%) as a clear oil.

Ethyl 3-ethoxy-4-(3,3-dimethylbut-1-ynyl)benzoate

This compound was prepared using the same procedure as detailed for ethyl 3-(2-morpholinoethoxy)-4-(3,3-dimethylbut-1-ynyl)benzoate.

4-(3,3-dimethylbut-1-ynyl)-3-ethoxybenzoic acid

This compound was prepared using the same procedure as detailed for 4-(3,3-dimethylbut-1-ynyl)-3-(2-morpholinoethoxy)benzoic acid. m/z=244 (M−1).

Intermediate 12

Preparation of 4-(3,3-dimethylbut-1-ynyl)-3-(2-hydroxy-2-methylpropxy)benzoic acid

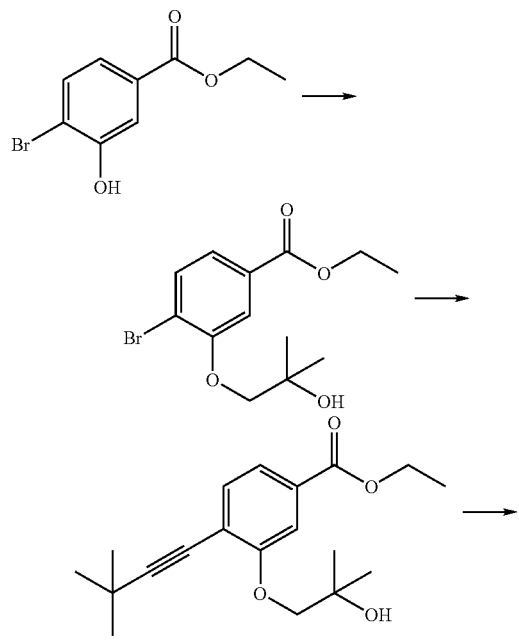

Ethyl 3-(2-hydroxy-2-methylpropoxy)-4-bromobenzoate

Ethyl 4-bromo-3-hydroxybenzoate (1.5 g, 6.12 mmol), potassium carbonate (5.07 g, 36.72 mmol) and 1-chloro-2-methylpropan-2-ol (0.75 mL, 7.34 mmol) were placed in 50 mL DMF and the reaction was heated at 80° C. for 18 h. The mixture was cooled and partitioned between EtOAc and water. The organic layer was separated, washed with water, brine, dried (Na$_2$SO$_4$), filtered, and the filtrate was concentrated under vacuum to an oil. Purification by column chromatography on silica gel using EtOAc/hexane (0-50%) gave the product (0.5 g, 26%) as a yellow oil.

Ethyl 3-(2-hydroxy-2-methylpropoxy)-4-(2-cyclopropylethynyl)benzoate

This compound was prepared using the same procedure as detailed for ethyl 3-(2-morpholinoethoxy)-4-(3,3-dimethylbut-1-ynyl)benzoate to give the product (0.18 g, 38%) as an oil.

4-(3,3-dimethylbut-1-ynyl)-3-(2-hydroxy-2-methylpropxy)benzoic acid

This compound was prepared using the same procedure as detailed for 4-(3,3-dimethylbut-1-ynyl)-3-(2-morpholinoethoxy)benzoic acid to give the product (0.15 g, 95%) as a solid. m/z=272.8 (M−1).

Intermediate 13

Preparation of 2-chloro-6-(3,3-dimethylbut-1-ynyl)nicotinic acid

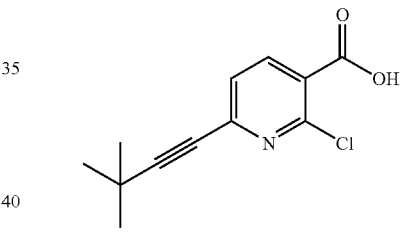

2,6-dichloropyridine-3-carboxylic acid (2.0 g, 10.42 mmol), 3,3-dimethylbut-1-yne (1.4 mL, 11.46 mmol), copper (I) iodide (0.198 g, 1.04 mmol) and bis(triphenylphosphine) palladium(II) chloride (1.46 g, 2.08 mmol) were stirred in 40 mL triethylamine at room temperature for 24 h. The solvent was removed in vacuo and the residue was purified by column chromatography using 10-50% MeOH/EtOAc to furnish 125 mg (5%) of the title compound as an orange solid. m/z=236 (M−1).

Intermediate 14

Preparation of (E)-4-(4,4,4-Trifluorobut-2-en-2-yl)benzoic acid

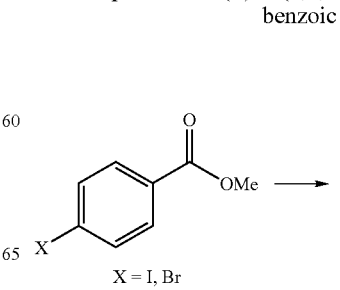

X = I, Br

-continued

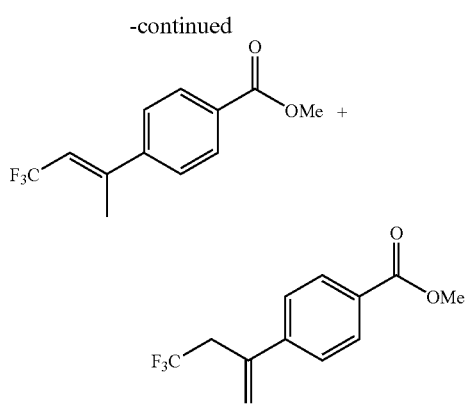

(E)-methyl 4-(4,4,4-trifluorobut-2-en-2-yl)benzoate. A mixture of methyl 4-iodobenzoate (2.62 g, 10 mmol), Et$_3$N (5 ml), acetonitrile (6 ml), Pd(OAc)2 (100 mg, 0.4 mmol) added 1,1,1-trifluoro-2-butene (2.20 g, 20 mmol) was sealed and heated at 125° C. for 20 h. After cooling, the mixture was treated with sat. Aq. Na$_2$CO$_3$ solution and extracted with EtOAc. The combined organic phases were washed with brine, dried (MgSO$_4$), and evaporated. The residue was purified by column chromatography on silica gel to give methyl (e)-methyl 4-(4,4,4-trifluorobut-2-en-2-yl)benzoate and methyl 4-(4,4,4-trifluorobut-1-en-2-yl)benzoate.

(E)-4-(4,4,4-trifluorobut-2-en-2-yl)benzoic acid. (e)-4-(4, 4,4-trifluorobut-2-en-2-yl)benzoic acid [lc-ms: tr=3.03 min, m/z=229 (m−1)] and 4-(4,4,4-trifluorobut-1-en-2-yl)benzoic acid [lc-ms: tr=2.82 min, m/z=229 (m−1)] were prepared from the corresponding methyl esters according to the general saponification procedure for the preparation of (e)-4-(3, 3,3-trifluoro-2-methylprop-1-enyl)benzoic acid.

Intermediate 15

Preparation of (e)-2-methyl-4-(3,3,3-trifluoroprop-1-enyl)benzoic acid

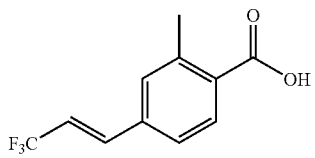

A mixture of 4-bromo-2-methylbenzoic acid (25 g, 0.12 mol), tri-o-tolylphosphine (7.1 g, 0.023 mol), tetra-N-butylammonium chloride (9.7 g, 0.035 mol), potassium acetate (22.8 g, 0.232 mol), 3,3,3-trifluoroprop-1-ene (89 g, 0.93 mol), palladium acetate (1.3 g, 0.0058 mol) and N,N-dimethylacetamide (150 mL, 1.6 mol) was sealed in a Parr instrument and stirred at 180° C. for 120 h. After cooling, the reaction mixture was filtered through Celite® and the filtrate was partitioned between EtOAc and 1N HCl (pH 2-3). The organic layer was separated and washed with brine, dried (Na$_2$SO$_4$) and concentrated under vacuum. The residue was purified by column chromatography on silica gel to give a crude product (which contained a small amount of the correspnding (Z)-isomer).

The (Z)-isomer and other impurities could be removed by column after transforming the acid into the corresponding methyl ester. Saponification of the methyl ester gave the pure acid as a white solid (16.5 g, 62%).

Intermediate 16

Preparation of (e)-4-(3,3,3-trifluoro-2-methylprop-1-enyl)benzoic acid

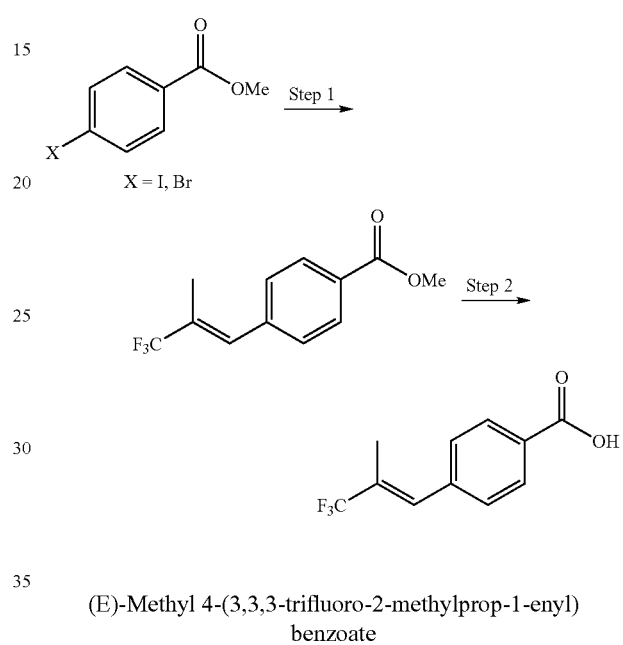

(E)-Methyl 4-(3,3,3-trifluoro-2-methylprop-1-enyl) benzoate

To a mixture of methyl 4-iodobenzoate (2.62 g, 10 mmol), Et$_3$N (5 mL), acetonitrile (6 mL), Pd(OAc)$_2$ (100 mg, 0.4 mmol) was added 2-trifluoromethylpropene (2.20 g, 20 mmol). The mixture was sealed and heated at 125° C. for 20 h. After cooling, the mixture was treated with sat. aq. Na$_2$CO$_3$ solution and extracted with EtOAc. The combined organic phases were washed with brine, dried (MgSO$_4$), and evaporated. The residue was purified by column chromatography on silica gel to give methyl (E)-4-(3,3,3-trifluoro-2-methylprop-1-enyl)benzoate.

(E)-4-(3,3,3-Trifluoro-2-methylprop-1-enyl)benzoic acid

To a stirred mixture of methyl (E)-4-(3,3,3-trifluoro-2-methylprop-1-enyl)benzoate (60 mg, 0.25 mmol) in THF (5 mL) and MeOH (5 mL) was added a 2N NaOH solution (1 mL). The mixture was stirred at room temperature for 10 h. After removal of the organic solvent in vacuo, the mixture was treated with water and acidified with 1N HCl to pH 2-3. The mixture was extracted with EtOAc (20 mL×3). The combined extracts were washed with brine, dried (Na$_2$SO$_4$), and evaporated. The residue was purified with column to give (E)-4-(3,3,3-trifluoro-2-methylprop-1-enyl)benzoic acid as a white solid. LC-MS: $t_R$=3.04 min, m/z=229 (M−1).

Intermediate 17

Preparation of 5-(3,3-dimethylbut-1-ynyl)picolinic acid

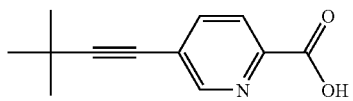

Methyl 5-(3,3-dimethylbut-1-ynyl)picolinate

To a 250 mL sealed reaction vessel was added methyl 5-bromopyridine-2-carboxylate (5 g, 23 mmol), copper(I) iodide (0.43 g, 2.3 mmol), bis(triphenylphosphine) palladium (II) chloride (3.23 g, 4.6 mmol), and triethylamine (80 mL). The mixture was allowed to stir for approximately 10 minutes upon which 3,3-dimethylbut-1-yne (2.83 g, 34.5 mmol) was added. The tube was sealed, stirred at room temperature overnight, and heated at 60° C. for one hour. The mixture was allowed to cool, and then concentrated under vacuum to a residue. The residue was purified by column chromatography on silica gel using EtOAc/hexanes (1:10) as eluent to give the product (4.62 g, 92%) as a tan solid which was used directly in the next step.

5-(3,3-dimethylbut-1-ynyl)picolinic acid

To a 500 mL round bottom flask was added methyl 5-(3,3-dimethylbut-1-ynyl)picolinate (4.5 g, 21 mmol), lithium hydroxide (5.02 g, 210 mmol), methanol (80 mL), and water (30 mL). The mixture was stirred at room temperature for 30 minutes, heated to reflux for 1 hour, then concentrated under vacuum. Water (100 mL) was added and the mixture was cooled to 0° C. Concentrated HCl was added slowly to the stirred solution until the pH of the solution reached 6. An off white precipitate formed and was filtered, washed with cold water (3×100 mL) and dried under vacuum to afford the product (3.97 g, 95%) as an off white solid. LC-MS 2.76 min, 202.9 (M−1).

Intermediate 18

Preparation of 4-(cyclopropylethynyl)-3-(cyclopropylmethoxy)benzoic acid

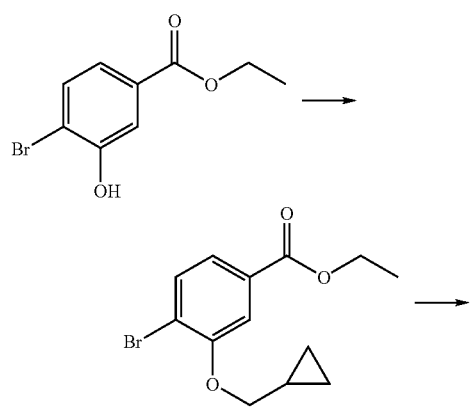

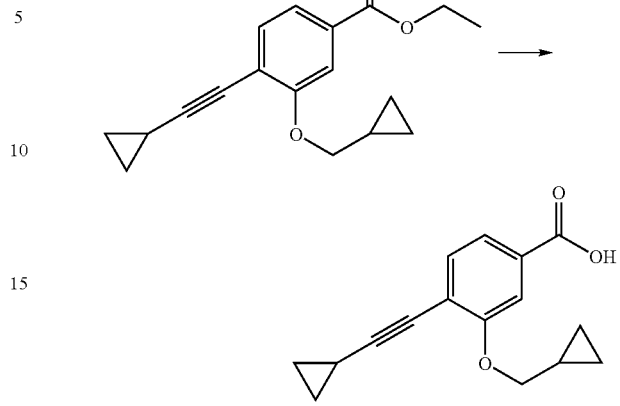

Ethyl 4-bromo-3-(cyclopropylmethoxy)benzoate

Ethyl 4-bromo-3-hydroxybenzoate (2.0 g, 8.2 mmol), potassium carbonate (3.4 g, 24.48 mmol and (chloromethyl)cyclopropane (1.13 mL, 12.24 mmol) were placed in 50 mL DMF and the reaction was heated at 80° C. for 18 h. The mixture was cooled and partitioned between EtOAc and water. The organic layer was separated, washed with water, brine, dried ($Na_2SO_4$), filtered, and the filtrate was concentrated to an oil. Purification by column chromatography on silica gel using 0-50% EtOAc/hexane gave the product (0.77 g, 31%) as a clear oil.

Ethyl 4-(2-cyclopropylethynyl)-3-(cyclopropylmethoxy)benzoate

Ethyl 4-bromo-3-(cyclopropylmethoxy)benzoate (0.77 g, 2.57 mmol), ethynylcyclopropane (0.45 mL of a 70% w/v solution in toluene, 3.86 mmol), copper(I) iodide (49 mg, 0.26 mmol) and bis(triphenylphosphine)palladium(II) chloride (0.36 g, 0.51 mmol) were placed in 50 mL triethylamine and stirred in a sealed tube at room temperature for 20 h. The reaction was diluted with MeOH and filtered through Celite®., then the filtrate was concentrated to an oil. Purification by column chromatography on silica gel using 25% EtOAc/hexane gave the product (0.47 g, 61%) as a brown oil.

4-(Cyclopropylethynyl)-3-(cyclopropylmethoxy) benzoic acid

Ethyl 4-(2-cyclopropylethynyl)-3-(cyclopropylmethoxy)benzoate (0.47 g, 1.65 mmol) and LiOH (120 mg, 4.96 mmol) were placed in a 3:1 mixture of methanol:water (50 mL) and heated at 60° C. for 3.5 h. The reaction was cooled and concentrated in vacuo to a volume of 20 mL, then placed in an ice-water bath and acidified to pH 5 with conc. HCl. A white solid precipitated which was filtered and washed thoroughly with water. The solid was dried in the vacuum oven to give the product (0.44 g, 98%). m/z=257.1 (M+1).

Intermediate 19

Preparation of 2-(3,3-dimethylbut-1-ynyl)pyrimidine-5-carboxylic acid

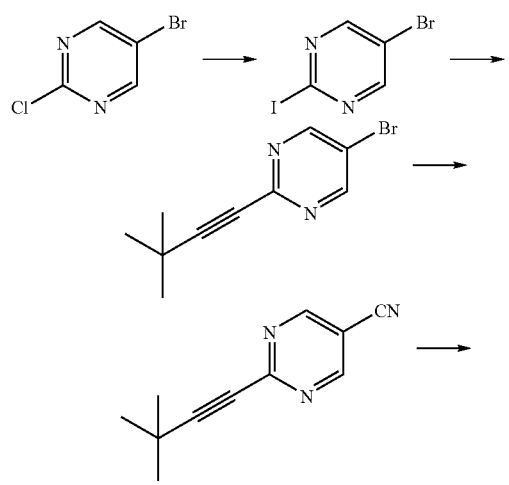

5-Bromo-2-iodo-pyrimidine

The title compound was prepared according to the procedure given *The Journal of Organic Chemistry*, 2002, 67, 6550-6552. In 57% hydiodic acid (aqeous) precooled to 0° C. was added to solid 5-Bromo-2-chloro-pyrimidine (3.36 g, 0.0174 mol) in a 100 ml round bottom flask. The mixture was stirred vigorously at 0° C. and after 4 hours, was allowed to warm to room temp and stirred overnight. The mixture was then poured over ice and carefully neutralized by addition of solid sodium bicarbonate. Solid sodium hydrogensulfite added until mixture became colorless then the mixture was extracted with EtOAc (2×200 mL). The combined organic extracts were washed with brine and dried (MgSO$_4$), filtered and concentrated under vacuum to leave a white solid (4.2 g) which was used without further purification.

5-bromo-2-(3,3-dimethylbut-1-ynyl)pyrimidine

A mixture of 5-Bromo-2-iodo-pyrimidine (2.53 g, 0.00888 mol), copper(I) iodide (0.169 g, 0.000888 mol), 1-butyne, 3,3-dimethyl- (1.17 mL, 0.00977 mol) and bis(triphenylphosphine)palladium(II) chloride (0.623 g, 0.000888 mol) in triethylamine (25 mL, 0.18 mol) was heated at 50° C. in a 150 mL sealed reaction vessel. After 16 hours, the mixture was cooled to r.t. and filtered through Celite®, the filter cake being washed repeatedly with ethyl acetate. The filtrate was concentrated under vacuum to leave a dark solid. Purification by column chromatography on silcia gel with an ethyl acetate: hexane (0-100% gradient) as eluent gave the product (1.9 g) as a solid.

2-(3,3-dimethylbut-1-ynyl)pyrimidine-5-carbonitrile

A mixture of 5-bromo-2-(3,3-dimethylbut-1-ynyl)pyrimidine (2.5 g, 0.010 mol) and copper cyanide (1.4 g, 0.016 mol) in N-methyl pyrrolidine was heated in a sealed tube at 200° C. for 24 hours. The mixture was allowed to cool to room temperature and filtered through Celite® and the filtrate was concentrated under vaccum. The residue was purified by column chromatography on silica gel with an ethyl acetate: hexane (0-50% gradient) to give the product (1.25 g).

2-(3,3-dimethylbut-1-ynyl)pyrimidine-5-carboxylic acid

A mixture 2-(3,3-dimethylbut-1-ynyl)pyrimidine-5-carbonitrile (1.0 g, 0.005 mol) and potassium hydroxide (2.8 g, 0.05 mol) in isopropanol (40 mL) and water (10 mL) was heated at reflux for three hours. The mixture was allowed to cool to room temperature and concentrated under vacuum. Water (200 mL) was added and the mixture was cooled to 0° C., then conc. HCl was added until a pH of 6 was obtained. The resulting off-white precipitate was collected by filtration and washed with water to give the product as a solid. m/z=205 (M+1).

Intermediate 20

Preparation of 4-(cyclopentylethynyl)-2-fluorobenzoic acid

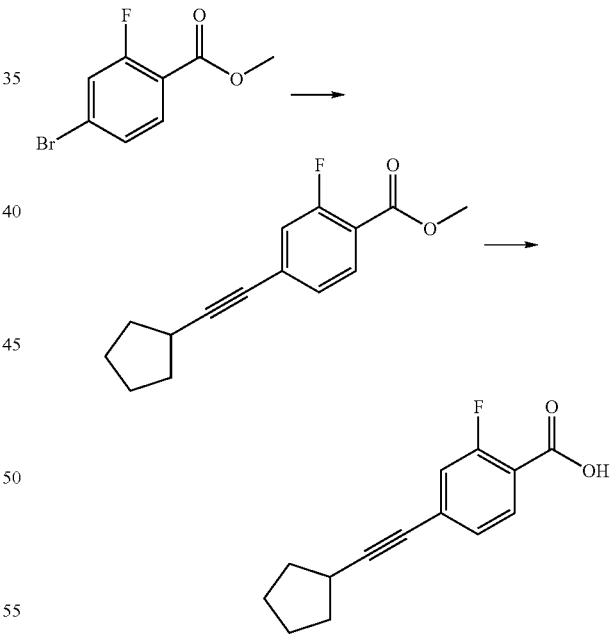

Methyl 4-(cyclopentylethynyl)-2-fluorobenzoate

4-Bromo-2-fluorobenzoic acid methyl ester (1.0 g, 4.0 mmol) was dissolved in triethylamine (5 mL). To the mixture was added copper iodide (38 mg, 5 mol %), followed by PdCl$_2$(PPh$_3$)$_2$ (140 mg, 5 mol %) and ethynylcyclopentane (0.85 mL, 6.3 mmol). The mixture was heated in a sealed pressure tube at 80° C. for 3 hours. After completion of the reaction, the triethylamine was removed under vacuum and the residue was dissolved in EtOAc and filtered through Celite®. The organic layer was washed with water, brine, and dried (Na$_2$SO$_4$), filtered and the mixture concentrated under vacuum. The residue was purified using column chromatography on sililca using EtOAc-hexane (0-100% gradient) as eluent to give the product (0.92 g).

4-(cyclopentylethynyl)-2-fluorobenzoic acid

Methyl 4-(cyclopentylethynyl)-2-fluorobenzoate was dissolved in 10 mL of MeOH and 10 mL of 2N LiOH and the mixture was refluxed overnight. The MeOH was removed under vacuum and the basic layer was washed with EtOAC, acidified, and re-extracted with EtOAC. The organic layer was washed with brine, dried (Na$_2$SO$_4$), filtered and concentrated under vacuum to give the desired product (645 mg) as a beige solid. m/z=233 (M+1).

Intermediate 21

Preparation of 2-chloro-6-(cyclopropylethynyl)nicotinic acid

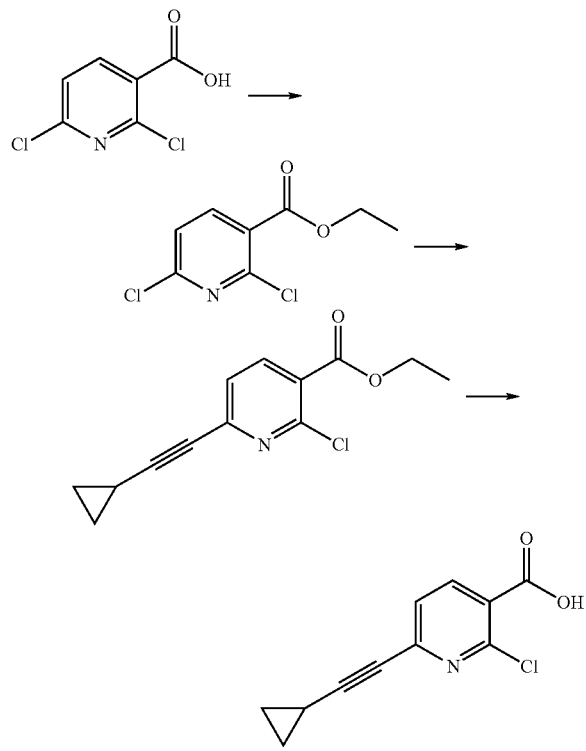

Ethyl 2,6-dichloropyridine-3-carboxylate 2,6-dichloropyridine-3-carboxylic acid (2.0 g, 10.42 mmol) was placed in 100 mL EtOH, 2 mL conc. H$_2$SO$_4$ was added and the mixture was refluxed for 18 h. The reaction mixture was cooled and the pH adjusted to 5 with satd. aqueous NaHCO$_3$ and then extracted with EtOAc. The organic layer was separated and dried (Na$_2$SO$_4$). Removal of solvent in vacuo furnished 2.1 g of the ethyl ester which was used in the next step without further purification. m/z=220.6 (M+1).

Ethyl 2-chloro-6-(2-cyclopropylethynyl)pyridine-3-carboxylate

Ethyl 2,6-dichloropyridine-3-carboxylate (2.0 g, 9.1 mmol), ethynylcyclopropane (1.6 mL of a 70% w/v solution in toluene, 13.63 mmol), copper(I) iodide (173 mg, 0.9 mmol), bis(triphenylphosphine) palladium(II) chloride (1.28 g, 1.82 mmol) were stirred in 40 mL triethylamine at room temperature for 24 h. The solvent was removed in vacuo and the residue was purified by column chromatography using 10-50% EtOAc/hexane to give the product (0.7 g, 31%) as a brown oil. m/z=250 (M+1).

2-chloro-6-(cyclopropylethynyl)nicotinic acid

The ester was hydrolyzed as follows: Ethyl 2-chloro-6-(2-cyclopropylethynyl)pyridine-3-carboxylate (0.7 g, 2.8 mmol) and lithium hydroxide (0.4 g, 16.86 mmol) were refluxed in a mixture of 30 mL MeOH and 10 mL water. The mixture was cooled and the methanol was removed in vacuo. The remaining solution was acidified to pH 2 with 1M HCl at 0° C. The precipitate was filtered and dried to give 0.4 g (57%) of the title compound. m/z=222.4 (M+1).

Intermediate 22

Preparation of (Z)-2-methoxy-4-(3,3,3-trifluoroprop-1-enyl)benzoic acid and preparation of (E)-2-methoxy-4-(3,3,3-trifluoromethylprop-1-enyl)benzoic acid

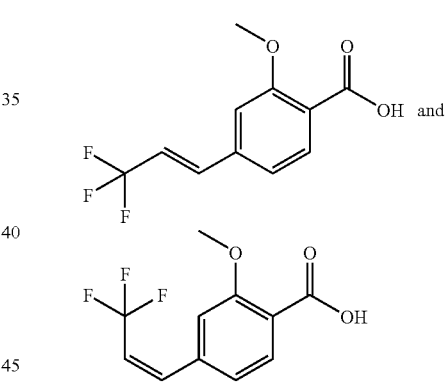

Methyl 4-formyl-2-methoxybenzoate

A slow stream of CO was passed into a suspension of methyl 4-bromo-2-methoxybenzoate (2.4 g, 0.010 mol), bis(triphenylphosphine)palladium(II) chloride (140 mg, 0.00020 mol), sodium formate (1.02 g, 0.0150 mol), and dry DMF (10 mL). The mixture was vigorously stirred at 110° C. for 2 h. After cooling, the mixture was treated with aqueous Na$_2$CO$_3$ solution and extracted with EtOAc. The extract was washed with brine, dried (Na$_2$SO$_4$), and concentrated. The residue was purified by column chromatography on silica gel with AcOEt-hexane as eluent (0 to 50%) to give a colorless oil.

Methyl (E)-4-(3,3,3-trifluoroprop-1-enyl)-2-methoxybenzoate and methyl (Z)-4-(3,3,3-trifluoroprop-1-enyl)-2-methoxybenzoate MS 4 Å (powder, 16 g) was added to a 1 M solution of TBAF in THF (20 mL, 20 mmol), and the mixture was stirred at room-temperature overnight under an argon atmosphere. To the mixture were added a solution of methyl 4-formyl-2-methoxybenzoate (420 mg, 0.0022 mol) and 2,2,2-trifluoroethyldiphenylphosphine oxide (1.23 g, 0.00432 mol) in THF (20 mL). After the mixture was stirred for 2 h, MS 4 Å was removed by filtration. The filtrate was concentrated and water (120 mL) was added. The mixture was extracted with AcOEt. The extract was washed with brine, dried ($Na_2SO_4$), and concentrated. The residue was purified by column chromatography on silica gel using AcOEt-hexane (0-15%) as eluent to give (E)-methyl 4-(3,3,3-trifluoroprop-1-enyl)-2-methoxybenzoate as a white solid, followed by (Z)-methyl 4-(3,3,3-trifluoroprop-1-enyl)-2-methoxybenzoate as a colorless oil.

(E)-4-(3,3,3-Trifluoroprop-1-enyl)-2-methoxybenzoic acid

A mixture of (E)-methyl 4-(3,3,3-trifluoroprop-1-enyl)-2-methoxybenzoate (340 mg, 0.0013 mol), MeOH (20 mL), and 2 N aqueous NaOH solution (1.5 mL) was stirred at 65° C. overnight. The solvents were removed under reduced pressure and the residue was treated with water, acidified with 1N HCl to pH 2-3, and extracted with EtOAc (50 mL×3). The combined organic layers were washed with brine, dried ($Na_2SO_4$), filtered and concentrated under vacuum to give the product as a white solid. LC-MS: 2.59 min, 244.8 (M−1).

(Z)-4-(3,3,3-trifluoroprop-1-enyl)-2-methoxybenzoic acid

A mixture of (Z)-methyl 4-(3,3,3-trifluoroprop-1-enyl)-2-methoxybenzoate (60.0 mg, 0.000230 mol), MeOH (10 mL), and 2 N aqueous NaOH solution (0.5 mL) was stirred at 65° C. for 5 h. After cooling the mixture, the solvent was removed under reduced pressure. The residue was treated with water, acidified with 1N HCl to pH 2-3, and extracted with EtOAc (30 mL×3). The combined organic layers were washed with brine, dried ($Na_2SO_4$), filtered and concentrated under vacuum to give the product as a syrup which became an off-white solid while standing at room temperature for a long time. LC-MS: 2.49 min, 244.8 (M−1).

Intermediate 23

Preparation of 4-(cyclopropylethynyl)-2-methylbenzoic acid

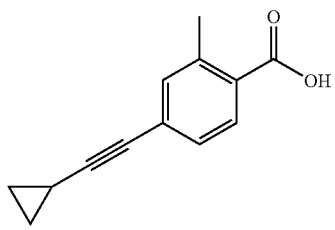

Methyl-4-bromo-2-methylbenzoate

4-Bromo-2-methylbenzoic acid (5.0 g, 23 mmol) was suspended in methanol (30 mL). To the mixture was added a solution of HCl in diethylether (1.0M, 30 mL). The mixture was refluxed for 24 hours and concentrated to dryness. The residue was dissolved in EtOAc and washed with saturated sodium bicarbonate. The organic layer was washed with brine, dried ($Na_2SO_4$), filtered and concentrated under vacuum to give the desired compound (5.5 g) as a brown oil.

4-(cyclopropylethynyl)-2-methylbenzoic acid

Methyl 4-Bromo-2-methylbenzoate (1.0 g, 4.4 mmol) was dissolved in triethylamine (5 mL). To the mixture was added copper iodide (43 mg, 5 mol %), followed by $PdCl_2(PPh_3)_2$ (157 mg, 5 mol %) and ethynylcyclopropane (1.43 ml, 12 mmol). The mixture was heated in a sealed pressure tube at 80° C. for 3 hours. After completion of the reaction, the triethylamine was evaporated and the residue was dissolved in EtOAc and filtered through Celite®. The organic layer was washed with water, brine, and dried ($Na_2SO_4$), then filtered and concentrated under vacuum. The residue was purified by column chromatography on sililca gel using EtOAc-hexane (0-100% gradient) as eluent to give the desired product (630 mg). The product was dissolved in 10 mL of MeOH and 10 mL of 2N LiOH and the mixture was refluxed overnight. The MeOH was evaporated and the basic layer was washed with EtOAC, acidified, and re-extracted with EtOAC. The organic layer was washed with brine, dried ($Na_2SO_4$), filtered and concentrated under vacuum to give the desired product as a beige solid (461 mg). m/z 201 (M+1).

Intermediate 24

Preparation of 4-(cyclopropylethynyl)-2-fluorobenzoic acid

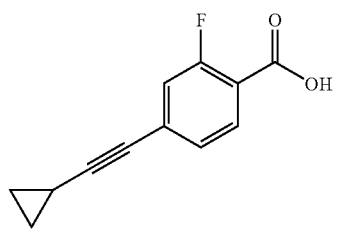

This compound was prepared using the same method as for 4-(3,3-dimethylbut-1-ynyl)-2-methylbenzoic acid, with the exception that cyclopopylacetylene was used as the alkyne coupling partner.

Intermediate 25

Preparation of 4-(3,3-dimethylbut-1-ynyl)-2-methoxybenzoic acid

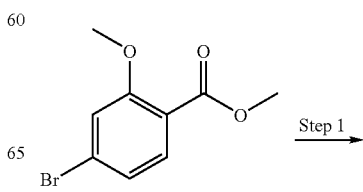

-continued

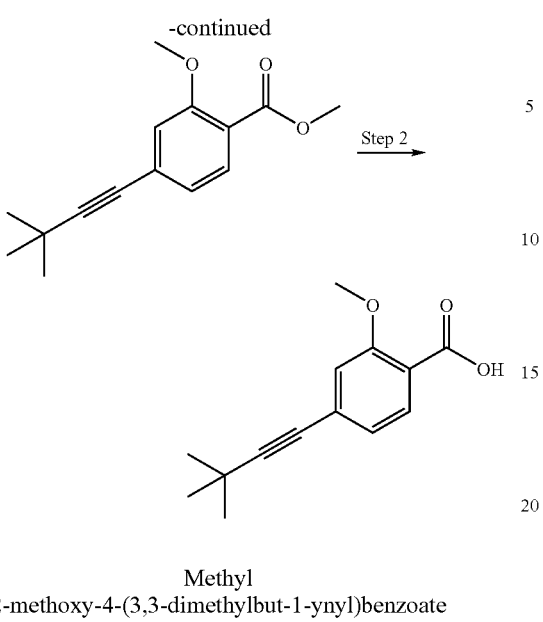

Methyl 2-methoxy-4-(3,3-dimethylbut-1-ynyl)benzoate

A mixture of methyl 4-bromo-2-methoxybenzoate (1.2 g, 0.0049 mol), copper(I) iodide (0.093 g, 0.00049 mol), 3,3-dimethyl-1-butyne (0.70 mL, 0.0059 mol) and bis(triphenylphosphine)palladium(II) chloride (0.34 g, 0.00049 mol) in Et$_3$N (10 mL) was heated at 100° C. in a 50 mL sealed reaction vessel for 16 hours. After cooling, the mixture was filtered through Celite® and the filter cake was washed repeatedly with ethyl acetate. The filtrate was concentrated under vacuum and the residue was purified by column chromatography on silica gel to give a viscous oil (1.10 g, 91%).

2-Methoxy-4-(3,3-dimethylbut-1-ynyl)benzoic acid

A mixture of methyl 2-methoxy-4-(3,3-dimethylbut-1-ynyl)benzoate (1.10 g, 0.00447 mol), MeOH (20 mL), and 2N aqueous NaOH solution (5 mL) was stirred at 65° C. overnight. After allowing to cool, the mixture was concentrated under vacuum. The residue was treated with water, and extracted with hexane. The aqueous layer was acidified with 1N HCl to pH 2-3, and extracted with EtOAc (50 mL×3). The combined organic layers were washed with brine, dried (Na$_2$O$_4$), filtered and concentrated under vacuum to give the product (870 mg, 84%) as a white solid. LC-MS: 3.22 min, 233.4 (M+1).

Intermediate 26

Preparation of 4-(cylopropylethynyl)-2,6-difluorobenzoic acid

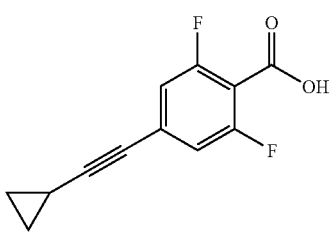

4-Bromo-2,6-difluoro-benzoic acid methyl ester (200 mg, 0.8 mmol) was dissolved in triethylamine (5 mL) and dichloropalladium(bis)triphenylphosphine (29 mg, 5 mol %) was added followed by copper iodide (8 mg, 5 mol %) and cyclpropylacetylene (0.09 mL, 0.96 mmol). The mixture was heated at reflux in a sealed tube for 1 hour. The mixture was cooled to room temperature and filtered through Celite® and evaporated. The residue was dissolved in dichloromethane and purified using a 0-100% EtOAc/Hexane gradient to give 178 mg (94%) of the ester compound. m/z=237 (M+1). The ester was hydrolysed using the methodology outlined for 4-(cyclopentylethynyl)-2-fluorobenzoic acid to give the desired acid product.

Intermediate 27

Preparation of 4-(cyclopentylethynyl)-2-methylbenzoic acid

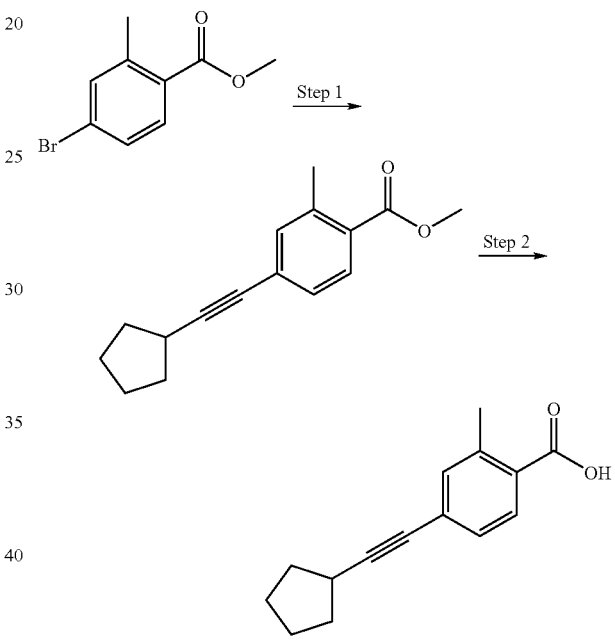

Methyl 4-(cyclopentylethynyl)-2-methylbenzoate

Methyl 4-bromo-2-methylbenzoate (1.0 g, 4.4 mmol) was dissolved in triethylamine (5 mL). To the mixture was added copper iodide (43 mg, 5 mol %), followed by PdCl$_2$(PPh$_3$)$_2$ (157 mg, 5 mol %) and ethynylcyclopentane (0.75 mL, 5.3 mmol). The mixture was heated in a sealed pressure tube at 80° C. for 3 hours. After completion of the reaction, the triethylamine was evaporated and the residue was dissolved in EtOAc and filtered through Celite®. The organic layer was washed with water, brine, and dried (Na$_2$SO$_4$), then filtered and concentrated under vacuum. The residue was purified by column chromatography on sililca gel using EtOAc-hexane (0-100% gradient) as eluet to give the desired product.

4-(cyclopentylethynyl)-2-methylbenzoic acid

The product from step 1 was dissolved in 10 mL of MeOH and 10 mL of 2N LiOH and the mixture was refluxed overnight. The MeOH was evaporated and the basic layer was washed with EtOAC, acidified, and re-extracted with EtOAC. The organic layer was washed with brine, dried (Na$_2$SO$_4$), filtered and concentrated under vacuum to give the desired product (461 mg) as a beige solid. m/z=243 (M+1).

Intermediate 28

Preparation of 4-(3,3-dimethylbut-1-ynyl)-2-methylbenzoic acid

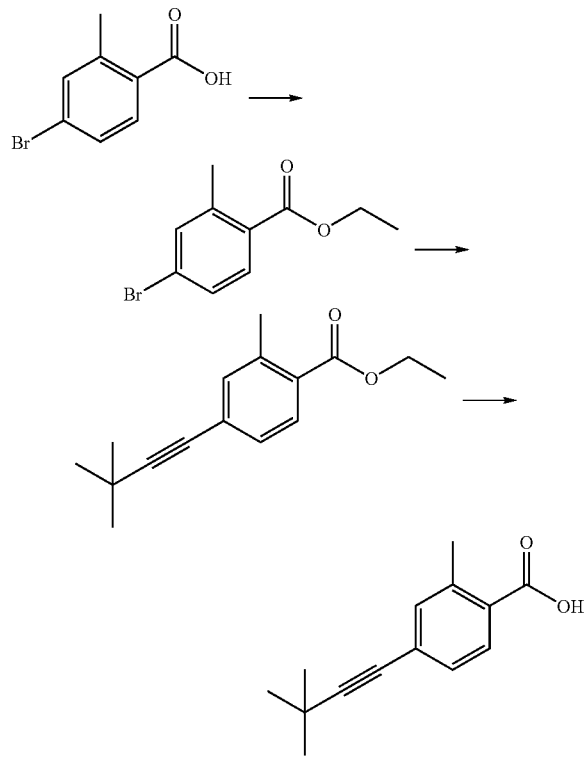

Ethyl 4-bromo-2-methylbenzoate 4-bromo-2-methylbenzoic acid (10 g, 46.5 mmol) was dissolved in 200 mL EtOH, 5 mL conc $H_2SO_4$ was added and the mixture was refluxed for 18 h. The reaction volume was reduced in vacuo to 50 mL, and neutralized to pH 7 with satd. aqueous $NaHCO_3$ and extracted with EtOAc. The organic layer was dried ($Na_2SO_4$), filtered and the filtrate was concentrated to give the product (6.5 g) as an oil.

Ethyl 2-methyl-4-(3,3-dimethylbut-1-ynyl)benzoate

Ethyl 4-bromo-2-methylbenzoate (6 g, 0.02 mol), 1-butyne, 3,3-dimethyl-(4.56 mL, 0.0382 mol) copper(I) iodide (0.47 g, 0.0025 mol) and bis(triphenylphosphine)palladium (II) chloride (3.46 g, 0.00493 mol) were placed in 40 mL triethylamine and stirred at room temperature overnight in a sealed tube. The reaction mixture was diluted with MeOH and filtered through Celite®. The filtrate was concentrated to a brown residue. The residue was purified by column chromatography on silica gel using hexanes as eluent to give the product (4.8 g, 42%) as a brown oil.

4-(3,3-dimethylbut-1-ynyl)-2-methylbenzoic acid

Ethyl 2-methyl-4-(3,3-dimethylbut-1-ynyl)benzoate (4.8 g, 0.020 mol) and lithium hydroxide (2.8 g, 0.058 mol) were placed in 3:1 mixture of methanol:water (80 mL) and heated at 60° C. for 3.5 h. TLC and LCMS indicated product formation. The reaction was cooled and concentrated in vacuo to a volume of 20 mL. The mixture was placed in an ice-water bath and acidified to pH 5 with conc. HCl. A white solid crashed out which was filtered and washed thoroughly with water. The solid was dried in a vacuum oven to give the product (4.1 g, 97%) as a solid. m/z=215.1 (M−1).

Intermediate 29

Preparation of (E)-2-fluoro-4-(3,3,3-trifluoroprop-1-enyl)benzoic acid

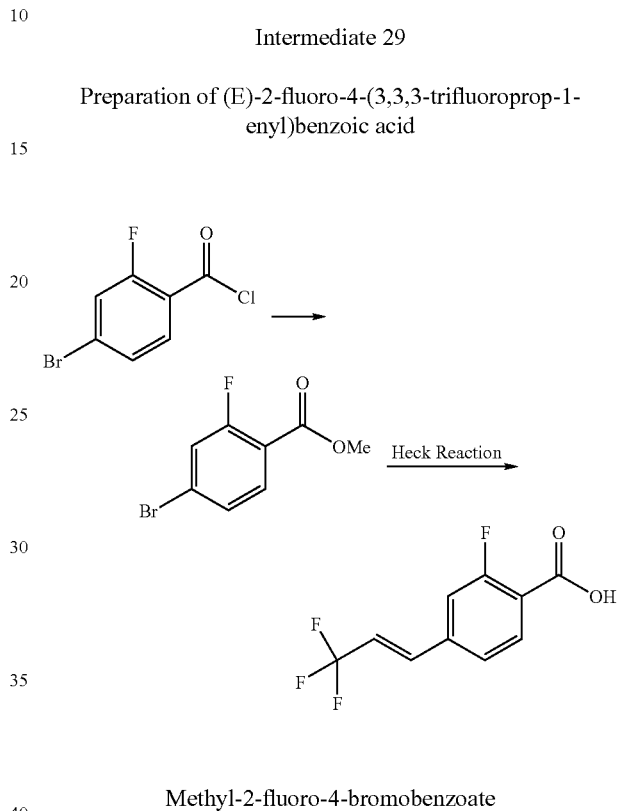

Methyl-2-fluoro-4-bromobenzoate

4-Bromo-2-fluorobenzoyl chloride (45.0 g, 0.190 mol) was slowly added to a solution of methanol (31 mL, 0.76 mol) and triethylamine (53 mL, 0.38 mol) at 0° C. and the mixture was stirred at room temperature overnight. The MeOH was removed under vacuum and the residue was dissolved in $CH_2Cl_2$ (500 mL). The organic layer was washed with water, dried ($Na_2SO_4$), and concentrated to give a white solid.

(E)-2-Fluoro-4-(3,3,3-trifluoroprop-1-enyl)benzoic acid

A mixture of methyl-2-fluoro-4-bromobenzoate (5.0 g, 0.021 mol), tri-o-tolylphosphine (1.31 g, 0.00429 mol), tetra-N-butylammonium bromide (2.08 g, 0.00644 mol), potassium acetate (4.2 g, 0.043 mol), 3,3,3-trifluoroprop-1-ene (20 g, 0.2 mol), palladium acetate (0.24 g, 0.0011 mol) was sealed in a Parr instrument and stirred at 180° C. for 96 h. After cooling, the reaction mixture was filtered through Celite® and the filtrate was partitioned bewteen EtOAc and 1 N aq. HCl. The organic layer was separated and washed with brine, dried ($Na_2SO_4$) and concentrated. The residue was chromatographed with hexane-EtOAc(5% AcOH) (0 to 60%) to give the product as a white solid. LC-MS: t=2.98 min, m/z=233.2 (M−1).

Intermediate 30

Preparation of (E)-2-fluoro-4-(3,3,3-trifluoroprop-1-enyl)benzoic acid and (Z)-2-fluoro-4-(3,3,3-trifluoroprop-1-enyl)benzoic acid

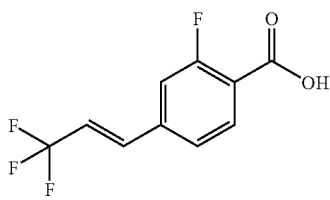

tert-Butyl 4-bromo-2-fluorobenzoate

To a stirred solution of 4-bromo-2-fluorobenzoic acid (3.0 g, 0.014 mol) in THF (50 mL) at 0° C. was added DMF (0.1 mL) and oxalyl chloride (1.5 mL, 0.018 mol). The mixture was stirred at 0° C. for 1 h and then warmed to rt. The solvent was removed under reduced pressure. The obtained acid chloride was added to a mixture of tert-butyl alcohol (5.0 g, 0.067 mol), pyridine (10 mL), and $CH_2Cl_2$ (50 mL) at 0° C. The mixture was stirred at rt for 3 h, and then at 50° C. overnight. The mixture was washed with water, 2 N NaOH, and brine, dried ($MgSO_4$), and concentrated under vacuum. The residue was purified by column to give a colorless oil (1.5 g, 45%).

tert-Butyl 2-fluoro-4-formylbenzoate

To a stirred solution of tert-butyl 4-bromo-2-fluorobenzoate (1.5 g, 5.45 mmol) in THF (70 mL) at −100° C. under argon was carefully added BuLi (2.5 M in hexane, 2.3 mL, 5.75 mmol). The mixture was kept at −100° C. to −80° C. for 1 h and then DMF (1.0 mL) in THF (5 mL) was added. After 1 h, the mixture was warmed to 0° C. and quenched by adding sat. aq $NH_4Cl$, and extracted with EtOAc. The organic layer was separated, washed with brine, dried ($MgSO_4$), and concentrated under vacuum. The residue was purified by column chromatography on silica gel using EtOAc/hexane (0-10%) as eluent to give the product (750 mg, 61%) as a white solid.

(E)-tert-Butyl 2-fluoro-4-(3,3,3-trifluoroprop-1-enyl) benzoate and (Z)-tert-butyl 2-fluoro-4-(3,3,3-trifluoroprop-1-enyl)benzoate Molecular sieves 4 Å (powder, 24 g) was added to a 1 M solution of TBAF in THF (30 mL, 30 mmol), and the mixture was stirred at room-temperature overnight under an argon atmosphere. To the mixture were added a solution of tert-butyl 2-fluoro-4-formylbenzoate (750 mg, 0.0033 mol) and 2,2,2-trifluoroethyldiphenylphosphine oxide (1.9 g, 0.0067 mol) in THF (30 mL). After the mixture was stirred for 2 h it was filtered. The filtrate was concentrated under vacuum and water (120 mL) was added. The mixture was extracted with AcOEt and the organic extract was washed with brine, dried ($Na_2SO_4$), and concentrated under vacuum. The residue was purified by column chromatography on silica gel using AcOEt-hexane (0-15%) as eluent to give (E)-tert-butyl 2-fluoro-4-(3,3,3-trifluoroprop-1-enyl)benzoate as a colorless oil (620 mg, 64%), followed by (Z)-tert-butyl 2-fluoro-4-(3,3,3-trifluoroprop-1-enyl)benzoate as a colorless oil (80 mg, 8%).

(E)-2-fluoro-4-(3,3,3-trifluoroprop-1-enyl)benzoic acid

A solution of (E)-tert-butyl 2-fluoro-4-(3,3,3-trifluoroprop-1-enyl)benzoate (500 mg, 0.002 mol) in $CH_2Cl_2$ (10 mL) and TFA (1.0 mL) was stirred at room temperature for 2 h. The solvent was removed under reduced pressure to give a white solid. LC-MS: 2.99 min, 233.2 (M−1).

(Z)-2-fluoro-4-(3,3,3-trifluoroprop-1-enyl)benzoic acid

A solution of (Z)-tert-butyl 2-fluoro-4-(3,3,3-trifluoroprop-1-enyl)benzoate (35 mg, 0.12 mmol) in $CH_2Cl_2$ (5 mL) and TFA (0.5 mL) was stirred at room temperature for 2 h. The solvent was removed under reduced pressure to give a white solid. LC-MS: 2.86 min, 233.2 (M−1).

Intermediate 31

Preparation of 4-(3,3-dimethylbut-1-ynyl)-2-fluorobenzoic acid

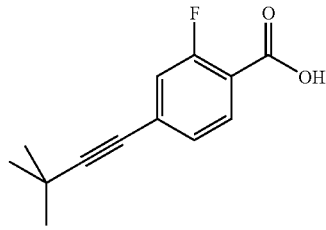

4-Bromo-2-fluoro-benzoic acid methyl ester

4-Bromo-2-fluorobenzoic acid (10 g, 0.04 mol) was suspended in 1,2-dichloroethane (60 mL, 0.8 mol) to which was added thionyl chloride (10 mL, 0.1 mol) followed by a drop of DMF. The mixture was heated to reflux for 1 hour. Excess thionyl chloride and 1,2-dichloroethane were stripped off and the crude product was treated with methanol (50 mL) and heated to reflux for an hour. The mixture was concentrated to dryness, dissolved in dichloromethane, treated with cold sat. sodium bicarbonate solution. The organic layer was dried, then concentrated under vacuum to obtain the title compound as a white solid.

4-(3,3-Dimethyl-but-1-ynyl)-2-fluoro-benzoic acid methyl ester

In a sealed reaction vessel was added bis(triphenylphosphine)palladium(II) chloride (1.03 g, 0.00145 mol) N,N-diisopropylethylamine (9.0 mL, 0.050 mol), copper(I) iodide (0.353 g, 0.00186 mol), and 1,4-dioxane (70 mL) in that order. 1-butyne, 3,3-dimethyl-(6.1 mL, 0.050 mol) was added and the vessel was allowed to stir at room temperature for 24 hrs. The mixture was filtered through Celite® and concentrated in vacuo. The mixture was chromatographed using a 0-20% ethyl acetate:hexanes gradient. The combined pure fractions were reduced in vacuo and dried on high vacuum to yield a light brown solid.

4-(3,3-Dimethyl-but-1-ynyl)-2-fluoro-benzoic acid

Methyl 2-fluoro-4-(3,3-dimethylbut-1-ynyl)benzoate (8.2 g, 0.035 mol) was suspended in a 3:1 mixture of $H_2O$ and methanol to which was added lithium hydroxide (2.5 g, 0.10 mol) all at once and the mixture was agitated over-night at ambient temperature. The mixture was then concentrated to ¾ the volume and acidified with 1N HCl until the pH read just acidic. The white precipitate was filtered, washed with water and vacuum dried at 80° C. for several hours. m/z=218.9 (M−1).

Intermediate 32

Preparation of 2-chloro-4-(3,3-dimethylbut-1-ynyl)benzoic acid

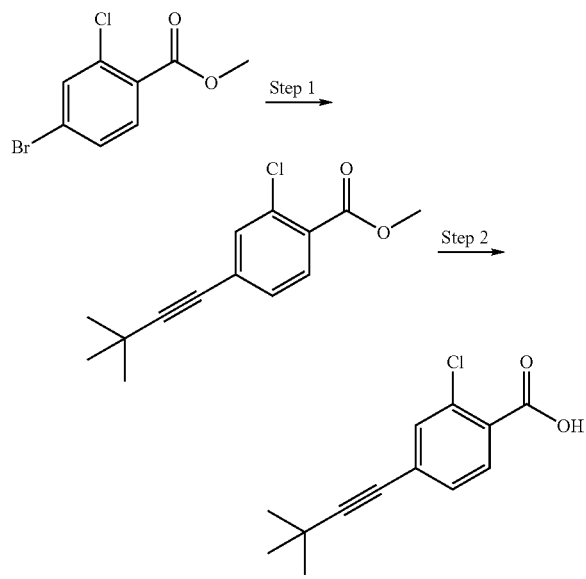

Methyl 2-chloro-4-(3,3-dimethylbut-1-ynyl)benzoate

A mixture of methyl 4-bromo-2-chlorobenzoate (400 mg, 0.0016 mol), copper(I) iodide (30 mg, 0.00016 mol), 3,3-dimethyl-1-butyne (0.29 mL, 0.0024 mol) and bis(triphenylphosphine)palladium(II) chloride (110 mg, 0.00016 mol) in Et₃N (5 mL) and DMF (2 mL) was heated at 100° C. in a 50 mL sealed reaction vessel for 32 hours. After cooling, the mixture was filtered through Celite® and the filter cake was washed repeatedly with ethyl acetate. The organic phase was washed with brine, dried (Na₂SO₄), and concentrated under vacuum. The residue was purified by column chromatography on silica gel to give the product (330 mg, 82%) as a light yellow oil.

2-Chloro-4-(3,3-dimethylbut-1-ynyl)benzoic acid

A mixture of methyl 2-chloro-4-(3,3-dimethylbut-1-ynyl) benzoate (330 mg, 0.0013 mol), 2N aq. NaOH (3.0 mL), THF (5 mL), and MeOH (5 mL) was stirred at rt for 5 h. The mixture was concentrated under vacuum and the residue was treated with water and acidified with 1N HCl to pH 2-3, and extracted with EtOAc. The organic layer was washed with brine, dried (Na₂SO₄), and concentrated under vacuum to give the product (305 mg, 98%) as a white solid. $t_R$=3.56 min, 234.9 & 236.9 (M−1).

Intermediate 33

Preparation of 2-chloro-4-(cyclopropylethynyl)benzoic acid

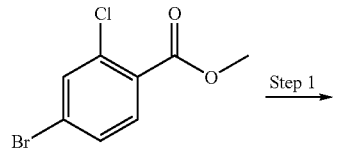

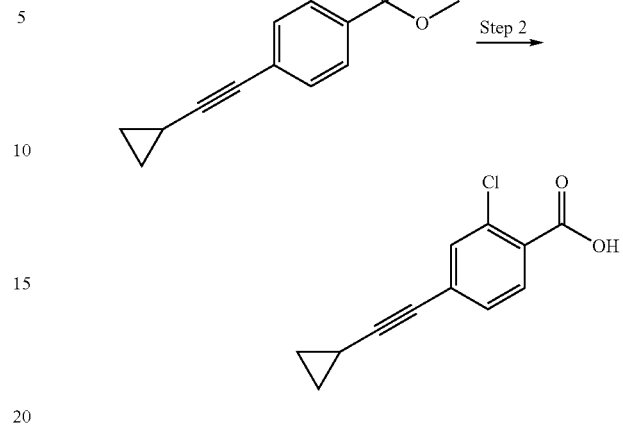

Methyl 2-chloro-4-(2-cyclopropylethynyl)benzoate

A mixture of methyl 4-bromo-2-chlorobenzoate (450 mg, 0.0018 mol), copper(I) iodide (34 mg, 0.00018 mol), 70% solution of cyclopropylacetylene (0.26 g, 0.0027 mol) in toluene and bis(triphenylphosphine)palladium(II) chloride (130 mg, 0.00018 mol) in Et₃N (5 mL) and DMF (3 mL) was heated at 100° C. in a 50 mL sealed reaction vessel for 36 hours. After cooling, the mixture was filtered through Celite® and the filter cake was washed repeatedly with ethyl acetate. The organic phase was washed with brine, dried (Na₂SO₄), filtered and concentrated under vacuum. The residue was purified by column chromatography on silica gel to give the product (320 mg, 76%) as a brown oil.

2-Chloro-4-(2-cyclopropylethynyl)benzoic acid

A mixture of methyl 2-chloro-4-(2-cyclopropylethynyl) benzoate (310 mg, 0.0013 mol), 2N aq. NaOH (3.0 mL), THF (5 mL), and MeOH (5 mL) was stirred at rt for 5 h. The mixture was concentrated under vacuum and the residue was treated with water and acidified with 1N HCl to pH 2-3, and extracted with EtOAc. The organic layer was washed with brine, dried (Na₂SO₄), filtered and concentrated under vacuum to give the product (270 mg, 93%) as a yellow solid. LC-MS: 3.18 min, 218.9 & 220.9 (M−1).

Intermediate 34

Preparation of (E)-2-chloro-4-(3,3,3-trifluoroprop-1-enyl)benzoic acid

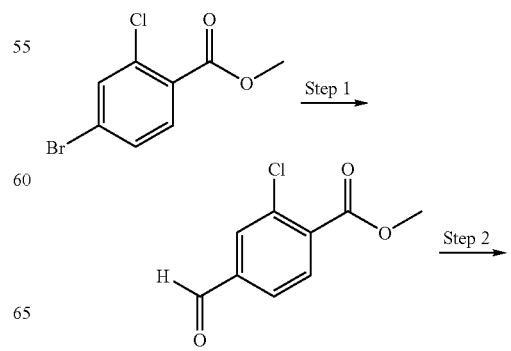

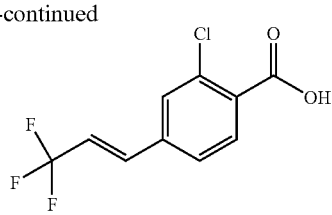

Methyl 2-chloro-4-formylbenzoate

A slow stream of CO was passed into a suspension of methyl 4-bromo-2-chlorobenzoate (1.50 g, 0.00601 mol), bis(triphenylphosphine)palladium(II) chloride (80 mg, 0.0001 mol), sodium formate (613 mg, 0.00902 mol), and dry DMF (10 mL). The mixture was vigorously stirred at 110° C. for 2 h. After cooling, the mixture was treated with aqueous Na$_2$CO$_3$ solution and extracted with EtOAc. The extract was washed with brine, dried (Na$_2$SO$_4$), and concentrated. The residue was chromatographed on silica gel with AcOEt-hexane to give the product as a colorless oil (becomes a white solid when stored in a refrigerator).

2-Chloro-4-((E)-3,3,3-trifluoroprop-1-enyl)benzoic acid

4 Å molecular sieves (powder, 16 g) was added to a 1 M solution of TBAF in THF (20 mL, 20 mmol), and the mixture was stirred at room-temperature overnight under an argon atmosphere. To the mixture were added a solution of methyl 2-chloro-4-formylbenzoate (210 mg, 0.0010 mol) and 2,2,2-trifluoroethyldiphenylphosphine oxide (600 mg, 0.0021 mol) in THF (15 mL). After the mixture was stirred for 2 h, the molecular sieves were removed by filtration. The filtrate was concentrated and water (120 mL) was added. The mixture was extracted with AcOEt. The organic extract was washed with brine, dried (Na$_2$SO$_4$), and concentrated. The residue was chromatographed on silica gel with AcOEt [1% HOAc]-hexane to give the product as a white solid. LC-MS: t=3.12 min, m/z=248.9 & 250.9 (M−1).

Intermediate 35

Preparation of 4-(cyclopropylethynyl)-2-(methylsulfonyl)benzoic acid

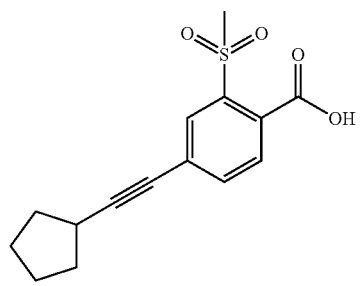

4-Bromo-2-methanesulfonyl acid methyl ester (250 mg, 0.85 mmol) was dissolved in triethylamine (5 mL). To the mixture was added copper iodide (9.0 mg, 5 mol %), followed by PdCl$_2$(PPh$_3$)$_2$ (32 mg, 5 mol %) and ethynylcyclopentane (0.135 ml, 1.0 mmol). The mixture was heated in a sealed pressure tube at 80° C. for 3 hours. After reaction completion, the triethylamine was removed under vacuum and the residue was dissolved in EtOAc and filtered through Celite®. The organic layer was washed with water, brine, and dried (Na$_2$SO$_4$). After filtration and concentration under vacuum, the residue was purified by column chromatography on sililca gel using EtOAc-hexane (0-100% gradient) as eluent to give methyl 4-(cyclopropylethynyl)-2-(methylsulfonyl)benzoate (240 mg). The product was dissolved in 10 mL of MeOH and 10 mL of 2N LiOH and the mixture was refluxed overnight. The MeOH was evaporated and the basic layer was washed with EtOAc, acidified, and re-extracted with EtOAc. The organic layer was washed with brine, dried (Na$_2$SO$_4$), filtered and concentrated under vacuum to give the product (165 mg) as a beige solid. m/z=293 (M+1).

Intermediate 36

Preparation of 4-(3,3-dimethylbut-1-ynyl)-2,6-difluorobenzoic acid

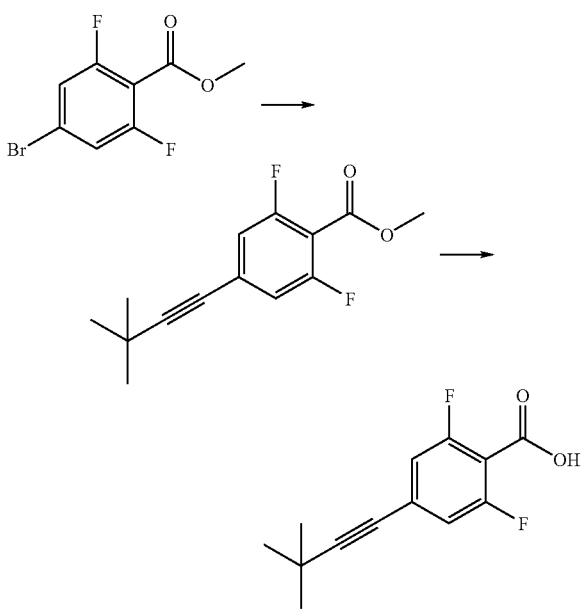

Methyl 4-bromo-2,6-difluorobenzoate 4-bromo-2,6-difluorobenzoic acid (7 g, 0.03 mol), methyl iodide (2.8 mL, 0.045 mol) and potassium carbonate (12.22 g, 0.08842 mol) were placed in 100 mL acetone in a sealed tube and heated at 50° C. overnight. The reaction was cooled, partitioned between EtOAc and water. The organic layer was dried (Na$_2$SO$_4$), filtered and the filtrate was concentrated to an oil. Purification by column chromatography on silica gel gave the product (1.3 g, 17%) along with 5 g of starting material.

Methyl 2,6-difluoro-4-(3,3-dimethylbut-1-ynyl)benzoate

Methyl 4-bromo-2,6-difluorobenzoate (1.3 g, 0.0052 mol), 1-butyne, 3,3-dimethyl-(0.96 mL, 0.0080 mol), copper(I)

iodide (200 mg, 0.001 mol) and bis(triphenylphosphine)palladium(II) chloride (0.73 g, 0.0010 mol) were placed in 50 mL triethylamine and stirred in a sealed tube at room temperature for 20 h. The reaction was diluted with MeOH and filtered through Celite®. The filtrate was concentrated to an oil and purified by column chromatography on silica gel using hexane as eluent to give the product (1.0 g, 80%) as a yellow oil.

4-(3,3-dimethylbut-1-ynyl)-2,6-difluorobenzoic acid

Methyl 2,6-difluoro-4-(3,3-dimethylbut-1-ynyl)benzoate (1.0 g, 0.004 mol) and lithium hydroxide (0.57 g, 0.012 mol) were placed in a 3:1 mixture of methanol:water (60 mL) and heated at 60° C. for 3.5 h. The reaction was cooled and concentrated in vacuo to a volume of 20 mL. The mixture was placed in an ice-water bath and acidified to pH 5 with coc. HCl. A white solid crashed out which was filtered and washed thoroughly with water. The solid was dried in the vacuum oven to give the product (0.79 g, 84%) as a solid. m/z=237.1 (M−1).

Intermediate 37

Preparation of 4-(3,3-dimethyl-1-ynyl)-2-fluoro-3-methoxybenzoic acid

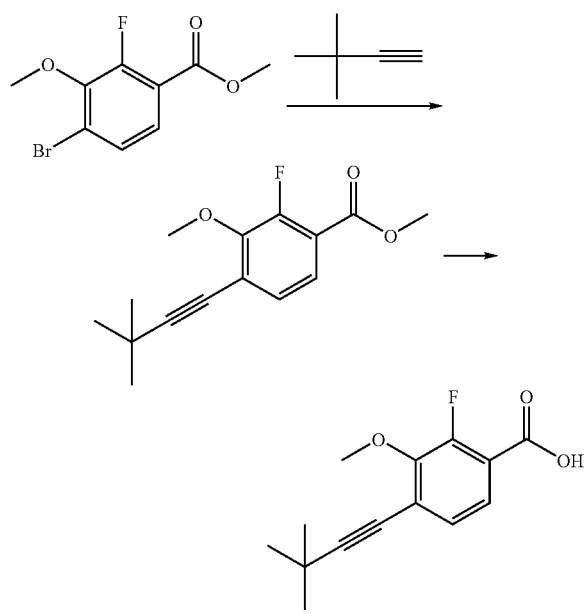

Methyl 2-fluoro-3-methoxy-4-(3,3-dimethylbut-1-ynyl)benzoate

Methyl 4-bromo-2-fluoro-3-methoxybenzoate (960 mg, 3.5 mmol), copper(I) iodide (70 mg, 0.4 mmol), and bis(triphenylphosphine)palladium(II) chloride (300 mg, 0.4 mmol) were suspended in Et₃N (10 mL) and DMF (4 mL). 1-Butyne, 3,3-dimethyl-(440 mg, 5.2 mmol) was added and the mixture was heated from room temperature to 100° C. in a sealed tube for 60 h. Solvent was removed, and the residue was dissolved in EtOAc, washed with water, brine and dried over Na₂SO₄. Purified by column chromatography on silica gel to give the product as a light yellow oil (760 mg, 79%).

2-Fluoro-3-methoxy-4-(3,3-dimethylbut-1-ynyl)benzoic acid

Methyl 2-fluoro-3-methoxy-4-(3,3-dimethylbut-1-ynyl) benzoate (760 mg, 2.7 mmol) was dissolved in MeOH (10 mL), NaOH (in 10 mL water) was added and stirred at 50° C. for 1 h. Solvent was removed, more water was added, neutralized by HCl till pH~2, white solid thus formed was filtered out, dried in vacuum oven (at 65° C.). Product was obtained as a white solid (760 mg, 93%).

Intermediate 38

Preparation of 2-chloro-4-(3,3-dimethylbut-1-ynyl)-5-fluorobenzoic acid

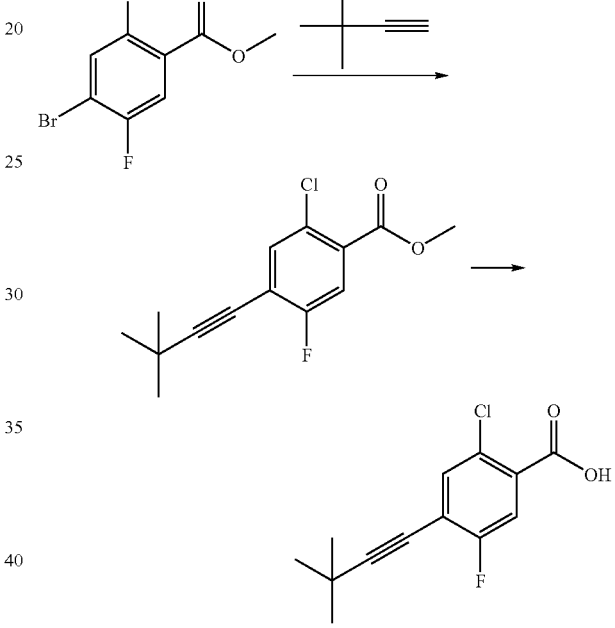

Methyl 2-chloro-5-fluoro-4-(3,3-dimethylbut-1-ynyl) benzoate

Methyl 4-bromo-2-chloro-5-fluorobenzoate (9.1 g, 32 mmol), copper(I) iodide (0.62 g, 3.2 mmol) and bis(triphenylphosphine)palladium(II) chloride (2.3 g, 3.2 mmol) were suspended in Et₃N (100 mL) and DMF (40 mL), 1-butyne, 3,3-dimethyl-(4.1 g, 48 mmol) was added and then the mixture was stirred at 100° C. in a sealed tube for 40 h. Solvent was removed, residue was dissolved in EtOAc, washed by water and brine, purified by column, product was obtained as a light yellow oil (6.1 g, 69%).

2-Chloro-5-fluoro-4-(3,3-dimethylbut-1-ynyl)benzoic acid

Methyl 2-chloro-5-fluoro-4-(3,3-dimethylbut-1-ynyl)benzoate (6.1 g, 22 mmol) was dissolved in MeOH (30 mL), sodium hydroxide (1.3 g, 33 mmol) (in 20 mL, water) was added and stirred at 60° C. overnight. Solvent was removed, residue was dissolved in water, neutralized by HCl till pH <2, extracted by EtOAc, washed by water, brine and dried over Na₂SO₄. Product was obtained as a beige solid (3.1 g, 52%).

Intermediate 39

Preparation of (E)-4-(3,3-dimethylbut-1-enyl)-2-methylbenzoic acid

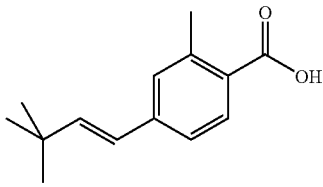

4-Bromo-2-methyl-benzoic acid methyl ester

To a suspension of 4-bromo-2-methylbenzoic acid (10.0 g, 0.0465 mol) in 1,2-dichloroethane (60 mL) was added thionyl chloride (28 g, 0.23 mol) and the mixture heated to reflux for 1 hour. The mixture was concentrated to dryness and vacuum dried. The crude acid chloride was dissolved in methanol (100 mL) and the solution was treated with triethylamine (4.7 g, 0.046 mol). The mixture was heated to reflux for an hour and then concentrated to dryness. The crude ester was dissolved in EtOAc, washed consecutively with sat. sodium bicarbonate solution and water. The organic phase was dried and concentrated to obtain the title ester.

(E)-4-(3,3-dimethylbut-1-enyl)-2-methylbenzoic acid methyl ester

A mixture of methyl 4-bromo-2-methylbenzoate (10.0 g, 0.0436 mol), tri-o-tolylphosphine (1.31 g, 0.00429 mol), cesium carbonate (6.99 g, 0.0214 mol), tetra-N-butylammonium chloride (1.79 g, 0.00644 mol), 1-butene, 3,3-dimethyl- (20 g, 0.2 mol), palladium acetate (0.24 g, 0.0011 mol) was sealed in a glass vessel and stirred at 150° C. for 96 h. After cooling, the reaction mixture was filtered through Celite® and the filtrate was partitioned bewteen EtOAc and water. The organic layer was separated and washed with brine, dried ($Na_2SO_4$) and concentrated. The residue was chromatographed with hexane-EtOAc to give the title compound as a white solid.

(E)-4-(3,3-dimethyl-but-1-enyl)-2-methylbenzoic acid

A solution of (E)-4-(3,3-dimethylbut-1-enyl)-2-methylbenzoic acid methyl ester (6.5 g, 0.028 mol) and lithium hydroxide (3.4 g, 0.14 mol) in a mixture of methanol (50 mL, 1 mol) and water (150 mL) was heated to reflux for 3 hours. Most of the methanol was stripped off and the aqueous solution was carefully acidified with conc. HCl. The white precipitate was filtered, washed with water and vacuum dried. m/z=217.1 (M−1).

Intermediate 40

Preparation of 3-methyl-4-(3,3,3-trifluoroprop-1-ynyl)benzoic acid

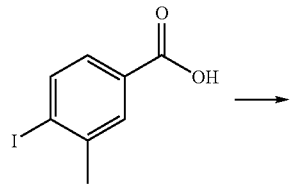

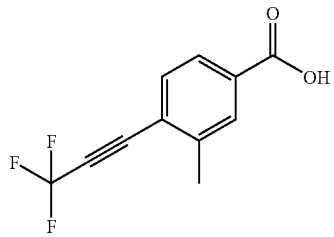

The method is based upon a procedure detailed by Yoneda et al in Bulletin Chemical Society Japan 1990, 63, 2124-2126. A solution of n-butyl lithium (2.5M in hexanes; 1 eq) was added carefully to a solution of 3,3,3-trifluoroprop-1-yne (1 eq) in THF at −78° C. under nitrogen. The mixture was stirred at −78° C. for 30 min then a solution of ZnCl2 (3 eq) in THF was added slowly. The mixture was allowed to warm to room temperature, stirred for 30 min then Pd(Ph3P)4 (5 mol %) was added, followed by 4-iodo-3-methylbenzoic acid (0.5 eq). The mixture was heated to 50° C. and stirred for 15 h, then heated further to 80° C. for 5 h, and finally at 100° C. overnight. After allowing to cool to room temperature the mixture was concentrated under vacuum to a crude residue. The residue was purified by column chromatography on silica gel to give the product as a solid. m/z=227 (M−1).

Preparation of Amine Building Blocks

Intermediate 41

Preparation of 2-((cyclopropylmethoxy)methyl)-2,3-dihydrobenzo[b][1,4]dioxin-6-amine

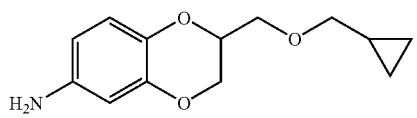

2-((cyclopropylmethoxy)methyl)-2,3-dihydro-6-nitrobenzo [b][1,4]dioxine (2,3-dihydro-6-nitrobenzo[b][1,4]dioxin-2-yl)methanol (500 mg, 0.002 mol) and sodium hydride (0.28 g, 0.0070 mol) were placed in a flask under nitrogen. The flask was placed in an ice bath and 25 mL DMF was added. The reaction was stirred at 0° C. for 10 minutes and then (chloromethyl)cyclopropane (440 µL, 0.0048 mol) was added. The mixture was warmed to room temp over 20 min then tetra-N-butylammonium bromide (1.53 g, 0.00475 mol) was added to the mixture and the reaction was stirred at room temperature overnight. The reaction was partitioned between EtOAc and water. The organic layer was separated, washed with brine, dried ($Na_2SO_4$), filtered and the filtrate was concentrated under vacuum to an oil. The oil was purified by column chromatography on silica gel using EtOAc/hexanes (10%) as eluent to give a yellow solid (0.33 g, 50%). m/z=266 (M+1).

2-((cyclopropylmethoxy)methyl)-2,3-dihydrobenzo[b][1,4]dioxin-6-amine 2-((Cyclopropylmethoxy)methyl)-2,3-dihydro-6-nitrobenzo[b][1,4]dioxine (0.33 g, 0.0012 mol) was dissolved in 20 mL dioxane. Sodium dithionite (2.2 g, 0.013 mol) was suspended in water (4 mL) and NH$_4$OH (2 mL) and then added to the dioxane solution. The reaction was stirred at room temp for 6 hrs. The mixture was filtered through filter paper and the filtrate concentrated under vacuum to a white solid. The solid was suspended in 10% EtOAc/hexanes and filtered. The filtrate was concentrated to a white solid and used for the next reaction without further purification. Yield of the title compound is 0.29 g (98%). m/z=235.8 (M+1).

Intermediate 42

Preparation of 1-methyl-1,2,3,4-tetrahydroquinolin-7-ylamine

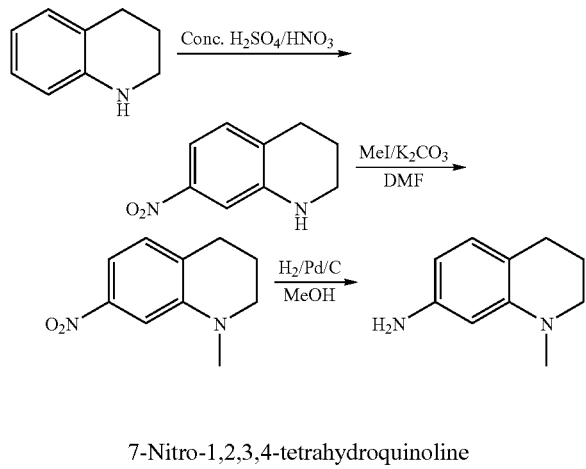

7-Nitro-1,2,3,4-tetrahydroquinoline

To a solution of 1,2,3,4-tetrahydoquinoline (6.5 g, 0.049 mol) in conc. Sulfuric acid (118 mL) at 0° C. was added a solution of con. nitric acid (4.9 mL) in conc. Sulfuric acid (12 mL) drop-wise over 3 hours so as to maintain the temperatute <5° C. The reaction mixture was then poured onto crushed ice and neutralized with solid potassium carbonate. The mixture was extracted with EtOAc (2×500 mL), the combined organic extracts were washed with water, dried and concentrated to give the crude product which was purified by column chromatography on silica-gel using EtOAc/hexane as eluent to obtain the title compound as an orange solid.

1-Methyl-7-nitro-1,2,3,4-tetrahydroquinoline. To a solution of the 7-nitro-1,2,3,4-tetrahydroquinoline (4.5 g, 25.25 mmol) in DMF (50 mL) was added potassium carbonate (15 g) followed by iodomethane (5.54 g, 39.0 mMol) and the mixture was agitated overnight at ambient temperature. The mixture was poured onto water and extracted with ether (3×200 mL). The combined ethereal extracts were washed with brine, dried and concentrated to give the crude product which was purified by column chromatography on silica-gel to obtain the title compound as an orange liquid.

1-Methyl-1,2,3,4-tetrahydroquinolin-7-ylamine

A mixture of the 1-methyl-7-nitro-1,2,3,4-tetrahydroquinoline (4.0 g, 20.81 mmol), Pd/C (10% w/w; 2 g) in methanol (100 mL) was hydrogenated at 10 PSI for 2 hours. The catalyst was filtered off, and the filtrate was concentrated under vacuum to give the crude product which was used as such without further purification.

Intermediate 43

Preparation of 3,4-dihydro-2H-benzo[b][1,4]oxazin-6-amine

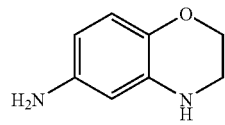

6-Nitro-2H-benzo[b][1,4]oxazin-3(4H)-one

Bromoacetyl bromide (4.84 g, 24 mmol, in 10 mL CHCl$_3$) was added dropwise to the suspension of 2-amino-4-nitrophenyl (3,08 g, 20 mmol), benzyltriethylammonium chloride (TEBA, 4.56 g, 20 mmol) and NaHCO$_3$ (6.72 g, 80 mmol) in 30 mL CHCl$_3$ with ice bath cooling. The mixture was stirred with ice bath cooling for 1.5 h then at 60° C. overnight. The solvent was removed under vacuum and water was added to the residue. A solid precipitated which was filtered and dried under vacuum to give the product (3.45 g, 89%) as a beige solid.

6-Amino-2H-benzo[b][1,4]oxazin-3(4H)-one

Pd/C (10%) was added to a suspension of 6-nitro-2H-benzo[b][1,4]oxazin-3(4H)-one (1.5 g) in MeOH (20 mL) and the reaction mixture was stirred under an atmosphere of hydrogen overnight. The mixture was filtered through Celite® and the filtrate was concentrated under vacuum to give the product (0.705 g, 56%) as a beige solid.

3,4-Dihydro-2H-benzo[b][1,4]oxazin-6-amine

6-Amino-2H-benzo[b][1,4]oxazin-3(4H)-one (590 mg, 3.6 mmol) was added to a THF solution of borane tetrahydrofuran complex (9 mL, 1M solution) and the reaction mixture was refluxed for 2.5 h. EtOH (2 mL) was added and stirred at 70° C. for 1 h before 1 mL HCl (conc.) was added. The mixture was stirred at 80° C. overnight then the volatiles were removed under vacuum to leave a crude reside. The residue was dissolved in water, NaOH was added until pH~10, and the mixture was extracted with CH$_2$Cl$_2$. The organic phase was washed with water and the solvent was removed under vacuum. The residue was purified by column chromatography on silica gel to give the product (274 mg, 51%) as a colorless oil.

Intermediate 44

Preparation of 3,4-dihydo-2H-benzo[b][1,4]oxazin-7-amine

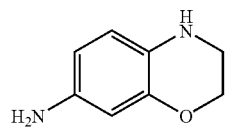

The above was prepared using the same procedure as for 3,4-dihydro-2H-benzo[b][1,4]oxazin-6-amine, except 2-amino-5-nitrophenol was used as starting material.

Intermediate 45

Preparation of 4-methyl-3,4-dihydro-2H-benzo[b][1,4]oxazin-7-amine

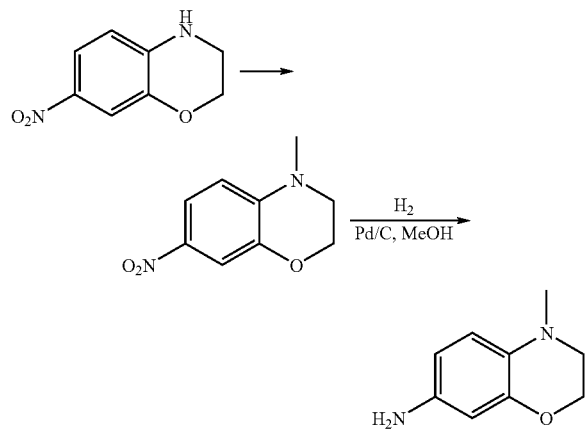

Potassium carbonate (800 mg, 6 mmol) and methyl iodide (1.3 g, 9 mmol) were added to a solution of 3,4-dihydro-7-nitro-2H-benzo[b][1,4]oxazine (540 mg, 3 mmol) in DMF (10 mL). The reaction mixture was stirred at room temperature overnight. Sodium hydride (100 mg, 95%) and methyl iodide (1.0 g) were added and the reaction mixture was stirred at room temperature overnight. The solvent was removed under vacuum and the residue was suspended in water. A solid precipitated which was filtered and washed with water. The bright yellow solid was then suspended in MeOH (20 mL) and Pd/C (10%) was added. The suspension was stirred under an atmosphere of hydrogen overnight, then filtered through Celite® and the filtrate concentrated under vacuum to give the product (470 mg) as a purple oil.

Intermediate 46

Preparation of 6-amino-2,2-dimethyl-2H-benzo[b][1,4]oxazin-3(4H)-one and 2,2-dimethyl-3,4-dihydro-2H-benzo[b][1,4]oxazin-6-amine

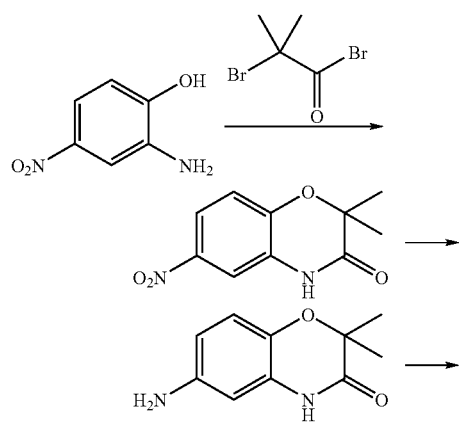

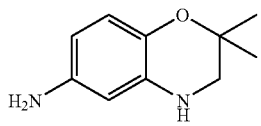

2,2-Dimethyl-6-nitro-2H-benzo[b][1,4]oxazin-3(4H)-one

2-Bromoisobutyryl bromide (10.3 g, 45 mmol, in 20 mL chloroform) was added dropwise to a suspension of 2-amino-4-nitrophenol (4.62 g, 30 mmol) and sodium bicarbonate (10.1 g, 120 mmol) in chloroform (250 mL) under nitrogen with ice bath cooling. The reaction mixture was stirred from 0° C. to room temperature overnight then the solvent was removed under vacuum. The residue was suspended in DMF (150 mL) and potassium carbonate (5.98 g, 45 mmol) was added, then the reaction mixture was stirred at 80° C. overnight. The solvent was removed under vacuum and water was added to the residue. The precipitate that emerged was filtered and dried under vacuum to give the product (4.5 g, 68%) as a light brown solid.

The remainder of the synthesis (hydrogenation of the nitro group and then borane reduction of the lactam) was performed using the general procedure described for 3,4-dihydro-2H-benzo[b][1,4]oxazin-6-amine.

Intermediate 47

Preparation of 7-amino-2,2-dimethyl-2H-benzo[b][1,4]oxazin-3(4H)-one and 2,2-dimethyl-3,4-dihydro-2H-benzo[b][1,4]oxazin-7-amine

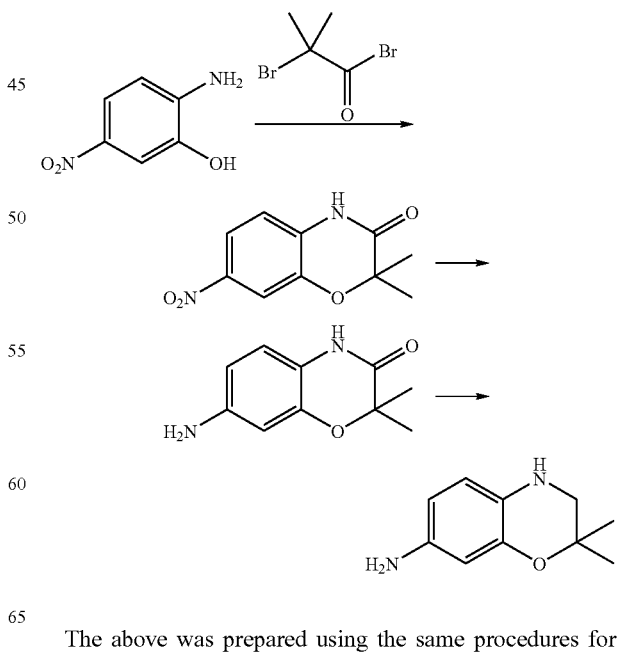

The above was prepared using the same procedures for 6-amino-2,2-dimethyl-2H-benzo[b][1,4]oxazin-3(4H)-one and 2,2-dimethyl-3,4-dihydro-2H-benzo[b][1,4]oxazin-6-amine except 2-amino-5-nitrophenol was used as the starting material.

Intermediate 48

Preparation of 6-chloro-3,4-dihydro-2H-benzo[b][1,4]oxazin-7-amine

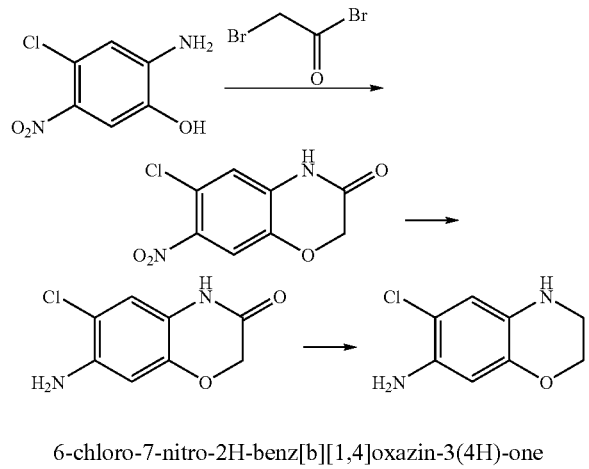

6-chloro-7-nitro-2H-benz[b][1,4]oxazin-3(4H)-one

This compound was prepared using the general procedure described for 2,2-Dimethyl-6-nitro-2H-benzo[b][1,4]oxazin-3(4H)-one above except 2-amino-4-chloro-5-nitrophenol was used as starting material.

7-Amino-6-chloro-2H-benzo[b][1,4]oxazin-3(4H)-one

Stannous chloride dihydrate (30 g, 0.13 mol) was added in portion to a solution of 6-chloro-7-nitro-2H-benzo[b][1,4]oxazin-3(4H)-one (6.7 g, 0.026 mol) in DMF (100 mL) with ice bath cooling. The mixture was allowed to warm to room temperature and was then stirred overnight. EtOAc (300 mL) and MeOH (300 mL) were added to the reaction mixture, Et$_3$N was added until pH >8 and the resulting suspension was filtered through Celite®. The solvent was removed under vacuum and the residue was suspended in water, extracted with EtOAc, dried (Na$_2$SO$_4$), filtered and concentrated under vacuum. The residue was triturated with ether to give the product (2.5 g, 45%) as a yellow solid.

6-chloro-3,4-dihydro-2H-benzo[b][1,4]oxazin-7-amine

Borane reduction performed using general procedure described above for 3,4-dihydro-2H-benzo[b][1,4]oxazin-6-amine except 7-Amino-6-chloro-2H-benzo[b][1,4]oxazin-3(4H)-one was used as starting material.

Intermediate 49

Preparation of (6-Amino-3H-imidazo[4,5-b]pyridin-2-yl)-methanol

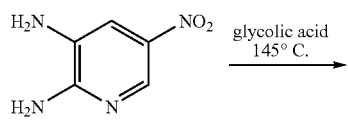

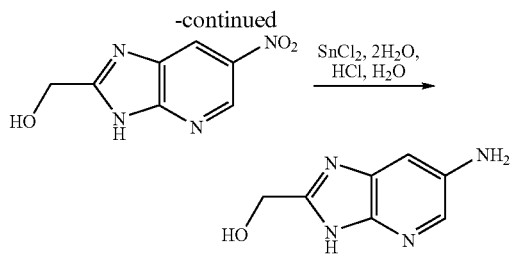

(6-Nitro-3H-imidazo[4,5-b]pyridin-2-yl)-methanol

Solid 2,3-Diamino-5-nitropyridine (prepared according to *J. Med. Chem.* 1997, 40, 3679-3686; 610 mg, 0.0040 mol) and solid glycolic acid (750 mg, 0.0099 mol) were combined in a sealed tube (left open) and heated to 145° C. and stirred for approx. 30-45 min (solid fuses together, liquifies then re-solidifies). After allowing to cool to rt the solid was extracted with 1N HCl. The aqueous mixture was concentrated under vacuum to leave a crude solid that was basified using conc. NH$_4$OH solution. The ammonia solution was concentrated under vacuum to leave a crude solid that was dry-loaded on to silica and purified by column chromatography (using the ISCO system) to give a solid (450 mg) that was used directly in the next step.

(6-Amino-3H-imidazo[4,5-b]pyridin-2-yl)-methanol

Stannous chloride dihydrate (1.6 g, 0.0070 mol) was added in one portion to a stirred solution of (6-nitro-3H-imidazo[4,5-b]pyridin-2-yl)-methanol (450 mg, 0.0023 mol) in 10% aqueous hydrochloric acid (20 mL) at 50° C. The mixture was stirred at 50° C. for approx. 2 hours then allowed to cool to room temperature. The mixture was cooled further to 0° C. and then basified to ca. pH 8 using conc. NH$_4$OH. The aqueous layer was then filtered through Celite® to remove tin salts, and the filtrate was concentrated under vacuum to leave a crude solid (380 mg; yield assumed quantitative) which was used directly in the next step (amide formation).

Intermediate 50

Preparation of (3-aminoquinolin-7-yl)methanol (prepared using the general procedure from *J. Am. Chem. Soc.* 1997, 119, 5591)

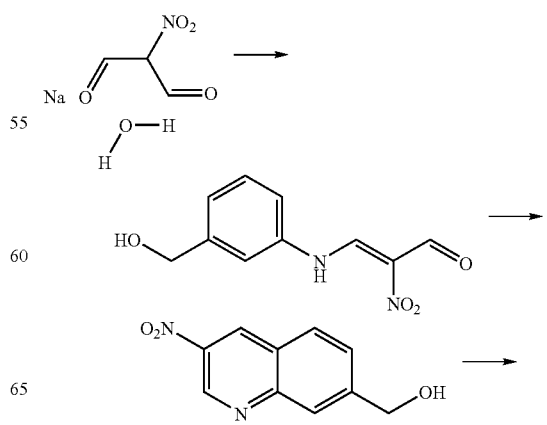

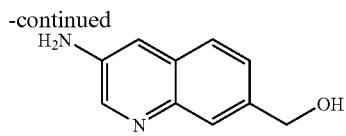

3-[3-(Hydroxymethyl)phenylamino]-2-nitroacrylaldehyde

3-Aminobenzyl alcohol (4.97 g, 0.0404 mol) was dissolved in 4 mL conc HCl. Sodium nitromalonaldehyde monohydrate (prepared from mucobromic acid according to the procedure in *Organic Syntheses Vol IV*, pp 844, 1963) (4.25 g, 0.0269 mol) was dissolved in 35 mL water and added to the amine solution (a yellow precipitate formed immediately)—a further 80 mL of water being added to aid stirring. After 10 min, the precipitate was filtered, washed with water and air dried overnight to give the product (4.3 g) as a yellow solid.

(3-Nitroquinolin-7-yl)methanol 3-(3-(Hydroxymethyl)phenylamino)-2-nitroacrylaldehyde (4.3 g, 19.4 mmol) was placed in 20 mL HOAc. 4.8 g of 3-aminobenzyl alcohol (4.8 g, 38.7 mmol) was dissolved in 5 mL conc HCl, then 20 mL HOAC was added to the HCl solution. This mixture was added to the reaction flask containing the 3-(3-(hydroxymethyl)phenylamino)-2-nitroacrylaldehyde in HOAc. The mixture was heated to reflux under nitrogen and after 20 min, benzene thiol (0.19 mL, 0.19 mmol) was added. The mixture was refluxed for 28 h (m/z=208.1). After allowing to cool, acid was removed under vacuum. The residue was dissolved in EtOAc/MeOH and loaded on a silica gel cartridge. Purification by column chromatography on silica gel using hexane/EtOAc (0-50%) then 10% MeOH/EtOAc as eluent gave the product (500 mg, 9%) as a brown solid.

(3-Aminoquinolin-7-yl)methanol (3-Nitroquinolin-7-yl)methanol (1.2 g, 0.0059 mol) and 400 mg of Pd/C (10% wt) were placed in 60 mL dry THF. The mixture was stirred under a hydrogen atmosphere (balloon) overnight. The reaction was filtered through Celite® and the filtrate concentrated to an oil. Purification by column chromatography on silica gel using MeOH/CH$_2$Cl$_2$ (0-10%) as eluent provided 0.9 g of an oily product. m/z=216.9 (+acetic acid). The product was suspended in MeOH and K$_2$CO$_3$ (200 mg) was added. This mixture was stirred at room temperature for 4 h. m/z=175.1. The mixture was filtered and the filtrate was concentrated under vacuum to give the product (172 mg, 19%) as a moist solid. $^1$H NMR (d$_4$-MeOD) δ 8.32 (1H, d), 7.69 (1H, s), 7.55 (1H, d), 7.34 (1H, dd), 7.23 (1H, d), 5.40 (2H, s).

Intermediate 51

Preparation of (6-amino-1H-indazol-3-yl)methanol

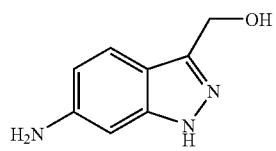

6-nitro-1H-indazole-3-carbaldehyde (500 mg, 0.003 mol) was dissolved in 50 mL THF. Lithium tetrahydroaluminate (400 mg, 0.01 mol) was added in 3 portions and the reaction mixture was stirred at room temperature overnight. Water (400 μL), 15% NaOH solution (400 μL), then water (1.2 mL) was added, and then the crystalline brown-yellow precipitate was filtered off. The filtrate was concentrate to an oil which was used directly in the next step without further purification. m/z=164.0. $^1$H NMR (d$_4$-MeOH) δ 7.2 (1H, d), 7.05 (1H, d), 6.85 (1H, dd), 4.74 (2H, s).

Intermediate 52

Preparation of (7-aminoquinolin-3-yl)methanol

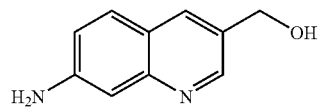

2-Dimethylaminomethylene-1,3-bis(dimethylimmonio)propane bis(tetrafluoroborate)

To a 3-neck flask equipped with a reflux condenser was added bromoacetic acid (25 g, 0.18 mol) and phosphoryl chloride (50 mL, 0.54 mol). The solution was cooled to 0° C. and N,N-dimethylformamide (84 mL, 1.1 mol) was added dropwise over 30 min. The resulting solution was heated at 110° C. for 3 h. As the mixture was heated, it began to exotherm and evolve CO$_2$. The mixture was then cooled to 0° C. and a solution of aqueous 50% tetrafluoroboric acid (63 g, 0.36 mol) in MeOH (100 mL) was added slowly over 1 h via an addition funnel. Isopropanol (100 mL) was added to the dark viscous solution. Solids precipitated and the slurry was stirred at 0° C. for 2 h. The solids were collected by filtration to provide the product (64 g, 72%) as a pale yellow solid.

Benzyl 3-aminophenylcarbamate

To a stirred solution of m-phenylenediamine (5.0 g, 0.046 mol) and N,N-diisopropylethylamine (8.0 mL, 0.046 mol) in CH$_2$Cl$_2$ (150 mL) at 0° C. was added slowly benzyl chloroformate (6.6 mL, 0.046 mol). The mixture was stirred at 0° C. for 2 h and then warmed to rt for 2 h. Aq. NaHCO$_3$ solution was added and the organic phase was separated, washed with brine, dried (Na$_2$SO$_4$) and concentrated. The residue was purified by column chromatography on silica gel to give the desired product (8.0 g, 71%) as a syrup. LC-MS: 2.11 min, 243.0 (M+1).

Benzyl 3-formylquinolin-7-ylcarbamate

A slurry of benzyl 3-aminophenylcarbamate (8.0 g, 0.033 mol) and 2-dimethylaminomethylene-1,3-bis(dimethylimmonio)propane bis(tetrafluoroborate) (31 g, 0.087 mol) in ethanol (400 mL) was heated at reflux for 24 h. The solution was concentrated under vacuum and the residue was dissolved in THF (200 mL) and 1N HCl (200 mL). The reation mixture was stirred at rt overnight, then poured into a saturated solution of sodium bicarbonate (200 mL), and extracted with EtOAc (2x). The combined organic layers were washed with brine, dried (Na$_2$SO$_4$), and concentrated under vacuum to afford the desired product (10.0 g, 99%) as a yellow solid. LC-MS: 2.84 min, 307.1 (M+1).

Benzyl 3-(hydroxymethyl)quinolin-7-ylcarbamate

To a stirred mixture of benzyl 3-formylquinolin-7-ylcarbamate (2.0 g, 0.0065 mol), THF (50 mL), MeOH (50 mL), and water (50 mL) was added sodium tetrahydroborate (0.25 g, 0.0065 mol). The mixture was stirred at rt until LC-MS indicated no SM. The mixture was acidified with 1N HCl and concentrated under vacuum, and then treated with aq. NaHCO$_3$ solution and EtOAc. The organic layer was separated and washed with brine, dried (Na$_2$SO$_4$), and evaporated. The residue was purified by column chromatography on silica gel using MeOH-EtOAc (0-10%) as eluent to give the product (1.3 g, 64%) as a light yellow solid. LC-MS: 1.83 min, 309.2 (M+1).

(7-Amino quinolin-3-yl)methanol

A mixture of benzyl 3-(hydroxymethyl)quinolin-7-ylcarbamate (480 mg, 0.0016 mol), 10% Pd-C (50 mg), and MeOH (50 mL) was stirred under H$_2$ (1 atm) for 1 h. The catalyst was filtered-off and the filtrate was concentrated to give the product as a yellow solid. LC-MS: 0.34 min, 175.1 (M+1).

Intermediate 53

Preparation of quinolin-7-amine

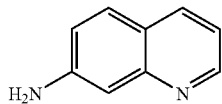

A mixture of 7-nitroquinoline (0.30 g, 0.0017 mol; Specs, Inc.), 10% Pd-C (50 mg), and MeOH (20 mL) was stirred under H$_2$ (1 atm) for 2 h. The mixture was filtered and the filtrate was concentrated to give a yellow solid (235 mg, 95%). LC-MS: 0.33 min, 145.1 (M+1). $^1$H NMR (DMSO-d$_6$): 8.58 (1H, dd, J=4.4, 1.6 Hz), 8.00 (1H, dd, J=8.0, 1.2 Hz), 7.60 (1H, d, J=8.8 Hz), 7.07 (1H, dd, J=8.0, 4.4 Hz), 6.98 (1H, dd, J=8.8, 2.0 Hz), 6.93 (1H, d, J=2.0 Hz), 5.75 (s, 2H).

Intermediate 54

Preparation of 5-amino-3-methylisoquinoline

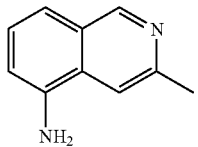

5-amino-3-methylisoquinoline

A mixture of 3-methyl-5-nitroisoquinoline (1.3 g, 0.0069 mol—prepared according to the procedure in WO 2004/024710), 10% Pd—C (100 mg) and MeOH (100 mL) was stirred under an atmosphere of hydrogen (1 atm) at rt for 2 h. The mixture was filtered and the filtrate was concentrated under vacuum to give a light yellow solid (1.1 g, 100%). LC-MS: 0.64 min, 159.1 (M+1).

Intermediate 55

Preparation of 1-chloroisoquinolin-5-amine

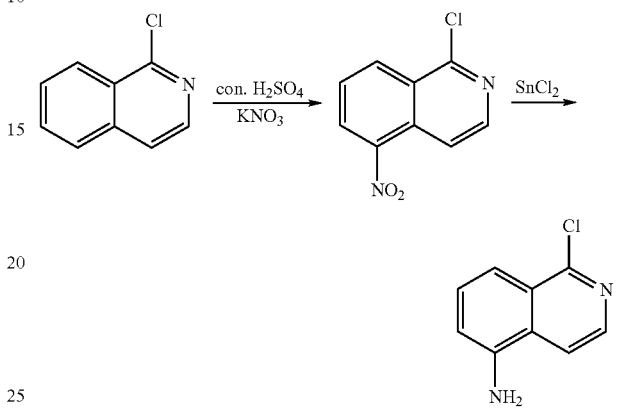

1-Chloro-5-nitroisoquinoline. A mixture of 1-chloroisoquinoline (6.0 g, 0.037 mol) in conc. H$_2$SO$_4$ (35 mL) was treated with a solution of fuming HNO$_3$ (10 mL) and potassium nitrate (4.0 g, 0.040 mol) in conc. H$_2$SO$_4$ (35 mL) at 0-5° C. The mixture was stirred at 0° C. for a further 90 min, and then poured into ice. The precipitate was collected, washed and dried to give the product as a yellow solid. LC-MS: 3.68 min, 209.2 & 211.1 (M+1).

1-Chloroisoquinolin-5-amine

A mixture of 1-chloro-5-nitroisoquinoline (450 mg, 0.0022 mol), stannous chloride dihydrate (2.4 g, 0.011 mol), and EtOAc (50 mL) was stirred under reflux under an atmosphere of nitrogen for 3 h. After cooling, the mixture was poured into ice-water and basified to pH 10.0 with aq. Na$_2$CO$_3$. The organic phase was separated and the aqueous phase was extracted with EtOAc. The combined organic layers were washed with brine, dried (Na$_2$SO$_4$) and concentrated under vacuum. The residue was purified by column chromatography on silica gel to give the product as a light yellow solid. LC-MS: 3.17 min, 179.2 & 181.2 (M+1).

Intermediate 56

Preparation of 7-amino-3,4-dihydro-2H-benzo[b][1,4]oxazin-3-yl)methanol and 8-amino-2,3,4,5-tetrahydrobenzo[b][1,4]oxazepin-3-ol

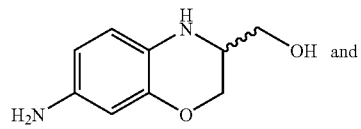

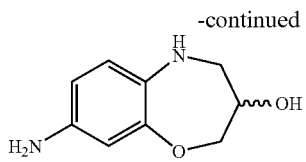

3,4-Dihydro-7-nitro-2H-benzo[b][1,4]oxazin-3-yl)methanol and 8-amino-2,3,4,5-tetrahydrobenzo[b][1,4]oxazepin-3-ol A mixture of 2-amino-5-nitrophenol (10.0 g, 0.0649 mol), potassium carbonate (13.4 g, 0.0973 mol), cesium fluoride (2.0 g, 0.013 mol) and 1-bromo-2,3-epoxypropane (5.37 mL, 0.0649 mol) in DMF (120 mL) was stirred under $N_2$ at rt overnight and then heated at 100° C. for 10 h. After cooling, the solvent was removed under vacuum and the residue was partitioned between water and EtOAc. The organic layer was washed with brine, dried ($Na_2SO_4$) and concentrated. The residue was purified by column with $CH_2Cl_2$-EtOAc (containing 5% $Et_3N$) (0 to 40%) to give an orange solid. LC-MS: 2.30 min, 211.1 (M+1).

7-Amino-3,4-dihydro-2H-benzo[b][1,4]oxazin-3-yl)methanol and 8-amino-2,3,4,5-tetrahydrobenzo[b][1,4]oxazepin-3-ol (3,4-Dihydro-7-nitro-2H-benzo[b][1,4]oxazin-3-yl)methanol (3.8 g, 0.018 mol) was hydrogenated at 40 PSi for 2 hours over 10% Pd/C. The mixture was filtered through Celite® and the filtrate was concentrated under vacuum to afford the crude product. Purification by column chromatography on silica-gel (EtOAc) gave the product as a dark brown oil. LC-MS: 0.36 min, 181.1 (M+1). $^1$H NMR (DMSO-$d_6$): 6.32 (1H, d, J=9.2 Hz), 6.01-5.97 (2H, m, 4.82-4.76 (2H, m), 4.29 (2H, s), 4.08 (1H, dd, J=10.4, 1.6 Hz), 3.79 (1H, dd, J=10.4, 6.8 Hz), 3.35 (2H, m), 3.17 (1H, m). 8-Amino-2,3,4,5-tetrahydrobenzo[b][1,4]oxazepin-3-ol was also isolated from above procedure as a minor byproduct.

Intermediate 57

Preparation of (S)-(3,4-dihydro-7-nitro-2H-benzo[b][1,4]oxazin-3-yl)methanol

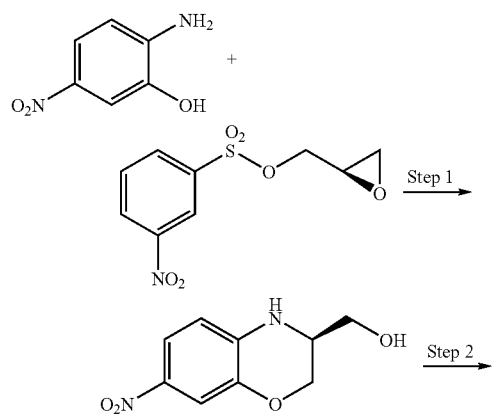

(S)-(3,4-dihydro-7-nitro-2H-benzo[b][1,4]oxazin-3-yl)methanol

Sodium hydride (0.810 g, 0.0202 mol) was added slowly to a mixture of 2-amino-5-nitrophenol (3.0 g, 0.019 mol) in dmf (50 ml) at 0° C. The mixture was stirred at rt for 1 h and then (r)-(oxiran-2-yl)methyl 3-nitrobenzenesulfonate (5.0 g, 0.019 mol) was added. The mixture was stirred at room temperature overnight and then DMF was removed under vacuum. The residue was partitioned between water and EtOAc. The organic layer was washed with aqueous $Na_2CO_3$ solution, brine, dried ($Na_2SO_4$) and concentrated under vacuum to give a brown solid (5.2 g). A mixture of the above brown solid, $K_2CO_3$ (2.0 g) and DMF (200 ml) was stirred at 120° C. under $N_2$ overnight. After cooling, the solvent was removed in vacuo and the residue was partitioned between water and EtOAc. The organic layer was washed with brine, dried ($Na_2SO_4$) and concentrated under vacuum. The residue was purified by column chromatography on silica gel with $CH_2Cl_2$-EtOAc (containing 5% $Et_3N$–0 to 60%) to give the product as a soft brown solid. LC-MS: 2.30 min, 211.1 (m+1).

(S)-(7-Amino-3,4-dihydro-2H-benzo[b][1,4]oxazin-3-yl)methanol

A mixture of (s)-(3,4-dihydro-7-nitro-2h-benzo[b][1,4]oxazin-3-yl)methanol (340 mg 0.0016 mol), 10% Pd/C (50 mg) and MeOH (50 ml) were stirred under an atmosphere of hydrogen (1 atm) for 3 h. LC-MS indicated completion of reaction. The mixture was filtered and the filtrate was concentrated under vacuum to give the product as a brown syrup. LC-MS: 0.36 min, 181.1 (m+1).

(R)-(7-amino-3,4-dihydro-2h-benzo[b][1,4]oxazin-3-yl)methanol was prepared using the same procedure as for (s)-(3,4-dihydro-7-nitro-2h-benzo[b][1,4]oxazin-3-yl)methanol, except (s)-(oxiran-2-yl)methyl 3-nitrobenzenesulfonate was used as starting material.

Intermediate 58

Preparation of (7-amino-2,3-dihydro-benzo[1,4]dioxin-2-yl)-methanol 9see 43P—Intermediate 19)

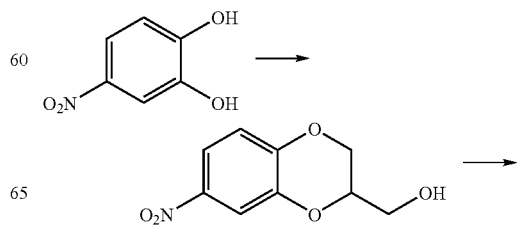

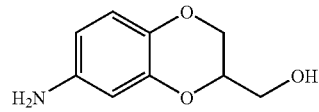

(7-Nitro-2,3-dihydro-benzo[1,4]dioxin-2-yl)-methanol 3.0 g of sodium hydrogen carbonate was suspended in 90 mL DMF. At 0° C. a solution of 5.15 g of 4-nitrocatechol was added dropwise over 15 min. Subsequently, 3.9 g of epichlorohydrin in 10 mL DMF were added over 15 min. Stirring was continued at room temperature, then at 80° C. overnight. The mixture was diluted with water and extracted three times with ethyl acetate, dried (anhyd. $Na_2SO_4$), filtered and concentrated under vacuum to give a yellow oil. The oil was purified by column chromatography on silica gel using EtOAc-hexanes (0-100% gradient) to give the product (2.8 g) as a yellow solid.

(7-amino-2,3-dihydro-benzo[1,4]dioxin-2-yl)-methanol (7-nitro-2,3-dihydro-benzo[1,4]dioxin-2-yl)-methanol (1.0 g, 4.7 mmol) was dissolved in methanol (30 ml) and palladium on activated carbon was added (0.10 g, 5% wt). The mixture was shaken on a parr shaker under $H_2(g)$ atmosphere (60 psi) for 24 hours. The mixture was filtered through Celite® and evaporated to give 722 mg of material as a white solid (86%), which was used as such for the next step. M/z=182 (m+1). Lc: 0.82 minutes.

Intermediate 59

Preparation of (6-Amino-2,3-dihydro-benzo[1,4]dioxin-2-yl)-methanol

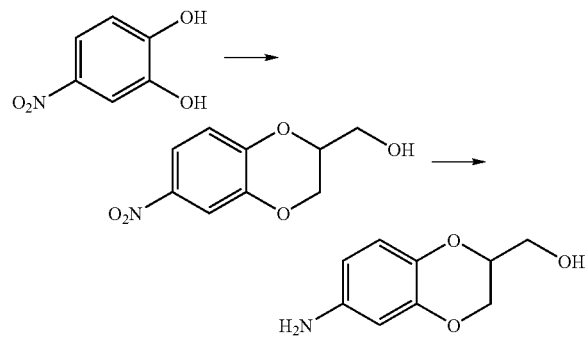

(6-Nitro-2,3-dihydro-benzo[1,4]dioxin-2-yl)-methanol 1.93 g of 60% sodium hydride was suspended in 90 mL DMF. At 0° C. a solution of 5.15 g of 4-nitrocatechol was added dropwise over 15 min. Subsequently, 3.9 g of epichlorohydrin in 10 mL DMF were added over 15 min. Stirring was continued at room temperature, then at 80° C. overnight. The mixture was diluted with water and extracted three times with ethyl acetate, dried ($Na_2SO_4$), filtered and concentrated under vacuum to give a yellow oil. The oil was purified by column chromatography on silica gel using a EtOAc-hexanes (0-100% gradient) to give the product (2.3 g) as a yellow solid.

(6-Amino-2,3-dihydro-benzo[1,4]dioxin-2-yl)-methanol (6-Nitro-2,3-dihydro-benzo[1,4]dioxin-2-yl)-methanol (1.0 g, 4.7 mmol) was dissolved in methanol (30 mL) and palladium on activated carbon was added (0.10 g, 5% wt). The mixture was shaken on a Parr Shaker under $H_2(g)$ atmosphere (60 PSI) for 24 hours. The mixture was filtered through Celite® and evaporated to give 646 mg of material as a white solid (77%), which was used as such for the next step. m/z=182 (M+1). LC: 0.82 minutes.

Intermediate 60

Preparation of (7-amino-3,4-dihydro-2H-pyrido[3,2-b][1,4]oxazin-3-yl)methanol

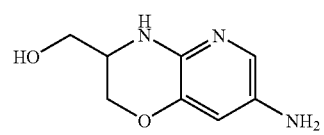

2-amino-3-methoxy-5-nitropyridine

Into a 250 mL sealed tube were combined 2-chloro-3-methoxy-5-nitropyridine (0.50 g, 0.00265 mol), concentrated ammonium hydroxide (5 mL, 0.1 mol) and ethanol (20 mL). The mixture was heated to 80° C. and stirred overnight. After allowing to cool to room temperature, the mixture was reduced in vacuo and the residue was taken up in ethyl acetate (50 mL), then washed with equal amounts of brine and water (1×50 mL each). The organic layer was dried ($Na_2SO_4$), filtered and concentrated under vacuum to leave a solid (0.312 g, 69%) which was used directly in the next step without further purification. LC-MS 1.94 min. M/Z=171.0 (M+1).

2-amino-3-hydroxy-5-nitropyridine

Into a 500 mL round bottom flask were combined 2-amino-3-methoxy-5-nitropyridine (0.300 g, 0.00177 mol) and solid pyridine hydrochloride (8.8 g, 0.076 mol). The solid mixture was heated at 150° C. (upon which the solids fused; the evolution of a gas was also apparent). The mixture was held at 150° C. for three hours upon which reaction was deemed complete by LC-MS. After allowing to cool to 80° C., the mixture was poured on to ice and the aqueous layer was extracted with ethyl acetate (3×100 ml). The combined organic extracts were washed with water (2×100 mL), dried ($Na_2SO_4$), filtered and concentrated under vacuum to leave a crude residue. The residue was purified by column chromatography on silica gel using a methanol:methylene chloride (0-10%) gradient as eluent to give the product as a solid (0.138 g, 49 %) which was used directly in the next step. LC-MS 1.28 min. m/z=155.9 (M+1).

(7-nitro-3,4-dihydro-2H-pyrido[3,2-b][1,4]oxazin-3-yl)methanol

Into a 75 mL sealed tube were combined 2-amino-3-hydroxy-5-nitropyridine (0.138 g, 0.000890 mol), N,N-dimethylfonnamide (4.1 mL) and potassium carbonate (0.39 g, 0.0028 mol). The mixture was allowed to stir at room temperature for 10 minutes then 1-bromo-2,3-epoxypropane (0.12 g, 0.00089 mol) was added in one portion. The flask was sealed, then heated to 110° C. and stirred overnight. After allowing to cool, the mixture was concentrated under vacuum to give a crude solid which was dissolved in EtOAc (75 mL), washed with water and brine, then dried ($Na_2SO_4$), filtered and concentrated under vacuum to leave a crude residue. The residue was purified by column chromatography on silica gel using $MeOH/CH_2Cl_2$ (0-10% gradient) as eluent to give a solid (0.092 g, 46%). LC-MS 1.92 min. M/Z=212.0 (M+1). $^1$H NMR ($d_6$-DMSO) δ 8.8 (d, 1 H), 7.8 (d, 1 H), 5.1 (t, 1H), 4.2 (m, 1 H), 4.0 (m, 1H), 3.62 (m, 1H), 3.45 (m, 1H), 3.21 (m, 1H).

(7-amino-3,4-dihydro-2H-pyrido[3,2-b][1,4]oxazin-3-yl)methanol

Into a 500 mL round bottom flask were combined (7-nitro-3,4-dihydro-2H-pyrido[3,2-b][1,4]oxazin-3-yl)methanol (0.320 g, 0.00152 mol), 10%-palladium on carbon (0.06 g, 0.0005 mol) and methanol (50 mL). The apparatus was evacuated, then hydrogen was introduced and the mixture was allowed to stir overnight (at 1 atm presuure). The mixture was then filtered through Celite® and the filtrate was concentrated under vacuum to yield an oil (0.252 g, 89%) which was used directly in the next step without further purification. (0.252 g, 89%) LC-MS 0.29 min. M/Z=181.9(M+1).

Intermediate 61

Preparation of (5-amino-1H-indol-2-yl)methanol

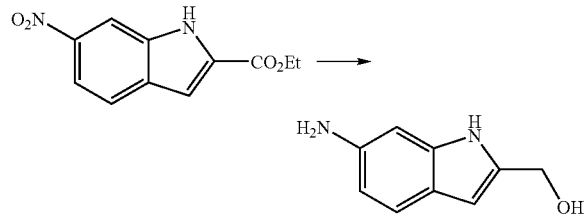

2-Ethoxycarbonyl-5-nitroindole (500 mg, 0.002 mol) was dissolved in 50 mL THF, added lithium tetrahydroaluminate (341 mg, 0.00898 mol) portionwise and stirred at room temperature overnight. Water (341 µL), 15% NaOH solution (341 µL), and water (1.1 mL) were added cautiously and the mixtured was filtered. The filtrate was concentrated under vacuum to give the product (300 mg, 98%) as an oil. m/z=162.9.

Intermediate 62

Preparation of (5-amino-1H-indazol-3-yl)methanol

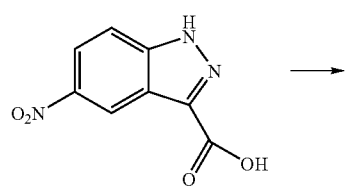

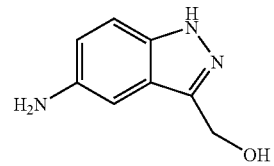

5-nitro-1H-indazole-3-carboxylic acid (500 mg, 0.002 mol) was dissolved in 50 mL THF, added lithium tetrahydroaluminate (366 mg, 0.00964 mol) portionwise and stirred at room temperature overnight. 65 mg (15%). Water (366 µL), 15% NaOH solution (366 µL), and water (1.1 mL) were added cautiously and the mixtured was filtered. The filtrate was concentrated under vacuum to give the product (65 mg, 15%) as an oil. m/z=160.0.

Preparation of Amido Compounds

Amide Formation

Method A: A Representative Synthesis of Benzamides Using an Automated Parallel Synthesis Method The appropriate benzoic acid (2 mmol) is dissolved or suspended in 15 ml of chloroform and treated with 20 mmol of thionyl chloride. The reaction mixture is refluxed for fifteen minutes and the solvents are removed under vacuum. The residue is dissolved in 4ml of anhydrous chloroform and 60 µl (30 µmole) of this solution is added to each well of the 96 well glass plates. Appropriate amine is then added to the corresponding well (60 µmole), followed by n,n-diisopropylethylamine (120 µmole). The plate is then heated at 65° C. for 15 minutes. The solvents are removed using an ht-12 genevac centrifugal evacuator and 100 µl of dmso is added to each well and the compounds are transferred to a 96-well polypropylene reaction plate. The plates are then sealed using an abgene plate sealer and submitted to lc-ms purification.

Method B: A Representative Synthesis of Benzamides Using an Automated Parallel Synthesis Method In one well of a 96-well polypropylene reaction plate was added the appropriate benzoic acid (6.03 mg, 30 µmol) in 15 µl of anhydrous pyridine. To the reaction was added TFFH (TFFH is fluoro-N,N,N',N'-tetramethylformamidinium hexafluorophosphate;12 mg, 45 µmol), followed by dilsopropylethylamine (6.0 mg, 45 µmol), followed by the appropriate amine (60 µmol). The reaction plate was heated at 50° C. for 15 minutes and the solvent was evaporated. The residue was dissolved in DMSO and purified using LC-MS based purification (50 mm×10 mm Phenomenex Gemini Column using a 10-100% acetonitrile-water gradient).

Method C:

To a mixture of the acid (0.4 mmol), N-(3-dimethylaminopropyl)-N'-ethylcarbodiimide hydrochloride (0.8 mmol), 1-Hydroxybenzotriazole hydrate (0.24 mmol) and $CH_2Cl_2$ (5 mL) was added the appropriate amine (0.5 mmol) and DIPEA (0.2 mL). The mixture was stirred at room temperature overnight, diluted with EtOAc, washed with brine, dried ($Na_2SO_4$), and concentrated. The residue was purified by column chromatography on silica gel to give the product.

Method D:

To a mixture of acid (1.0 mmol), N-(3-Dimethylaminopropyl)-N'-ethylcarbodiimide hydrochloride (385 mg, 2.0 mmol), 1-hydroxybenzotriazole hydrate (0.5-1.0 mmol), DMF (2 mL) and $CH_2Cl_2$ (5 mL) was added amine (1.2 mmol) and diisopropylethylamine (0.5 mL). The mixture was stirred at room temperature overnight, diluted with EtOAc, washed with brine, dried ($Na_2SO_4$), and concentrated. The residue was purified by column to give the amide.

Method E:

To a stirred solution of acid (1.0 mmol) in dry $CH_2Cl_2$ (10 mL) and DMF (2 drops) at 0° C. was added oxalyl chloride (1.5 mmol). The mixture was stirred at 0° C. for 1 h and then warmed to rt for 3 h. The solvent was removed in vacuo. A solution of the obtained acid chloride in $CH_2Cl_2$ (2 mL) was added to a solution of amine (1.0 mmol) in $CH_2Cl_2$ (3 mL) and pyridine (2 mL) at 0° C. The reaction mixture was stirred at rt overnight, and then diluted with EtOAc. The organic phase was washed with aq. $NaHCO_3$ solution and brine, dried ($Na_2SO_4$), and concentrated. The residue was purified by chromatography to give the amide.

Method F:

To a stirred solution of acid (0.25 mmol) in dry THF or $CH_2Cl_2$ (5 mL) and DMF (1 drop) at 0° C. was added oxalyl chloride (0.40 mmol). The mixture was stirred at 0° C. for 1 h and then warmed to rt. The solvent was removed in vacuo. A solution of the obtained acid chloride in $CH_2Cl_2$ (2 mL) was added to a solution of amine (0.25 mmol) in $CH_2Cl_2$ (10 mL), $Et_3N$ (0.2 mL), DMAP (5 mg) at 0° C. The reaction mixture was stirred at rt overnight, and then diluted with EtOAc (100 mL). The organic phase was washed with aq. $NaHCO_3$ solution and brine, dried, and concentrated. The residue was purified by chromatography to give the amide.

Method G:

To a cooled (0° C.) and well stirred suspension of the appropriate acid (1 eq) in $CH_2Cl_2$ (ca. 3 mL per mmol) and DMF (catalytic quantity) is added oxalyl chloride (1.5 eq) slowly drop-wise and the mixture is agitated for one hour. The mixture is concentrated under vacuum and the residue re-suspended in $CH_2Cl_2$. The appropriate amine (0.5-1.0 eq) is then added and the mixture is stirred for 1-48 hours before being worked-up and purified.

Method H:

N,N-Diisopropylethylamine (1 eq) was added in one portion to a stirred mixture of 2-methyl-4-(3,3-dimethylbut-1-ynyl)benzoic acid (1 eq) and N,N,N',N'-tetramethyl-O-(7-azabenzotriazol-1-yl)uronium hexafluorophosphate (1.05 eq) in N,N-dimethylformamide (ca. 3 mL per 0.5 mmol of starting acid) at room temperature. The mixture was stirred at room temperature for approx. 2 hours then a solution of the appropriate amine (1 eq) in DMF (1 mL) was added in one portion. The mixture was stirred overnight then worked-up by pouring in to $H_2O$ (30 mL) and EtOAc (30 mL). The aqueous and organic layers were partitioned and the aqueous was extracted with EtOAc (2×30 mL). The combined organic extracts were washed with brine (1×30 mL), dried ($Na_2SO_4$), filtered and the solvent removed under vacuum to leave a crude residue. Appropriate purification was employed to furnish the desired final compound.

Method I:

A mixture of the acid (1 mmol), N-(3-dimethylaminopropyl)-N'ethylcarbodiimide hydrochloride (3 mmol), 1-hydroxybenzotriazole hydrate (1.5 mmol) and the amine (2 mmol) was stirred in DMF at room temperature overnight. The mixture was partitioned between EtOAc and water. The organic layer was separated and washed with saturated aqueous $NaHCO_3$, water, brine, dried ($Na_2SO_4$), filtered and the filtrate was concentrated in vacuo to a residue which was purified by flash column chromatography.

Method J:

DIPEA (0.92 mmol) was added to the solution of appropriate acid (0.46 mmol), appropriate amine (0.69 mmol) and TFFH (0.69 mmol) in anhydrous pyridine (3 mL) and the reaction mixture was stirred at 60° C. overnight. Volatiles were removed and the residue was suspended in water, extracted by EtOAc and the organic phase was washed by water, brine and was dried over $Na_2SO_4$, solvent was removed and the residue was chromatographed to give the product.

Method K:

DIPEA (0.92 mmol) was added to the solution of appropriate acid (4.0 mmol), appropriate amine (3.2 mmol) and TFFH (6.0 mmol) in anhydrous pyridine (10 mL) and the reaction mixture was stirred at 70° C. overnight. Volatiles were removed and the residue was dissolved in EtOAc and the organic phase was washed by water, $Na_2CO_3$ aqueous solution, brine and was dried over $Na_2SO_4$, solvent was removed and the residue was chromatographed to yield the product.

Method L:

To a solution of acid (0.5 mmol), N-(3-Dimethylaminopropyl)-N'-ethylcarbodiimide hydrochloride (1.0 mmol), 1-hydroxybenzotriazole hydrate (1.0 mmol) in DMF (5 mL) and $CH_2Cl_2$ (5 mL) were added amine (0.75 mmol) and diusopropylethylamine (1.0 mmol). The mixture was stirred at 40° C. overnight before diluted with EtOAc, washed with brine, dried over $Na_2SO_4$ and concentrated. The residue was purified by column to give the amide.

Method M:

The amine (1 eq) was added in one portion to a stirred solution of the acid (1 eq), N-(3-Dimethylaminopropyl)-N'-ethylcarbodiimide hydrochloride (1 eq), 4-N,N-dimethylaminopyridine (1 eq) and $Et_3N$ (2 eq) in $CH_2Cl_2$ (ca. 3 mL per 0.125 mmol) and the mixture stirred until completion of the reaction (typically left overnight). The mixture was diluted with more $CH_2Cl_2$ (30 mL) and washed with $H_2O$ (1×20 mL), then dried ($Na_2SO_4$), filtered and concentrated under vacuum. The residue was purfied by column chromatography on silica gel or preparative thin-layer chromatography.

Compound 54

To a stirred solution of 4-(3,3,3-trifluoroprop-1-ynyl)benzoic acid (50 mg, 0.23 mmol) in THF (5 mL) and DMF (1 drop) at 0° C. was added oxalyl chloride (0.10 mL, 1.2 mmol). The mixture was stirred at 0° C. for 1 h and then warmed to rt. The solvent was removed in vacuo, and the obtained acid chloride in $CH_2Cl_2$ (2 mL) was added to a solution of (5-aminobenzo[d]thiazol-2-yl)methanol (20 mg, 0.11 mmol) in CH$_2$Cl$_2$ (5 mL), Et$_3$N (0.2 mL), DMAP (5 mg) at 0° C. The reaction mixture was stirred at rt overnight, and then diluted with EtOAc (100 mL). The organic phase was washed with aq. NaHCO$_3$ solution and brine, dried (MgSO$_4$), and concentrated under vacuum. The residue was purified by column chromatography on silica gel to give the ester. The ester was dissolved in MeOH (10 mL) and K$_2$CO$_3$ (300 mg) was added. The mixture was stirred at rt for 3 h, and then treated with water and EtOAc. The organic layer was separated, washed with brine, dried (Na$_2$SO$_4$), and concentrated. The residue was purified by preparative thin-layer chromatography with acetone-hexane (1:1) to give a white solid (10 mg).

Compound 69

A mixture of N-(1-acetyl-3,3-dimethylindolin-6-yl)-4-(3,3-dimethylbut-1-ynyl)benzamide (20 mg), CH$_3$CN (3 mL), and 5N aq. HCl (1 mL) was refluxed at 80° C. for 10 h. After cooling, the mixture was treated with aq. Na$_2$CO$_3$ and extracted with EtOAc. The combined organic layers were washed with brine, dried (Na$_2$SO$_4$), and concentrated under vacuum. The residue was purified by PLC to give a light yellow solid (10 mg).

Compound 112

A mixture of 4-(2-cyclopentylethynyl)benzoic acid (42.6 mg, 0.000199 mol), (6-amino-2,3-dihydrobenzo[b][1,4]dioxin-2-yl)methanol (36.2 mg, 0.000200 mol), EDCI (1 eq.) and DIEA (2 eq.) in 10 ml of DCM was stirred at 50° C. overnight. The reaction mixture was washed by brine and dried over sodium sulfate. The residue was separated by NP column after removal of the solvent. A tan solid product was obtained (53%).

Compound 116

A mixture of 4-(2-cyclopentylethynyl)benzoic acid (23 mg, 0.10 mmol), EDCI (1 eq.), and DIPEA (2 eq.) in 10 mL of CH$_2$Cl$_2$ was stirred at rt for 20 minutes. To this solution was added (6-amino-2,3-dihydrobenzo[b][1,4]dioxin-2-yl)methyl methanesulfonate (27 mg, 0.10 mmol) in 5 ml of CH$_2$Cl$_2$. The reaction mixture was then stirred at rt overnight. A yellow solid was obtained after regular work up and chromatographic separation.

Compound 117

A mixture of 4-(2-cyclopentylethynyl)benzoic acid (43 mg, 0.00020 mol), 3,4-dihydro-2H-benzo[b][1,4]oxazin-7-amine (35 mg, 0.00020 mol), EDC (1.0 eq.) and HOBt (1.0 eq) in 20 ml of DCM was stirred at rt overnight. The reaction mixture was washed with brine and dried over sodium sulfate. The solvent was removed d the residue was separated by chromatography. A light yellow solid product (42 mg) was obtained.

Compound 197

A mixture of 2-methyl-N-(2-methylbenzo[d]thiazol-5-yl)-4-(3,3-dimethylbut-1-ynyl)benzamide (50 mg, 0.14 mmol), selenium dioxide (46 mg, 0.41 mmol), and 1,4-dioxane (10 mL) was stirred under an atmosphere of nitrogen at 80° C. overnight. After cooling, the mixture was filtered through Celite® and the filtrate was treated with aq. NaHCO$_3$ and extracted with EtOAc. The organic layer was washed with brine, dried (Na$_2$SO$_4$), and concentrated under vacuum. The residue was dissolved in THF-H$_2$O (2:1) (10 mL) and NaBH$_4$ (50 mg) was added slowly. The mixture was stirred at rt for 2 h and then acidified with 1N HCl. After treated with aq. NaHCO$_3$, the mixture was extracted with EtOAc. The combined organic layers were washed with brine, dried (Na$_2$SO$_4$), and concentrated under vacuum. The residue was purified by preparative thin-layer chromatography to give N-(benzo[d]thiazol-5-yl)-2-methyl-4-(3,3-dimethylbut-1-ynyl)benzamide (compound 198-11 mg) as a light yellow solid and N-(2-(hydroxymethyl)benzo[d]thiazol-5-yl)-2-methyl-4-(3,3-dimethylbut-1-ynyl)benzamide (compound 197-27 mg) as a light yellow solid.

Compound 225

(E)-4-(3,3,3-trifluoroprop-1-enyl)-2-methyl-N-(2-methylbenzo[d]thiazol-5-yl)benzamide (200 mg, 0.0005 mol) and selenium dioxide (177 mg, 0.00160 mol) were placed in 20 mL dioxane and the reaction was heated at 80° C. overnight under nitrogen. The reaction was cooled and filtered through Celite®. The filtrate was partitioned between EtOAc and NaHCO$_3$. The organic layer was separated, washed with water, brine, dried (Na$_2$SO$_4$) and concentrated under vacuum. The residue was dissolved in THF/H$_2$O (2:1; 20 mL) and NaBH$_4$ (200 mg, 5.3 mmol) was added in three batches. The mixture was stirred at room temperature for 2 h, then quenched by addition of 1N HCl. The mixture was basified by addition of sat'd NaHCO$_3$ and extracted with EtOAc. The organic layer was washed with water, brine, dried (Na$_2$SO$_4$) and concentrated under vacuum. The residue was purified by column chromatography on silica gel using EtOAc/hexane (0-100%) as eluent and then again using MeOH/CH$_2$Cl$_2$ (0-3%) as eluent to give the product (40 mg) as a solid. m/z=392.6 Further purification by preparative HPLC (water/acetonitrile) gave the product (35 mg) as a white solid. m/z=392.6.

Compound 228

To a stirred solution of (E)-4-(3,3,3-trifluoroprop-1-enyl)-2-methylbenzoic acid (0.20 g, 0.87 mmol) in CH$_2$Cl$_2$ (50 mL) and DMF (2 drops) at 0° C. was added oxalyl chloride (0.11 mL 1.3 mmol). The mixture was stirred at 0° C. for 1 h and then warmed to rt for 2 h. The solvent was removed in vacuo. The above acid chloride was added to a solution of (7-aminoquinolin-3-yl)methanol (76 mg, 0.43 mmol) in CH$_2$Cl$_2$ (5 mL) and pyridine (10 mL). The reaction mixture was stirred at rt overnight, and then concentrated in vacuo. The residue was treated with EtOAc and aq. NaHCO$_3$ solution. The organic layer was separated, washed with brine, dried (Na$_2$SO$_4$), and concentrated under vacuum. The residue was purified by column chromatography on silica gel using EtOAc/hexane (0-50%) as eluent to give the ester [95 mg, m/z: 599.2 (M+1)]. The ester was dissolved in MeOH (5 mL) and K$_2$CO$_3$ (200 mg) was added. The mixture was stirred at rt for 3 h, and then methanol was removed under vacuum. The residue was treated with water and EtOAc. The organic layer was separated, washed with brine, dried (Na$_2$SO$_4$), and concentrated under vacuum. The residue was purified by preparative thin-layer chromatography with acetone-CH$_2$Cl$_2$ (1:1) to give a white solid (43 mg, 24%). LC-MS: 2.29 min, 387.7 (M+1).

Compound 229

To a stirred solution of 7,8-Dihydro-5H-pyrano[4,3-b]pyridin-3-ylamine (50 mg, 0.3 mmol) in anhydrous DMF (2 mL) was added a stirred solution of (E)-4-(3,3,3-trifluoroprop-1-enyl)-2-methylbenzoic acid (91.96 mg, 0.4 mmol), N-(3-dimethylaminopropyl)-N'-ethylcarbodiimide hydrochloride (76.59 mg, 0.4 mmol), HOBt (62.98 mg, 0.46 mmol), 4-N,N-dimethylaminopyridine (2 mg, 0.02 mmol) and DIPEA (139 µL, 0.8 mmol) in anhydrous DMF (3 mL). The reaction was stirred overnight at room temperature. The reaction mixture was poured into saturated NaHCO$_3$ solution (50 mL) and extracted with EtOAc (3×50 mL). The combined organics were washed with brine (3×50 mL), dried (MgSO$_4$), filtered and concentrated under vacuum. Purification by column chromatography on silica gel (0 to 5% MeOH in DCM over 60 minutes) gave the desired product (39 mg, 30%) as an off-white solid.

General Method for Automated parallel LC-MS Purification of Libraries

The libraries were purified using a Perkin Elmer API100 mass spectrometer coupled to Shimadzu LC pumps. The chromatographic method employed was 10-100% gradient of acetonitrile to water over 8 minutes at a flow rate of 6 ml per minute. The column used was a 10×50 mm YMC C18 and the compounds were collected using a Gilson 204 fraction collector.

Following the methods described above and the appropriate reagents, starting materials and purification methods known to those skilled in the art, the amide compounds of this invention were or can be prepared.

The synthetic and biological examples presented herein are offered to illustrate this invention and are not to be construed in any way as limiting the scope of this invention. In the examples below, all temperatures are in degrees Celsius (unless otherwise indicated).

The compounds that have been prepared in accordance with the invention are presented in Table 1, below. The syntheses of these representative compounds were carried out in accordance with the methods set forth above, and activity of the compounds was measured by percent inhibition in a calcium uptake assay, the details of which are described below.

Calcium Uptake Assay

Functional activity of compounds against the VR1 receptor was determined by measuring changes in intracellular calcium in HEK 293 cells expressing hVR1. Compounds were examined for their ability to inhibit agonist-induced calcium influx. Dual wavelength ratiometric dye, Fura2, was used as an indicator of relative levels of [Ca$^{2+}$] in a 96-well format using a Flex Station®, Molecular Devices.

Cell Line and Culture Conditions:

hVR1 was cloned into a pcDNA5/TO vector from Invitrogen and stably transformed into T-REx HEK 293 cell line from Invitrogen. HEK 293 cells expressing hVR1 were grown to confluency (24 hour culture) on PDL-coated, plastic 96-well black-walled plates, in the presence of DMEM medium containing 5% PenStrep, 5% Glutamax, 200 µg/mL Hygromycin, 5 µg/mL Blasticidin and 10% heat inactivated FBS. Twenty-four hours prior to assay, cells were transferred to DMEM media containing 1 µg/mL doxycycline. Prior to the assay, cells were loaded with 5 µg/mL Fura-2 (Molecular Probes) in saline solution (130 mM NaCl, 3 mM KCl, 1 mM CaCl$_2$, 0.6 mM MgCl$_2$, 10 mM HEPES, 10 mM glucose and 50 mM sucrose pH 7.4) at 37° C. for 40 minutes. The dye was then aspirated and replaced with 100 µL saline before commencement of the assay in Flex Station®.

Agonist Concentration and Compound Dilutions:

The agonist EC$_{50}$ was determined at the start of the assay and compound IC$_{50}$ experiments were run using an agonist concentration equal to its EC$_{50}$ as stimulus. The agonists used were capsaicin (EC$_{50}$=2.5 nM) and protons (saline solution plus 10 mM citric acid buffered to pH 5.7 with HCl). Compounds were tested at concentrations ranging from 10 nM to 3.3 µM.

The assay consists of two stages: a pre-treatment phase followed by a treatment phase. 50 µl of a compound solution was added to the cells (Pre-treatment). In some instances, following pre-treatment, 50 µl of the test compound in a saline solution at pH 5.1 was added (Treatment). Compounds were tested as follows: For the pre-treatment phase, 50 µL of 3× concentration of test compound in saline is added to cells containing 100 µL of saline to achieve a final concentration of x. For the treatment phase, at a determined time after pre-treatment, 50 µL of test compound plus agonist solution is added to cells at the relevant concentrations.

Recordings were made at 4 second intervals at wavelengths of 340 nm and 380 nm and the fluorescence ratio analyzed. Responses were measured as peak fluorescence ratio after compound-agonist addition minus baseline fluorescence ratio prior to treatment and were calculated using the SoftMaxPro software from Molecular Devices. Percent inhibition was calculated as follows and is depicted in Table 1:

$$\text{Percentage inhibition} = \left[1 - \frac{(\text{Compound Response} - \text{Control Response})}{(\text{Agonist Response} - \text{Control Response})}\right] \times 100$$

TABLE 1

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 1 | 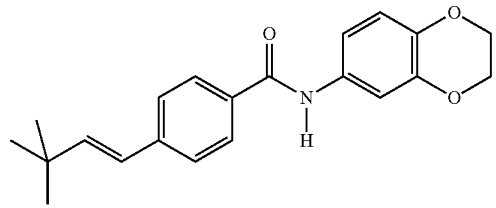 | 338.29 (337.42) | A | | 83 |
| 2 | 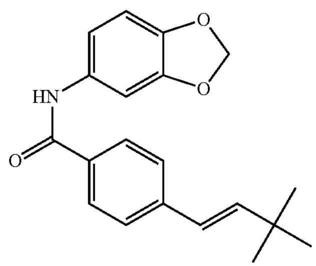 | 324.33 (323.40) | A | | |
| 3 | 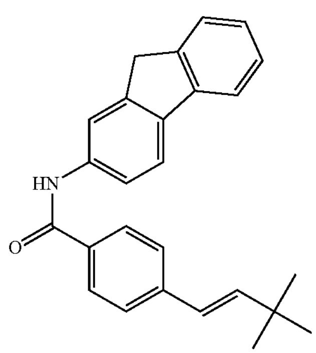 | | A | | |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 4 | 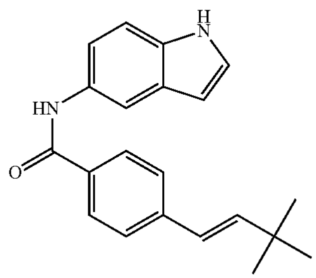 | 319.08 (318.42) | A | | |
| 5 | 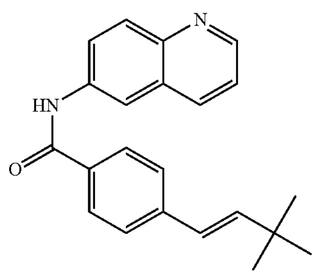 | 331.27 (330.43) | A | | |
| 6 | 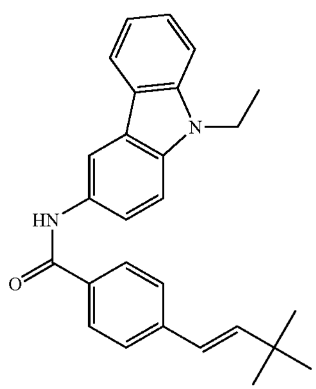 | | A | | |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 7 | 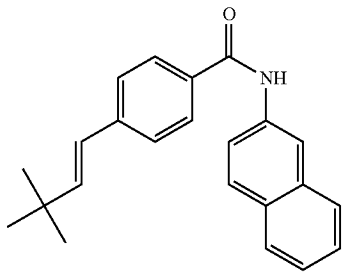 | | A | | |
| 8 | 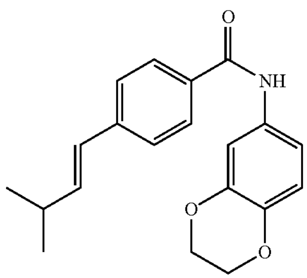 | 324.31 (323.40) | A | | 26 |
| 9 | 305.29 (304.40) | A | | 37 |

TABLE 1-continued

AMIDE COMPOUNDS

| ID | STRUCTURE | MS observed (calcd) | Method of Synth. | $^1$H NMR | Low pH % Inhib. @ 0.3 μM |
|---|---|---|---|---|---|
| 10 | 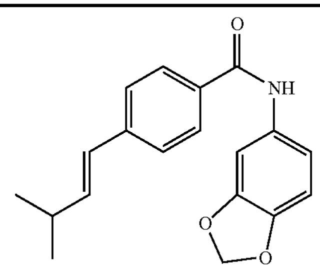 | 310.30 (309.37) | A | | |
| 11 | 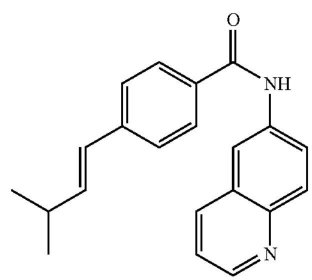 | 317.19 (316.41) | A | | 34 |
| 12 | 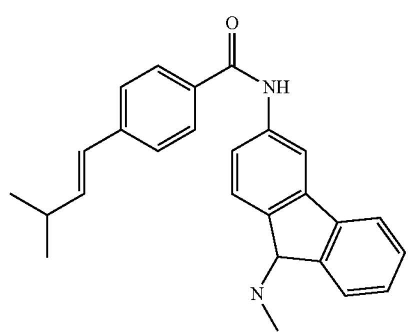 | 383.27 (382.51) | A | | |

TABLE 1-continued
AMIDE COMPOUNDS
| ID | STRUCTURE | MS observed (calcd) | Method of Synth. | ¹H NMR | Low pH % Inhib. @ 0.3 μM |
|---|---|---|---|---|---|
| 13 | 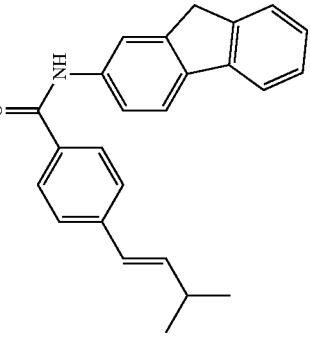 | 354.18 (353.47) | A | | 11 |
| 14 | 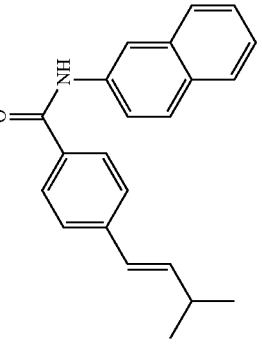 | 316.19 (315.42) | A | | |
| 15 | 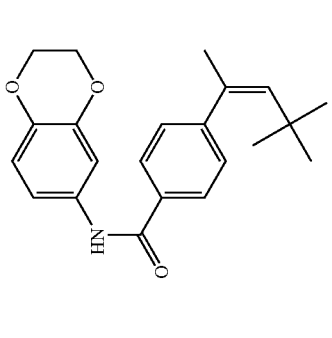 | 352.28 (351.45) | A | | |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 16 | ![indole structure] | 333.28 (332.45) | A | | 21 |
| 17 | ![benzodioxole structure] | 338.29 (337.42) | A | | |
| 18 | ![quinoline structure] | 345.09 (344.46) | A | | 12 |

TABLE 1-continued

AMIDE COMPOUNDS

| ID | STRUCTURE | MS observed (calcd) | Method of Synth. | $^1$H NMR | Low pH % Inhib. @ 0.3 μM |
|---|---|---|---|---|---|
| 19 | 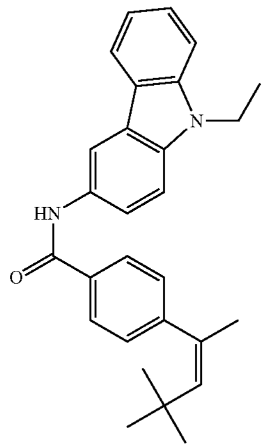 | 411.28 (410.56) | A | | 14 |
| 20 | 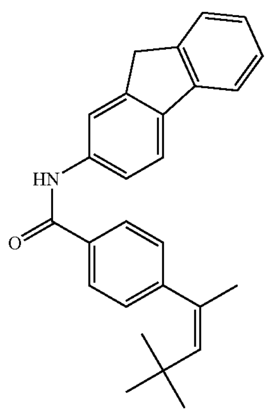 | | A | | |

TABLE 1-continued
AMIDE COMPOUNDS
| ID | STRUCTURE | MS observed (calcd) | Method of Synth. | ¹H NMR | Low pH % Inhib. @ 0.3 μM |
|---|---|---|---|---|---|
| 21 | 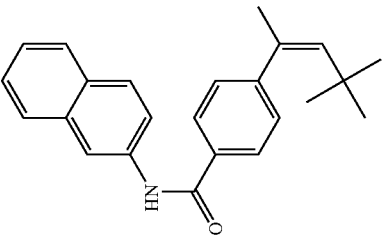 | 344.18 (343.47) | A | | |
| 22 | 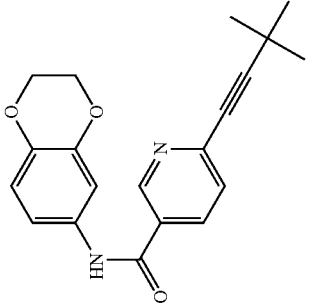 | 337.39 (336.39) | A | | 106 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 23 | (isoquinolin-5-yl amide of 6-(3,3-dimethylbut-1-ynyl)nicotinamide) | 330.27 (329.41) | B |  | 98 |
| 24 | (quinolin-3-yl amide of 6-(3,3-dimethylbut-1-ynyl)nicotinamide) | 330.26 (329.41) | B | (d₆-DMSO) δ 10.91(s, 1H), 9.14(d, 2H) 8.84(d, 1H), 8.37(dd, 1H), 8.02-7.97(m, 2H), 7.58-7.72(m, 3H), 1.34(s, 9H) | 101 |
| 25 | (1-methylindol-5-yl amide of 6-(3,3-dimethylbut-1-ynyl)nicotinamide) | 332.28 (331.42) | B |  | 105 |

TABLE 1-continued
AMIDE COMPOUNDS
| ID | STRUCTURE | MS observed (calcd) | Method of Synth. | $^1$H NMR | Low pH % Inhib. @ 0.3 μM |
|---|---|---|---|---|---|
| 26 | 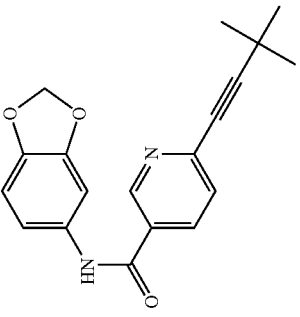 | 323.19 (322.37) | B | | 104 |
| 27 | 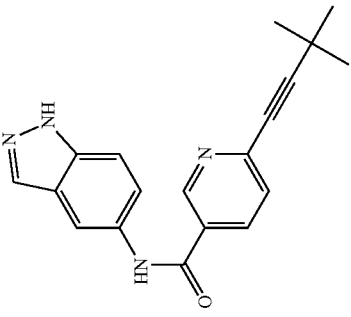 | 319.08 (318.38) | B | | |
| 28 | 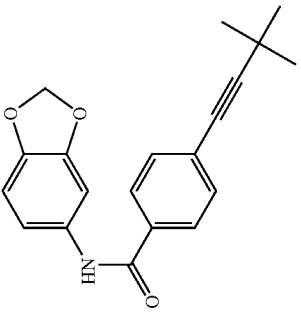 | 322.26 (321.38) | B | | 102 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 29 | 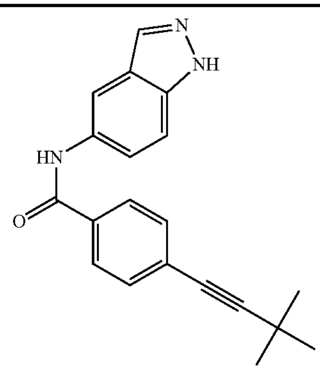 | 318.16 (317.39) | I | (d₆-DMSO) δ 13.0(1H, s), 10.35(1H, s), 8.25(1H, s), 8.15(1H, s), 7.95(2H, d), 7.65(1H, d), 7.55-7.48(3H, m), 1.46(9H, s) | |
| 30 | 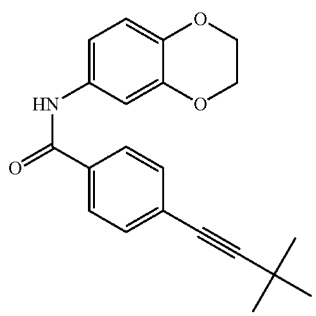 | 336.44 (335.41) | I | (CDCl₃) δ 7.78(2H, d), 7.61(1H, s), 7.52(2H, d), 7.05(1H, d), 6.83(1H, d), 4.25(4H, m), 1.45(9H, s) | 105 |
| 31 | 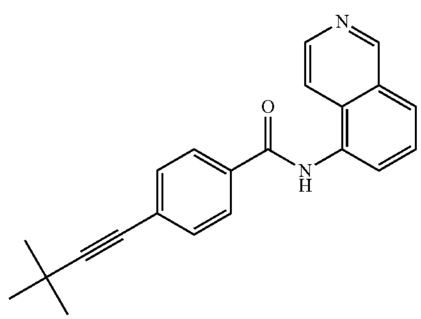 | 329.30 (328.42) | I | (d₆-DMSO) δ 10.8(1H, s), 9.75(1H, s), 8.71(1H, d), 8.42(1H, d), 8.34(1H, d), 8.21(1H, d), 8.15(2H, d), 7.95(1H, t), 7.55(2H, d), 1.45(9H, s) | 108 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 32 | 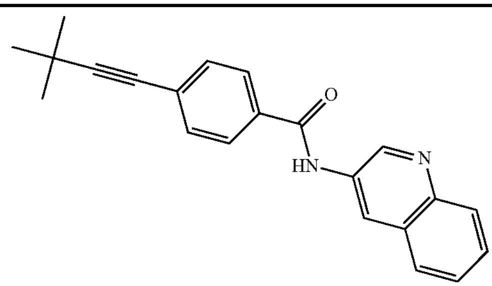 | 329.29 (328.42) | I | (CDCl₃) δ 8.85(1H, d), 8.71(1H, d), 8.15(1H, d), 8.05(1H, s), 7.95(2H, d), 7.65(1H, t), 7.61(1H, t), 7.55(2H, d), 1.45(9H, s) | 101 |
| 33 | 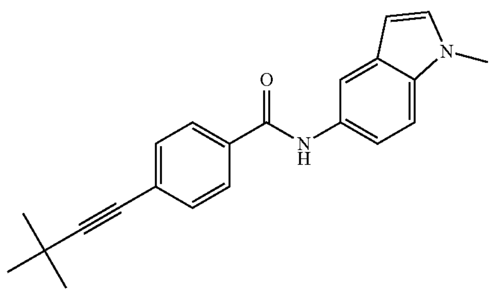 | 331.29 (330.43) | I | (CDCl₃) δ 7.95(1H, s), 7.82(2H, d), 7.5(2H, d), 7.4(1H, d), 7.3(1H, d), 7.08(1H, d), 6.48(1H, d), 3.8(3H, s), 1.35(9H, s) | 105 |
| 34 | 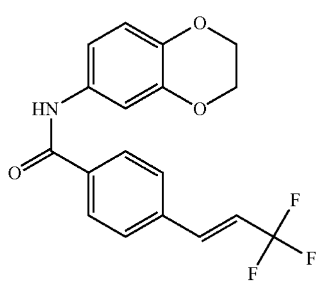 | 350.29 (349.31) | L | (d₆-DMSO) δ 10.14(1H, s), 7.97(2H, d), 7.83(2H, d), 7.40-7.39(m, 2H), 7.21-7.18(m, 1H), 6.96-6.90(m, 1H), 6.83(1H, d), 4.24-4.21(m, 4H). | 97 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 35 | (isoquinolin-5-yl amide of 4-(3,3,3-trifluoroprop-1-enyl)benzamide) | 343.09 (342.32) | L | (d₆-DMSO) δ 10.61(1H, s), 9.37(1H, d), 8.53(1H, d), 8.14(2H, d), 8.07(1H, d), 7.93-7.85(m, 4H), 7.74(1H, t), 7.46(1H, dd), 7.00-6.94(m, 1H). | 106 |
| 36 | (quinolin-3-yl amide of 4-(3,3,3-trifluoroprop-1-enyl)benzamide) | 343.10 (342.32) | J | (d₆-DMSO) δ 10.78(1H, s), 9.16(1H, d), 8.86(1H, d), 8.09(2H, d), 8.00-7.97(2H, m), 7.91(2H, d), 7.70-7.66(1H, m), 7.62-7.58(1H, m), 7.48-7.43(1H, m), 7.00-6.94(1H, m). | 54 |
| 37 | (1-methylindol-5-yl amide of 4-(3,3,3-trifluoroprop-1-enyl)benzamide) | 345.09 (344.34) | L | (d₆-DMSO) δ 10.18(1H, s), 8.04-7.95(3H, m), 7.86-7.80(2H, m), 7.48-7.34(3H, m), 7.31(1H, d), 6.98-6.89(1H, m), 6.41(1H, d), 3.79(3H, s). | 17 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 38 | 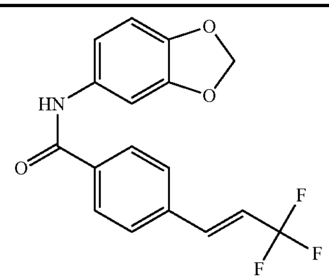 | 336.39 (335.29) | A | | |
| 39 | 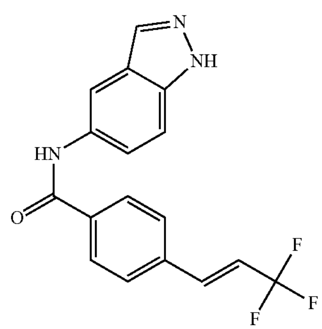 | 332.28 (331.30) | A | | |
| 40 | 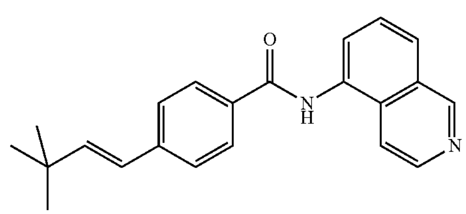 | 331.20 (330.43) | J | (d₆-DMSO) δ 10.50(1H, s), 9.37(1H, s), 8.53(1H, dd), 8.10-8.04(3H, m), 7.91(1H, dd), 7.85(1H, dd), 7.76-7.70(2H, m), 7.60(1H, d), 6.56(1H, d), 6.43(1H, d), 1.14(9H, s). | 86 |

TABLE 1-continued

AMIDE COMPOUNDS

| ID | STRUCTURE | MS observed (calcd) | Method of Synth. | ¹H NMR | Low pH % Inhib. @ 0.3 µM |
|---|---|---|---|---|---|
| 41 | 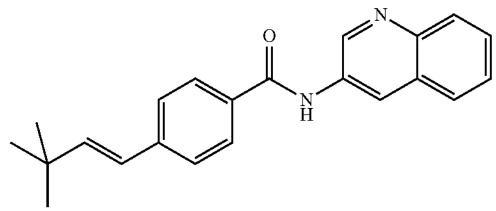 | 331.20 (330.43) | J | (d₆-DMSO) δ 10.66(1H, s), 9.16(1H, d), 8.85(1H, d), 8.03-7.96(4H, m), 7.70-7.58(4H, m), 6.56(1H, d), 6.43(1H, d), 1.14(9H, s). | 101 |
| 42 | 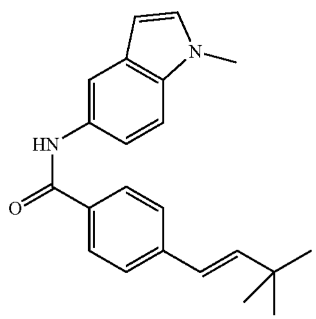 | 333.40 (332.45) | L | (d₆-DMSO) δ 10.13(1H, s), 8.00-7.94(3H, m), 7.66-7.64(1H, m), 7.56-7.54(1H, m), 7.48-7.38(2H, m), 7.31(1H, dd), 6.52(1H, d), 6.42-6.38(2H, m), 3.78(3H, s), 1.11(9H, s). | 98 |
| 43 | 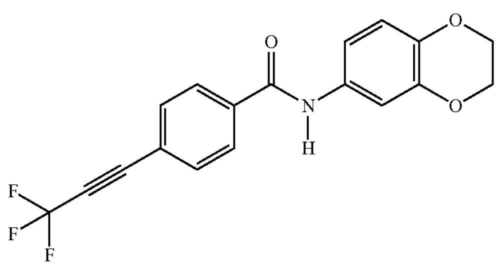 | 347.90 (347.30) | same as Compd. 112 | (d₆-DMSO) δ 10.26(s, 1H), 8.03(d, 2H, J=8.4Hz), 7.89(d, 2H, J=8.4Hz), 7.37(d, 1H, J=2.4Hz), 7.19(dd, 1H, J=8.8, 2.4Hz), 6.83(d, 1H, J=8.8Hz), 4.23(m, 4H). | 105 |

TABLE 1-continued

AMIDE COMPOUNDS

| ID | STRUCTURE | MS observed (calcd) | Method of Synth. | $^1$H NMR | Low pH % Inhib. @ 0.3 μM |
|---|---|---|---|---|---|
| 44 | N-methylindole-6-yl amide of 6-(3,3-dimethylbut-1-yn-1-yl)pyridine-3-carboxamide | 332.30 (331.42) | B | | 87 |
| 45 | isoquinolin-5-yl amide of 4-(3,3,3-trifluoroprop-1-yn-1-yl)benzamide | 339.20 (340.31) | I | (d$_6$-DMSO) δ 10.73(s, 1H) 9.38(s, 1H) 8.53(d, 1H) 8.19(d, 2H) 8.08(d, 1H) 7.98-7.85(m, 4H) 7.75(t, 1H) | 99 |
| 46 | quinolin-3-yl amide of 4-(3,3,3-trifluoroprop-1-yn-1-yl)benzamide | 339.26 (340.31) | same as Compd. 112 | (d$_6$-DMSO) δ 10.07(s, 1H), 9.14(d, 1H, J=2.4Hz), 8.86(d, 1H, J=2.4Hz), 8.15(d, 2H, J=8.4Hz), 8.01-7.95(m, 4H), 7.69(m, 1H), 7.61(m, 1H). | |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 47 | *4-(cyclopropylethynyl)-N-(quinolin-3-yl)benzamide* | 313.30 (312.37) | B | (d₆-DMSO) δ 10.73(s, 1H) 9.14(d, 1H) 8.85(d, 1H) 8.03-7.95(m, 4H) 7.71-7.54(m, 4H) 1.65-1.56(m, 1H) 0.97-0.91(m, 2H) 0.82-0.76(m, 2H) | 55 |
| 48 | *4-(cyclopropylethynyl)-N-(isoquinolin-5-yl)benzamide* | 313.31 (312.37) | B | (d₆-DMSO) δ 10.58(s, 1H) 9.36(s, 1H) 8.52(d, 1H) 8.08-8.02(m, 3H) 7.86(dd, 2H) 7.73(t, 1H) 7.56(d, 2H) 1.65-1.57(m, 1H) 0.97-0.91(m, 2H) 0.83-0.76(m, 2H) | 99 |
| 49 | *4-(cyclopropylethynyl)-N-(2,3-dihydrobenzo[b][1,4]dioxin-6-yl)benzamide* | 320.30 (319.36) | B | (d₆-DMSO) δ 10.10(s, 1H) 7.88(d, 2H) 7.48(d, 2H) 7.37(d, 1H) 7.19(dd, 1H) 6.82(d, 1H) 4.27-4.19(m, 4H) 1.63-1.54(m, 1H) 0.89-0.96(m, 2H) 0.80-0.75(m, 2H) | 96 |

TABLE 1-continued

AMIDE COMPOUNDS

| ID | STRUCTURE | MS observed (calcd) | Method of Synth. | ¹H NMR | Low pH % Inhib. @ 0.3 µM |
|----|-----------|---------------------|------------------|--------|--------------------------|
| 50 | 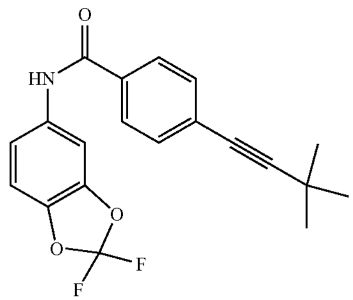 | 358.40 (357.36) | B | (d$_6$-DMSO) δ 10.48(s, 1H) 7.95-7.90(m, 3H) 7.53-7.49(m, 3H) 7.40(d, 1H) 1.31(s, 9H) | 5 |
| 52 | 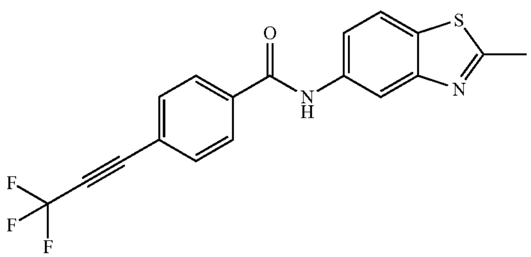 | 361.20 (360.36) | F | (d$_6$-DMSO) δ 10.61(s, 1H), 8.42(d, 1H, J=2.0Hz), 8.10(d, 2H, J=8.4Hz), 7.99(d, 1H, J=8.4Hz), 7.93(d, 2H, J=8.4Hz), 7.77(dd, 1H, J=8.4, 2.0Hz), 2.80(s, 3H). | 101 |
| 53 | 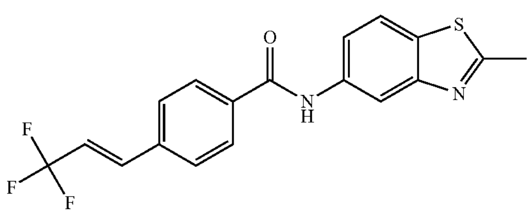 | 363.30 (362.38) | K | (d$_6$-DMSO) δ 10.50(1H, s), 8.43(1H, d), 8.04(3H, d), 7.98(2H, d), 7.77(1H, dd), 7.44(1H, dd), 6.98-6.93(1H, m), 2.80(3H, s). | 81 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 54 | benzothiazole-CH₂OH linked via amide to phenyl-C≡C-CF₃ | 377.10 (376.36) | See "Prepn. of amido compd.s" | (d₆-DMSO) δ 10.63(s, 1H), 8.44(d, 1H, J=2.4Hz), 8.10(d, 2H, J=8.4Hz), 8.05(d, 1H, J=8.8Hz), 7.93(d, 2H, J=8.4Hz), 7.78(dd, 1H, J=8.8, 2.4Hz), 6.26(t, 1H, J=6.0Hz), 4.86(d, 2H, J=6.0Hz). | 76 |
| 55 | benzothiazole-CH₂OH linked via amide to phenyl-CH=CH-CH₂-CF₃ | 379.10 (378.38) | same as Compd. 54 | (d₆-DMSO): δ 10.50(s, 1H), 8.46(d, 1H, J=2.0Hz), 8.04(d, 3H, J=8.4Hz), 7.88(d, 2H, J=8.4Hz), 7.79(dd, 1H, J=8.4, 2.0Hz), 7.48-7.42(m, 1H), 6.95(dq, 1H, J=16.4, 6.8Hz), 6.26(t, 1H, J=5.6Hz), 4.86(d, 2H, J=5.6Hz). | 101 |
| 56 | 2-methylbenzothiazole linked via amide to phenyl-C≡C-C(CH₃)₃ | 349.20 (348.47) | I | (d₆-DMSO) δ 10.45(1H, s), 8.43(1H, d), 7.99-7.95(3H, m), 7.77(1H, dd), 7.52(2H, m), 2.75(3H, s), 1.45(9H, s) | 104 |
| 57 | 3-oxo-3,4-dihydro-2H-benzo[b][1,4]oxazine linked via amide to phenyl-CH=CH-CF₃ | 363.30 (362.31) | C | (d₆-DMSO) δ 10.79(1H, s), 10.27(1H, s), 7.98(2H, d), 7.84(2H, d), 7.52(1H, d), 7.45-7.40(1H, m), 7.25(1H, dd), 6.96-6.90(2H, m), 4.54(2H, s). | 58 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 58 | 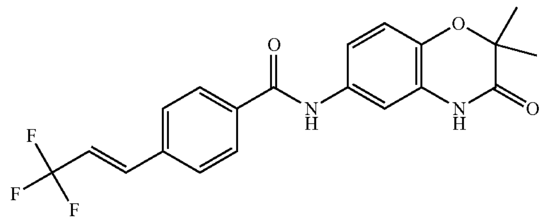 | 391.50 (390.37) | C | (d₆-DMSO) δ 10.70(1H, s), 10.26(1H, s), 7.98(2H, d), 7.84(2H, d), 7.51(1H, d), 7.43(1H, dd), 7.25(1H, dd), 6.96-6.90(2H, m), 1.39(6H, s). | 19 |
| 59 | 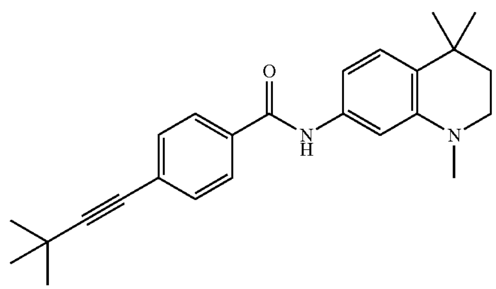 | 375.00 (374.53) | I | (CDCl₃) d 7.77(2H, d), 7.65(1H, s), 7.47(2H, d), 7.15(1H, d), 7.05(1H, s), 6.78(1H, dd), 3.25(2H, dd), 2.92(3H, s), 1.75(2H, dd), 1.33(9H, s), 1.27(6H, s) | 83 |
| 60 | 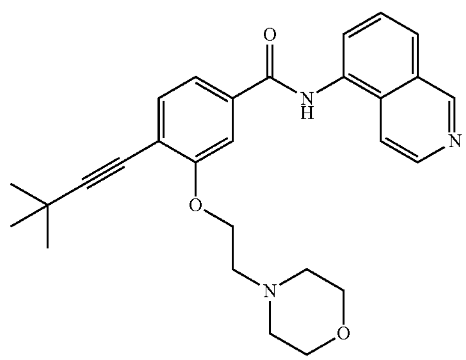 | 458.30 (457.58) | I | (d₆-DMSO) δ 10.54(1H, s), 9.35(1H, s), 8.52(1H, d), 8.15(1H, d), 7.85(1H, d), 7.82(1H, d), 7.75(1H, t), 7.68(1H, d), 7.65(1H, d), 7.45(1H, d), 4.25(2H, t), 3.58(4H, t), 2.78(2H, t), 2.58(4H, m), 1.45(9H, s) | 69 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 61 | 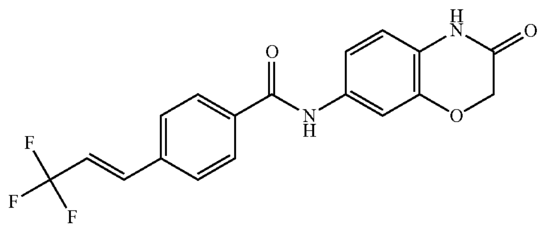 | 363.30 (362.31) | C | (d₆-DMSO) δ 10.69(1H, s), 10.24(1H, s), 7.98(2H, d), 7.84(2H, d), 7.48-7.34(3H, m), 6.96-6.85(2H, m), 4.57(2H, s). | 10 |
| 62 | 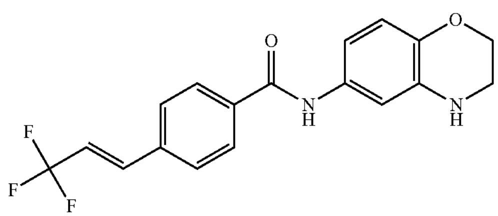 | 349.10 (348.33) | C | (d₆-DMSO) δ 9.95(1H, s), 7.96(2H, d), 7.82(2H, d), 7.42(1H, dd), 7.11(1H, d), 6.94-6.88(1H, m), 6.80(1H, dd), 6.59(1H, d), 5.86(1H, brs), 4.09(2H, t), 3.27(2H, t). | 14 |
| 63 | 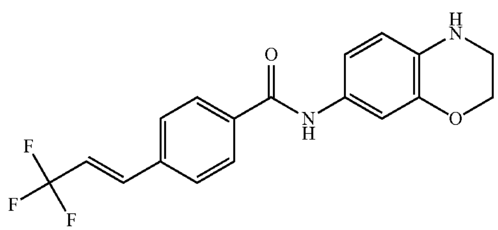 | 348.70 (348.33) | C | (d₆-DMSO) δ 9.94(1H, s), 7.95(2H, d), 7.82(2H, d), 7.41(1H, dd), 7.15(1H, d), 7.06(1H, dd), 6.91(1H, dd), 6.52(1H, d), 5.62(1H, s), 4.12(2H, t), 3.32-3.24(2H, m). | 123 |
| 64 | 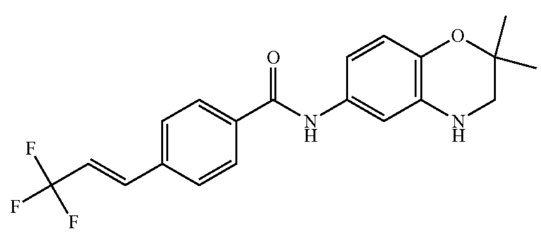 | 376.70 (376.38) | C | (d₆-DMSO) δ 9.95(1H, s), 7.96(2H, d), 7.44-7.39(1H, m), 7.13(1H, d), 6.94-6.88(1H, m), 6.81(1H, dd), 6.56(1H, d), 5.96(1H, brs), 2.98(2H, d), 1.23(6H, s) | 10 |

TABLE 1-continued

AMIDE COMPOUNDS

| ID | STRUCTURE | MS observed (calcd) | Method of Synth. | $^1$H NMR | Low pH % Inhib. @ 0.3 μM |
|---|---|---|---|---|---|
| 65 | (isoquinolin-5-yl amide of 3-ethoxy-4-(3,3-dimethylbut-1-ynyl)benzamide) | 372.90 (372.47) | I | (d$_6$-DMSO) δ 10.54(1H, s), 9.45(1H, s), 8.52(1H, d), 8.15(1H, d), 7.95(1H, d), 7.90(1H, d), 7.75(1H, t), 7.65(2H, m), 7.45(1H, d), 4.22(2H, q), 1.45(3H, t), 1.35(9H, s) | 109 |
| 66 | (isoquinolin-5-yl amide of 2-chloro-6-(3,3-dimethylbut-1-ynyl)nicotinamide) | 364.20 (363.85) | I | (d$_6$-DMSO) δ 10.85(1H, s), 9.4(1H, s), 8.27(1H, d), 8.15(1H, m), 8.05(2H, d), 7.88(2H, m), 7.75(1H, t), 1.8(9H, s) | 10 |
| 67 | (3,3-dimethyl-1-(2-morpholinoethyl)indolin-6-yl amide of 4-(3,3-dimethylbut-1-ynyl)benzamide) | | F | (d$_6$-DMSO): δ 10.25(s, 1H), 8.13(br s, 1H), 7.94(d, 2H, J=8.4Hz), 7.47(d, 2H, J=8.4Hz), 7.62-7.47(m, 1H), 7.18(d, 1H, J=8.4Hz), 4.26(t, 2H, J=5.2Hz), 3.73(s, 2H), 3.54(s, 4H), 2.65(s, 2H), 2.44(d,4H, J=4.4Hz), 1.31(s, 9H), 1.28(s, 6H). | 8 |

TABLE 1-continued

AMIDE COMPOUNDS

| ID | STRUCTURE | MS observed (calcd) | Method of Synth. | $^1$H NMR | Low pH % Inhib. @ 0.3 μM |
|---|---|---|---|---|---|
| 68 | 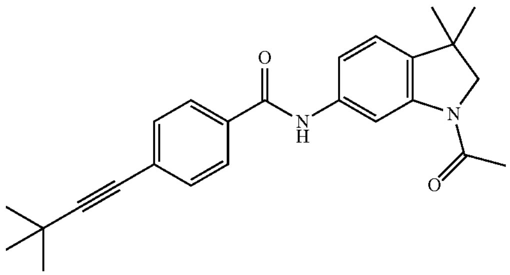 | 389.20 (388.51) | F | (d$_6$-DMSO) δ 10.26(s, 1H), 8.36(d, 1H, J=2.0Hz), 7.94(d, 2H, J=8.4Hz), 7.55(dd, 1H, J=8.4, 2.0Hz), 7.47(d, 2H, J=8.4Hz), 7.19(d, 1H, J=8.4Hz), 3.86(s, 2H), 2.16(s, 3H), 1.31(s, 9H), 1.30(s, 6H). | 140 |
| 69 | 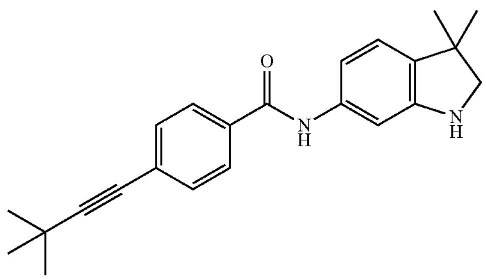 | 347.20 (346.48) | See "Prepn. of amido compd.s" | (d$_6$-DMSO) δ 9.97(s, 1H), 7.90(d, 2H, J=8.4Hz), 7.47(d, 2H, J=8.4Hz), 7.04(s, 1H), 6.90(s, 2H), 5.55(s, 1H), 3.17(s, 2H), 1.31(s, 9H), 1.21(s, 6H). | 103 |
| 70 | 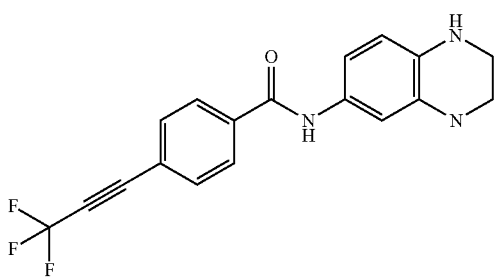 | 345.10 (346.31) | same as Compd. 112 | (d$_6$-DMSO) δ 10.07(s, 1H), 8.01(d, 2H, J=8.4Hz), 7.87(d, 2H, J=8.4Hz), 7.15(d, 1H, J=2.0Hz), 7.07(dd, 1H, J=8.4, 2.0Hz), 6.52(d, 1H, J=8.4Hz), 5.65(s, 1H), 4.12(t, 2H, J=4.4Hz), 3.26(m, 2H). | 185 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 71 | 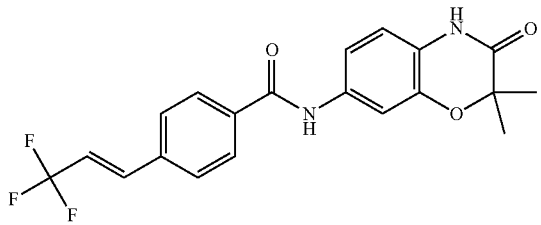 | 391.40 (390.37) | C | (d6-DMSO) δ 10.59(1H, s), 10.23(1H, s), 7.97(2H, d), 7.84(2H, d), 7.48(1H, d), 7.45-7.40(1H, m), 7.33(1H, dd), 6.96-6.84(2H, m)), 1.40(6H, s). | 10 |
| 72 | 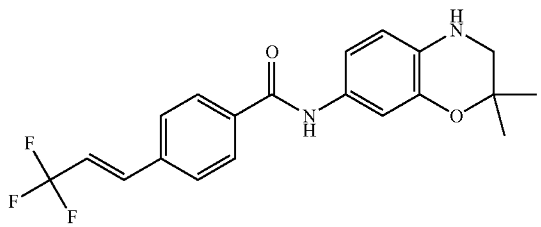 | 377.00 (376.38) | C | (d₆-DMSO) δ 9.92(1H, s), 7.94(2H, d), 7.82(2H, d), 7.42(1H, dd), 7.12(1H, d), 7.03(1H, dd), 6.91(1H, dd), 6.54(1H, d), 5.73(1H, t), 2.91(2H, d), 1.24(6H, s). | 124 |
| 73 | 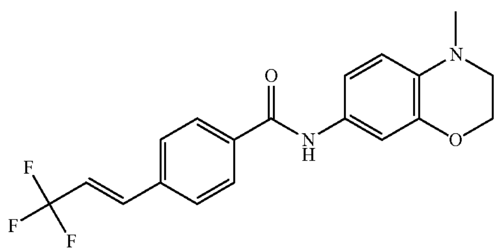 | 363.30 (362.35) | C | d₆-DMSO δ 10.01(1H, s), 7.96(2H, d), 7.83(2H, d), 7.41(1H, dd), 7.19-7.17(2H, m), 6.92(1H, dd), 6.67(1H, dd), 4.24(2H, t), 3.18(2H, t), 2.80(3H, s). | 94 |
| 74 | 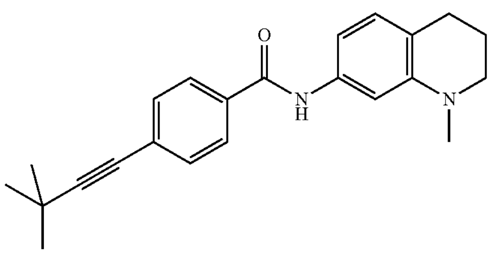 | 347.20 (346.48) | A | | 119 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 75 | 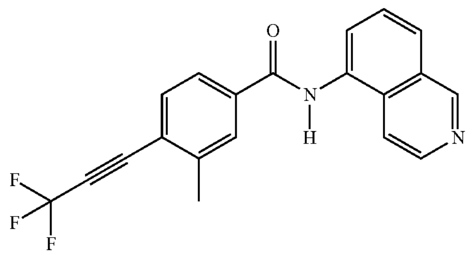 | 355.10 (354.33) | same as Compd. 112 | | 102 |
| 76 | 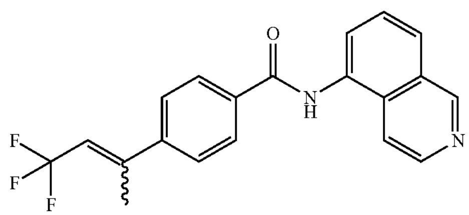 | 357.20 (356.35) | E | (d$_6$-DMSO) δ 10.61(s, 1H), 9.37(s, 1H), 8.53(d, 1H, J=6.0Hz), 8.16-7.65(m, 8H), 6.37(q, 1H, J=8.8Hz), 2.07(s, 3H). | 88 |
| 77 | 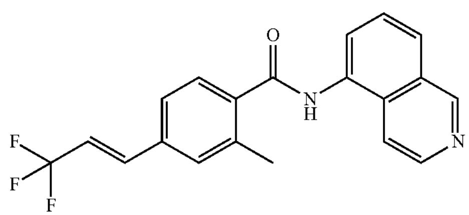 | 357.20 (356.35) | E | (d$_6$-DMSO) δ 10.53(s, 1H), 9.36(s, 1H), 8.55(d, 1H, J=5.6Hz), 8.04(d, 1H, J=8.0Hz), 8.02(s, 1H), 7.95(d, 1H, J=5.6Hz), 7.80-7.65(m, 4H), 7.42-7.35(m, 1H), 6.88(dq, 1H, J=16.4, 6.8Hz), 2.50(s, 3H). | 90 |
| 78 | 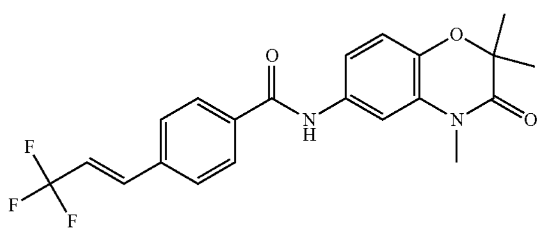 | 405.20 (404.39) | C | (d$_6$-DMSO) δ 10.31(1H, s), 8.00(2H, d), 7.86(2H, d), 7.64(1H, d), 7.46-7.41(2H, m), 6.98-6.89(2H, m), 3.28(3H, s), 1.40(6H, s). | 32 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 79 | 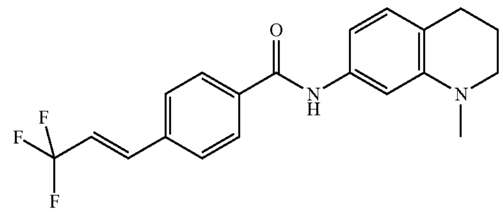 | 361.30 (360.38) | A | | 98 |
| 80 | 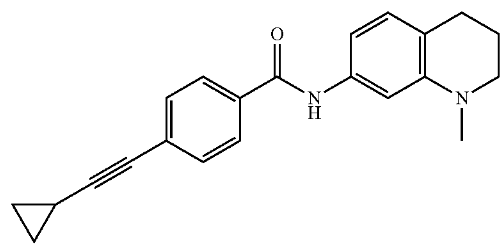 | 331.30 (330.43) | A | | 92 |
| 81 | 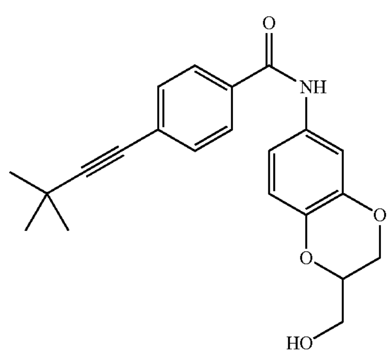 | 366.00 (365.43) | B | | 98 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 82 | *structure* | 366.00 (365.43) | B | | 76 |
| 83 | *structure* | 391.30 (390.41) | C | (d$_6$-DMSO) δ 10.00(1H, s), 7.98(2H, d), 7.83(2H, d), 7.44-7.40(1H, m), 7.17(1H, d), 7.01(1H, dd), 6.95-6.89(1H, m), 6.60(1H, d), 2.98(2H, s), 2.86(3H, s), 1.26(6H, s). | |
| 84 | *structure* | 377.10 (376.34) | C | (d$_6$-DMSO) δ 10.31(1H, s), 8.01(2H, d), 7.86(2H, d), 7.65(1H, d), 7.45-7.41(2H, m), 7.01-6.91(2H, m), 4.64(2H, s), 3.27(3H, s). | 45 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 85 | 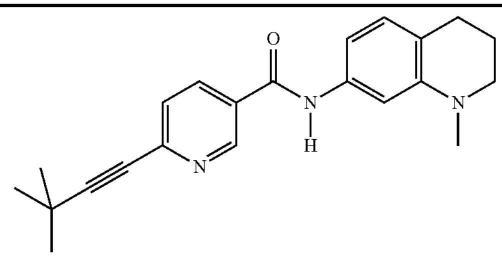 | 348.10 (347.46) | D | | 34 |
| 86 | 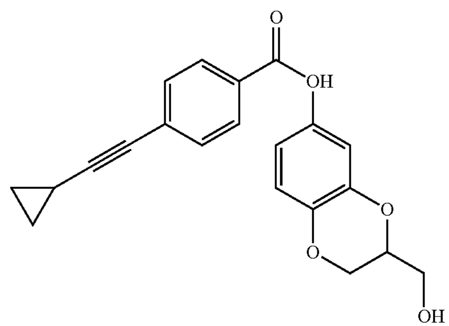 | 350.10 (349.39) | B | | 83 |
| 87 | 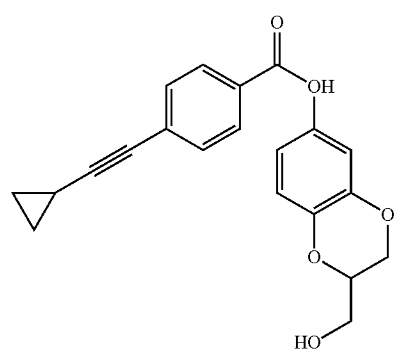 | 350.10 (349.39) | B | | 98 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 88 | 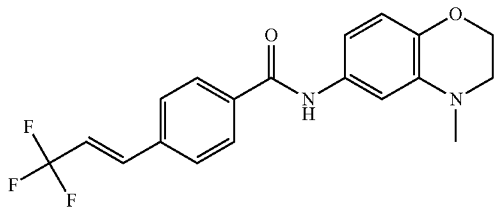 | 363.10 (362.35) | C | d₆-DMSO) δ 10.01(1H, s), 7.98(2H, d), 7.83(2H, d), 7.44-7.40(1H, m), 7.15(1H, d), 7.01(1H, dd), 6.95-6.89(1H, m), 6.62(1H, d), 4.22-4.19(2H, m), 3.25-3.22(2H, m), 2.82(3H, s), | 48 |
| 89 | 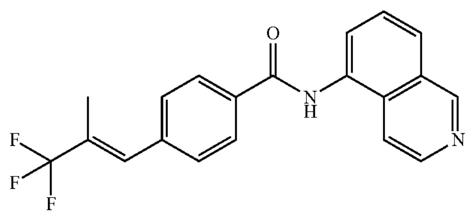 | 357.10 (356.35) | E | (d₆-DMSO) δ 10.61(s, 1H), 9.37(s, 1H), 8.53(d, 1H, J=6.0Hz), 8.15(d, 2H, J=8.0Hz), 8.07(d, 1H, J=8.4Hz), 7.92(d, 1H, J=6.8Hz), 7.86(d, 1H, J=6.0Hz), 7.74(t, 1H, J=8.0Hz), 7.67(d, 2H, J=8.0Hz), 7.29(s, 1H), 2.07(s, 3H). | 92 |
| 90 | 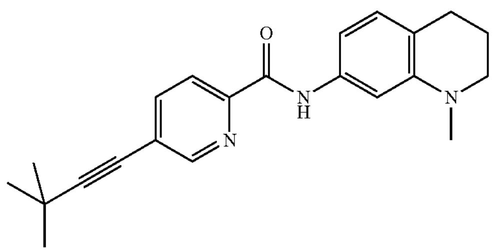 | 348.20 (347.46) | D | | |
| 91 | 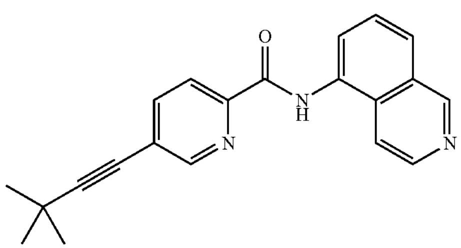 | 330.31 (329.41) | B | (d₆-DMSO) δ 10.99(s, 1H) 9.37(s, 1H) 8.75(dd, 1H) 8.55(d, 1H) 8.17-8.13(m, 1H) 8.09-8.03(m, 3H) 7.79-7.71(m, 2H) 1.35(s, 9H) | 21 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 92 | 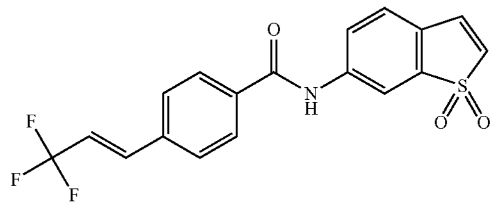 | 380.10 (379.36) | J | (d₆-DMSO) δ 10.75(1H, s), 8.28(1H, s), 8.04-8.00(3H, m), 7.89(2H, d), 7.63-7.59(2H, m), 7.47-7.42(1H, m), 7.32(1H, d), 6.96(1H, dd). | 71 |
| 93 | 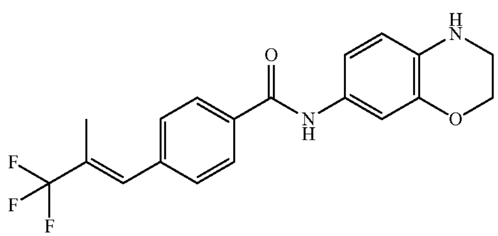 | 363.40 (362.35) | D | (d₆-DMSO) δ 9.95(s, 1H), 7.97(d, 2H, J=8.4Hz), 7.59(d, 2H, J=8.4Hz), 7.24(s, 1H), 7.15(d, 1H, J=2.4Hz), 7.07(dd, 1H, J=8.4, 2.4Hz), 6.52(d, 1H, J=8.4Hz), 5.62(s, 1H), 4.12(t, 2H, J=4.4Hz), 3.25(m, 2H), 2.04(s, 3H). | 105 |
| 94 | 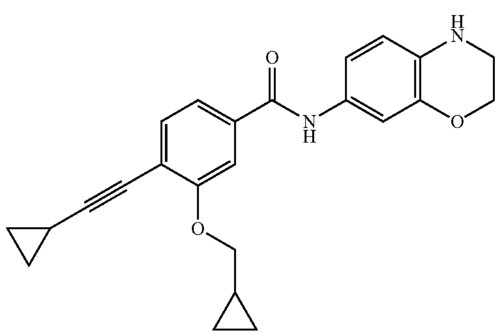 | 389.20 (388.47) | I | (CDCl₃) δ 7.55(1H, s), 7.42(2H, m), 7.13(1H, d), 7.05(1H, s), 7.03(1H, d), 6.65(1H, d), 4.25(2H, m), 3.95(2H, d), 3.71(1H, s), 3.42(2H, m), 1.44(1H, m), 1.25(1H, m), 0.95-0.85(4H, m), 0.63(2H, dd), 0.43(2H, dd) | 85 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 95 | (structure) | 337.30 (336.40) | same as Compd. 112 | (d$_6$-DMSO) δ 1.34(s, 9H); 3.26(brs, 2H); 4.13(brs, 2H); 5.71(s, 1H); 6.54(d, J=8.3Hz, 1H); 7.03(dd, J=8.3, 2.4Hz, 1H); 7.13(d, J=2.4Hz, 1H); 9.17(s, 2H);10.23(s, 1H). | 102 |
| 96 | (structure) | 363.40 (362.35) | D | (d$_6$-DMSO) δ 9.94(s, 1H), 7.95(d, 2H, J=8.4Hz), 7.71(d, 2H, J=8.4Hz), 7.15(d, 1H, J=2.4Hz), 7.07(dd, 1H, J=8.8, 2.4Hz), 6.52(d, 1H, J=8.8Hz), 6.32(q, 1H, J=9.2Hz), 5.61(s, 1H),4.12(t, 2H, J=4.4Hz), 3.26(m, 2H), 2.30(m, 3H). | 99 |
| 97 | (structure) | 380.00 (379.34) | B | | 101 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 98 | 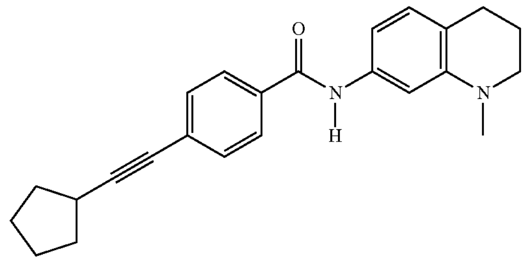 | 359.30 (358.49) | same as Compd. 112 | (d₆-DMSO) δ 9.96(s, 1H), 7.91(d, 2H, J=8.4Hz), 7.48(d, 2H, J=8.4Hz), 7.00(m, 2H), 6.82(d, 1H, J=8.4Hz), 3.18(t, 2H, J=5.6Hz), 2.90(m, 1H), 2.82(s, 3H), 2.65(t, 2H, J=6.0Hz), 2.05-1.95(m,2H), 1.91-1.84(m, 2H), 1.74-1.55(m, 6H). | 78 |
| 99 | 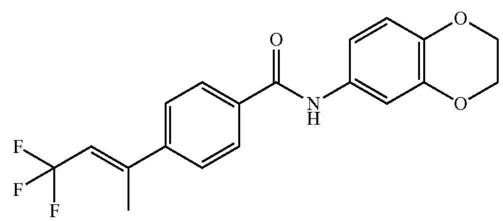 | 364.40 (363.34) | D | (d₆-DMSO) δ 10.14(s, 1H), 7.97(d, 2H, J=8.4Hz), 7.74(d, 2H, J=8.4Hz), 7.39(d, 1H, J=2.4Hz), 7.20(dd, 1H, J=8.8, 2.4Hz), 6.82(d, 1H, J=8.8Hz), 6.33(q, 1H, J=8.8Hz), 4.26-4.20(m, 4H), 2.30(m, 3H). | 94 |
| 100 | 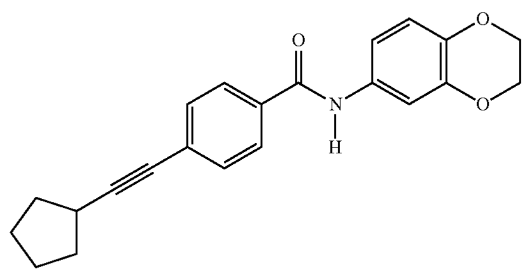 | 348.00 (347.42) | same as Compd. 112 | (d₆-DMSO) δ 10.10(s, 1H), 7.90(d, 2H, J=8.4Hz), 7.49(d, 2H, J=8.4Hz), 7.37(d, 1H, J=2.4Hz), 7.19(dd, 1H, J=8.8, 2.4Hz), 6.81(d, 1H, J=8.8Hz), 4.26-4.19(m, 4H), 2.89(m,1H), 2.02-1.95(m, 2H), 1.75-1.55(m, 6H). | 42 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 101 | 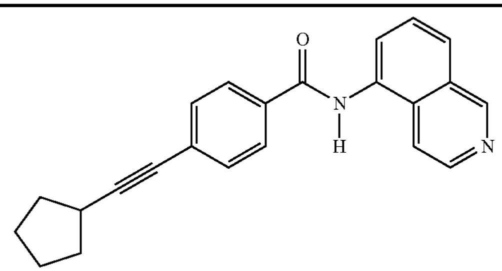 | 341.10 (340.43) | same as Compd. 112 | (d$_6$-DMSO) δ 10.57(s, 1H), 9.36(s, 1H), 8.52(d, 1H, J=6.0Hz), 8.07-8.04(m, 3H), 7.89(d, 1H, J=8.0Hz), 7.83(d, 1H, J=6.0Hz), 7.73(t, 1H, J=8.0Hz), 7.55(d, 2H, J=8.4Hz), 2.92(m,1H), 2.05-1.95(m, 2H), 1.75-1.55(m, 6H). | 94 |
| 102 | 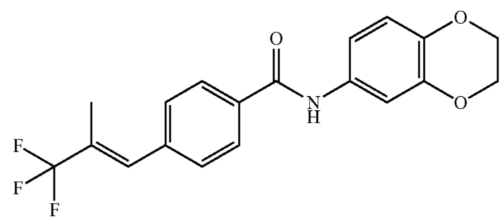 | 364.40 (363.34) | D | (d$_6$-DMSO) δ 10.15(s, 1H), 7.98(d, 2H, J=8.4Hz), 7.61(d, 2H, J=8.4Hz), 7.39(d, 1H, J=2.4Hz), 7.25(s, 1H), 7.20(dd, 1H, J=8.8, 2.4Hz), 6.83(d, 1H, J=8.8Hz), 4.26-4.20(m, 4H), 2.04(s, 3H). | 91 |
| 103 | 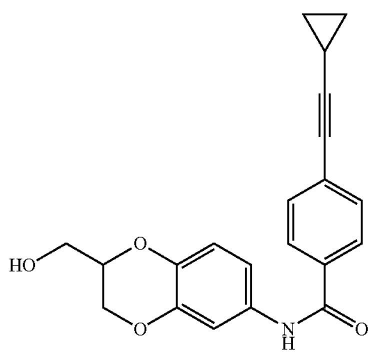 | 349.90 (349.39) | B | | 92 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 104 | 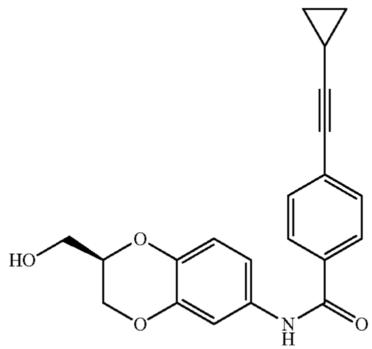 | 350.20 (349.39) | B | | 91 |
| 105 | 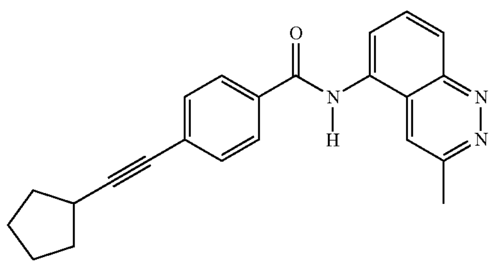 | 356.20 (355.44) | same as Compd. 112 | (d₆-DMSO) δ 10.63(s, 1H), 8.34(dt, 1H, J=8.0, 1.2Hz), 8.08-8.04(m, 3H), 7.94(dd, 1H, J=7.6, 1.2Hz), 7.90(t, 1H, J=7.6Hz), 7.58-7.54(m, 2H), 2.93(m, 1H), 2.88(s, 3H), 2.05-1.95(m, 2H),1.75-1.55(m, 6H). | |
| 106 | 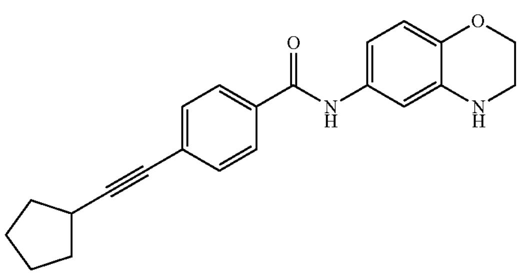 | 347.36 (346.43) | same as Compd. 112 | (d₆-DMSO) δ 9.92(s, 1H), 7.88(d, 2H, J=8.4Hz), 7.47(d, 2H, J=8.4Hz), 7.11(d, 1H, J=2.4Hz), 6.78(dd, 1H, J=8.4, 2.4Hz), 6.58(d, 1H, J=8.4Hz), 5.86(s, 1H), 4.08(t, 2H, J=4.4Hz), 3.26(m,1H), 2.89(m, 1H), 2.04-1.94(m, 2H), 1.74-1.55(m, 6H). | 5 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 107 | 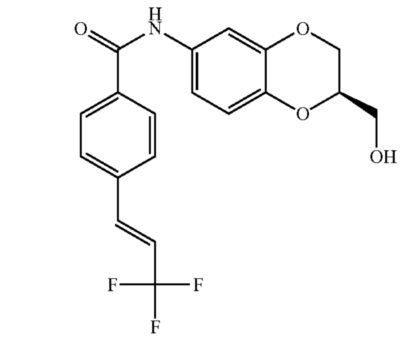 | 380.10 (379.34) | A | | 116 |
| 108 | 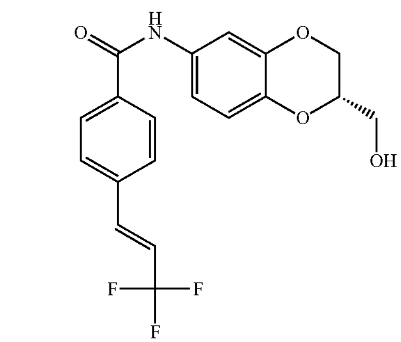 | 380.00 (379.34) | A | | 116 |
| 109 | 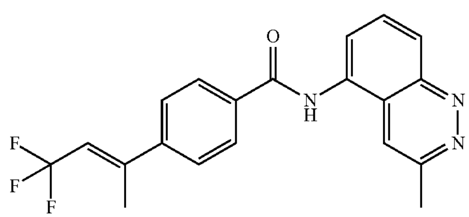 | 372.30 (371.37) | E | (d$_6$-DMSO) δ 10.66(s, 1H), 8.35(dt, 1H, J=8.4, 1.2Hz), 8.14(d, 2H, J=8.4Hz), 8.07(s, 1H), 7.96(dd, 1H, J=7.6, 1.2Hz), 7.91(t, 1H, J=8.0Hz), 7.80(d, 2H, J=8.4Hz), 6.37(q, 1H, J=8.8Hz), 2.89(s, 3H), 2.34(m, 3H). | |

TABLE 1-continued

AMIDE COMPOUNDS

| ID | STRUCTURE | MS observed (calcd) | Method of Synth. | ¹H NMR | Low pH % Inhib. @ 0.3 µM |
|---|---|---|---|---|---|
| 110 | 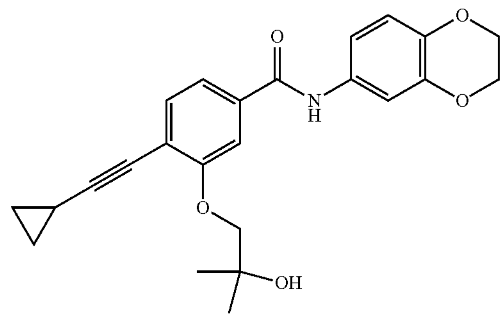 | 408.40 (407.47) | I | | 1 |
| 111 | 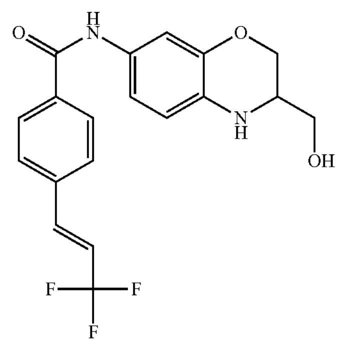 | 378.70 (378.35) | B | | 116 |
| 112 | 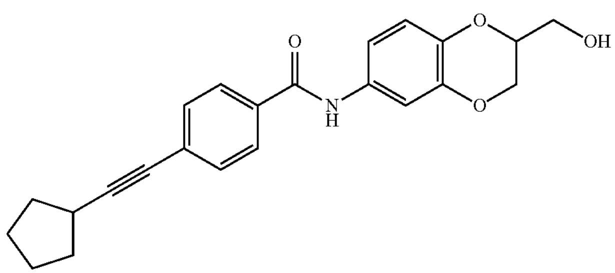 | 378.00 (377.44) | See "Prepn. of amido compd.s" | (d₆-DMSO) δ 10.10(s, 1H), 7.89(d, 2H, J=8.4Hz), 7.49(d, 2H, J=8.4Hz), 7.38(d, 1H, J=2.4Hz), 7.20(dd, 1H, J=8.4, 2.4Hz), 6.83(d, 1H, J=8.4Hz), 5.05(t, 1H, J=5.6Hz), 4.32(dd, 1H, J=11.2,2.4Hz), 4.13(m, 1H), 3.99(dd, 1H, J=11.2, 7.6Hz), 3.68-3.56(m, 2H), 2.89(m, 1H), 2.04-1.94(m, 2H), 1.77-1.54(m, 6H). | 88 |

TABLE 1-continued

AMIDE COMPOUNDS

| ID | STRUCTURE | MS observed (calcd) | Method of Synth. | $^1$H NMR | Low pH % Inhib. @ 0.3 μM |
|---|---|---|---|---|---|
| 113 | (phthalazine-methyl linked via amide to phenyl-CH=CH-CF$_3$) | 358.30 (357.34) | E | (d$_6$-DMSO) δ 10.65(s, 1H), 8.35(dt, 1H, J=8.4, 1.2Hz), 8.14(d, 2H, J=8.4Hz), 8.09(s, 1H), 7.97(dd, 1H, J=7.6, 1.2Hz), 7.91(dd, 1H, J=8.4, 7.6Hz), 7.90(d, 2H, J=8.4Hz), 7.50-7.44(m, 1H), 6.97(dq, 1H, J=16.4, 7.2Hz), 2.89(s, 3H). | 9 |
| 114 | (isoquinoline-methyl linked via amide to phenyl-CH=CH-CF$_3$) | 357.20 (356.35) | E | (d$_6$-DMSO) δ 10.51(s, 1H), 9.27(s, 1H), 8.14(d, 2H, J=8.4Hz), 8.01(d, 1H, J=8.4Hz), 7.90(d, 2H, J=8.4Hz), 7.85(d, 1H, J=7.6Hz), 7.69(s, 1H), 7.63(t, 1H, J=8.0Hz), 7.50-7.44(m, 1H), 6.97(dq, 1H, J=16.4, 7.2Hz), 2.62(s, 3H). | 90 |
| 115 | (quinoxaline linked via amide to phenyl-CH=CH-CF$_3$) | 344.30 (343.31) | E | (d$_6$-DMSO) δ 10.80(s, 1H), 8.91(d, 1H, J=1.6Hz), 8.85(d, 1H, J=1.6Hz), 8.70(d, 1H, J=2.4Hz), 8.20(dd, 1H, J=9.2, 2.4Hz), 8.10(d, 1H, J=9.2Hz), 8.08(d, 2H, J=8.4Hz), 7.90(d, 2H, J=8.4Hz), 7.49-7.43(m, 1H), 6.97(dq, 1H, J=16.4, 7.2Hz). | 90 |
| 116 | (2-methoxymethyl-benzodioxine linked via amide to phenyl-C≡C-cyclopentyl) | 456.20 (455.53) | See "Prepn. of amido compd.s" | (d$_6$-DMSO) δ 10.16(s, 1H), 7.90(d, 2H, J=8.4Hz), 7.50(d, 2H, J=8.4Hz), 7.44(d, 1H, J=2.4Hz), 7.24(dd, 1H, J=8.8, 2.4Hz), 6.91(d, 1H, J=8.8Hz), 4.55-4.35(m, 4H),4.07(dd, 1H, J=11.6, 6.8Hz), 3.26(s, 3H), 2.90(m, 1H), 2.04-1.93(m, 2H), 1.73-1.52(m, 6H). | 10 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 117 | 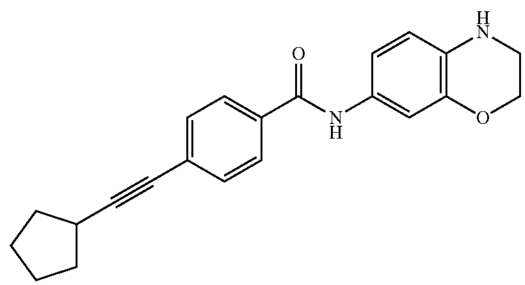 | 347.10 (346.43) | See "Prepn. of amido compds." | | 98 |
| 118 | 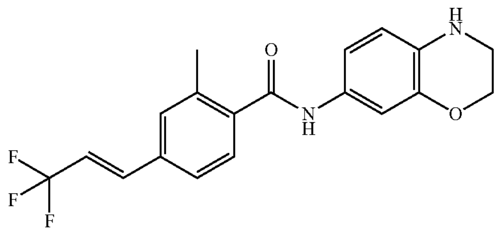 | 363.40 (362.35) | D | (d$_6$-DMSO) δ 9.93(s, 1H), 7.63(s, 1H), 7.59(d, 1H, J=8.0Hz), 7.44(d, 1H, J=8.0Hz), 7.37-7.31(m, 1H), 7.11(d, 1H, J=2.4Hz), 7.01(dd, 1H, J=8.8, 2.4 Hz), 6.82(dq, 1H, J=16.4, 7.2Hz), 6.50(d, 1H, J=8.8Hz), 5.59(s, 1H), 4.11(t, 2H,J=4.4Hz), 3.24(m, 2H), 2.37(s, 3H). | 103 |
| 119 | 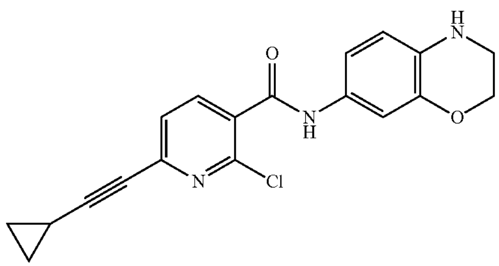 | 354.20 (353.81) | I | (d$_6$-DMSO) δ 10.25(1H, s), 7.9(1H, d), 7.55(1H, d), 7.15(1H, s), 6.95(1H, d), 6.55(1H, d), 5.78(1H, s), 4.25(2H, m), 3.35(2H, m), 1.85(1H, m), 1.05(2H, m), 0.95(2H, m) | |
| 120 | 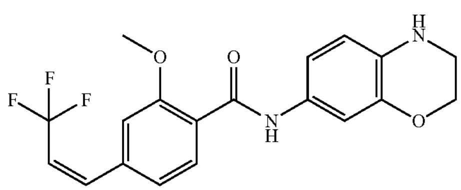 | 379.20 (378.35) | D | (d$_6$-DMSO) δ 9.77(s, 1H), 7.64(d, 1H, J=8.0Hz), 7.24(d, 1H, J=12.8Hz), 7.15(s, 1H), 7.13(d, 1H, J=2.0Hz), 7.08(d, 1H, J=8.0Hz), 7.01(dd, 1H, J=8.4, 2.4Hz), 6.50(d, 1H, J=8.4Hz), 6.18(dq, 1H, J=12.8, 9.6Hz), 5.59(s, 1H), 4.11(t, 2H,J=4.4Hz), 3.91(s, 3H), 3.25(m, 2H). | 19 |

TABLE 1-continued

AMIDE COMPOUNDS

| ID | STRUCTURE | MS observed (calcd) | Method of Synth. | $^1$H NMR | Low pH % Inhib. @ 0.3 μM |
|---|---|---|---|---|---|
| 121 | 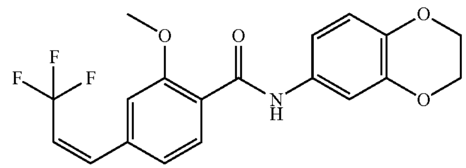 | 380.20 (379.34) | D | (d$_6$-DMSO) δ 9.78(s, 1H), 7.62(d, 1H, J=8.0Hz), 7.36(d, 1H, J=2.4Hz), 7.24(d, 1H, J=12.4Hz), 7.15(s, 1H), 7.13(dd, 1H, J=8.8, 2.4Hz), 7.08(d, 1H, J=8.0Hz), 6.80(d, 1H, J=9.2Hz), 6.19(dq, 1H, J=12.4, 9.2Hz), 4.22(m, 4H), 3.88(s, 3H). | 19 |
| 122 | 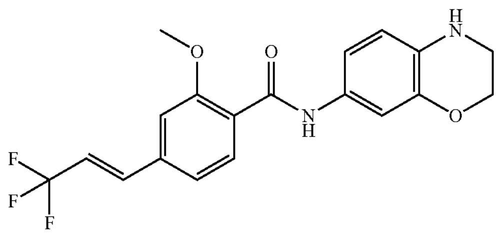 | 379.20 (378.35) | F | (d$_6$-DMSO) δ 9.76(s, 1H), 7.65(d, 1H, J=8.0Hz), 7.49(s, 1H), 7.42–7.33(m, 2H), 7.13(d, 1H, J=2.4Hz), 7.00(dd, 1H, J=8.4, 2.4Hz), 6.94(dq, 1H, J=16.4, 7.2Hz), 6.50(d, 1H, J=8.8Hz), 5.59(s, 1H), 4.11(t, 2H, J=4.4Hz), 3.94(s, 3H), 3.25(m, 2H). | 19 |
| 123 | 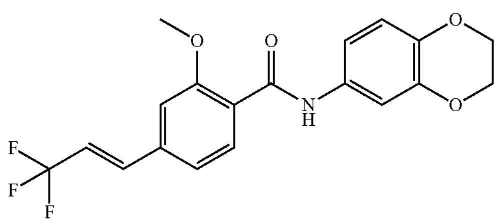 | 380.10 (379.34) | F | (d$_6$-DMSO) δ 9.97(s, 1H), 7.64(d, 1H, J=8.0Hz), 7.50(s, 1H), 7.43–7.34(m, 3H), 7.12(dd, 1H, J=8.8, 2.4Hz), 6.95(dq, 1H, J=16.4, 7.2Hz), 6.80(d, 1H, J=8.8Hz), 4.22(m, 4H), 3.93(s, 3H). | 19 |
| 124 | 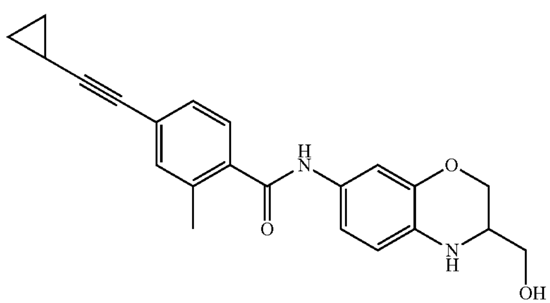 | 363.0 (362.43) | B | | 112 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 125 | 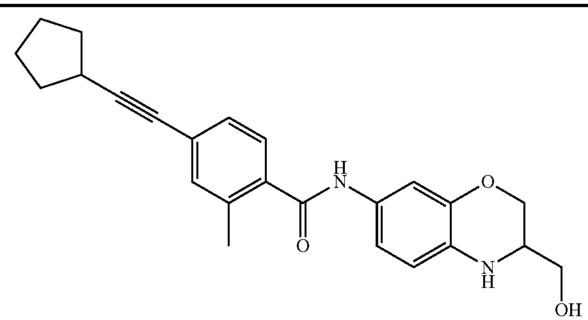 | 391.0 (390.49) | B | | 112 |
| 126 | 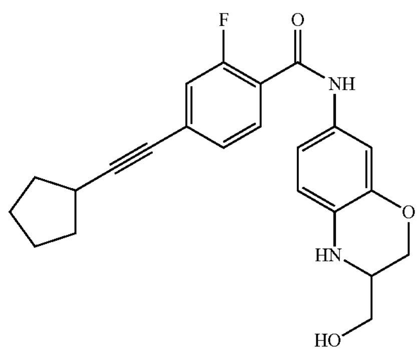 | 395.30 (394.45) | B | | 96 |
| 127 | 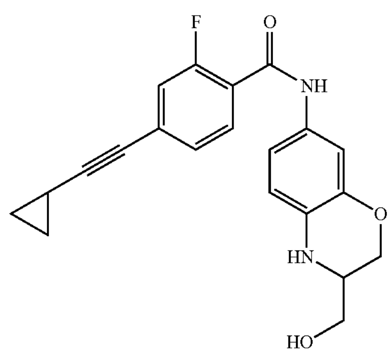 | 367.30 (366.40) | B | (d$_6$-DMSO) δ 10.00(s, 1H) 7.55(t, 1H) 7.32(dd, 1H) 7.27(dd, 1H) 7.09(d, 1H) 6.99(dd, 1H) 6.54(d, 1H) 5.7(s, 1H) 4.87(t, 1H) 4.11(dd 1H) 3.92(dd 1H) 3.45-3.27(m, 3H) 1.63-1.54(m, 1H) 0.96-0.896(m, 2H) 0.81-0.75(m, 2H) | 100 |

TABLE 1-continued

AMIDE COMPOUNDS

| ID | STRUCTURE | MS observed (calcd) | Method of Synth. | $^1$H NMR | Low pH % Inhib. @ 0.3 μM |
|---|---|---|---|---|---|
| 128 | 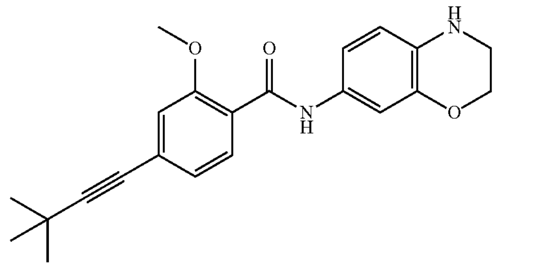 | 365.50 (364.45) | D | (d$_6$-DMSO) δ 9.71(s, 1H), 7.61(d, 1H, J=8.0Hz), 7.12(d, 1H, J=2.4Hz), 7.06(d, 1H, J=1.6Hz), 7.02(dd, 1H, J=8.0, 1.6Hz), 6.99(dd, 1H, J=8.4, 2.4Hz), 6.50(d, 1H, J=8.4Hz), 5.59(s, 1H), 4.11(t, 2H, J=4.4Hz), 3.91(s, 3H), 3.25(m, 2H), 1.31(s, 9H). | 12 |
| 129 | 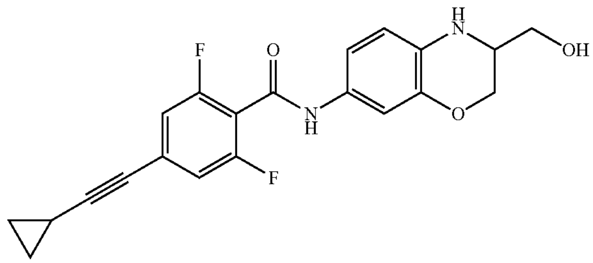 | 385.40 (384.39) | D | (d$_6$-DMSO) δ 10.36(s, 1H), 7.23(d, 2H, J=8.0Hz), 7.06(d, 1H, J=2.4Hz), 6.95(dd, 1H, J=8.4, 2.4Hz), 6.55(d, 1H, J=8.4Hz), 5.73(s, 1H), 4.86(t, 1H, J=5.2Hz), 4.11(dd, 1H, J=10.4, 2.0Hz), 3.92(dd, 1H, J=10.4, 6.0Hz), 3.43-3.32(m, 2H), 3.30(m, 1H),1.59(m, 1H), 0.96-0.91(m, 2H), 0.81-0.77(m, 2H). | 104 |
| 130 | 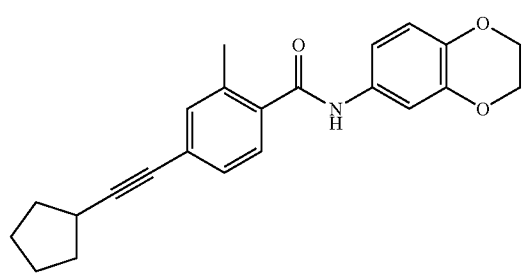 | 355.20 (354.36) | D | (d$_6$-DMSO) δ 10.36(s, 1H), 7.23(d, 2H, J=8.0Hz), 7.05(d, 1H, J=2.4Hz), 6.95(dd, 1H, J=8.4, 2.4Hz), 6.51(d, 1H, J=8.4Hz), 5.67(s, 1H), 4.11(t, 2H, J=4.4Hz), 3.25(m, 2H), 1.59(m, 1H), 0.96-0.91(m, 2H), 0.81-0.76(m, 2H). | 104 |

TABLE 1-continued

AMIDE COMPOUNDS

| ID | STRUCTURE | MS observed (calcd) | Method of Synth. | ¹H NMR | Low pH % Inhib. @ 0.3 µM |
|---|---|---|---|---|---|
| 131 | (structure) | 393.50 (392.38) | D | (d₆-DMSO) δ 9.93(s, 1H), 7.63(s, 1H), 7.59(d, 1H, J=8.0Hz), 7.44(d, 1H, J=8.0Hz), 7.34(m, 1H), 7.13(d, 1H, J=2.4Hz), 7.02(dd, 1H, J=8.4, 2.4Hz), 6.83(dq, 1H, J=16.4, 7.2Hz), 6.54(d, 1H, J=8.4Hz), 5.64(s, 1H), 4.86(t, 1H, J=5.2Hz), 4.11(dd, 1H,J=10.4, 2.0Hz), 3.92(dd, 1H, J=10.4, 5.6Hz), 3.44-3.32(m, 2H), 3.30(m, 1H), 2.37(s, 3H). | 104 |
| 132 | (structure) | 446.50 (445.56) | I | (d₆-DMSO) δ 10.25(1H, s), 7.45(2H, m), 7.35(2H, m), 7.15(1H, d), 6.85(1H, d), 4.25(2H, m), 4.05(1H, m), 3.65(2H, m), 3.55(2H, m), 2.65(1H, m) 2.35(3H, s), 2.1-1.95(2H, m), 1.85-1.5(6H, m), 1.5(1H, m), 1.45(2H, m), 1.25(2H, m) | |
| 133 | (structure) | 434.30 (433.55) | I | (d₆-DMSO) δ 10.25(1H, s), 7.45(2H, m), 7.35(2H, m), 7.15(1H, d), 6.85(1H, d), 4.25(2H, m), 4.05(1H, m), 3.65(2H, m), 3.55(2H, m), 2.45(3H, s), 1.85(9H, s), 1.5(1H, m), 1.45(2H, m), 1.25(2H, m). | |

TABLE 1-continued

AMIDE COMPOUNDS

| ID | STRUCTURE | MS observed (calcd) | Method of Synth. | $^1$H NMR | Low pH % Inhib. @ 0.3 µM |
|---|---|---|---|---|---|
| 134 | 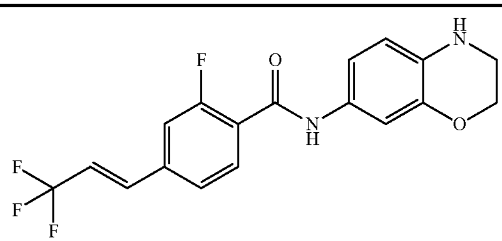 | 367.80 (366.32) | D | (d$_6$-DMSO) δ 10.04(s, 1H), 7.74(d, 1H, J=11.2Hz), 7.66(t, 1H, J=8.0Hz), 7.61(d, 1H, J=8.0Hz), 7.44-7.37(m, 1H), 7.10(d, 1H, J=2.4Hz), 7.00(dd, 1H, J=8.4, 2.4Hz), 6.96(m, 1H), 6.51(d, 1H, J=8.4Hz), 5.63(s, 2H), 4.11(t, 2H, J=4.4Hz), 3.25(m, 2H). | 108 |
| 135 | 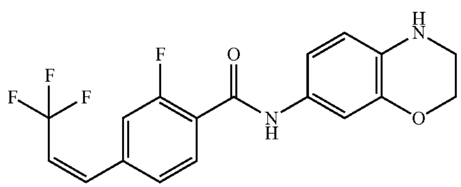 | 367.20 (366.32) | D | (d$_6$-DMSO) δ 10.06(s, 1H), 7.67(t, 1H, J=7.6Hz), 7.34-7.29(m, 2H), 7.25(d, 1H, J=12.8Hz), 7.10(d, 1H, J=2.4Hz), 7.01(dd, 1H, J=8.4, 2.4Hz), 6.51(d, 1H, J=8.4Hz), 6.25(dq, 1H, J=12.4, 9.2Hz), 5.63(s, 1H), 4.10(t, 2H, J=4.4Hz), 3.25(m, 2H). | 29 |
| 136 | 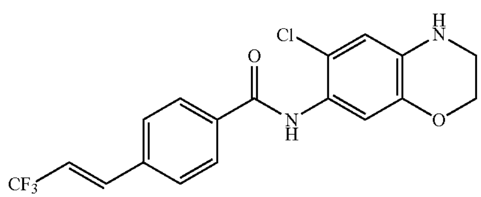 | 382.90 (382.77) | K | (d$_6$-DMSO) δ 9.80(1H, s), 7.99(2H, d), 7.82(2H, d), 7.42(1H, dd), 6.92(1H, dd), 6.78(1H, s), 6.67(1H, s), 6.09(1H, brs), 4.13(2H, t), 3.28(2H, t). | 50 |
| 137 | 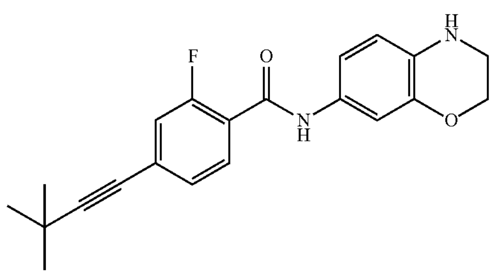 | 352.70 (352.41) | C | (d$_6$-DMSO) δ 9.98(1H, s), 7.57(1H, t), 7.32-7.25(2H, m), 7.08(1H, d), 6.99(1H, dd), 6.51(1H, d), 5.62(1H, brs), 4.11(2H, t), 3.24(2H, t), 1.30(9H, s). | 103 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 138 | (structure: N-(3-(hydroxymethyl)-3,4-dihydro-2H-benzo[b][1,4]oxazin-7-yl)-2-fluoro-4-(3,3-dimethylbut-1-yn-1-yl)benzamide) | 382.70 (382.44) | C | (d₆-DMSO) δ 9.99(1H, s), 7.57(1H, t), 7.32-7.25(2H, m), 7.09(1H, d), 6.99(1H, dd), 6.54(1H, d), 5.69(1H, brs), 4.86(1H, t), 4.12(1H, dd), 3.91(1H, dd), 3.43-3.28(3H, m), 1.30(9H, s). | 107 |
| 139 | (structure: N-(3,4-dihydro-2H-benzo[b][1,4]oxazin-6-yl)-4-(cyclopentylethynyl)-2-methylbenzamide) | 360.90 (360.46) | C | (d₆-DMSO) δ 9.88(1H, s), 7.34(1H, d), 7.28(1H, s), 7.25-7.23(1H, m), 7.09(1H, d), 7.00(1H, dd), 6.49(1H, d), 5.57(1H, brs), 4.10(2H, t), 3.26-3.23(2H, m), 2.89-2.73(1H, m), 2.32(3H, s), 1.99-1.97(2H, m), 1.73-1.70(2H, m), 1.63-1.56(4H, m). | 95 |
| 140 | (structure: N-(2,3-dihydrobenzo[b][1,4]dioxin-6-yl)-4-(cyclopentylethynyl)-2-methylbenzamide) | 361.90 (361.44) | C | (d₆-DMSO) δ 10.12(1H, s), 7.38-7.25(4H, m), 7.12(1H, dd), 6.79(1H, d), 4.23-4.20(4H, m), 2.89-2.85(1H, m), 2.33(3H, s), 2.02-1.95(2H, m), 1.73-1.68(2H, m), 1.65-1.55(4H, m). | 33 |

TABLE 1-continued

AMIDE COMPOUNDS

| ID | STRUCTURE | MS observed (calcd) | Method of Synth. | $^1$H NMR | Low pH % Inhib. @ 0.3 µM |
|---|---|---|---|---|---|
| 141 | 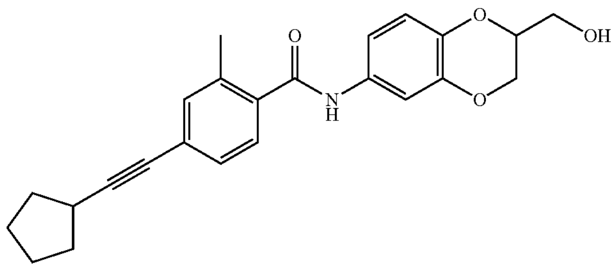 | 392.00 (391.47) | C | (d$_6$-DMSO) δ 10.12(1H, s), 7.38-7.35(2H, m), 7.30(1H, s), 7.26(1H, d), 7.13(1H, dd), 6.83-6.81(1H, m), 5.06-5.03(1H, m), 4.31(1H, dd), 4.12-4.10(1H, m), 4.01-3.96(1H, m), 3.66-3.58(2H, m), 2.89-2.85(1H, m), 2.33(3H,s), 2.02-1.95(2H, m), 1.73-1.67(2H, m), 1.65-1.55(4H, m). | 87 |
| 142 | 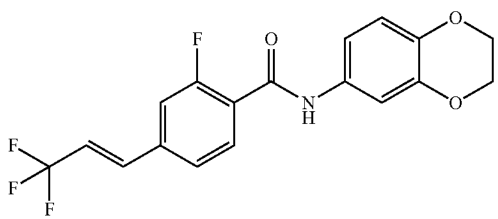 | 368.10 (367.30) | D | (d$_6$-DMSO) δ 10.27(s, 1H), 7.76(d, 1H, J=10.4Hz), 7.69(t, 1H, J=8.0Hz), 7.63(dd, 1H, J=8.0, 1.2Hz), 7.45-7.37(m, 1H), 7.33(d, 1H, J=2.8Hz), 7.12(dd, 1H, J=8.8, 2.8Hz), 6.98(dq, 1H, J=16.4, 7.2Hz), 6.82(d, 1H, J=8.8Hz), 4.23(m, 4H). | 70 |
| 143 | 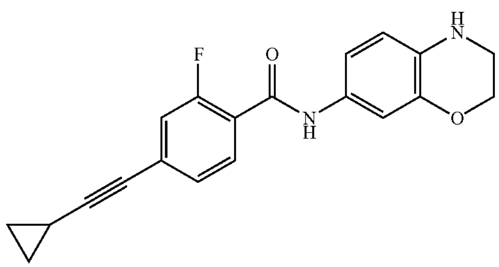 | 337.80 (336.37) | D | (d$_6$-DMSO) δ 9.98(s, 1H), 7.55(t, 1H, J=7.6Hz), 7.31(dd, 1H, J=11.2, 1.6Hz), 7.26(dd, 1H, J=8.0, 1.6Hz), 7.08(d, 1H, J=2.4Hz), 6.99(dd, 1H, J=8.4, 2.4Hz), 6.50(d, 1H, J=8.4Hz), 5.62(s, 1H), 4.11(t, 2H, J=4.4Hz), 3.25(m, 2H), 1.58(m, 1H), 0.96-0.90(m,2H), 0.80-0.75(m, 2H). | 100 |
| 144 | 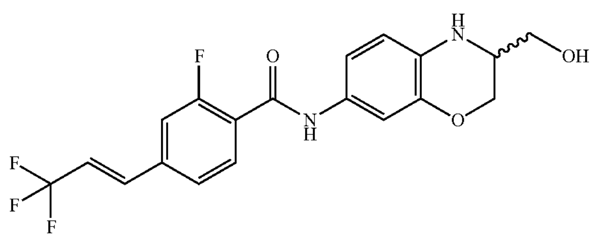 | 397.20 (396.34) | D | (d$_6$-DMSO) δ 10.04(s, 1H), 7.74(d, 1H, J=11.2Hz), 7.66(t, 1H, J=8.0Hz), 7.61(d, 1H, J=8.0Hz), 7.41(m, 1H), 7.11(d, 1H, J=2.4Hz), 7.01(dd, 1H, J=8.4, 2.4Hz), 6.97(m, 1H), 6.55(d, 1H, J=8.4Hz), 5.69(s, 1H), 4.86(t, 1H, J=5.2Hz), 4.12(dd, 1H, J=10.4, 2.4Hz),3.92(dd, 1H, J=10.4, 5.6Hz), 3.45-3.32(m, 2H), 3.30(m, 1H). | 105 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 145 | 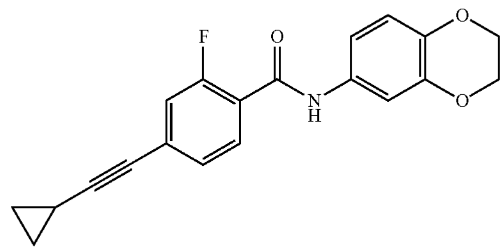 | 338.40 (337.35) | D | (d₆-DMSO) δ 10.22(s, 1H), 7.58(t, 1H, J=7.6Hz), 7.34(dd, 1H, J=11.2, 1.6Hz), 7.31(d, 1H, J=2.4Hz), 7.28(dd, 1H, J=8.0, 1.6Hz), 7.10(dd, 1H, J=8.8, 2.4Hz), 6.81(d, 1H, J=8.8Hz), 4.22(m, 4H), 1.58(m, 1H), 0.96-0.90(m, 2H), 0.80-0.76(m, 2H). | 41 |
| 146 | 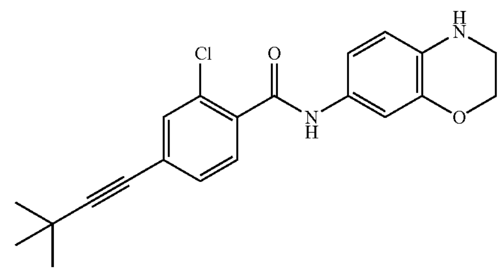 | 369.20 (368.87) | D | (d₆-DMSO) δ 10.09(s, 1H), 7.49(d, 1H, J=1.6Hz), 7.47(d, 1H, J=8.0Hz), 7.38(dd, 1H, J=8.0, 1.6Hz), 7.08(d, 1H, J=2.4Hz), 6.98(dd, 1H, J=8.4, 2.4Hz), 6.50(d, 1H, J=8.4Hz), 5.62(s, 1H), 4.11(t, 2H, J=4.4Hz), 3.25(m, 2H), 1.30(s, 9H). | 93 |
| 147 | 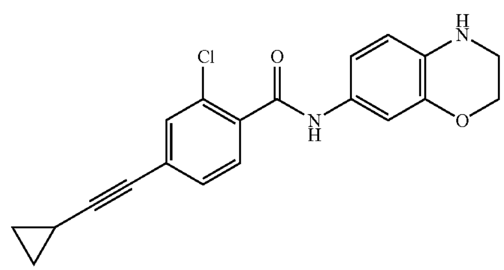 | 352.80 (352.82) | D | (d₆-DMSO) δ 10.08(s, 1H), 7.51(d, 1H, J=1.6Hz), 7.46(d, 1H, J=7.6Hz), 7.38(dd, 1H, J=7.6, 1.6Hz), 7.07(d, 1H, J=2.4Hz), 6.98(dd, 1H, J=8.4, 2.4Hz), 6.50(d, 1H, J=8.4Hz), 5.61(s, 1H), 4.10(t, 2H, J=4.4Hz), 3.25(m, 2H), 1.57(m, 1H), 0.95-0.88(m, 2H), 0.80-0.75(m, 2H). | 88 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 148 | 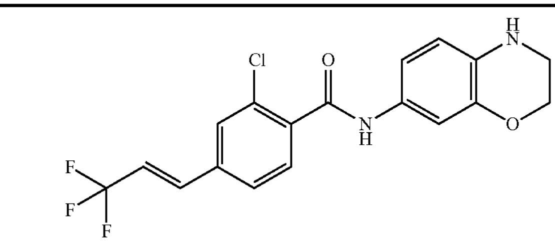 | 382.90 (382.77) | D | (d₆-DMSO) δ 10.12(s, 1H), 7.93(d, 1H, J=1.2Hz), 7.75(dd, 1H, J=8.0, 1.2Hz), 7.58(d, 1H, J=8.0Hz), 7.43-7.37(m, 1H), 7.09(d, 1H, J=2.4Hz), 6.99(dd, 1H, J=8.8, 2.4Hz), 6.96(m, 1H), 6.51(d, 1H, J=8.8Hz), 5.62(s, 1H), 4.11(t, 2H, J=4.4Hz), 3.25(m, 2H). | 104 |
| 149 | 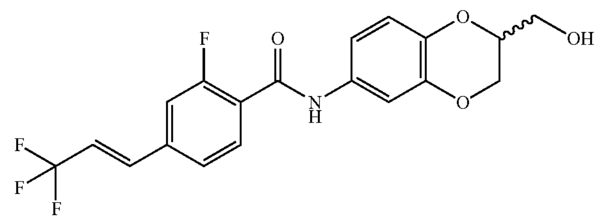 | 398.20 (397.33) | F | (d₆-DMSO) δ 10.28(s, 1H), 7.76(d, 1H, J=11.2Hz), 7.69(t, 1H, J=7.6Hz), 7.63(d, 1H, J=8.4Hz), 7.42(m, 1H), 7.34(d, 1H, J=2.4Hz), 7.13(dd, 1H, J=8.4, 2.4Hz), 6.98(dq, 1H, J=16.4, 7.2Hz), 6.84(d, 1H, J=8.4Hz), 5.06(t, 1H, J=5.6Hz), 4.32(dd, 1H, J=11.6, 2.0Hz), 4.13(m, 1H), 4.00(dd, 1H, J=11.6, 8.0Hz), 3.68-3.56(m, 2H). | 71 |
| 150 | 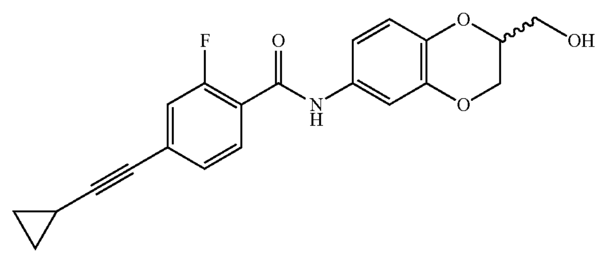 | 368.20 (367.38) | D | (d₆-DMSO) δ 10.22(s, 1H), 7.58(t, 1H, J=8.0Hz), 7.36-7.31(m, 2H), 7.28(dd, 1H, J=8.0, 1.6Hz), 7.12(dd, 1H, J=8.4, 2.4Hz), 6.83(d, 1H, J=8.4Hz), 5.05(t, 1H, J=5.6Hz), 4.32(dd, 1H, J=11.2, 2.0Hz), 4.13(m, 1H), 3.99(dd, 1H, J=11.2, 7.6Hz), 3.68-3.56(m, 2H), 1.58(m, 1H), 0.96-0.90(m, 2H), 0.81-0.76(m, 2H). | 75 |
| 151 | 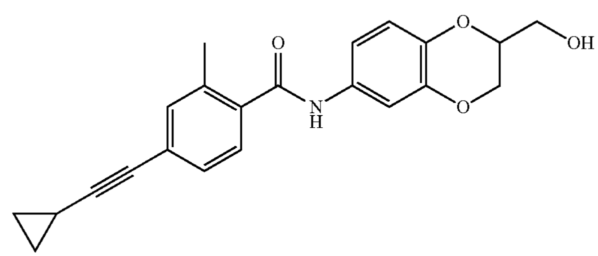 | 363.90 (363.42) | C | (d₆-DMSO) δ 10.12(1H, s), 7.37-7.34(2H, m), 7.29(1H, s), 7.26(1H, d), 7.13(1H, dd), 6.81(1H, d), 5.06-5.03(1H, m), 4.31(1H, dd), 4.14-4.10(1H, m), 4.01-3.96(1H, m), 3.66-3.57(2H, m), 2.32(3H, s), 1.58-1.54(1H, m), 0.92-0.88(2H, m), 0.76-0.72(2H, m). | 108 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 152 | 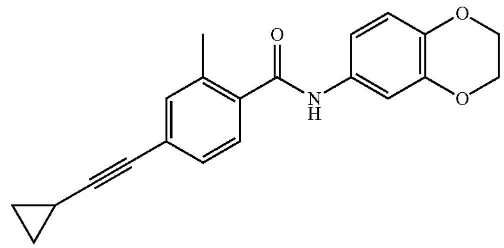 | 334.00 (333.39) | C | (d$_6$-DMSO) δ 10.11(1H, s), 7.37-7.33(2H, m), 7.29-7.24(2H, m), 7.12(1H, dd), 6.80(1H, d), 4.23-4.20(4H, m), 2.32(3H, s), 1.58-1.54(1H, m), 0.92-0.88(2H, m), 0.76-0.72(2H, m). | 73 |
| 153 | 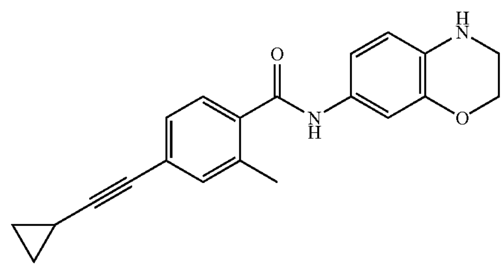 | 332.80 (332.41) | C | (d$_6$-DMSO) δ 9.88(1H, s), 7.33(1H, d), 7.27(1H, s), 7.24(1H, d), 7.09(1H, d), 7.00(1H, dd), 6.49(1H, d), 5.57(1H, brs), 4.10(2H, t), 3.29-3.23(2H, m), 2.33(3H, s), 1.57-1.53(1H, m), 0.92-0.87(2H, m), 0.76-0.72(2H, m). | 104 |
| 154 | 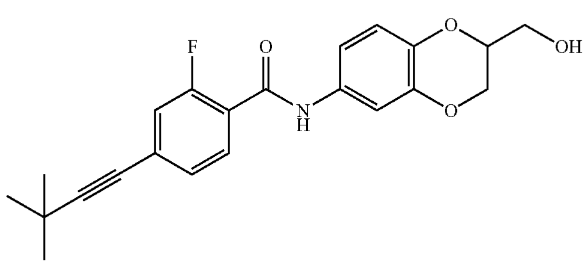 | 383.70 (383.42) | C | (d$_6$-DMSO) δ 10.23(1H, s), 7.59(1H, t), 7.34-7.27(3H, m), 7.12(1H, dd), 6.83(1H, d), 5.05(1H, t), 4.32(1H, dd), 4.13-4.11(1H, m), 4.02-3.97(1H, m), 3.64-3.58(2H, m), 1.30(9H, s). | 95 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 155 | 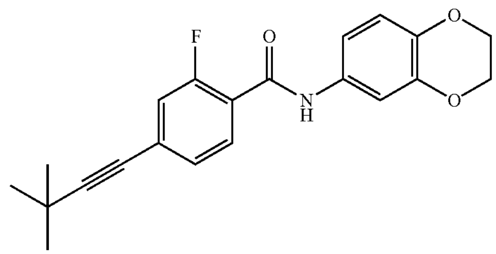 | 353.70 (353.40) | C | (d₆-DMSO) δ 10.22(1H, s), 7.59(1H, s), 7.34-7.27(3H, m), 7.11(1H, dd), 6.82(1H, d), 4.24-4.20(4H, m), 1.30(9H, s). | 95 |
| 156 | 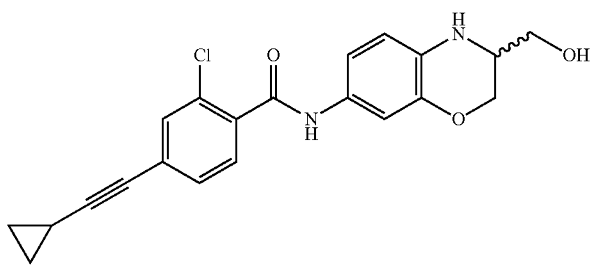 | 383.10 (382.85) | D | (d₆-DMSO) δ 10.08(s, 1H), 7.51(d, 1H, J=1.6Hz), 7.46(d, 1H, J=8.0Hz), 7.39(dd, 1H, J=8.0, 1.6Hz), 7.08(d, 1H, J=2.0Hz), 6.98(dd, 1H, J=8.4, 2.4Hz), 6.54(d, 1H, J=8.4Hz), 5.67(s, 1H), 4.86(t, 1H, J=5.6Hz), 4.11(dd, 1H, J=10.8, 2.4Hz), 3.92(dd, 1H, J=10.8, 5.6Hz), 3.43-3.33(m, 2H), 3.30(m, 1H), 1.58(m, 1H), 0.96-0.89(m, 2H), 0.81-0.76(m, 2H). | 102 |
| 157 | 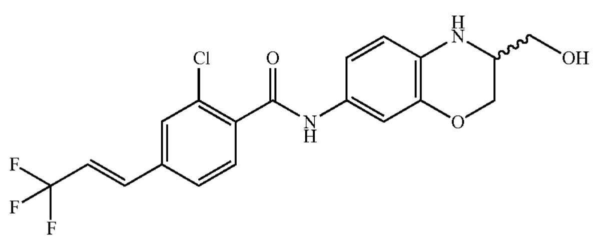 | 413.30 (412.80) | D | (d₆-DMSO) δ 10.12(s, 1H), 7.93(d, 1H, J=1.2Hz), 7.75(dd, 1H, J=8.0, 1.6Hz), 7.58(d, 1H, J=8.0Hz), 7.40(m, 1H), 7.10(d, 1H, J=2.4Hz), 7.00(dd, 1H, J=8.8, 2.4Hz), 6.97(m, 1H), 6.54(d, 1H, J=8.8Hz), 5.68(s, 1H), 4.86(t, 1H, J=5.6Hz), 4.11(dd, 1H, J=10.8, 2.4Hz), 3.92(dd, 1H, J=10.8, 5.6Hz), 3.44-3.32(m, 2H), 3.30(m, 1H). | 107 |

TABLE 1-continued

AMIDE COMPOUNDS

| ID | STRUCTURE | MS observed (calcd) | Method of Synth. | ¹H NMR | Low pH % Inhib. @ 0.3 µM |
|---|---|---|---|---|---|
| 158 | 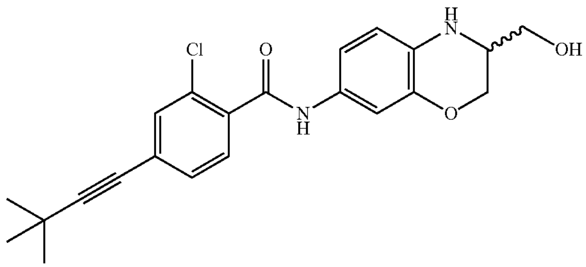 | 399.00 (398.89) | F | (d₆-DMSO) δ 10.09(s, 1H), 7.49(d, 1H, J=1.6Hz), 7.47(d, 1H, J=8.0Hz), 7.38(dd, 1H, J=8.0, 1.6Hz), 7.09(d, 1H, J=2.4Hz), 6.99(dd, 1H, J=8.4, 2.4Hz), 6.54(d, 1H, J=8.4Hz), 5.68(s, 1H), 4.86(t, 1H, J=5.6Hz), 4.12(dd, 1H, J=10.8, 2.0Hz), 3.92(dd, 1H, J=10.8, 5.6Hz), 3.44-3.32(m, 2H), 3.30(m, 1H), 1.30(s, 9H). | 107 |
| 159 | 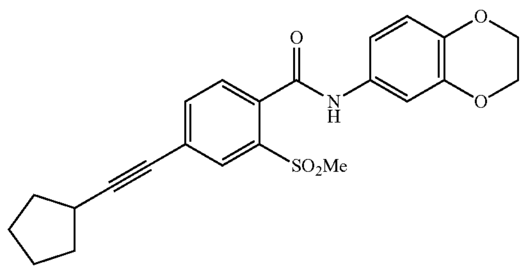 | 426.30 (425.51) | I | (d₆-DMSO) δ 10.5(1H, s), 7.9(1H, s), 7.85(1H, d), 7.75(1H, d), 7.25(1H, s), 7.15(1H, d), 6.85(1H, d), 4.25(4H, m), 3.95(3H, s), 2.85(1H, m), 2.2-1.95(2H, m), 1.85-1.5(6H, m) | |
| 160 | 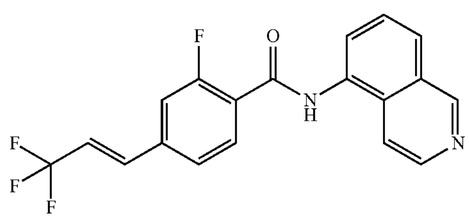 | 361.10 (360.31) | E | (d₆-DMSO) δ 10.61(s, 1H), 9.37(s, 1H), 8.57(d, 1H, J=6.0Hz), 8.10-8.00(m, 2H), 7.94(d, 1H, J=5.6Hz), 7.90-7.81(m, 2H), 7.76-7.67(m, 2H), 7.50-7.40(m, 1H), 7.01(m, 1H). | 96 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 161 | 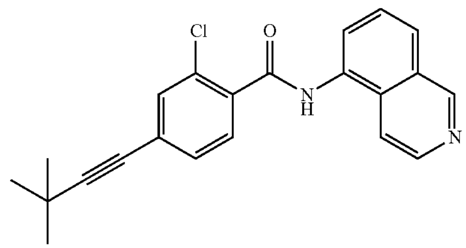 | 363.10 (362.86) | J | (CDCl₃) δ 9.30(1H, s), 8.60(1H, dd), 8.52(1H, s), 8.41(1H, d), 7.88(2H, d), 7.75(1H, d), 7.68(1H, t), 7.54(1H, s), 7.43(1H, d), 1.32(9H, s). | 95 |
| 162 | 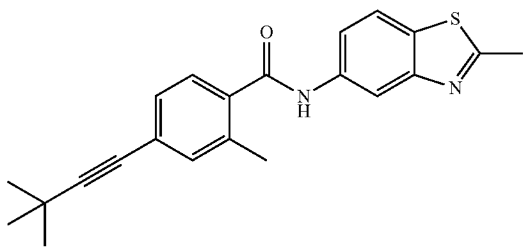 | 363.20 (362.50) | I | | 89 |
| 163 | 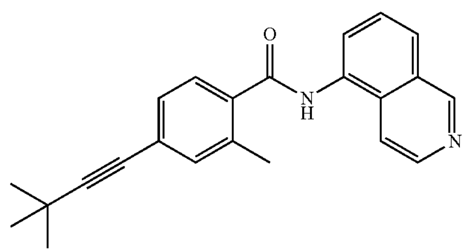 | 343.10 (342.44) | I | (d₆DMSO) δ 10.5(1H, s), 9.4(1H, s), 8.6(1H, d), 8.15(2H, m), 7.85(1H, d), 7.75(1H, t), 7.35(1H, d), 7.55(2H, m), 2.45(3H, s), 1.8(9H, s) | 98 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 164 | 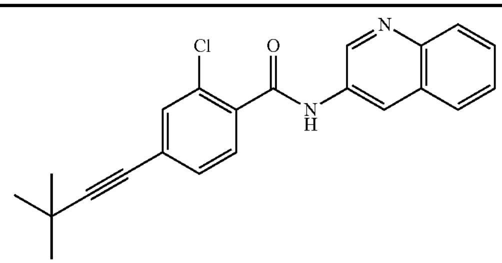 | 362.90 (362.86) | J | (CDCl₃) δ 8.91(1H, dd), 8.83(1H, dd), 8.30(1H, s), 8.08(1H, d), 7.86(1H, d), 7.81(1H, d), 7.69-7.65(1H, m), 7.59-7.51(1H, m), 7.42(1H, dd), 7.41(1H, dd), 1.30(9H, s). | 105 |
| 165 | 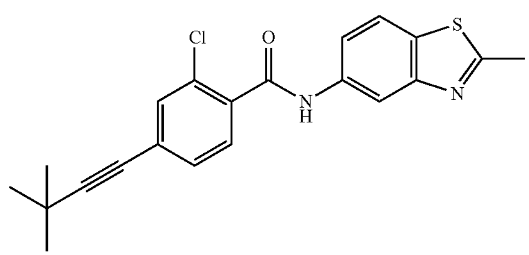 | 383.20 (382.92) | J | (CDCl₃) δ 8.18(1H, d), 8.09(1H, s), 7.81-7.72(3H, m), 7.48(1H, d), 7.37(1H, dd), 2.84(3H, s), 1.31(9H, s). | 107 |
| 166 | 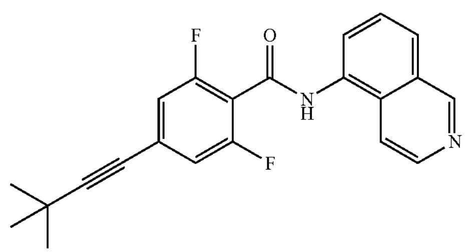 | 355.10 (364.40) | I | (d₆-DMSO) δ 11.0(1H, s), 9.4(1H, s), 8.6(1H, d), 8.15(2H, m), 7.85(1H, d), 7.75(1H, t), 7.55(2H, m), 1.8(9H, s) | 99 |

TABLE 1-continued
AMIDE COMPOUNDS
| ID | STRUCTURE | MS observed (calcd) | Method of Synth. | ¹H NMR | Low pH % Inhib. @ 0.3 µM |
|---|---|---|---|---|---|
| 167 | 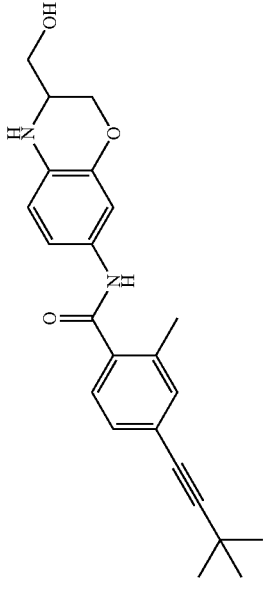 | 379.10 (378.48) | I | (d₆-DMSO) δ 9.8(1H, s), 7.45-7.25(3H, m), 7.15(1H, s), 6.98(1H, d), 6.52(1H, d), 5.75(1H, s), 4.80(1H, t), 4.2(1H, m), 3.85(1H, m), 3.65(2H, m), 2.45(3H, s), 1.9(9H, s) | 107 |
| 168 | 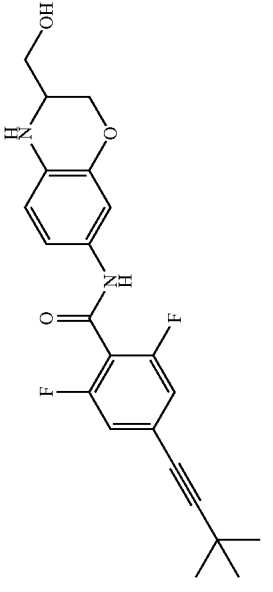 | 400.90 (400.43) | I | (d₆-DMSO) δ 10.4(1H, s), 7.25(2H, d), 7.15(1H, s), 6.91(1H, d), 6.52(1H, d), 5.75(1H, s), 4.80(1H, t), 4.2(1H, m), 3.85(1H, m), 3.65(2H, m), 1.9(9H, s) | 104 |
| 169 | Chiral 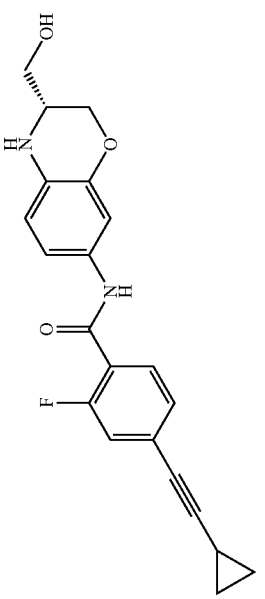 | 367.10 (366.40) | D | (d₆-DMSO) δ 10.00(s, 1H) 7.55(t 1H) 7.32(dd, 1H) 7.27(dd, 1H) 7.09(d, 1H) 6.99(dd, 1H) 6.54(d, 1H) 5.7(s, 1H) 4.87(t, 1H) 4.11(dd 1H) 3.92(dd 1H)3.45-3.27(m, 3H) 1.63-1.54(m, 1H) 0.96-0.896(m, 2H) 0.81-0.75(m, 2H) | 112 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 170 | Chiral structure | 383.20 (382.44) | D | (d₆-DMSO) δ 9.99(1H, s), 7.57(1H, t), 7.32-7.25(2H, m), 7.09(1H, d), 6.99(1H, dd), 6.54(1H, d), 5.69(1H, brs), 4.86(1H, t), 4.12(1H, dd), 3.91(1H, dd), 3.43-3.28(3H, m), 1.30(9H, s). | 108 |
| 171 | Chiral structure | 367.30 (366.40) | D | (d₆-DMSO) δ 10.00(s, 1H) 7.55(t 1H) 7.32(dd, 1H) 7.27(dd, 1H) 7.09(d, 1H) 6.99(dd, 1H) 6.54(d, 1H) 5.7(s, 1H) 4.87(t, 1H) 4.11(dd 1H) 3.92(dd, 1H) 3.45-3.27(m, 3H)1.63-1.54(m, 1H) 0.96-0.896(m, 2H) 0.81-0.75(m, 2H) | 112 |
| 172 | Chiral structure | 383.20 (382.44) | D | (d₆-DMSO) δ 9.99(1H, s), 7.57(1H, t), 7.32-7.25(2H, m), 7.09(1H, d), 6.99(1H, dd), 6.54(1H, d), 5.69(1H, brs), 4.86(1H, t), 4.12(1H, dd), 3.91(1H, dd), 3.43-3.28(3H, m), 1.30(9H, s). | 109 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 173 | 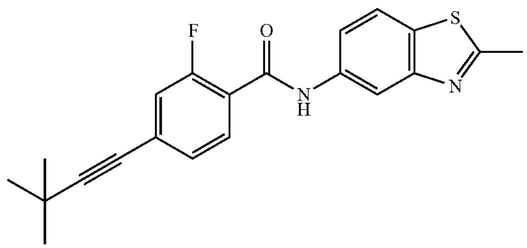 | 367.20 (366.46) | A | | 109 |
| 174 | 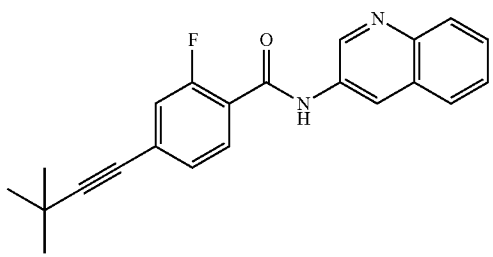 | 347.20 (346.41) | A | | 97 |
| 175 | 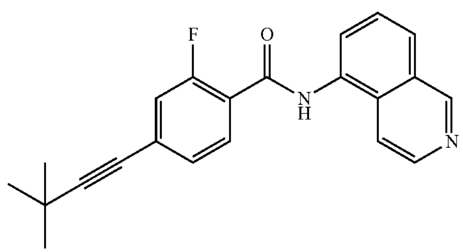 | 347.30 (346.41) | A | | 95 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 176 | 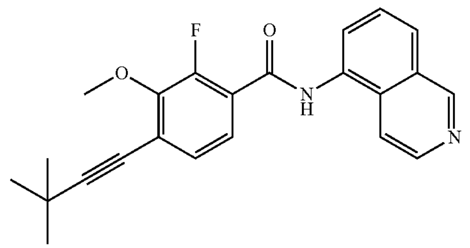 | 376.60 (376.43) | J | (CDCl₃) δ 9.30(1H, s), 8.91-8.86(1H, m), 8.63(1H, d), 8.49(1H, d), 7.88-7.83(2H, m), 7.74-7.66(2H, m), 7.32-7.26(1H, m), 4.09(3H, s), 1.38(9H, s). | 89 |
| 177 | 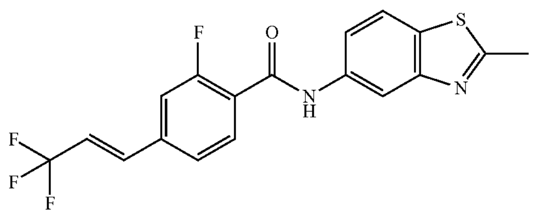 | 380.90 (380.37) | F | (d₆-DMSO) δ 10.67(s, 1H), 8.40(d, 1H, J=2.0Hz), 7.99(d, 1H, J=8.4Hz), 7.80(d, 1H, J=11.6Hz), 7.76(d, 1H, J=7.6Hz), 7.70-7.65(m, 2H), 7.47-7.41(m, 1H), 7.01(dq, 1H, J=16.4,7.2Hz), 2.80(s, 3H). | 85 |
| 178 | 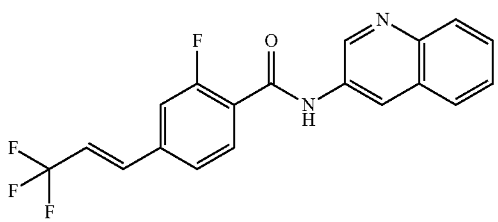 | 361.20 (360.31) | E | (d₆-DMSO) δ 10.97(s, 1H), 9.04(d, 1H, J=2.4Hz), 8.85(d, 1H, J=2.0Hz), 7.99(d, 2H, J=8.4Hz), 7.83(m, 2H), 7.69(m, 2H), 7.61(t, 1H, J=8.0Hz), 7.49-7.42(m, 1H), 7.03(dq,1H, J=16.4, 7.2Hz). | 9 |
| 179 | 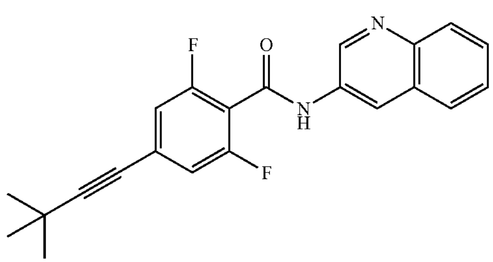 | 365.10 (364.40) | I | (d₆-DMSO) δ 11.5(1H, s), 9.1(1H, s), 8.8(1H, s), 7.9(2H, d), 7.75-7.50(2H, m), 7.48-7.35(2H, m), 1.8(9H, s) | 100 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 180 | (2-methylbenzothiazol-5-yl amide of 2,6-difluoro-4-(3,3-dimethylbut-1-ynyl)benzoic acid) | 384.90 (384.45) | G | (d₆-DMSO) δ 11.0(1H, s), 8.45(1H, s), 8.0(1H, d), 7.65(1H, d), 7.35(2H, m), 2.75(3H, s), 1.8(9H, s) | 99 |
| 181 | (quinolin-3-yl amide of 2-methyl-4-(3,3-dimethylbut-1-ynyl)benzoic acid) | 343.10 (342.44) | I | (d₆-DMSO) δ 10.8(1H, s), 9.1(1H, s), 8.8(1H, s), 7.9(2H, d), 7.75-7.50(3H, m), 7.48-7.35(2H, m), 2.38(3H, s), 1.8(9H, s) | 102 |
| 182 | Chiral (3-hydroxymethyl-3,4-dihydro-2H-benzo[1,4]oxazin-7-yl amide of 2-chloro-4-(3,3-dimethylbut-1-ynyl)benzoic acid) | 399.20 (398.89) | D | (d₆-DMSO) δ 10.09(s, 1H), 7.49(d, 1H, J=1.6Hz), 7.47(d, 1H, J=8.0Hz), 7.38(dd, 1H, J=8.0, 1.6Hz), 7.09(d, 1H, J=2.4Hz), 6.99(dd, 1H, J=8.4, 2.4Hz), 6.54(d, 1H, J=8.4Hz), 5.68(s, 1H), 4.86(t, 1H, J=5.6Hz),4.12(dd, 1H, J=10.8, 2.0Hz), 3.92(dd, 1H, J=10.8, 5.6Hz), 3.44-3.32(m, 2H), 3.30(m, 1H), 1.30(s, 9H). | 103 |

TABLE 1-continued

AMIDE COMPOUNDS

| ID | STRUCTURE | MS observed (calcd) | Method of Synth. | $^1$H NMR | Low pH % Inhib. @ 0.3 μM |
|---|---|---|---|---|---|
| 183 | Chiral, N-(3-(hydroxymethyl)-3,4-dihydro-2H-benzo[b][1,4]oxazin-7-yl)-2-chloro-4-(3,3-dimethylbut-1-ynyl)benzamide | 399.30 (398.89) | D | (d$_6$-DMSO) δ 10.09(s, 1H), 7.49(d, 1H, J=1.6Hz), 7.47(d, 1H, J=8.0Hz), 7.38(dd, 1H, J=8.0, 1.6Hz), 7.09(d, 1H, J=2.4Hz), 6.99(dd, 1H, J=8.4, 2.4Hz), 6.54(d, 1H, J=8.4Hz), 5.68(s, 1H), 4.86(t, 1H, J=5.6Hz), 4.12(dd, 1H, J=10.8, 2.0Hz), 3.92(dd, 1H, J=10.8, 5.6Hz), 3.44-3.32(m, 2H), 3.30(m, 1H), 1.30(s, 9H). | 98 |
| 184 | Chiral, N-(3-(hydroxymethyl)-3,4-dihydro-2H-benzo[b][1,4]oxazin-7-yl)-2-methyl-4-(3,3-dimethylbut-1-ynyl)benzamide | 379.20 (378.48) | D | (d$_6$-DMSO) δ 9.91(1H, s), 7.35(d, 1H), 7.27(s, 1H), 7.23(d, 1H), 7.11(d, 1H), 7.01(dd, 1H), 6.53(d, 1H), 5.65(s, 1H), 4.87(t, 1H), 4.11(dd, 1H), 3.92(dd, 1H), 3.43-3.34(m, 2H), 3.31(m, 1H), 2.32(s, 3H), 1.30(s, 9H) | 102 |
| 185 | N-(2-(hydroxymethyl)-2,3-dihydrobenzo[b][1,4]dioxin-6-yl)-2-methyl-4-((E)-2-(trifluoromethyl)vinyl)benzamide | 394.30 (393.37) | C | (d$_6$-DMSO) δ 10.18(1H, s), 7.65(1H, s), 7.61(1H, d), 7.47(1H, d), 7.37(1H, d), 7.33(1H, d), 7.15(1H, dd), 6.88-6.81(2H, m), 5.07(1H, t), 4.34-4.31(1H, m), 4.15-5.10(1H, m),3.68-3.57(2H, m), 3.41-3.29(1H, m), 2.36(3H, s). | 92 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 186 | 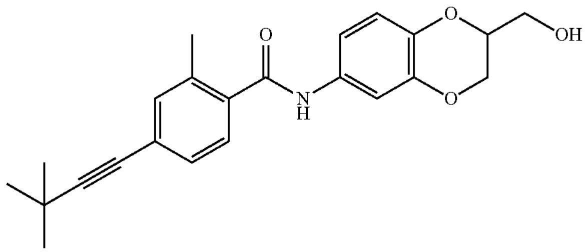 | 380.20 (379.46) | C | (d₆-DMSO) δ 10.15(1H, s), 7.40-7.36(2H, m), 7.30(1H, s), 7.25(1H, d), 7.15(1H, dd), 6.83(1H, d), 5.07(1H, t), 4.32(1H, dd), 4.13-4.09(1H, m), 4.02-3.97(1H, m), 3.65-3.60(2H, m), 2.34(3H, s), 1.30(9H, s). | 91 |
| 187 | 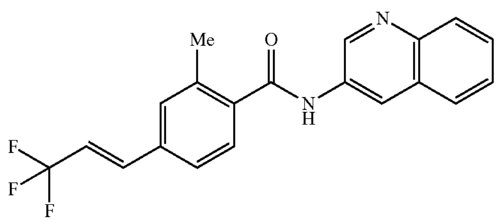 | 357.10 (356.35) | E | (d₆-DMSO) δ 10.86(s, 1H), 9.04(d, 1H, J=2.4Hz), 8.88(d, 1H, J=2.4Hz), 7.98(d, 2H, J=8.8Hz), 7.72-7.58(m, 5H), 7.43-7.35(m, 1H), 6.90(dq, 1H, J=16.4, 7.2Hz), 2.46(s, 3H). | 98 |
| 188 | 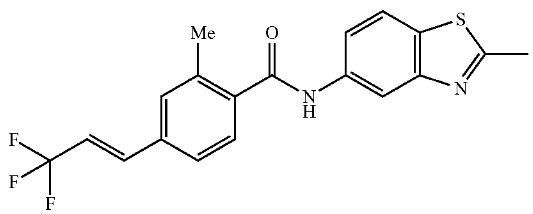 | 377.00 (376.40) | F | (d₆-DMSO) δ 10.56(s, 1H), 8.42(d, 1H, J=2.0Hz), 7.97(d, 1H, J=8.4Hz), 7.71(dd, 1H, J=8.4, 2.0Hz), 7.68(s, 1H), 7.65(d, 1H, J=8.0Hz), 7.57(d, 1H, J=8.0Hz), 7.41-7.34(m, 1H), 6.88(dq, 1H, J=16.4, 7.2Hz), 2.80(s, 3H), 2.43(s, 3H). | 83 |
| 189 | 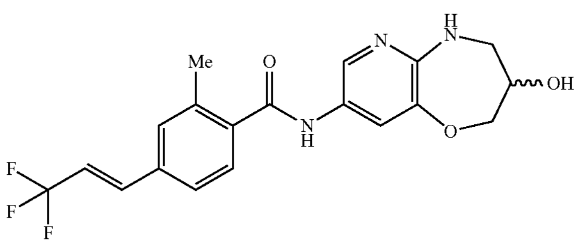 | 393.30 (392.38) | D | (d₆-DMSO) δ 10.03(s, 1H), 7.64(s, 1H), 7.60(d, 1H, J=8.0Hz), 7.45(d, 1H, J=8.0Hz), 7.39-7.31(m, 1H), 7.22(d, 1H, J=2.4Hz), 7.13(dd, 1H, J=8.4, 2.4Hz), 6.84(dq, 1H, J=16.4, 7.2Hz), 6.66(d, 1H, J=8.4Hz), /5.25(s, 1H), 4.99(d, 1H,J=5.2Hz), 4.19(dd, 1H, J=12.0, 3.6Hz), 3.87(m, 1H), 3.79(dd, 1H, J=12.0, 5.2Hz), 3.28(m, 1H), 2.96(m, 1H), 2.37(s, 3H). | 87 |

TABLE 1-continued

AMIDE COMPOUNDS

| ID | STRUCTURE | MS observed (calcd) | Method of Synth. | $^1$H NMR | Low pH % Inhib. @ 0.3 μM |
|---|---|---|---|---|---|
| 190 | 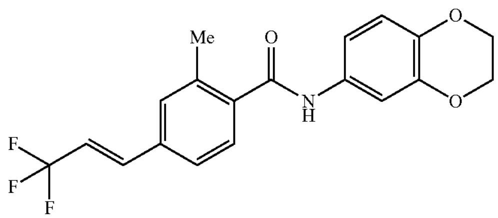 | 364.40 (363.34) | D | (d$_6$-DMSO) δ 10.18(s, 1H), 7.65(s, 1H), 7.61(d, 1H, J=8.0Hz), 7.47(d, 1H, J=8.0Hz), 7.38-7.32(m, 2H), 7.13(dd, 1H, J=8.8, 2.8Hz), 6.86(dq, 1H, J=16.4, 7.2Hz), 6.81(d, 1H, J=8.8Hz), 4.22(m, 4H), 2.38(s, 3H). | 87 |
| 191 | 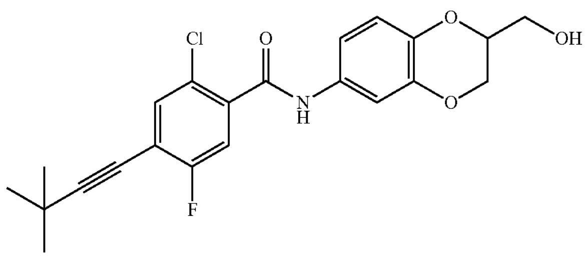 | 418.50 (417.87) | C | (d$_6$-DMSO) δ 10.40(1H, s), 7.65(1H, d), 7.59(1H, d), 7.32(1H, d), 7.10(1H, dd), 6.85(1H, d), 5.07(1H, t), 4.33(1H, dd), 4.14-4.08(1H, m), 4.02-3.98(1H, m), 3.65-3.60(2H, m), 1.31(9H, s). | 83 |
| 192 | 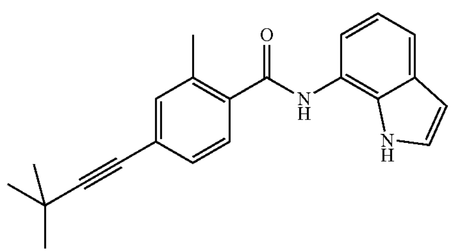 | 329.30 (330.43) | M | (CDCl$_3$) δ 10.05(1H, br. s), 7.75(1H, m), 7.53(2H, dd), 7.35-7.28(3H, m), 7.05(1H, app. t), 6.77(1H, dd), 6.59(1H, m), 2.52(3H, s), 1.34(9H, s) | |
| 193 | Chiral | 397.10 (396.34) | D | (d$_6$-DMSO) δ 10.04(s, 1H), 7.74(d, 1H, J=11.2Hz), 7.66(t, 1H, J=8.0Hz), 7.61(d, 1H, J=8.0Hz), 7.41(m, 1H), 7.11(d, 1H, J=2.4Hz), 7.01(dd, 1H, J=8.4, 2.4Hz), 6.97(m, 1H), 6.55(d, 1H, J=8.4Hz), 5.69(s, 1H), 4.86(t, 1H, J=5.2Hz), 4.12(dd, 1H, J=10.4, 2.4Hz), 3.92(dd, 1H, J=10.4, 5.6Hz), 3.45-3.32(m, 2H), 3.30(m, 1H). | 103 |

TABLE 1-continued

AMIDE COMPOUNDS

| ID | STRUCTURE | MS observed (calcd) | Method of Synth. | $^1$H NMR | Low pH % Inhib. @ 0.3 μM |
|---|---|---|---|---|---|
| 194 | Chiral; benzoxazine-hydroxymethyl amide with 2-methyl-4-(3,3-dimethylbut-1-ynyl)benzamide | 379.20 (378.48) | D | (d$_6$-DMSO) δ 9.91(1H, s), 7.35(d, 1H), 7.27(s, 1H), 7.23(d, 1H), 7.11(d, 1H), 7.01(dd, 1H), 6.53(d, 1H), 5.65(s, 1H), 4.87(t, 1H), 4.11(dd, 1H), 3.92(dd, 1H), 3.43-3.34(m, 2H), 3.31(m, 1H), 2.32(s, 3H), 1.30(s, 9H) | 102 |
| 195 | Chiral; benzoxazine-hydroxymethyl amide with 2-methyl-4-(3,3,3-trifluoropropenyl)benzamide | 393.20 (392.38) | D | (d$_6$-DMSO) δ 9.93(s, 1H), 7.63(s, 1H), 7.59(d, 1H, J=8.0Hz), 7.44(d, 1H, J=8.0Hz), 7.34(m, 1H), 7.13(d, 1H, J=2.4Hz), 7.02(dd, 1H, J=8.4, 2.4Hz), 6.83(dq, 1H, J=16.4, 7.2Hz), 6.54(d, 1H, J=8.4Hz), 5.64(s, 1H), 4.86(t, 1H, J=5.2Hz), 4.11(dd, 1H, J=10.4, 2.0Hz), 3.92(dd, 1H, J=10.4, 5.6Hz), 3.44-3.32(m, 2H), 3.30(m, 1H), 2.37(s, 3H). | 60 |
| 196 | 3-methylisoquinolin-5-yl amide of 2-methyl-4-(3,3,3-trifluoropropenyl)benzamide | 371.20 (370.38) | E | (d$_6$-DMSO) δ 10.44(s, 1H), 9.26(s, 1H), 7.98(m, 2H), 7.79(s, 1H), 7.76-7.60(m, 4H), 7.40(d, 1H, J=16.0Hz), 6.89(m, 1H), 2.64(s, 3H), 2.50(s, 3H). | 86 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 197 | *[structure: N-(2-(hydroxymethyl)benzothiazol-5-yl)-2-methyl-4-(3,3-dimethylbut-1-ynyl)benzamide]* | 379.10 (378.50) | See "Prepn. of amido compd.s" | (d₆-DMSO) δ 10.52(s, 1H), 8.41(d, 1H, J=2.0Hz), 8.02(d, 1H, J=8.8Hz), 7.72(dd, 1H, J=8.8, 2.0Hz), 7.47(d, 1H, J=8.4Hz), 7.33(s, 1H), 7.29(d, 1H, J=8.4Hz), 6.26(t, 1H, J=6.0Hz), 4.86(d, 2H, J=6.0Hz), 2.38(s, 3H), 1.31(s, 9H). | 107 |
| 198 | *[structure: N-(benzothiazol-5-yl)-2-methyl-4-(3,3-dimethylbut-1-ynyl)benzamide]* | 349.20 (348.47) | See "Prepn. of amido compd.s" | (CDCl₃) δ 9.03(s, 1H), 8.36(s, 1H), 7.94(d, 1H, J=8.4Hz), 7.81(d, 1H, J=8.0Hz), 7.65(s, 1H), 7.46(d, 1H, J=8.0Hz), 7.32(s, 1H), 7.29(d, 1H, J=8.0Hz), 2.50(s, 3H), 1.33(s, 9H). | 101 |
| 199 | *[structure: N-(1-chloroisoquinolin-5-yl)-2-methyl-4-(3,3-dimethylbut-1-ynyl)benzamide]* | 377.10 (376.89) | E | (d₆-DMSO) δ 10.62(s, 1H), 8.36(d, 1H, J=6.0Hz), 8.22(d, 1H, J=8.4Hz), 8.09(d, 1H, J=7.2Hz), 7.99(d, 1H, J=6.0Hz), 7.87(t, 1H, J=8.0Hz), 7.66(d, 1H, J=7.6Hz), 7.35(s, 1H), 7.32(d, 1H, J=8.0Hz), 2.45(s, 3H), 1.32(s, 9H). | 67 |
| 200 | *[structure: N-(1-chloroisoquinolin-5-yl)-2-methyl-4-(3,3,3-trifluoroprop-1-enyl)benzamide]* | 391.30 (390.80) | E | (d₆-DMSO) δ 10.65(s, 1H), 8.41(d, 1H, J=6.0Hz), 8.22(d, 1H, J=8.4Hz), 8.13(d, 1H, J=6.8Hz), 8.01(d, 1H, J=6.0Hz), 7.88(t, 1H, J=8.0Hz), 7.77-7.66(m, 3H), 7.43-7.36(m, 1H), 6.89(dq, 1H, J=16.0, 6.8Hz), 2.50(s, 3H). | 55 |

TABLE 1-continued

AMIDE COMPOUNDS

| ID | STRUCTURE | MS observed (calcd) | Method of Synth. | $^1$H NMR | Low pH % Inhib. @ 0.3 μM |
|---|---|---|---|---|---|
| 210 | 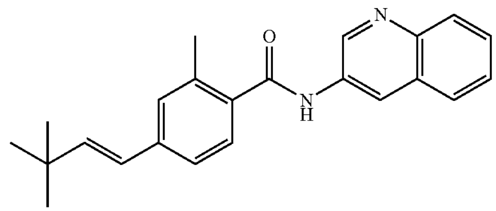 | 345.20 (344.46) | H | | 106 |
| 212 | 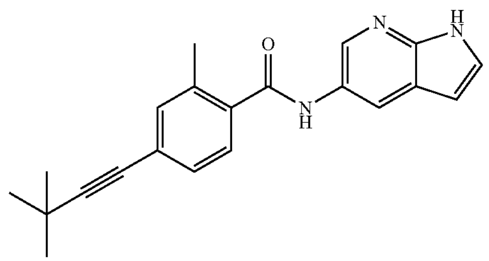 | 330.30 (331.42) | H | (d$_6$-DMSO) δ 10.95(1H, br. s), 9.75(1H, s), 8.82(2H, m), 7.86-7.78(2H, m), 7.61-7.55(2H, m), 6.80(1H, m), 2.78(3H, s), 1.64(9H, s) | 97 |
| 213 | 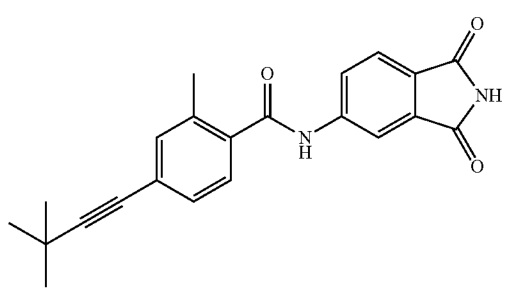 | 361.20 (360.42) | F | | 88 |

TABLE 1-continued

AMIDE COMPOUNDS

| ID | STRUCTURE | MS observed (calcd) | Method of Synth. | $^1$H NMR | Low pH % Inhib. @ 0.3 μM |
|---|---|---|---|---|---|
| 214 | benzimidazole-NH-C(O)-2-methyl-4-(3,3-dimethylbut-1-ynyl)phenyl | 332.30 (331.42) | F | | 74 |
| 215 | 2-methylbenzimidazole-NH-C(O)-2-methyl-4-(3,3-dimethylbut-1-ynyl)phenyl | 346.20 (345.45) | F | | 86 |
| 216 | 7-(hydroxymethyl)quinolin-3-yl-NH-C(O)-2-methyl-4-(3,3-dimethylbut-1-ynyl)phenyl | 373.10 (372.47) | I | (MeOD) δ 8.88(1H, d), 8.72(1H, d), 7.88(1H, s), 7.82(1H, d), 7.55(1H, dd), 7.4(1H, d), 7.21(1H, s), 7.2(1H, d), 5.45(2H, s), 2.38(3H, s), 1.25(9H, s) | 31 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 217 | (2-oxo-benzoxazol-6-yl carboxamide with 2-methyl-4-(3,3-dimethylbut-1-ynyl)phenyl) | 348.80 (348.41) | I | d₆-DMSO δ 11.5(1H, s), 10.4(1H, s), 7.79(1H, d), 7.42-7.38(2H, m), 7.31(1H, s), 7.25(1H, d), 7.05(1H, d), 2.35(3H, s), 1.25(9H, s) | 59 |
| 218 | (2-hydroxymethyl-imidazopyridine carboxamide) | 363.30 (362.44) | H | (MeOD) δ 8.48(1H, s), 8.38(1H, s), 7.36(1H, d), 7.20-7.16(2H, m), 3.28(2H, m), 2.36(3H, s), 1.23(9H, s) | 6 |
| 221 | (quinolin-8-yl carboxamide with 2-methyl-4-(3,3,3-trifluoropropenyl)phenyl) | 358.00 (356.35) | E | (d₆-DMSO) δ 10.27(s, 1H), 8.92(dd, 1H, J=4.4, 1.6Hz), 8.72(d, 1H, J=7.6Hz), 8.46(dd, 1H, J=8.4, 1.2Hz), 7.80-7.64(m, 6H), 7.42-7.37(m, 1H), 6.95-6.85(m, 1H), 2.52(s, 3H) | — |
| 222 | (quinolin-6-yl carboxamide with 2-methyl-4-(3,3,3-trifluoropropenyl)phenyl) | 357.60 (356.35) | E | (d₆-DMSO) δ 10.71(s, 1H), 8.81(dd, 1H, J=4.4, 1.6Hz), 8.57(d, 1H, J=2.0Hz), 8.34(dd, 1H, J=8.4, 1.2Hz), 8.00(d, 1H, J=9.2Hz), 7.92(dd, 1H, J=9.2, 2.4Hz), 7.70(s, 1H), 7.66(d, 1H, J=7.6Hz), 7.60(d, 1H, J=8.0Hz), 7.51(dd, 1H, J=8.4, 4.0Hz), 7.41-7.35(m, 1H), 6.94-6.84(m, 1H), 2.44(s, 3H) | 82 |

TABLE 1-continued

AMIDE COMPOUNDS

| ID | STRUCTURE | MS observed (calcd) | Method of Synth. | $^1$H NMR | Low pH % Inhib. @ 0.3 μM |
|---|---|---|---|---|---|
| 223 | (quinoline-5-yl amide of 2-methyl-4-(3,3,3-trifluoroprop-1-enyl)benzoic acid) | 357.80 (356.35) | E | (d$_6$-DMSO) δ 10.55(s, 1H), 8.94(dd, 1H, J=4.0, 1.6Hz), 8.49(d, 1H, J=8.0Hz), 7.95(t, 1H, J=4.8Hz), 7.85-7.65(m, 5H), 7.59(dd, 1H, J=8.4, 4.0Hz), 7.42-7.36(m, 1H), 6.95-6.84(m, 1H), 2.50(s, 3H). | |
| 224 | (quinoline-7-yl amide of 2-methyl-4-(3,3,3-trifluoroprop-1-enyl)benzoic acid) | 357.80 (356.35) | E | (d$_6$-DMSO) δ 10.72(s, 1H), 8.86(dd, 1H, J=4.0, 1.6Hz), 8.57(s, 1H), 8.30(dd, 1H, J=8.4, 1.2Hz), 7.95(d, 1H, J=8.4Hz), 7.87(dd, 1H, J=8.8, 1.6Hz), 7.70(s, 1H), 7.67(d, 1H, J=8.0Hz), 7.60(d, 1H, J=7.6Hz), 7.44(dd, 1H, J=8.0, 4.0Hz), 7.42-7.35(m, 1H), 6.88(dq, 1H, J=16.4, 7.2Hz), 2.45(s, 3H). | 82 |
| 225 | (2-hydroxymethyl-benzothiazol-5-yl amide of 2-methyl-4-(3,3,3-trifluoroprop-1-enyl)benzoic acid) | 392.40 (393.00) | See "Prepn. of amido compd.s" | (d$_6$-DMSO) δ 10.5(1H, s), 8.45(1H, d), 8.05(1H, d), 7.75-7.62(3H, m), 7.55(1H, d), 7.35(1H, dd), 6.85(1H, m), 6.25(1H, t), 4.85(2H, d), 2.38(3H, s) | 110 |
| 228 | (3-hydroxymethyl-quinolin-6-yl amide of 2-methyl-4-(3,3,3-trifluoroprop-1-enyl)benzoic acid) | 387.70 (386.38) | See "Prepn. of amido compd.s" | (d$_6$-DMSO) δ 10.70(s, 1H), 8.82(d, 1H, J=2.4Hz), 8.56(s, 1H), 8.17(s, 1H), 7.94(d, 1H, J=8.8Hz), 7.86(dd, 1H, J=8.8, 2.0Hz), 7.70(s, 1H), 7.66(d, 1H, J=8.0Hz), 7.60(d, 1H, J=8.0Hz), 7.42-7.35(m, 1H), 6.94-6.84(m, 1H), 5.44(t, 1H, J=5.6Hz), 4.70(d, 2H, J=5.6Hz), 2.45(s, 3H). | 100 |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 229 | 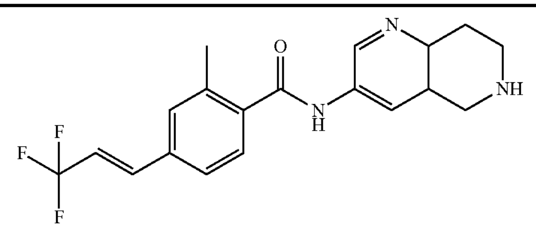 | 361.70 (361.37) | See "Prepn. of amido compds." | (d₆-DMSO) δ 10.79(1H, s), 9.60(2H, br. s), 8.75(1H, m), 8.22(1H, s), 7.70-7.65(2H, m), 7.59(1H, d), 7.39(1H, app. d), 6.90(1H, m), 4.38(2H, app. t), 3.48(2H, m), 3.11(2H, app. t), 2.41(3H, s) | 54 |
| 230 | 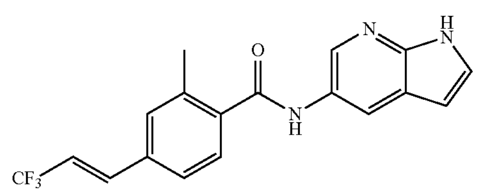 | 346.10 (345.33) | I | (MeOD) δ 8.45(2H, dd), 7.65-7.55(3H, m), 7.48(1H, d), 7.35(1H, dd), 6.65(1H, s), 6.55(1H, d), 2.58(3H, s) | 99 |
| 231 | 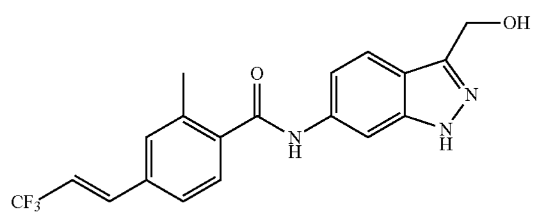 | 375.60 (375.35) | I | (MeOD) δ 7.75(1H, d), 7.68(1H, d), 7.58-7.48(3H, m), 7.35(1H, dd), 6.88(1H, dd), 6.65(1H, m), 4.78(2H, s), 2.38(3H, s) | |
| 232 | 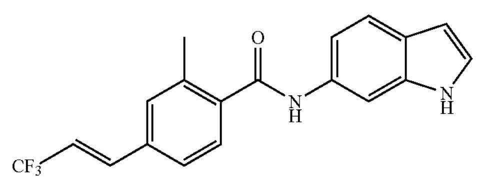 | 345.60 (344.34) | I | (MeOD) δ 8.05(1H, d), 7.62-7.55(4H, m), 7.35(1H, dd), 7.25(1H, d), 7.15(1H, dd), 6.65(1H, m), 6.49(1H, d), 2.38(3H, s) | |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 233 | 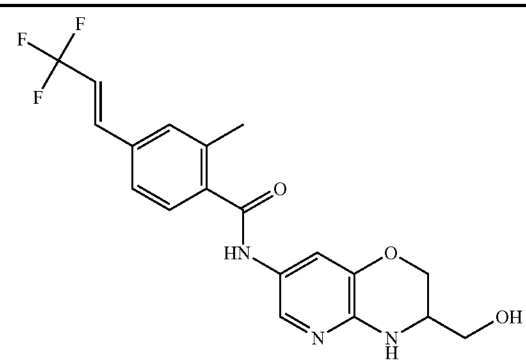 | 393.60 (393.37) | G | (d₆-DMSO) δ 9.93(s, 1H), 8.59(d, 1H), 7.95(s, 1H), 7.62(dd, 1H), 7.59(d, 1H), 6.83-6.79(m, 1H), 6.81(d, 1H), 6.58(d, 1H), 5.01(t, 1H) 4.19-4.07(m, 2H), 3.65-3.57(m, 2H), 3.56-3.48(m, 1H), 3.44-3.36(m, 1H), 2.32(s, 3H) | 100 |
| 235 | 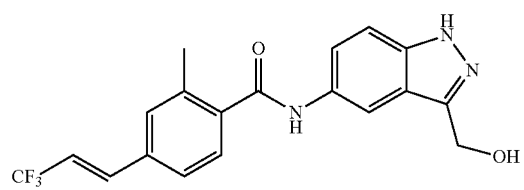 | 377.80 (375.35) | F | (MeOD) δ 8.45(1H, s), 7.65-7.45(5H, m), 7.25(1H, dd), 6.55(1H, m), 4.95(2H, s), 2.45(3H, s) | |
| 236 | 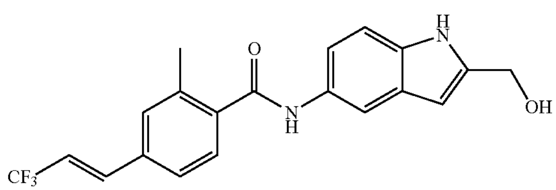 | 375.20 (374.37) | F | (d₆-DMSO) δ 10.95(1H, s), 10.10(1H, s), 7.95(1H, s), 7.65(1H, s), 7.62(1H, d), 7.51(1H, d), 7.35(1H, dd), 7.29-7.25(2H, m), 6.85(1H, m), 6.25(1H, s), 5.25(1H, t), 4.55(2H, d), 2.41(3H, s) | |
| 237 | 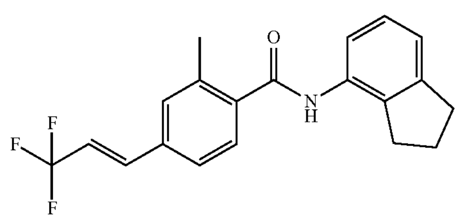 | 345.80 (345.37) | M | (CDCl₃) δ 7.89(1H, d), 7.53(1H, d), 7.35-7.30(2H, m), 7.21(1H, t), 7.16(1H, app. t), 7.09(1H, d), 6.26(1H, m), 2.98(2H, t), 2.84(2H, t), 2.54(3H, s), 2.13(2H, quintet) | |

TABLE 1-continued

AMIDE COMPOUNDS

| ID | STRUCTURE | MS observed (calcd) | Method of Synth. | ¹H NMR | Low pH % Inhib. @ 0.3 μM |
|---|---|---|---|---|---|
| 238 | 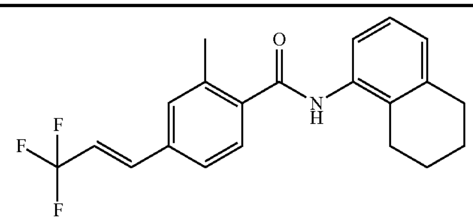 | 360.00 (359.39) | M | (CDCl$_3$) δ 7.80(1H, d), 7.53(1H, d), 7.36-7.12(4H, m), 6.98(1H, d), 6.26(1H, m), 2.80(2H, t), 2.63(2H, t), 2.55(3H, s), 1.89-1.82(2H, m), 1.82-1.74(2H, m) | |
| 239 | 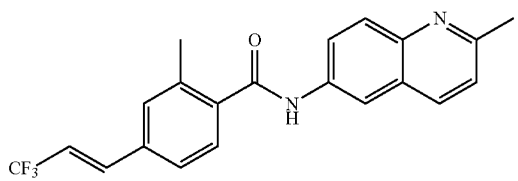 | 370.60 (370.38) | F | (d$_6$-DMSO) δ 10.55(1H, s), 8.5(1H, s), 8.22(1H, d), 7.90-7.85(2H, m), 7.69-7.64(2H, m), 7.59(1H, d), 7.44-7.35(2H, m), 6.87(1H, m), 2.65(3H, s), 2.41(3H, s) | |
| 240 | 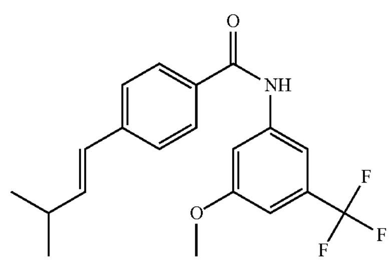 | 364.29 (363.38) | | | 75 (at 1 μM) |

Acid Stimulation Assay:

The Acid-induced changes in the intracellular calcium concentration were monitored using FDSS 6000 (Hamamatsu Photonics, Japan), a fluorometric imaging system. The cell suspension in resting buffer (HBSS supplemented with 10 mM HEPES, pH 7.4) was pre-incubated with varying concentrations of the test compounds or resting buffer (buffer control) for 15 minutes at room temperature under dark conditions. The cells were automatically added the stimulating solution (HBSS supplemented with MES, final assay buffer pH5.8) by the FDSS 6000. The $IC_{50}$ values of VR1 antagonists were determined from the half of the increase demonstrated by buffer control samples after acidic stimulation, and the results obtained with selected compounds of the invention are set forth in Table 2, below.

TABLE 2

$IC_{50}$ Data for Selected Amido Compounds

| ID | $IC_{50}$ (nM) |
|---|---|
| 35 | 2.50 |
| 45 | 1.00 |
| 70 | 5.00 |
| 96 | 3.00 |
| 107 | 5.00 |
| 108 | 5.00 |
| 111 | 5.00 |
| 118 | 5.00 |
| 127 | 5.00 |
| 138 | 3.00 |
| 166 | 8.00 |
| 167 | 7.00 |
| 170 | 3.00 |
| 172 | 3.00 |
| 176 | 4.00 |
| 187 | 3.00 |
| 193 | 3.00 |
| 194 | 3.00 |
| 195 | 3.00 |
| 197 | 3.00 |
| 198 | 3.00 |
| 210 | 3.00 |
| 214 | 3.00 |
| 225 | 0.90 |
| 233 | 3.00 |

Half-Life in Human Liver Microsomes (HLM)

Exemplary compounds of the invention were tested (1 µM), and were incubated with 3.3 mM $MgCl_2$ and 0.78 mg/mL HLM (HL101) in 100 mM potassium phosphate buffer (pH 7.4) at 37° C. on the 96-deep well plate. The reaction mixture was split into two groups, a non-P450 and a P450 group. NADPH was only added to the reaction mixture of the P450 group. An aliquot of samples of the P450 group was collected at 0, 10, 30, and 60 minute time points, where the 0 minute time point indicated the time when NADPH was added into the reaction mixture of the P450 group. An aliquot of samples of the non-P450 group was collected at −10 and 65 minute time points. Collected aliquots were extracted with an acetonitrile solution containing an internal standard. The precipitated protein was spun down in a centrifuge (2000 rpm, 15 min). The compound concentration in supernatant was measured by LC/MS/MS system. The half-life value ($T_{1/2}$) was obtained by plotting the natural logarithm of the peak area ratio of compounds/internal standard versus time. The slope of the line of best fit through the points yields the rate of metabolism (k). This was converted to a half-life value using following equations: Half-life=ln 2/k. The results of the tests and corresponding $T_{1/2}$ values are set forth in Table 3, below.

TABLE 3

T-Half Life In Hours For Exemplary Compounds

| ID | Half Life (hr) |
|---|---|
| 22 | 1.18 |
| 31 | 0.4 |
| 34 | 1.15 |
| 35 | 0.49 |
| 36 | 1.71 |
| 45 | 0.02 |
| 46 | 0.02 |
| 48 | 0.33 |
| 52 | 0.03 |
| 60 | 0.35 |
| 63 | 0.4 |
| 65 | 0.42 |
| 74 | 1.22 |
| 79 | 1.33 |
| 89 | 0.53 |
| 93 | 0.65 |
| 94 | 0.48 |
| 95 | 0.3 |
| 96 | 0.34 |
| 103 | 0.31 |
| 104 | 0.28 |
| 111 | 0.75 |
| 112 | 0.8 |
| 118 | 1.03 |
| 122 | 1.25 |
| 123 | 1.88 |
| 124 | 1.01 |
| 125 | 0.67 |
| 126 | 1.86 |
| 127 | 1.37 |
| 129 | 1.72 |
| 131 | 1.97 |
| 134 | 1.56 |
| 144 | 1.18 |
| 157 | 1.37 |
| 158 | 1.43 |
| 160 | 0.58 |
| 162 | 1.43 |
| 163 | 1.16 |
| 164 | 2.03 |
| 172 | 1.24 |
| 181 | 1.02 |
| 184 | 0.64 |
| 187 | 9.47 |
| 188 | 1.34 |
| 207 | 6.63 |
| 225 | 3.26 |
| 228 | 1.27 |

Pharmacokinetic Evaluation of Compounds Following Intravenous and Oral Administration in Rats.

Male Sprague-Dawley rats are acclimatized for at least 24 hours prior to experiment initiation. During acclimation period, all animals receive food and water ad libitum. However, food but not water is removed from the animal's cages at least 12 hours before initiation of the experiment. During the first 3 hours of experimentation, the animals receive only water ad libitum. At least three animal each are tested for intravenous and oral dosage. For intravenous formulation, compounds were dissolved (0.25 to 1 mg/mL) in a mixture of 3% dimethyl sulfoxide, 40% PEG 400 and the rest percentage of 40% Captisol in water (w/v). For oral formulation, compounds of this invention are dissolved (2 mg/mL) in a mixture of 5% of 10% Tween 80 in water (v/v) and 95% of 0.5% methyl cellulose in water (w/v). The animals are weighed before dosing. The determined body weight is used to calculate the dose volume for each animal.

For intravenous dosing: Dose volume (mL/kg)=1 mg/kg/ formulation concentration (mg/mL).

In instances where the formulation concentrations were less than 0.5 mg/mL, the dosing volume is about 2 mL/kg. PO rats are typically dosed through oral gavage at 2.5 ml/kg to achieve a dose level of 5 mg/kg. For IV dosing, blood samples are collected (using a pre-heparinized syringe) via the jugular vein catheter at 2, 5, 15, 30, 60, 120, 180, 300, 480, and 1440 minutes post dosing. For PO dosing, blood samples are collected (using a pre-heparinized syringe) via the jugular vein catheter before dosing and at 5, 15, 30, 60, 120, 180, 300, 480, and 1440 minutes post dosing. About 250 uL of blood is obtained at each time point from the animal. Equal volumes of 0.9% normal saline are replaced to prevent dehydration. The whole blood samples are maintained on ice until centrifugation. Blood samples are then centrifuged at 14,000 rpm for 10 minutes at 40° C. and the upper plasma layer transferred into a clean vial and stored at −80° C. The resulting plasma samples are then analyzed by liquid chromatography-tandem mass spectrometry. Following the measurement of plasma samples and dosing solutions, plasma concentration-time curve is plotted. Plasma exposure is calculated as the area under the concentration-time curve extrapolated to time infinite ($AUC_{inf}$). The $AUC_{inf}$ is averaged and the oral bioavailability (%F) for individual animal is calculated as:

AUCinf (PO)/AUCinf (IV, average), normalized to their respective dose levels. The %F is reported as the mean %F of all oral dosed animals.

EXAMPLE 1

Calcium Imaging Assay

VR1 protein is a heat-gated cation channel that exchanges approximately ten calcium ions for every sodium ion resulting in neuronal membrane depolarization and elevated intracellular calcium levels. Therefore the functional activity of compounds at the VR1 receptor may be determined by measuring changes in intracellular calcium levels in neurons such as the dorsal root ganglion.

DRG neurons were grown on PDL coated 96-well black-walled plates, in the presence of DMEM medium containing 5% Penstrep, 5% Glutamax, 200 µg/ml hygromycin, 5 µg/ml blasticide and 10% heat inactivated FBS. Prior to assay, cells were loaded with 5 µg/ml Fura2 in normal saline solution at 37° C. for 40 minutes. Cells were then washed with normal saline to remove dye before commencement of the experiment.

The plated neurons were transferred into a chamber on the stage of a Nikon eclipse TE300 microscope after which neurons were allowed to attain a stable fluorescence for about 10 minutes before beginning the experiment. The assay consists of two stages, a pretreatment phase followed by a treatment phase. First, a solution of the test compound was added from a multivalve perfusion system to the cells for 1 minute (pretreatment). Immediately following, capsaicin (250 nM) was added in the presence of the test compound (treatment) for a specific period between 20 and 60 seconds.

Fura2 was excited at 340 and 380 nm to indicate relative calcium ion concentration. Changes in wavelength measurements were made throughout the course of the experiment. The fluorescence ratio was calculated by dividing fluorescence measured at 340 nm by that at 380 nm. Data were collected using Intelligent Imaging's Slidebook software. All compounds that inhibited capsaicin induced calcium influx greater than 75% were considered positives.

Table 4 provides the data obtained. FIG. 1 demonstrates results obtained when compound 225 is administered with capsaicin. Fluorescence reflecting calcium ion influx is reduced.

TABLE 4

| Compound ID | Concentration | Treatment time (sec) | % inhibition of capsaicin induced calcium influx |
|---|---|---|---|
| 225 | 3 nM | 20 | >75 |

EXAMPLE 2

High Throughput Analysis of VR1 Antagonists for Determination of In Vitro Efficacy Using a Calcium Imaging Assay Inhibition of the capsacin response in the presence and absence of the test compound was measured and assessed, using the method for the calcium uptake assay, described hereinabove with respect to the data presented in Table 1. Such data is also graphically depicted in FIGS. 2-6, where significant reduction of the capsaicin response is observed in the presence of the representative test compound. No such reduction in response is observed in the absence of the test compound.

EXAMPLE 3

Whole-Cell Patch Clamp Electrophysiology

Dorsal root ganglion (DRG) neurons were recovered from either neonatal or adult rats and plated onto poly-D-lysine coated glass coverslips. The plated neurons were transferred into a chamber to allow drug solutions to be added to the cells using a computer-controlled solenoid-valve based perfusion system. The cells were imaged using standard DIC optics. Cells were patched using finely-pulled glass electrodes. Voltage-clamp electrophysiology experiments were carried out using an Axon Instruments Multiclamp amplified controlled by pCLAMP8 software.

The cells were placed into a whole-cell voltage clamp and held at a voltage of −80 mV while monitoring the membrane current in gap-free recording mode. 500 nM capsaicin was added for 30 seconds as a control. Test compounds at various concentrations were added to the cells for 1 minute prior to a 30 second capsaicin application. Differences between control experiments and drug positive capsaicin experiments were used to determine the efficacy of each test compound. All compounds that inhibited capsaicin induced current greater than 50% were considered positives. The data obtained for compound 240 is set forth in Table 5.

TABLE 5

| Compound ID | Concentration | Treatment time (seconds) | % inhibition of capsaicin induced current |
|---|---|---|---|
| 240 | 100 nM | 20 | 50 |

All publications, patents and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. All such modifications coming within the scope of the appended claims are intended to be included therein.

What is claimed is:

1. A compound according to formula (I):

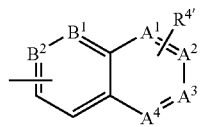

or a pharmaceutically acceptable salt, stereoisomer or tautomer thereof, wherein:
each of W, Z and X is $CR^4$ and Y is $CR^{4''}$;
L is —($CR^5$=$CR^6$)— or —(C≡C)—;
$R^1$ is quinolinyl substituted with hydrogen, $C_1$-$C_6$ alkyl, hydroxyl $C_1$-$C_6$ alkyl, $C_1$-$C_6$ alkylamino, $C_1$-$C_6$ alkoxy, amino $C_1$-$C_6$ alkoxy, substituted amino $C_1$-$C_6$ alkoxy, di $C_1$-$C_6$ alkylamino $C_1$-$C_6$ alkoxy, cycloalkyl $C_1$-$C_6$ alkoxy, $C_1$-$C_6$ alkoxycarbonyl, $C_1$-$C_6$ alkylarylamino, aryl $C_1$-$C_6$ alkyloxy, amino, aryl, aryl $C_1$-$C_6$ alkyl, substituted sulfonyl, sulfanyl, aminosulfonyl, arylsulfonyl, azido, carboxy, carbamoyl, cyano, cycloheteroalkyl, di $C_1$-$C_6$ alkylamino, halo, heteroaryloxy, heteroaryl, heteroalkyl, hydroxyl, nitro or thio;
$R^3$ is $CR^{6'}R^7R^8$;
each $R^4$ is independently hydrogen, $C_1$-$C_6$ alkyl, hydroxyl $C_1$-$C_6$ alkyl, $C_1$-$C_6$ alkylamino, $C_1$-$C_6$ alkoxy, amino $C_1$-$C_6$ alkoxy, substituted amino $C_1$-$C_6$ alkoxy, di $C_1$-$C_6$ alkylamino $C_1$-$C_6$ alkoxy, cycloalkyl $C_1$-$C_6$ alkoxy, $C_1$-$C_6$ alkoxycarbonyl, $C_1$-$C_6$ alkylarylamino, aryl $C_1$-$C_6$ alkyloxy, amino, aryl, aryl $C_1$-$C_6$ alkyl, substituted sulfonyl, sulfanyl, aminosulfonyl, arylsulfonyl, azido, carboxy, carbamoyl, cyano, cycloheteroalkyl, di $C_1$-$C_6$ alkylamino, halo, heteroaryloxy, heteroaryl, heteroalkyl, hydroxyl, nitro or thio;
$R^{4''}$ is substituted alkyl, methyl, halo, substituted sulfonyl, alkoxy, or amino;
each of $R^5$ and $R^6$ is independently H, halo, or $C_1$-$C_6$ alkyl; and
$R^{6'}$ is hydrogen, halo or $C_1$-$C_6$ alkyl; each of $R^7$ and $R^8$ is independently halo or $C_1$-$C_6$ alkyl; or $R^7$ and $R^8$ together form a $C_3$-$C_8$ cycloalkyl ring.

2. A compound according to claim 1 wherein each of $R^5$ and $R^6$ is independently H, or $C_1$-$C_6$ alkyl.

3. A compound according to claim 1 wherein $R^1$ is

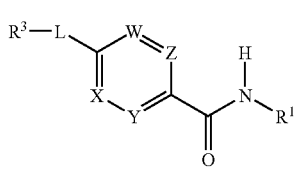

wherein, each ring is optionally substituted with one or more $R^{4'}$, and $R^{4'}$ is $C_1$-$C_6$ alkyl, halo, or hydroxy $C_1$-$C_6$ alkyl.

4. A compound according to claim 1 wherein $R^1$ is:

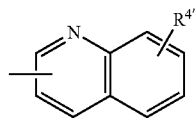

wherein $A^1$ is N; each of $A^2$, $A^3$ and $A^4$ is CH; and each of $B^1$ and $B^2$ is CH; one of $A^2$, $A^3$ and $A^4$ substitued with $R^{4'}$, and $R^{4'}$ is $C_1$-$C_6$ alkyl or hydroxy $C_1$-$C_6$ alkyl.

5. A compound according to claim 1 wherein $R^1$ is:

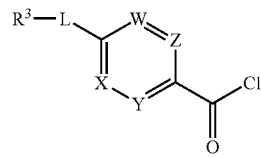

and wherein $R^{4'}$ is H, $C_1$-$C_6$ alkyl, halo, or hydroxy $C_1$-$C_6$ alkyl.

6. A compound according to claim 1 wherein $R^1$ is:

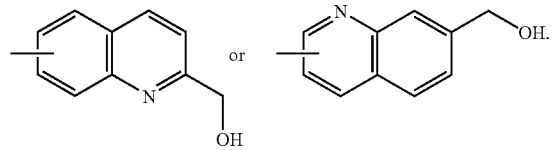

7. A compound according to claim 1 wherein each of $R^{4''}$ is methyl, chloro, trifluoromethyl, fluoro, or $SO_2Me$.

8. A compound according to claim 1 wherein $R^4$ is H.

9. A compound according to claim 1 wherein L is —($CR^5$=$CR^6$)—; and wherein each of $R^5$ and $R^6$ is independently H or $C_1$-$C_6$ alkyl.

10. A compound according to claim 1 wherein L is —CH=CH—.

11. A compound according to claim 1 wherein L is —C≡C—.

12. A compound according to claim 1 wherein $R^3$ is cyclopropyl, cyclobutyl, cyclopentyl, cyclohexyl or cycloheptyl.

13. A compound according to claim 1 wherein $R^3$ is $CF_3$.

14. A compound according to claim 1 wherein $R^3$ is t-Bu.

15. A pharmaceutical composition comprising a pharmaceutically acceptable carrier and a pharmaceutically effective amount of a compound of claim 1.

16. The pharmaceutical composition of claim 15 wherein the carrier is a parenteral carrier, oral or topical carrier.

17. A method for preparing a compound of claim 1 which comprises contacting a compound of the formula

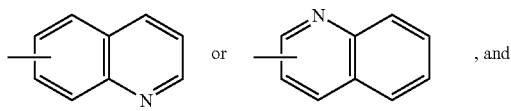

with a compound of the formula $R^1R^2NH$ under conditions sufficient to form a compound according to claim 1; wherein $R^2$ is H.

18. A method for treating a disease or condition which comprises administering to a patient in need of such treatment a therapeutically effective amount of a compound of claim 1, wherein the disease or condition is selected from the group consisting of acute cerebral ischemia, pain, post herpetic neuralgia, neuralgia, nerve injury, burn, headache, migraine, carpal tunnel syndrome, fibromyalgia, neuritis, sciatica, pelvic hypersensitivity incontinence, micturition disorder, renal colic, cystitis, rheumatoid arthritis, osteoarthritis, multiple sclerosis, pulmonary disease, gastroesophageal reflux disease (GERD), dysphagia, ulcer, irritable bowel syndrome (IBS), inflammatory bowel disease (IBD), colitis, Crohn's disease, ischemia, cerebrovascular ischemia, emesis and obesity.

19. The method of claim 18 wherein the compound is administered in combination with another pharmacologically active agent.

20. A compound according to claim 1 wherein the compound is selected from:

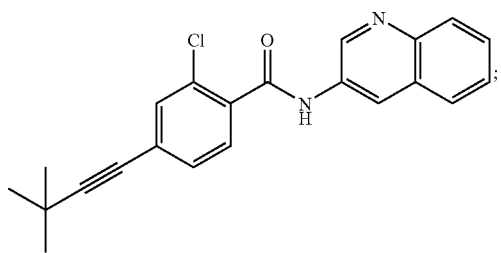

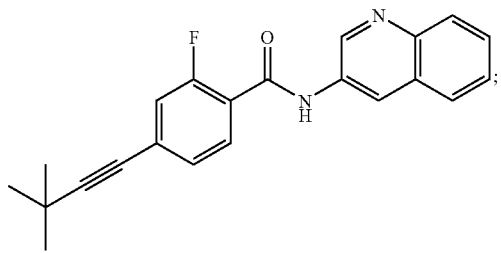

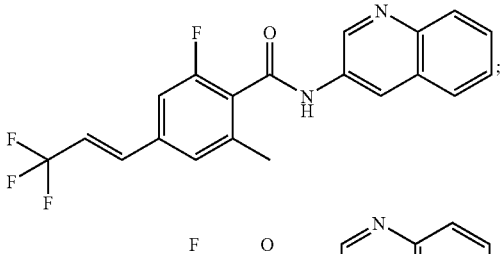

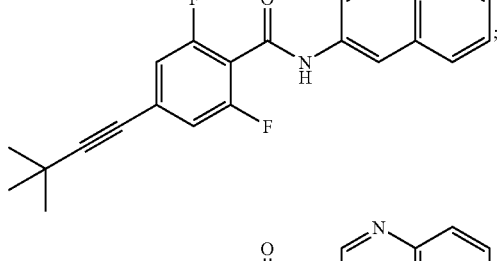

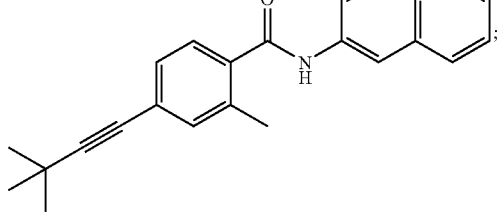

-continued

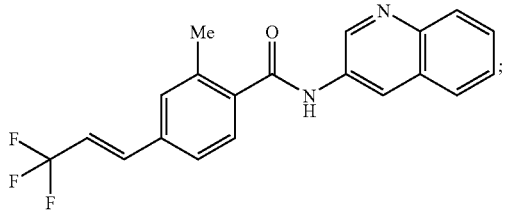

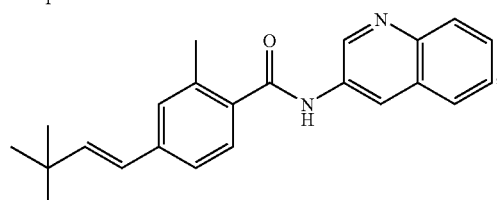

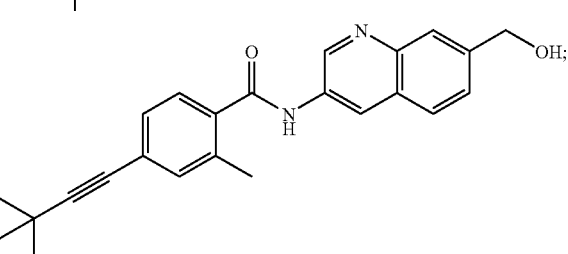

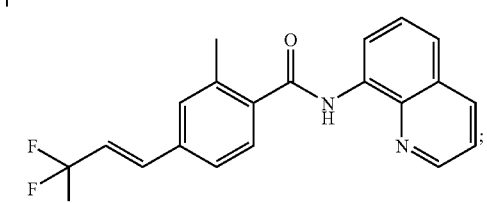

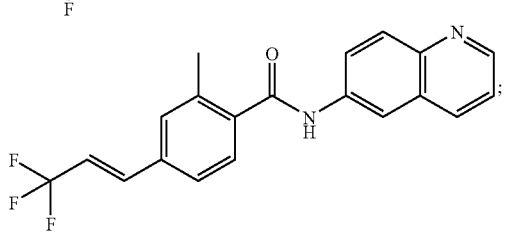

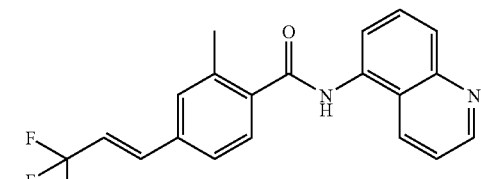

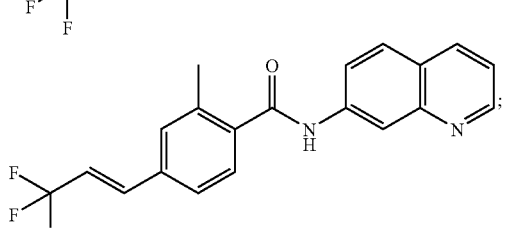

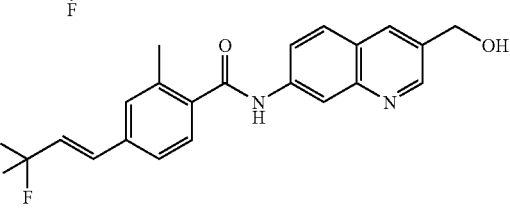

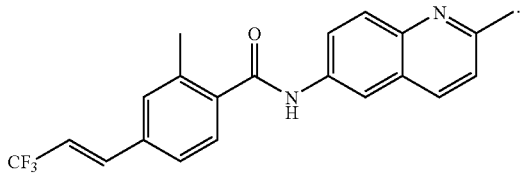

21. A compound according to claim 1 wherein the compound is selected from:
2-chloro-4-(3,3-dimethylbut-1-ynyl)-N-(quinolin-3-yl)benzamide;
4-(3,3-dimethylbut-1-ynyl)-2-fluoro-N-(quinolin-3-)benzamide;
(E)-2-fluoro-N-(quinolin-3-yl)-4-(3,3,3-trifluoroprop-1-enyl)benzamide;
4-(3,3-dimethylbut-1-ynyl)-2,6-difluoro-N-(quinolin-3-yl)benzamide;
4-(3,3-dimethylbut-1-ynyl)-2-methyl-N-(quinolin-3-)benzamide;
(E)-2-methyl-N-(quinolin-3-yl)-4-(3,3,3-trifluoroprop-1-enyl)benzamide;
(E)-4-(3,3-dimethylbut-1-enyl) -2-methly-N-(quinolin-3-yl)benzamide;
4-(3,3-dimethylbut-1-ynyl)-N-(7-(hydroxymethyl)quinolin-3-yl)-2-methylbenzamide;
(E)-2-methyl-N-(quinolin-8-yl)-4-(3,3,3-trifluoroprop-1-enyl)benzamide;
(E)-2-methyl-N-(quinolin-6-yl)-4-(3,3,3-trifluoroprop-1-enyl)benzamide;
(E)-2-methyl-N-(quinolin-5-yl)-4-(3,3,3-trifluoroprop-1-enyl)benzamide;
(E)-2-methyl-N-(quinolin-7-yl)-4-(3,3,3-trifluoroprop-1-enyl)benzamide;
(E)-N-(-3-(hydroxymethyl)quinolin-7-yl)-2-methyl-4-(3,3,3-trifluoroprop-1-enyl) benzamide;
(E)-2-methyl-N-(2-methylquinolin-6-yl)-4-(3,3,3-trifluoroprop-1-enyl)benzamide.

22. A compound according to claim 1 wherein $R^1$ is quinolinyl, optionally substituted with one or more $R^{4'}$, wherein $R^{4'}$ is $C_1$-$C_6$ alkyl, halo, or hydroxy $C_1$-$C_6$ alkyl.

23. The method of claim 18, wherein the disease or condition is a pain selected from the group consisting of chronic pain, acute pain, nociceptive pain, neuropathic pain, inflammatory pain, rheumatoid arthritic pain, osteoarthritic pain, back pain, visceral pain, dental pain, pelvic pain, menstrual pain and post stroke pain.

24. The method of claim 18, wherein the disease or condition is a pulmonary disease selected from the group consisting of asthma, cough, chronic obstructive pulmonary disease (COPD) and broncho constriction.

* * * * *